US011213482B1

(12) United States Patent
Gambotto et al.

(10) Patent No.: US 11,213,482 B1
(45) Date of Patent: Jan. 4, 2022

(54) SARS-COV-2 SUBUNIT VACCINE AND MICRONEEDLE ARRAY DELIVERY SYSTEM

(71) Applicant: University of Pittsburgh—Of the Commonwealth System of Higher Education, Pittsburgh, PA (US)

(72) Inventors: Andrea Gambotto, Pittsburgh, PA (US); Louis Falo, Jr., Wexford, PA (US); Eun Kim, Allison Park, PA (US)

(73) Assignee: University of Pittsburgh—Of the Commonwealth System of Higher Educat, Pittsburgh, PA (US)

( * ) Notice: Subject to any disclaimer, the term of this patent is extended or adjusted under 35 U.S.C. 154(b) by 0 days.

(21) Appl. No.: 17/009,121

(22) Filed: Sep. 1, 2020

Related U.S. Application Data

(60) Provisional application No. 62/989,208, filed on Mar. 13, 2020, provisional application No. 62/985,498, filed on Mar. 5, 2020.

(51) Int. Cl.

| | |
|---|---|
| ***A61K 39/00*** | (2006.01) |
| ***A61K 9/00*** | (2006.01) |
| ***A61B 5/15*** | (2006.01) |
| ***A61K 47/58*** | (2017.01) |
| ***A61K 39/39*** | (2006.01) |

(52) U.S. Cl.
CPC ...... *A61K 9/0021* (2013.01); *A61B 5/150984* (2013.01); *A61K 39/39* (2013.01); *A61K 47/58* (2017.08); *A61K 2039/505* (2013.01)

(58) Field of Classification Search
CPC .................................................. A61K 9/0021
See application file for complete search history.

(56) References Cited

U.S. PATENT DOCUMENTS

| | | | |
|---|---|---|---|
| 4,722,848 | A | 2/1988 | Paoletti et al. |
| 5,091,309 | A | 2/1992 | Schlesinger et al. |
| 5,217,879 | A | 6/1993 | Huang et al. |
| 5,589,466 | A | 12/1996 | Felgner et al. |
| 5,593,972 | A | 1/1997 | Weiner et al. |
| 5,643,579 | A | 7/1997 | Hung et al. |
| 5,817,637 | A | 10/1998 | Weiner et al. |
| 5,837,511 | A | 11/1998 | Falck-Pedersen et al. |
| 5,851,806 | A | 12/1998 | Kovesdi et al. |
| 5,880,103 | A | 3/1999 | Urban et al. |
| 5,994,106 | A | 11/1999 | Kovesdi et al. |
| 6,127,175 | A | 10/2000 | Vigne et al. |
| 6,194,388 | B1 | 2/2001 | Krieg et al. |
| 6,207,646 | B1 | 3/2001 | Krieg et al. |
| 6,214,806 | B1 | 4/2001 | Krieg et al. |
| 6,218,371 | B1 | 4/2001 | Krieg et al. |
| 6,239,116 | B1 | 5/2001 | Krieg et al. |
| 6,339,068 | B1 | 1/2002 | Krieg et al. |
| 6,406,705 | B1 | 6/2002 | Davis et al. |
| 6,429,199 | B1 | 8/2002 | Krieg et al. |
| 6,482,616 | B1 | 11/2002 | Kovesdi et al. |
| 7,067,309 | B2 | 6/2006 | Imler et al. |
| 7,195,896 | B2 | 3/2007 | Kovesdi et al. |
| 8,834,423 | B2 | 9/2014 | Falo, Jr. et al. |
| 2003/0096787 | A1 | 5/2003 | Perricaudet et al. |
| 2005/0112554 | A1 | 5/2005 | Shao et al. |
| 2009/0022735 | A1 | 1/2009 | Chong et al. |
| 2011/0098651 | A1 | 4/2011 | Falo, Jr. et al. |
| 2014/0350472 | A1 | 11/2014 | Falo, Jr. et al. |
| 2015/0126923 | A1 | 5/2015 | Falo, Jr. et al. |
| 2016/0271381 | A1 | 9/2016 | Falo, Jr. et al. |
| 2017/0050010 | A1 | 2/2017 | McAllister et al. |
| 2018/0272621 | A1 | 9/2018 | Falo, Jr. et al. |
| 2020/0031874 | A1 | 1/2020 | Gambotto et al. |

FOREIGN PATENT DOCUMENTS

| | | | |
|---|---|---|---|
| WO | 9428152 | A1 | 12/1994 |
| WO | 9502697 | A1 | 1/1995 |
| WO | 9516772 | A1 | 6/1995 |
| WO | 9534671 | A1 | 12/1995 |
| WO | 9622378 | A1 | 7/1996 |
| WO | 9712986 | A2 | 4/1997 |
| WO | 9721826 | A2 | 6/1997 |
| WO | 03022311 | A1 | 3/2003 |
| WO | 2017066768 | A1 | 4/2017 |
| WO | WO 2019136133 | | 7/2019 |
| WO | WO 2020232394 | | 11/2020 |

OTHER PUBLICATIONS

Wu et al (Nature vol. 579, pp. 265-269) (Year: 2020).*
Al-Omari et al., "MERS coronavirus outbreak: Implications for emerging viral infections", Diagnostic Microbiology and Infectious Disease, 2019, pp. 265-285, vol. 93.
Altschul et al., "Basic Local Alignment Search Tool", J. Mol. Biol., 1990, pp. 403-410, vol. 215.
Altschul et al., "Gapped BLAST and PSI-BLAST: a new generation of protein database search programs", Nucleic Acids Research, 1997, pp. 3389-3402, vol. 25, No. 17.
Ausubel et al., "Current Protocols in Molecular Biology", 2003, Units 7.7.1-7.7.23, John Wiley & Sons, Inc, New York.
Balmert et al., "Dissolving undercut microneedle arrays for multicomponent cutaneous vaccination", Journal of Controlled Release, 2020, pp. 336-346, vol. 317.
Bandyopadhyay, et al., "Expression of Complete Chicken Thymidine Kinase Gene Inserted in a Retrovirus Vector", Molecular and Cellular Biology, 1984, pp. 749-754, vol. 4, No. 4.
Bediz et al., "Dissolvable Microneedle Arrays for Intradermal Delivery of Biologics: Fabrication and Application", Pharm Res, 2014, pp. 117-135, vol. 31.
Bhardwaj et al., "Foldon-guided self-assembly of ultra-stable protein filbers", Protein Science, 2008, pp. 1475-1485, vol. 17.
Buchschacher et al., "Human Immunodeficiency Virus Vectors for Inductible Expression of Foreign Genes", Journal of Virology, 1992, pp. 2731-2739, vol. 66, No. 5.

(Continued)

*Primary Examiner* — Albert M Navarro
(74) *Attorney, Agent, or Firm* — Fish & Richardson P.C.

(57) ABSTRACT

A recombinant coronavirus vaccine is provided. Methods of making and delivering the coronavirus vaccine also are provided. A microneedle array is provided, along with methods of making and using the microneedle array.

27 Claims, 39 Drawing Sheets
(4 of 39 Drawing Sheet(s) Filed in Color)
Specification includes a Sequence Listing.

(56) References Cited

OTHER PUBLICATIONS

Chen et al., "Crystal Structure of the Receptor-Binding Domain from Newly Emerged Middle East Respiratory Syndrome Coronavirus", Journal of Virology, 2013, pp. 10777-10783, vol. 87, No. 19.
Corpet, "Multiple sequence alignment with hierarchical clustering", Nucleic Acids Research, 1988, pp. 10881-10890, vol. 16, No. 22.
Cuesta et al., "Improved stability of multivalent antibodies containing the human collagen XV trimerization domain", mAbs, 2012, pp. 226-232, vol. 4, No. 2.
Datta et al., "A Subset of Toll-Like Receptor Ligands Induces Cross-presentation by Bone Marrow-Derived Dendritic Cells", The Journal of Immunology, 2003, 4102-4110, vol. 170.
Demuth et al. "Composite Dissolving Microneedles for Coordinated Control of Antigen and Adjuvant Delivery Kinetics in Transcutaneous Vaccination", Adv. Funct. Mater., 2013, pp. 161-172, vol. 23.
Demuth et al., "Implantable Silk Composite Microneedles for Programmable Vaccine Release Kinetics and Enhanced Immunogenicity in Transcutaneous Immunization", Adv. Healthcare Mater., 2014, pp. 47-58, vol. 3.
Ding et al., "Microneedle arrays for the transcutaneous immunization of diphtheria and influenza in BALB/c mice", Journal of Controlled Release, 2009, pp. 71-78, vol. 136.
Economidou et al., "3D printing applications for transdermal drug delivery", International Journal of Pharmaceutics, 2018, pp. 415-424, vol. 544.
Feng et al., "Progressive Sequence Alignment as a Prerequisite to Correct Phylogenetic Trees", J Mol Evol, 1987, pp. 351-360, vol. 25.
Fernando et al., "Safety, tolerability, acceptability and immunogenicity of an influenza vaccine delivered to human skin by a novel high-density microprojection array patch (Nanopatch)", Vaccine, 2018, pp. 3779-3788, vol. 36.
Fink et al., "In Vivo Expression of B-Galactosidase in Hippocampal Neurons by HSV-Mediated Gene Transfer", Human Gene Therapy, 1992, pp. 11-19, vol. 3.
Frolov et al., "Alphavirus-based expression vectors: Strategies and applications", Proc. Natl. Acad. Sci., 1996, pp. 11371-11377, vol. 93.
Gao et al., "Protection of Mice and Poultry from Lethal H5N1 Avian Influenza Virus through Adenovirus-Based Immunization", Journal of Virology, 2006, pp. 1959-1964, vol. 80, No. 4.
Gates et al., "Replication of Vertical Features Smaller than 2 nm by Soft Lithography", J. Am. Chem. Soc., 2003, pp. 14986-14987, vol. 125.
Gorziglia et al., "Expression of the OSU Rotavirus Outer Capsid Protein VP4 by an Adenovirus Recombinant", Journal of Virology, 1992, pp. 4407-4412, vol. 66, No. 7.
Grundner et al., "Anaylsis of the neutralizing antibody response elicited in rabbits by repeated inoculation with trimeric HIV-1 envelope glycoproteins", Virology, 2005, pp. 33-46, vol. 331.
Hardy et al., "Construction of Adenovirus Vectors through Cre-Iox Recombination", Journal of Virology, 1997, pp. 1842-1849, vol. 71, No. 3.
He et al., "Skin-Derived Dendritic Cells Induce Potent CD8 T Cell Immunity in Recombinant Lentivector-Mediated Genetic Immunization", Immunity, 2006, pp. 643-656, vol. 24.
Helgason et al. (Editors), "Basic Cell Culture Protocols (Methods in Molecular Biology)", 2013, Fourth Edition, Humana Press, New York.
Henikoff et al., "Amino acid substitution matrices from protein blocks", Proc. Natl. Acad. Sci. USA, 1992, pp. 10915-10919, vol. 89.
Herweijer et al., "A Plasmid-Based Self-Amplifying Sindbis Virus Vector", Human Gene Therapy, 1995, pp. 1161-1167, vol. 6.
Higgins et al., "CLUSTAL: a package for performing multiple sequence alignment on a microcomputer", Gene, 1988, pp. 237-244, vol. 73.
Jeong et al., "PDMS-Based Elastomer Tuned Soft, Stretchable, and Sticky for Epidermal Electronics", Adv. Mater., 2016, pp. 5830-5836. vol. 28.
Johnson et al., "Cytotoxicity of a Replication-Defective Mutant of Herpes Simplex Virus Type 1", Journal of Virology, 1992, pp. 2952-2965, vol. 66, No. 5.
Goole et al., "3D printing in pharmaceutics: A new tool for designing customized drug delivery systems", International Journal of Pharmaceutics, 2016, pp. 376-394, vol. 499.
Kabashima et al., "The immunological anatomy of the skin", Nature Review—Immunology, 2019, pp. 19-30, vol. 19.
Kalali et al., "Double-Stranded RNA Induces an Antiviral Defense Status in Epidermal Keratinocytes through TLR3-, PKR-, and MDA5/RIG-I-Mediated Differential Signaling", The Journal of Immunology, 2008, pp. 2694-2704, vol. 181.
Kashem et al., "Antigen-Presenting Cells in the Skin", Annu. Rev. Immunol., 2017, pp. 469-499, vol. 35.
Kaushik et al., "Why is Trehalose an Exceptional Protein Stabilizer?", The Journal of Biological Chemistry, 2003, pp, 26458-26465, vol. 278, No. 29.
Khanafer et al., "Effects of strain rate, mixing ratio, and stress-strain definition on the mechanical behavior of the polydimethylsiloxane (PDMS) material as related to its biological applications", Biomed Microdevices, 2009, pp. 503-508, vol. 11.
Kim et al., "Immunogenicity of an adenoviral-based Middle East Respiratory Syndrome coronavirus vaccine in BALB/c mice", Vaccine, 2014, pp. 5975-5982, vol. 32.
Kim et al., "Preventative Vaccines for Zika Virus Outbreak: Preliminary Evaluation", EBioMedicine, 2016, pp. 315-320, vol. 13.
Korkmaz et al., "Theraputic intradermal delivery of tumor necrosis factor—alpha antibodies using tip-loaded dissolvable microneedle arrays", Acta Biomaterialia, 2015, pp. 96-105, vol. 24.
Korkmaz et al., "Tip-loaded Dissolvable Microneedle Arrays Effectively Deliver Polymer-Conjugated Antibody Inhibitors of Tumor—Necrosis-Factor-Alpha Into Human Skin", Journal of Pharmaceutical Sciences, 2016, pp. 3453-3457, vol. 105.
Krammer et al., "A Carboxy-Terminal Trimerization Domain Stabilizes Conformational Epitopes on the Stalk Domain of Soluble Recombinant Hemagglutinin Substrates", PLoS ONE, 2012, vol. 7, No. 8, e43603.
Lee et al., "Dissolving microneedles for transdermal drug delivery", Biomaterials, 2008, pp. 2113-2124, vol. 29.
Li et al., "Immunogenicity and Protection Efficacy of Monomeric and Trimeric Recombinant SARS Coronavirus Spike Protein Subunit Vaccine Candidates", Viral Immunology, 2013, pp. 126-132, vol. 26, No. 2.
Li et al., "Rapidly Seperable microneedle patch for the sustained release of a contraceptive", Nature Biomedical Engineering, 2019, pp. 220-229, vol. 3.
Lin et al., "3D printed, bio-inspired prototypes and analytical models for structured suture interfaces with geometrically—tuned deformation and failure behavior", Journal of the Mechanics and Physics of Solids, 2014, pp. 166-182, vol. 73.
Lopez-Boado et al., "Bordetella bronchiseptica Flagellin Is a Proinflammatory Determinant for Airway Epithelial Cells", Infection and Immunity, 2005, pp. 7525-7534, vol. 73, No. 11.
Losic et al., "Rapid Fabrication of Micro and Nanoscale Patterns by Replica Molding from Diatom Biosilica", Adv. Funct. Mater., 2007, pp. 2439-2446, vol. 17.
Lu et al., "Molecular basis of binding between novel human coronavirus MERS-CoV and its receptor CD26", Nature, 2013, pp. 227-231, vol. 500.
Lu et al., "Structure-based discovery of Middle East respiratory syndrome coronavirus fusion inhibitor", Nature Communications, 2014, vol. 5, DOI: 10.1038/ncomms4067.
Madzak et al., "Efficient in vivo encapsidation of a shuttle vector into pseudo-simian virus 40 virions using a shuttle virus as helper", Journal of General Virology, 1992, pp. 1533-1536, vol. 73.
Mann et al., "Varying the Position of a Retrovirus Packaging Sequence Results in the Encapsidation of Both Unspliced and Spliced RNAs", Journal of Virology, 1985, pp. 401-407, vol. 54, Nol. 2.

(56) References Cited

OTHER PUBLICATIONS

McCrudden et al., "Laser-engineered dissolving microneedle arrays for protein delivery: potential for enhanced intradermal vaccination", Journal of Pharmacy and Pharmacology, 2014, pp. 409-425, vol. 67.
Miller et al., "Generation of Helper-Free Amphotropic Retroviruses That Transduce a Dominant-Acting, Methotrexate-Resistant Dihydrofolate Reductase Gene", Mollecular and Cellular Biology, 1985, pp. 431-437, vol. 5, No. 3.
Needleman et al., "A General Method Applicable to the Search for Similarities in the Amino Acid Sequence of Two Proteins", J. Mol. Biol., 1970, pp. 443-453, vol. 48.
Nimmerjahn et al., "Divergent Immunoglobulin G Subclass Activity Through Selective Fc Receptor Binding", Science, 2005, pp. 1510-1512, vol. 310.
Nishiura et al., "Identifying determinants of heterogeneous transmission dynamics of the Middle East respiratory syndrome (MERS) outbreak in the Republic of Korea, 2015: a retrospective epidemiological analysis", BMJ Open, 2016, e009936, DOI: 10.1136/bmjopen-2015-009936.
Ohi et al., "Construction and replication of an adeno-associated virus expression vector that contains human B-globin cDNA", Gene, 1990, pp. 279-282, vol. 89.
Page et al., "Construction and Use of a Human Immunodeficiency Virus Vector for Analysis of Virus Infectivity", Journal of Virology, 1990, pp. 5270-5276, vol. 64, No. 11.
Papanikolopoulou et al., "Formation of Highly Stable Chimeric Trimers by Fusion of an Adenovirus Fiber Shaft Fragment with the Foldon Domain of Bacteriophage T4 Fibritin", Journal of Biological Chemistry, 2004, pp. 8991-8998, vol. 279, No. 10.
Park et al., "Epidemiological investigation of MERS-CoV spread in a single hospital in South Korea, May to Jun. 2015", Euro Surveill., 2015, Article ID 21169, vol. 20, No. 25.
Pearson et al., "Improved tools for biological sequence comparison", Proc. Natl. Acad. Sci. USA, 1988, pp. 2444-2448, vol. 85.
Pearson, "Using the FASTA program to search protein and DNA sequence databases", Meth. Mol. Bio, 1994, pp. 309-331, vol. 24.
Peruzzi et al., "A novel Chimpanzee serotype-based adenoviral vector as a delivery tool for cancer vaccines", Vaccine, 2009, pp. 1293-1300, vol. 27.
Petropoulos et al., "Using Avian Retroviral Vectors for Gene Transfer", Journal of Virology, 1992, pp. 3391-3397, vol. 66, No. 6.
Prasad et al., "3D Printing technologies for drug delivery: a review", Drug Development and Industrial Pharmacy, 2016, pp. 1019-1031, vol. 42, No. 7.
Prausnitz, "Engineering Microneedle Patches for Vaccination and Drug Delivery to Skin", Annu. Rev. Chem. Biomol. Eng., 2017, pp. 177-200, vol. 8.
Quantin et al., "Adenovirus as an expression vector in muscle cells in vivo", Proc. Natl. Acad. Sci. USA, 1992, pp. 2581-2584, vol. 89.
Rad et al., "High-fidelity replication of thermoplastic microneedles with open microfluidic channels", Microsystems & Nanoengineering, 2017, Article No. 17034, vol. 3.
Raj et al., "Dipeptidyl peptidase 4 is a functional receptor for the emerging human coronavirus—EMC", Nature, 2013, pp. 251-256, vol. 495.
Rosenfeld et al., "In Vivo Transfer of the Human Cystic Fibrosis Transmembrane Conductance Regulator Gene to the Airway Epithelium", Cell, 1992, pp. 143-155, vol. 68.
Rouphael et al., "The safety, immunogenicity, and acceptability of inactivated influenza vaccine delivered by microneedle patch (TIV-MNP 2015): a randomised, partly blinded, placebo-controlled, phase 1 trial", Lancet, 2017, pp. 649-658, vol. 390.
Schlesinger, "Alphaviruses—vectors for the expression of heterologous genes", Trends Biotechnol., 1993, pp. 18-22, vol. 11, No. 1.
Schulz et al., "Toll-like receptor 3 promotes cross-priming to virus-infected cells", Nature, 2005, pp. 887-892, vol. 433.
Shanmugam et al., "Synthetic Toll Like Receptor-4 (TLR-4) Agonist Peptides as a Novel Class of Adjuvants", PLoS ONE, 2012, Article No. e30839, vol. 7, No. 2.
Skountzou et al., "*Salmonella flagellins* are potent adjuvants for intranasally administered whole inactivated influenza vaccine", Vaccine, 2010, pp. 4103-4112, vol. 28.
Smith et al., "Comparison of Biosequences", Advances in Applied Mathematics, 1981, pp. 482-489, vol. 2.
Song et al., "Synthesis and Characterization of a Native, Oligomeric Form of Recombinant Severe Acute Respiratory Syndrome Coronavirus Spike Glycoprotein", Journal of Virology, 2004, pp. 10328-10335, vol. 78, No. 19.
Song et al., "An avian influenza A (H7N9) virus vaccine candidate based on the fusion protein of hemagglutinin globular head and *Salmonella typhimurium* flagellin", BMC Biotechnology, 2015, vol. 15, No. 79, DOI 10.1186/s12896-015-0195-z.
Sorge et al., "Amphotropic Retrovirus Vector System for Human Cell Gene Transfer", Molecular and Cellular Biology, 1984, pp. 1730-1737, vol. 4, No. 9.
Steitz et al., "A Candidate H1N1 Pandemic Influenza Vaccine Elicits Protective Immunity in Mice", PLoS ONE, 2010, Article No. e10492, vol. 5, No. 5.
Stover et al., "New use of BCG for recombinant vaccines", Nature, 1991, pp. 456-460, vol. 351.
Stratford-Perricaudet et al., "Evaluation of the Transfer and Expression in Mice of an Enzyme-Encoding Gene Using a Human Adenovirus Vector", Human Gene Therapy, 1990, pp. 241-256, vol. 1.
Sullivan et al., "Dissolving polymer microneedle patches for influenza vaccination", Nature Medicine, 2010, pp. 915-921, vol. 16, No. 8.
Tai et al., "A recombinant receptor-binding domain of MERS-CoV in trimeric form protects human dipeptidyl peptidase 4 (hDPP4) transgenic mice from MERS-CoV infection", Virology, 2016, pp. 375-382, vol. 499.
Takahashi et al., "Induction of CD8 cytotoxic T cells by immunization with purified HIV-1 envelope protein in ISCOMs", Nature, 1990, pp. 873-875, vol. 344.
Tang et al., "Cardiac cell-integrated microneedle patch for treating myocardial infarction", Sci. Adv., 2018, Article No. eaat9365, vol. 4.
Tang et al., "On the origin and continuing evolution of SARS-CoV-2", National Science Review, 2020, pp. 1012-1023, vol. 7.
Tao et al., "Structure of bacteriophage T4 fibritin: a segmented coiled coil and the role of the C-terminal domain", Structure, 1997, pp. 789-798, vol. 5.
Tewari et al., "Poly (I:C) is an effective adjuvant for antibody and multi-functional CD4+ T cell responses to Plasmodium falciparum circumsporozoite protein (CSP) and aDEC-CSP in non human primates", Vaccine, 2010, pp. 7256-7266, vol. 28.
Than et al., "Self-implantable double-layered micro-drug-reservoirs for efficient and controlled ocular drug delivery", Nature Communications, 2018, vol. 9, No. 4433, DOI: 10.1038/s41467-018-06981-w.
Verbaan et al., "Improved piercing of microneedle arrays in dermatomed human skin by an impact insertion method", Journal of Controlled Release, 2008, pp. 80-88, vol. 128.
Wang et al., "Structure of MERS-CoV spike receptor-binding domain complexed with human receptor DPP4", Cell Research, 2013, pp. 986-993, vol. 23.
Weldon et al., "Effect of Adjuvants on Responses to Skin Immunization by Microneedles Coated with Influenza Subunit Vaccine", PLoS ONE, 2012, Article No. e41501, vol. 7, No. 7.
World Health Organization, "2018 Annual review of diseases prioritized under the Research and Development Blueprint", 2018, Available from: http://www.who.int/blueprint/priority-diseases/en/.
World Health Organization, "MERS Situation Update Nov. 2019", MERS-CoV Situation Update from the Eastern Mediterranean Region, 2019, Available at https://www.who.int/emergencies/mers-cov/en/.
Wilkinson et al., "Constitutive and enhanced expression from the CMV major IE promoter in a defective adenovirus vector", Nucleic Acid Research, 1992, pp. 2233-2239, vol. 20, No. 9.
Yang et al., "Highly Stable Trimers Formed by Human Immunodeficiency Virus Type 1 Envelope Glycoproteins Fused with the Trimeric Motif of T4 Bacteriophage Fibritin", Journal of Virology, 2002, pp. 4634-4642, vol. 76, No. 9.

(56) References Cited

OTHER PUBLICATIONS

Yang et al., "Engineering of Fc Fragments with Optimized Physicochemical Properties Implying Improvement of Clinical Potentials for Fc-Based Therapeutics", Frontiers in Immunology, 2018, Article No. 1860, vol. 8.
Yu et al., "Intranasal vaccination of recombinant H5N1 HA1 proteins fused with foldon and Fc induces strong mucosal immune responses with neutralizing activity: Implication for developing novel mucosal influenza vaccines", Human Vaccines & Immunotherapeutics, 2015, pp. 2831-2838, vol. 11, No. 12.
Zaki et al., "Isolation of a Novel Coronavirus from a Man with Pneumonia in Saudi Arabia", The New England Journal of Medicine, 2012, pp. 1814-1820, vol. 367, No. 19.
Zhao et al., "Enhanced immunization via dissolving microneedle array-based delivery system incorporating subunit vaccine and saponin adjuvant", International Journal of Nanomedicine, 2017, pp. 4763-4772, vol. 12.
Zhao et al., "Transdermal immunomodulation: Principles, advances, and perspectives", Advanced Drug Delivery Reviews, 2018, pp. 3-19, vol. 127.
Berkner, "Development of adenovirus vectors for the expression of heterologous genes," Biotechniques, Jul./Aug. 1988, 6(7):616-629.
Berkner, "Expression of Heterologous Sequences in Adenoviral Vectors," Curr. Top. Microbiol. Immunology, 1992, 158:39-66.
Breakfield et al., "Gene Transfer into the Nervous System," Mol. Neurobiology, Dec. 1987, 1:339-371.
Condon et al. "DNA-based immunization by in vivo transfection of dendritic cells," Nat. Medicine, Oct. 1996, 2(10):1122-1128.
Devereaux et al., "A comprehensive set of sequence analysis programs for the VAX," Nucleic Acids Research, Jan. 1984, 12(1 Pt. 1):387-395.
Freese et al., "HSV-1 Vector Mediated Neuronal Gene Delivery: Strategies for Molecular Neuroscience and Neurology," Biochem. Pharmacology, Nov. 1990, 40(10):2189-2199.
GenBank Accession No. ACY88831.1, "flagellin [*Salmonella enterica* subsp. *enterica serovar Typhimurium* str. 14028S]," Mar. 22, 2017, 1 page.
GenBank Accession No. JX869059.2, "Human betacoronavirus 2c EMC/2012, complete genome," Dec. 4, 2012, 12 pages.
GenBank Accession No. U62024.1. "Recombination vector pAdlox, complete sequence," Feb. 27, 1997, 2 pages.
Higgins et al., "Fast and sensitive multiple sequence alignments on a microcomputer," Comput. Appl. Biosci. Communication, Apr. 1989, 5(2):151-153.
Huang et al., "Parallelization of a local similarity algorithm," Comput. Appl. Biosciences, Apr. 1992, 8(2):155-65.
Johnston et al., "Mechanical characterization of bulk Sylgard 184 for microfluidics and microengineering," J. Micromech. Microengineering, Feb. 28, 2014, 24:035017, 7 pages.
Mackett et al., "Vaccinia virus: a selectable eukaryotic cloning and expression vector. 1982," Biotechnology, 1992, 24:495-499.
Margolskee, "Epstein-Barr Virus Based Expression Vectors," Curr. Top. Microbial. Immunology, 1992, 158:67-95.
Miller, "Retroviral Vectors," Curr. Top. Microbiol. Immunology, 1992, 158:1-24.
Molecular Cloning: A Laboratory Manual, 4th ed, Sambrook et al. (eds.), 2012, Chapter 11, 883-888.
Morelli et al., "CD4+ T Cell Responses Elicited by Different Subsets of Human Skin Migratory Dendritic Cells," J. Immunology, Jan. 2006, 175(12):7905-7915.
Mowat et al., "ISCOMS—a novel strategy for mucosal immunization?," Immunol. Today, Nov. 1991, 12(11):383-385.
Muzyczka, "Use of Adeno-Associated Virus as a General Transduction Vector for Mammalian Cells," Curr. Top. Microbiol. Immunology, 1992, 158:97-129.
Ahmed et al., "Preliminary Indentification of Potential Vaccine Targets for the COVID-19 Coronavirus (SARS-CoV-2) Based on SARS-CoV Immunological Studies," Viruses, Feb. 25, 2020, 12(3):254, 15 pages.
PCT International Search Report and Written Opinion in International Appln. No. PCT/US2021/021192, dated Jun. 22, 2021, 14 pages.

* cited by examiner atgTTCGTGttcctgGTCctgCTCCCACTGGTGTCCTCGCAGtgcGTGaacCTGACCACCcgcacccAGc
tgCCCCCTGCGTACACCaacTCCatcACCAGGggcgtcTACTATCCCgacaagGTGTTTCGAagtTCCGT
TctgcacTCGacccAAgacCTGttcCTCcccttcttcAGCaacgtgacctggTTCcatGCTatccacgta
tcgGGTACGaacgggACCaagcgcTTCgacaaccccGTCCTGCCCttcaacgacGGCgtgtacTTTgcaT
CCaccGAGaagtcgaacATTATCAGGGGGtggattttcggcACCacccTAGACtcgaagacacagTCGct
gCTGatcgtgaacaacGCGaccaatGTCgtcATCaagGTTTGCgaattcCAGttcTGCAATGACCCCttc
ctgGGAgtctactaccacAAGAACaacaagagctggatggagAGTgagttcAGAGTGTATTCCTCCGCTA
ACaattgcACCttcgagtacGTATCCcagcccttcCTGatggacctggagggcAAGcagGGGaactttAA
AaatctgCGCgagttcgtgTTTaagAACATCgacggcTACttcaagatcTATAGTaagcacacaCCCATA
AATctgGTCCGCgacCTGCCGCAAggcttctccgctTTGGAACCCCTCgtggacCTGCCGATTGGGATCa
acatcACACGTTTTcagACTCTCctggccCTGcacCGGagttacCTGACAcccGGTgacTCCTCCtcagg
ctggACTGCCGGGGCCgccGCTtactacGTCGGCtatTTGcagcccAGAACTTTCCTCctgaagTATaac
GAGAACggcACGatcACCGATgccGTGGATTGTGCGctgGACCCGctgTCGGAGACAaagtgcACGctga
agTCGTTTACCgtggagaagGGGatctaccagACATCTaacttccgggttcagcccACTgagTCCatcgt
gcgcttccccaacatcACGAATCTCtgccccttcggcGAGgtgttcAACGCAactCGCttcgccAGTgtg
tacgcctggAACCGCaagCGGATTtccAATTGTGTCGCTGACtacagtGTGCTTtacaacTCTGCCTCAt
tcAGTACGttcAAGTGTTACggcgtgTCCCCGaccaagctgAATGATctgtgcTTCaccaacGTAtacGC
CGACTCGTTTGTCatcCGCGGCGATGAAgtgAGGcagatcGCGcccGGCcagACGGGCaagATCGCCgac
tacaacTACaagCTGCCCgatgatttcACTggctgtGTTATTGCTtggAATAGTaacAATctggactcga
agGTCGGGGGGaactacaactatCTCTATAGGCTCttcAGAAAAAGTAATCTGaagcctttcgagCGCGA
CatcTCGACTgagATATATcagGCAGGCtccacccCCTGCaacggcGTGGAGgggTTTaattgctacTTC
cccCTTcagagctacggcTTTcagccaacaAACggcgtaGGCTATCAGcccTACCGCgtggtggtgctgT
CAttcGAACTCctgcacgccCCCGCAaccGTCtgcggcCCTaagaagAGTACGaacCTGGTGaagAACaa
gTGCGTCAACttcAATttcAACggcctcACCggcacaGGGGTGctgaccgagTCCaacAAGaagtttCTC
CCGTTCcagcagTTTGGGAGGGACatcGCAgacACTaccgacgcggtgAGGgacccacagaccttggaga
taCTGGACatcactCCTTGCAGCTTCGGGGGCgtgTCGgtcATAACTcccGGCactaacACCTCAAACca
gGTCGCCgtgCTCtaccagGACgtgAACTGTaccgaggtgCCCgtgGCGATTcacgccgaccagctgACA
cccACGtggAGGgtgtactccaccGGAAGTAATGTCttccagacccGCgccgggTGTctgATAGGCGCCg
agcacGTCaacaacTCGTACgagGGATCCTGA

FIG. 2A

MFVFLVLLPLVSSQCVNLTTRTQLPPAYTNSITRGVYYPDKVFRSSVLHSTQDLFLPFFS
NVTWFHAIHVSGTNGTKRFDNPVLPFNDGVYFASTEKSNIIRGWIFGTTLDSKTQSLLIV
NNATNVVIKVCEFQFCNDPFLGVYYHKNNKSWMESEFRVYSSANNCTFEYVSQPFLMDLE
GKQGNFKNLREFVFKNIDGYFKIYSKHTPINLVRDLPQGFSALEPLVDLPIGINITRFQT
LLALHRSYLTPGDSSSGWTAGAAAYYVGYLQPRTFLLKYNENGTITDAVDCALDPLSETK
CTLKSFTVEKGIYQTSNFRVQPTESIVRFPNITNLCPFGEVFNATRFASVYAWNRKRISN
CVADYSVLYNSASFSTFKCYGVSPTKLNDLCFTNVYADSFVIRGDEVRQIAPGQTGKIAD
YNYKLPDDFTGCVIAWNSNNLDSKVGGNYNYLYRLFRKSNLKPFERDISTEIYQAGSTPC
NGVEGFNCYFPLQSYGFQPTNGVGYQPYRVVVLSFELLHAPATVCGPKKSTNLVKNKCVN
FNFNGLTGTGVLTESNKKFLPFQQFGRDIADTTDAVRDPQTLEILDITPCSFGGVSVITP
GTNTSNQVAVLYQDVNCTEVPVAIHADQLTPTWRVYSTGSNVFQTRAGCLIGAEHVNNSY
EGS*

FIG. 2B

2019-nCoV-S1H (2010bp, 669aa)

atgTTCGTGttcctgGTCctgCTCCCACTGGTGTCCTCGCAGtgcGTGaacCTGACCACCcgcacccAGc
tgCCCCCTGCGTACACCaacTCCatcACCAGGggcgtcTACTATCCCgacaagGTGTTTCGAagtTCCGT
TctgcacTCGacccAAgacCTGttcCTCcccttcttcAGCaacgtgacctggTTCcatGCTatccacgta
tcgGGTACGaacgggACCaagcgcTTCgacaaccccGTCCTGCCCttcaacgacGGCgtgtacTTTgcaT
CCaccGAGaagtcgaacATTATCAGGGGGtggattttcggcACCacccTAGACtcgaagacacagTCGct
gCTGatcgtgaacaacGCGaccaatGTCgtcATCaagGTTTGCgaattcCAGttcTGCAATGACCCCttc
ctgGGAgtctactaccacAAGAACaacaagagctggatggagAGTgagttcAGAGTGTATTCCTCCGCTA
ACaattgcACCttcgagtacGTATCCcagcccttcCTGatggacctggagggcAAGcagGGGaactttAA
AaatctgCGCgagttcgtgTTTaagAACATCgacggcTACttcaagatcTATAGTaagcacacaCCCATA
AATctgGTCCGCgacCTGCCGCAAggcttctccgctTTGGAACCCCTCgtggacCTGCCGATTGGGATCa
acatcACACGTTTTcagACTCTCctggccCTGcacCGGagttacCTGACAcccGGTgacTCCTCCtcagg
ctggACTGCCGGGGCCgccGCTtactacGTCGGCtatTTGcagcccAGAACTTTCCTCctgaagTATaac
GAGAACggcACGatcACCGATgccGTGGATTGTGCGctgGACCCGctgTCGGAGACAaagtgcACGctga
agTCGTTTACCgtggagaagGGGatctaccagACATCTaacttccgggttcagcccACTgagTCCatcgt
gcgcttccccaacatcACGAATCTCtgccccttcggcGAGgtgttcAACGCAactCGCttcgccAGTgtg
tacgcctggAACCGCaagCGGATTtccAATTGTGTCGCTGACtacagtGTGCTTtacaacTCTGCCTCAt
tcAGTACGttcAAGTGTTACggcgtgTCCCCGaccaagctgAATGATctgtgcTTCaccaacGTAtacGC
CGACTCGTTTGTCatcCGCGGCGATGAAgtgAGGcagatcGCGcccGGCcagACGGGCaagATCGCCgac
tacaacTACaagCTGCCCgatgatttcACTggctgtGTTATTGCTtggAATAGTaacAATctggactcga
agGTCGGGGGGaactacaactatCTCTATAGGCTCttcAGAAAAAGTAATCTGaagcctttcgagCGCGA
CatcTCGACTgagATATATcagGCAGGCtccacccCCTGCaacggcGTGGAGgggTTTaattgctacTTC
cccCTTcagagctacggcTTTcagccaacaAACggcgtaGGCTATCAGcccTACCGCgtggtggtgctgT
CAttcGAACTCctgcacgccCCCGCAaccGTCtgcggcCCTaagaagAGTACGaacCTGGTGaagAACaa
gTGCGTCAACttcAATttcAACggcctcACCggcacaGGGGTGctgaccgagTCCaacAAGaagtttCTC
CCGTTCcagcagTTTGGGAGGGACatcGCAgacACTaccgacgcggtgAGGgacccacagaccttggaga
taCTGGACatcactCCTTGCAGCTTCGGGGGCgtgTCGgtcATAACTcccGGCactaacACCTCAAACca
gGTCGCCgtgCTCtaccagGACgtgAACTGTaccgaggtgCCCgtgGCGATTcacgccgaccagctgACA
cccACGtggAGGgtgtactccaccGGAAGTAATGTCttccagacccGCgccgggTGTctgATAGGCGCCg
agcacGTCaacaacTCGTACgagGGATCCcaccatCACcacCACcacTGA

FIG. 3A

MFVFLVLLPLVSSQCVNLTTRTQLPPAYTNSITRGVYYPDKVFRSSVLHSTQDLFLPFFS
NVTWFHAIHVSGTNGTKRFDNPVLPFNDGVYFASTEKSNIIRGWIFGTTLDSKTQSLLIV
NNATNVVIKVCEFQFCNDPFLGVYYHKNNKSWMESEFRVYSSANNCTFEYVSQPFLMDLEGKQG
NFKNLREFVFKNIDGYFKIYSKHTPINLVRDLPQGFSALEPLVDLPIGINITRFQT
LLALHRSYLTPGDSSSGWTAGAAAYYVGYLQPRTFLLKYNENGTITDAVDCALDPLSETK
CTLKSFTVEKGIYQTSNFRVQPTESIVRFPNITNLCPFGEVFNATRFASVYAWNRKRISN
CVADYSVLYNSASFSTFKCYGVSPTKLNDLCFTNVYADSFVIRGDEVRQIAPGQTGKIAD
YNYKLPDDFTGCVIAWNSNNLDSKVGGNYNYLYRLFRKSNLKPFERDISTEIYQAGSTPC
NGVEGFNCYFPLQSYGFQPTNGVGYQPYRVVVLSFELLHAPATVCGPKKSTNLVKNKCVN
FNFNGLTGTGVLTESNKKFLPFQQFGRDIADTTDAVRDPQTLEILDITPCSFGGVSVITP
GTNTSNQVAVLYQDVNCTEVPVAIHADQLTPTWRVYSTGSNVFQTRAGCLIGAEHVNNSY
EGSHHHHHH*

FIG. 3B

2019-nCoV-S1fRS09 (2094bp, 697aa)

atgTTCGTGttcctgGTCctgCTCCCACTGGTGTCCTCGCAGtgcGTGaacCTGACCACCcgcacccAGc
tgCCCCCTGCGTACACCaacTCCatcACCAGGggcgtcTACTATCCCgacaagGTGTTTCGAagtTCCGT
TctgcacTCGacccAAgacCTGttcCTCcccttcttcAGCaacgtgacctggTTCcatGCTatccacgta
tcgGGTACGaacgggACCaagcgcTTCgacaaccccGTCCTGCCCttcaacgacGGCgtgtacTTTgcaT
CCaccGAGaagtcgaacATTATCAGGGGGtggattttcggcACCacccTAGACtcgaagacacagTCGct
gCTGatcgtgaacaacGCGaccaatGTCgtcATCaagGTTTGCgaattcCAGttcTGCAATGACCCCttc
ctgGGAgtctactaccacAAGAACaacaagagctggatggagAGTgagttcAGAGTGTATTCCTCCGCTA
ACaattgcACCttcgagtacGTATCCcagcccttcCTGatggacctggagggcAAGcagGGGaactttAA
AaatctgCGCgagttcgtgTTTaagAACATCgacggcTACttcaagatcTATAGTaagcacacaCCCATA
AATctgGTCCGCgacCTGCCGCAAggcttctccgctTTGGAACCCCTCgtggacCTGCCGATTGGGATCa
acatcACACGTTTTcagACTCTCctggccCTGcacCGGagttacCTGACAcccGGTgacTCCTCCtcagg
ctggACTGCCGGGGCCgccGCTtactacGTCGGCtatTTGcagcccAGAACTTTCCTCctgaagTATaac
GAGAACggcACGatcACCGATgccGTGGATTGTGCGctgGACCCGctgTCGGAGACAaagtgcACGctga
agTCGTTTACCgtggagaagGGGatctaccagACATCTaacttccgggttcagcccACTgagTCCatcgt
gcgcttccccaacatcACGAATCTCtgccccttcggcGAGgtgttcAACGCAactCGCttcgccAGTgtg
tacgcctggAACCGCaagCGGATTtccAATTGTGTCGCTGACtacagtGTGCTTtacaacTCTGCCTCAt
tcAGTACGttcAAGTGTTACggcgtgTCCCCGaccaagctgAATGATctgtgcTTCaccaacGTAtacGC
CGACTCGTTTGTCatcCGCGGCGATGAAgtgAGGcagatcGCGcccGGCcagACGGGCaagATCGCCgac
tacaacTACaagCTGCCCgatgatttcACTggctgtGTTATTGCTtggAATAGTaacAATctggactcga
agGTCGGGGGGaactacaactatCTCTATAGGCTCttcAGAAAAAGTAATCTGaagcctttcgagCGCGA
CatcTCGACTgagATATATcagGCAGGCtccacccCCTGCaacggcGTGGAGgggTTTaattgctacTTC
cccCTTcagagctacggcTTTcagccaacaAACggcgtaGGCTATCAGcccTACCGCgtggtggtgctgT
CAttcGAACTCctgcacgccCCCGCAaccGTCtgcggcCCTaagaagAGTACGaacCTGGTGaagAACaa
gTGCGTCAACttcAATttcAACggcctcACCggcacaGGGGTGctgaccgagTCCaacAAGaagtttCTC
CCGTTCcagcagTTTGGGAGGGACatcGCAgacACTaccgacgcggtgAGGgacccacagaccttggaga
taCTGGACatcactCCTTGCAGCTTCGGGGGCgtgTCGgtcATAACTcccGGCactaacACCTCAAACca
gGTCGCCgtgCTCtaccagGACgtgAACTGTaccgaggtgCCCgtgGCGATTcacgccgaccagctgACA
cccACGtggAGGgtgtactccaccGGAAGTAATGTCttccagacccGCgccgggTGTctgATAGGCGCCg
agcacGTCaacaacTCGTACgagGGATCCGGGTACatccccGAGgcccctCGCGATggcCAAgctTATGT
GCGAaaggacGGGgagtgggtgctgctcTCCaccttcctgGCCcccccccacGCACTGAGCTGA

FIG. 4A

MFVFLVLLPLVSSQCVNLTTRTQLPPAYTNSITRGVYYPDKVFRSSVLHSTQDLFLPFFS
NVTWFHAIHVSGTNGTKRFDNPVLPFNDGVYFASTEKSNIIRGWIFGTTLDSKTQSLLIV
NNATNVVIKVCEFQFCNDPFLGVYYHKNNKSWMESEFRVYSSANNCTFEYVSQPFLMDLE
GKQGNFKNLREFVFKNIDGYFKIYSKHTPINLVRDLPQGFSALEPLVDLPIGINITRFQT
LLALHRSYLTPGDSSSGWTAGAAAYYVGYLQPRTFLLKYNENGTITDAVDCALDPLSETK
CTLKSFTVEKGIYQTSNFRVQPTESIVRFPNITNLCPFGEVFNATRFASVYAWNRKRISN
CVADYSVLYNSASFSTFKCYGVSPTKLNDLCFTNVYADSFVIRGDEVRQIAPGQTGKIAD
YNYKLPDDFTGCVIAWNSNNLDSKVGGNYNYLYRLFRKSNLKPFERDISTEIYQAGSTPC
NGVEGFNCYFPLQSYGFQPTNGVGYQPYRVVVLSFELLHAPATVCGPKKSTNLVKNKCVN
FNFNGLTGTGVLTESNKKFLPFQQFGRDIADTTDAVRDPQTLEILDITPCSFGGVSVITP
GTNTSNQVAVLYQDVNCTEVPVAIHADQLTPTWRVYSTGSNVFQTRAGCLIGAEHVNNSY
EGSGYIPEAPRDGQAYVRKDGEWVLLSTFLAPPHALS*

FIG. 4B

2019-nCoV-S1fRS09H (2133bp, 710aa)

atgTTCGTGttcctgGTCctgCTCCCACTGGTGTCCTCGCAGtgcGTGaacCTGACCACCcgcacccAGc
tgCCCCCTGCGTACACCaacTCCatcACCAGGggcgtcTACTATCCCgacaagGTGTTTCGAagtTCCGT
TctgcacTCGacccAAgacCTGttcCTCcccttcttcAGCaacgtgacctggTTCcatGCTatccacgta
tcgGGTACGaacgggACCaagcgcTTCgacaaccccGTCCTGCCCttcaacgacGGCgtgtacTTTgcaT
CCacccGAGaagtcgaacATTATCAGGGGGtggattttcggcACCacccCTAGACtcgaagacacagTCGct
gCTGatcgtgaacaacGCGaccaatGTCgtcATCaagGTTTGCgaattcCAGttcTGCAATGACCCCttc
ctgGGAgtctactaccacAAGAACaacaagagctggatggagAGTgagttcAGAGTGTATTCCTCCGCTA
ACaattgcACCttcgagtacGTATCCcagcccttcCTGatggacctggagggcAAGcagGGGaactttAA
AaatctgCGCgagttcgtgTTTaagAACATCgacggcTACttcaagatcTATAGTaagcacacaCCCATA
AATctgGTCCGCgacCTGCCGCAAggcttctccgctTTGGAACCCCTCgtggacCTGCCGATTGGGATCa
acatcACACGTTTTcagACTCTCctggccCTGcacCGGagttacCTGACAcccGGTgacTCCTCCtcagg
ctggACTGCCGGGGCCgccGCTtactacGTCGGCtatTTGcagcccAGAACTTTCCTCctgaagTATaac
GAGAACggcACGatcACCGATgccGTGGATTGTGCGctgGACCCGctgTCGGAGACAaagtgcACGctga
agTCGTTTACCgtggagaagGGGatctaccagACATCTaacttccgggttcagcccACTgagTCCatcgt
gcgcttccccaacatcACGAATCTCtgccccttcggcGAGgtgttcAACGCAactCGCttcgccAGTgtg
tacgcctggAACCGCaagCGGATTtccAATTGTGTCGCTGACtacagtGTGCTTtacaacTCTGCCTCAt
tcAGTACGttcAAGTGTTACggcgtgTCCCCGaccaagctgAATGATctgtgcTTCaccaacGTAtacGC
CGACTCGTTTGTCatcCGCGGCGATGAAgtgAGGcagatcGCGcccGGCcagACGGGCaagATCGCCgac
tacaacTACaagCTGCCCgatgatttcACTggctgtGTTATTGCTtggAATAGTaacAATctggactcga
agGTCGGGGGGaactacaactatCTCTATAGGCTCttcAGAAAAAGTAATCTGaagcctttcgagCGCGA
CatcTCGACTgagATATATcagGCAGGCtccacccCCTGCaacggcGTGGAGgggTTTaattgctacTTC
cccCTTcagagctacggcTTTcagccaacaAACggcgtaGGCTATCAGcccTACCGCgtggtggtgctgT
CAttcGAACTCctgcacgccCCCGCAaccGTCtgcggcCCTaagaagAGTACGaacCTGGTGaagAACaa
gTGCGTCAACttcAATttcAACggcctcACCggcacaGGGGTGctgaccgagTCCaacAAGaagtttCTC
CCGTTCcagcagTTTGGGAGGGACatcGCAgacACTaccgacgcggtgAGGgacccacagaccttggaga
taCTGGACatcactCCTTGCAGCTTCGGGGGCgtgTCGgtcATAACTcccGGCactaacACCTCAAACca
gGTCGCCgtgCTCtaccagGACgtgAACTGTaccgaggtgCCCgtgGCGATTcacgccgaccagctgACA
cccACGtggAGGgtgtactccaccGGAAGTAATGTCttccagacccGCgccgggTGTctgATAGGCGCCg
agcacGTCaacaacTCGTACgagGGATCCGGGTACatccccGAGgcccctCGCGATggcCAAgctTATGT
GCGAaaggacGGGgagtgggtgctgctcTCCaccttcctgGCCcccccccacGCACTGAGCGAGaacTTA
tacttcgagGGCcaccatcaccaccaccatTGA

FIG. 5A

MFVFLVLLPLVSSQCVNLTTRTQLPPAYTNSITRGVYYPDKVFRSSVLHSTQDLFLPFFS
NVTWFHAIHVSGTNGTKRFDNPVLPFNDGVYFASTEKSNIIRGWIFGTTLDSKTQSLLIV
NNATNVVIKVCEFQFCNDPFLGVYYHKNNKSWMESEFRVYSSANNCTFEYVSQPFLMDLEGKQG
NFKNLREFVFKNIDGYFKIYSKHTPINLVRDLPQGFSALEPLVDLPIGINITRFQT
LLALHRSYLTPGDSSSGWTAGAAAYYVGYLQPRTFLLKYNENGTITDAVDCALDPLSETK
CTLKSFTVEKGIYQTSNFRVQPTESIVRFPNITNLCPFGEVFNATRFASVYAWNRKRISN
CVADYSVLYNSASFSTFKCYGVSPTKLNDLCFTNVYADSFVIRGDEVRQIAPGQTGKIAD
YNYKLPDDFTGCVIAWNSNNLDSKVGGNYNYLYRLFRKSNLKPFERDISTEIYQAGSTPC
NGVEGFNCYFPLQSYGFQPTNGVGYQPYRVVVLSFELLHAPATVCGPKKSTNLVKNKCVN
FNFNGLTGTGVLTESNKKFLPFQQFGRDIADTTDAVRDPQTLEILDITPCSFGGVSVITP
GTNTSNQVAVLYQDVNCTEVPVAIHADQLTPTWRVYSTGSNVFQTRAGCLIGAEHVNNSY
EGSGYIPEAPRDGQAYVRKDGEWVLLSTFLAPPHALSENLYFEGHHHHHH*

FIG. 5B

SARS-CoV-2-S1-3

ATGTTCGTGTTCTTGGTGCTTCTGCCGTTGGTGAGTTCTCAGTGCGTCAACCTGACCACCCGAACCCAGCTCCCCCC
CGCCTACACCAACAGCATCACCCGGGGCGTCTACTACCCAGACAAGGTGTTTCGGTCTAGCGTGCTGCACTCCACC
CAGGACCTGTTCCTCCCCTTCTTCTCCAACGTGACCTGGTTCCACGCGATCCACGTGTCGGGAACGAACGGAACTA
AGCGCTTCGACAACCCTGTGCTCCCCTTTAACGATGGCGTGTATTTCGCTTCAACCGAGAAATCGAACATCATTCGC
GGTTGGATCTTCGGCACCACCCTGGACAGTAAGACTCAGTCCCTCCTGATCGTGAACAATGCCACAAACGTTGTGA
TCAAGGTCTGCGAGTTCCAGTTTTGCAACGACCCTTTCCTGGGCGTGTACTACCACAAGAATAACAAGTCCTGGAT
GGAGTCAGAATTCAGGGTGTACAGCTCAGCCAACAACTGCACATTCGAGTATGTGTCCCAGCCCTTTCTGATGGAT
CTGGAGGGCAAGCAGGGGAACTTCAAGAATCTACGTGAATTCGTGTTCAAGAACATCGATGGCTATTTCAAAATC
TACTCGAAGCACACGCCCATCAATCTGGTAAGGGACCTGCCTCAGGGGTTCTCGGCCCTGGAGCCACTCGTCGATC
TGCCGATTGGCATCAACATCACCCGCTTTCAAACCCTCCTGGCCCTCCACAGGTCCTACCTGACGCCCGGCGATTCG
TCGAGTGGGTGGACGGCAGGCGCAGCTGCGTACTACGTGGGGTACCTGCAGCCACGAACCTTCCTGCTGAAGTAC
AACGAGAACGGCACGATTACCGACGCGGTTGATTGCGCCTTGGACCCGCTCTCCGAAACCAAGTGCACCCTGAAG
AGCTTCACCGTGGAGAAGGGAATCTACCAGACGAGTAACTTCCGCGTGCAGCCGACCGAGAGTATTGTTCGGTTC
CCCAACATCACCAACTTGTGCCCATTTGGCGAGGTCTTCAACGCCACCCGCTTCGCAAGCGTGTACGCCTGGAACC
GCAAGAGAATCTCCAATTGCGTGGCCGACTACAGCGTCCTGTACAACTCGGCCTCGTTCAGTACGTTCAAGTGCTA
CGGGGTGTCCCCCACCAAGCTCAATGACCTCTGCTTTACCAACGTGTACGCTGATTCGTTCGTAATCAGGGGTGAC
GAGGTGCGCCAGATCGCCCCAGGCCAGACTGGGAAGATCGCTGACTATAACTATAAGCTCCCCGACGACTTTACC
GGCTGCGTCATCGCCTGGAACTCCAACAACCTGGATTCGAAGGTGGGAGGCAACTACAATTACCTGTATCGCCTCT
TCAGGAAGTCAAATCTGAAGCCTTTCGAGAGGGACATATCGACCGAGATCTACCAGGCGGGAAGTACCCCCTGCA
ACGGGGTGGAGGGGTTCAACTGCTACTTCCCGCTGCAGTCGTACGGCTTCCAGCCTACCAACGGGGTCGGGTACC
AGCCCTACCGCGTGGTGGTGCTCAGTTTCGAGCTCTTGCATGCCCCCGCTACAGTGTGCGGACCGAAGAAGTCCAC
AAACCTGGTGAAGAACAAGTGCGTTAACTTTAACTTCAACGGACTCACTGGCACCGGCGTGCTGACTGAGTCGAA
CAAGAAGTTTCTGCCCTTCCAGCAGTTTGGCCGCGACATCGCAGACACCACCGATGCCGTGCGGGACCCCCAGAC
CCTCGAGATCCTGGACATCACCCCCTGCTCCTTCGGCGGAGTCTCCGTCATAACCCCCGGGACAAACACGTCGAAT
CAGGTGGCTGTGCTCTATCAAGATGTAAATTGTACAGAGGTGCCCGTGGCAATCCACGCGGACCAGCTGACCCCA
ACCTGGCGCGTTTACAGCACCGGCAGTAACGTGTTCCAGACACGCGCTGGTTGCCTCATCGGCGCCGAACACGTG
AACAACTCGTATGAGGGATCCTGA

FIG. 6A

SARS-CoV-2-S1-3-NP

ATGTTCGTGTTCTTGGTGCTTCTGCCGTTGGTGAGTTCTCAGTGCGTCAACCTGACCACCCGAACCCAGCTCCCCCCCGCCTACA
CCAACAGCATCACCCGGGGCGTCTACTACCCAGACAAGGTGTTTCGGTCTAGCGTGCTGCACTCCACCCAGGACCTGTTCCTCC
CCTTCTTCTCCAACGTGACCTGGTTCCACGCGATCCACGTGTCGGGAACGAACGGAACTAAGCGCTTCGACAACCCTGTGCTCC
CCTTTAACGATGGCGTGTATTTCGCTTCAACCGAGAAATCGAACATCATTCGCGGTTGGATCTTCGGCACCACCCTGGACAGTA
AGACTCAGTCCCTCCTGATCGTGAACAATGCCACAAACGTTGTGATCAAGGTCTGCGAGTTCCAGTTTTGCAACGACCCTTTCC
TGGGCGTGTACTACCACAAGAATAACAAGTCCTGGATGGAGTCAGAATTCAGGGTGTACAGCTCAGCCAACAACTGCACATTC
GAGTATGTGTCCCAGCCCTTTCTGATGGATCTGGAGGGCAAGCAGGGGAACTTCAAGAATCTACGTGAATTCGTGTTCAAGAA
CATCGATGGCTATTTCAAAATCTACTCGAAGCACACGCCCATCAATCTGGTAAGGGACCTGCCTCAGGGGTTCTCGGCCCTGGA
GCCACTCGTCGATCTGCCGATTGGCATCAACATCACCCGCTTTCAAACCCTCCTGGCCCTCCACAGGTCCTACCTGACGCCCGGC
GATTCGTCGAGTGGGTGGACGGCAGGCGCAGCTGCGTACTACGTGGGGTACCTGCAGCCACGAACCTTCCTGCTGAAGTACA
ACGAGAACGGCACGATTACCGACGCGGTTGATTGCGCCTTGGACCCGCTCTCCGAAACCAAGTGCACCCTGAAGAGCTTCACC
GTGGAGAAGGGAATCTACCAGACGAGTAACTTCCGCGTGCAGCCGACCGAGAGTATTGTTCGGTTCCCCAACATCACCAACTT
GTGCCCATTTGGCGAGGTCTTCAACGCCACCCGCTTCGCAAGCGTGTACGCCTGGAACCGCAAGAGAATCTCCAATTGCGTGG
CCGACTACAGCGTCCTGTACAACTCGGCCTCGTTCAGTACGTTCAAGTGCTACGGGGTGTCCCCCACCAAGCTCAATGACCTCT
GCTTTACCAACGTGTACGCTGATTCGTTCGTAATCAGGGGTGACGAGGTGCGCCAGATCGCCCCAGGCCAGACTGGGAAGAT
CGCTGACTATAACTATAAGCTCCCCGACGACTTTACCGGCTGCGTCATCGCCTGGAACTCCAACAACCTGGATTCGAAGGTGG
GAGGCAACTACAATTACCTGTATCGCCTCTTCAGGAAGTCAAATCTGAAGCCTTTCGAGAGGGACATATCGACCGAGATCTAC
CAGGCGGGAAGTACCCCCTGCAACGGGGTGGAGGGGTTCAACTGCTACTTCCCGCTGCAGTCGTACGGCTTCCAGCCTACCAA
CGGGGTCGGGTACCAGCCCTACCGCGTGGTGGTGCTCAGTTTCGAGCTCTTGCATGCCCCCGCTACAGTGTGCGGACCGAAGA
AGTCCACAAACCTGGTGAAGAACAAGTGCGTTAACTTTAACTTCAACGGACTCACTGGCACCGGCGTGCTGACTGAGTCGAAC
AAGAAGTTTCTGCCCTTCCAGCAGTTTGGCCGCGACATCGCAGACACCACCGATGCCGTGCGGGACCCCCAGACCCTCGAGAT
CCTGGACATCACCCCCTGCTCCTTCGGCGGAGTCTCCGTCATAACCCCCGGGACAAACACGTCGAATCAGGTGGCTGTGCTCTA
TCAAGATGTAAATTGTACAGAGGTGCCCGTGGCAATCCACGCGGACCAGCTGACCCCAACCTGGCGCGTTTACAGCACCGGCA
GTAACGTGTTCCAGACACGCGCTGGTTGCCTCATCGGCGCCGAACACGTGAACAACTCGTATGAGGGATCCATGTCTGATAAT
GGACCCCAAAATCAGCGAAATGCACCCCGCATTACGTTTGGTGGACCCTCAGATTCAACTGGCAGTAACCAGAATGGAGAACG
CAGTGGGGCGCGATCAAAACAACGTCGGCCCCAAGGTTTACCCAATAATACTGCGTCTTGGTTCACCGCTCTCACTCAACATGG
CAAGGAAGACCTTAAATTCCCTCGAGGACAAGGCGTTCCAATTAACACCAATAGCAGTCCAGATGACCAAATTGGCTACTACC
GAAGAGCTACCAGACGAATTCGTGGTGGTGACGGTAAAATGAAAGATCTCAGTCCAAGATGGTATTTCTACTACCTAGGAACT
GGGCCAGAAGCTGGACTTCCCTATGGTGCTAACAAAGACGGCATCATATGGGTTGCAACTGAGGGAGCCTTGAATACACCAA
AAGATCACATTGGCACCCGCAATCCTGCTAACAATGCTGCAATCGTGCTACAACTTCCTCAAGGAACAACATTGCCAAAAGGCT
TCTACGCAGAAGGGAGCAGAGGCGGCAGTCAAGCCTCTTCTCGTTCCTCATCACGTAGTCGCAACAGTTCAAGAAATTCAACT
CCAGGCAGCAGTAGGGGAACTTCTCCTGCTAGAATGGCTGGCAATGGCGGTGATGCTGCTCTTGCTTTGCTGCTGCTTGACAG
ATTGAACCAGCTTGAGAGCAAAATGTCTGGTAAAGGCCAACAACAACAAGGCCAAACTGTCACTAAGAAATCTGCTGCTGAG
GCTTCTAAGAAGCCTCGGCAAAAACGTACTGCCACTAAAGCATACAATGTAACACAAGCTTTCGGCAGACGTGGTCCAGAACA
AACCCAAGGAAATTTTGGGGACCAGGAACTAATCAGACAAGGAACTGATTACAAACATTGGCCGCAAATTGCACAATTTGCCC
CCAGCGCTTCAGCGTTCTTCGGAATGTCGCGCATTGGCATGGAAGTCACACCTTCGGGAACGTGGTTGACCTACACAGGTGCC
ATCAAATTGGATGACAAAGATCCAAATTTCAAAGATCAAGTCATTTTGCTGAATAAGCATATTGACGCATACAAAACATTCCCA
CCAACAGAGCCTAAAAAGGACAAAAAGAAGAAGGCTGATGAAACTCAAGCCTTACCGCAGAGACAGAAGAAACAGCAAACT
GTGACTCTTCTTCCTGCTGCAGATTTGGATGATTTCTCCAAACAATTGCAACAATCCATGAGCAGTGCTGACTCAACTCAGGCCT
AA

FIG. 6B

SARS-CoV-2-S1-3-2ANP

ATGTTCGTGTTCTTGGTGCTTCTGCCGTTGGTGAGTTCTCAGTGCGTCAACCTGACCACCCGAACCCAGCTCCCCCCCGCCTACA
CCAACAGCATCACCCGGGGCGTCTACTACCCAGACAAGGTGTTTCGGTCTAGCGTGCTGCACTCCACCCAGGACCTGTTCCTCC
CCTTCTTCTCCAACGTGACCTGGTTCCACGCGATCCACGTGTCGGGAACGAACGGAACTAAGCGCTTCGACAACCCTGTGCTCC
CCTTTAACGATGGCGTGTATTTCGCTTCAACCGAGAAATCGAACATCATTCGCGGTTGGATCTTCGGCACCACCCTGGACAGTA
AGACTCAGTCCCTCCTGATCGTGAACAATGCCACAAACGTTGTGATCAAGGTCTGCGAGTTCCAGTTTTGCAACGACCCTTTCC
TGGGCGTGTACTACCACAAGAATAACAAGTCCTGGATGGAGTCAGAATTCAGGGTGTACAGCTCAGCCAACAACTGCACATTC
GAGTATGTGTCCCAGCCCTTTCTGATGGATCTGGAGGGCAAGCAGGGGAACTTCAAGAATCTACGTGAATTCGTGTTCAAGAA
CATCGATGGCTATTTCAAAATCTACTCGAAGCACACGCCCATCAATCTGGTAAGGGACCTGCCTCAGGGGTTCTCGGCCCTGGA
GCCACTCGTCGATCTGCCGATTGGCATCAACATCACCCGCTTTCAAACCCTCCTGGCCCTCCACAGGTCCTACCTGACGCCCGGC
GATTCGTCGAGTGGGTGGACGGCAGGCGCAGCTGCGTACTACGTGGGGTACCTGCAGCCACGAACCTTCCTGCTGAAGTACA
ACGAGAACGGCACGATTACCGACGCGGTTGATTGCGCCTTGGACCCGCTCTCCGAAACCAAGTGCACCCTGAAGAGCTTCACC
GTGGAGAAGGGAATCTACCAGACGAGTAACTTCCGCGTGCAGCCGACCGAGAGTATTGTTCGGTTCCCCAACATCACCAACTT
GTGCCCATTTGGCGAGGTCTTCAACGCCACCCGCTTCGCAAGCGTGTACGCCTGGAACCGCAAGAGAATCTCCAATTGCGTGG
CCGACTACAGCGTCCTGTACAACTCGGCCTCGTTCAGTACGTTCAAGTGCTACGGGGTGTCCCCCACCAAGCTCAATGACCTCT
GCTTTACCAACGTGTACGCTGATTCGTTCGTAATCAGGGGTGACGAGGTGCGCCAGATCGCCCCAGGCCAGACTGGGAAGAT
CGCTGACTATAACTATAAGCTCCCCGACGACTTTACCGGCTGCGTCATCGCCTGGAACTCCAACAACCTGGATTCGAAGGTGG
GAGGCAACTACAATTACCTGTATCGCCTCTTCAGGAAGTCAAATCTGAAGCCTTTCGAGAGGGACATATCGACCGAGATCTAC
CAGGCGGGAAGTACCCCCTGCAACGGGGTGGAGGGGTTCAACTGCTACTTCCCGCTGCAGTCGTACGGCTTCCAGCCTACCAA
CGGGGTCGGGTACCAGCCCTACCGCGTGGTGGTGCTCAGTTTCGAGCTCTTGCATGCCCCCGCTACAGTGTGCGGACCGAAGA
AGTCCACAAACCTGGTGAAGAACAAGTGCGTTAACTTTAACTTCAACGGACTCACTGGCACCGGCGTGCTGACTGAGTCGAAC
AAGAAGTTTCTGCCCTTCCAGCAGTTTGGCCGCGACATCGCAGACACCACCGATGCCGTGCGGGACCCCCAGACCCTCGAGAT
CCTGGACATCACCCCCTGCTCCTTCGGCGGAGTCTCCGTCATAACCCCCGGGACAAACACGTCGAATCAGGTGGCTGTGCTCTA
TCAAGATGTAAATTGTACAGAGGTGCCCGTGGCAATCCACGCGGACCAGCTGACCCCAACCTGGCGCGTTTACAGCACCGGCA
GTAACGTGTTCCAGACACGCGCTGGTTGCCTCATCGGCGCCGAACACGTGAACAACTCGTATGAGGGATCCGGCCAGTGTACA
AACTACGCCCTGCTTAAATTAGCCGGCGACGTGGAGTCAAACCCCGGCCCCGTCGACGCCACCATGTCTGATAATGGACCCCA
AAATCAGCGAAATGCACCCCGCATTACGTTTGGTGGACCCTCAGATTCAACTGGCAGTAACCAGAATGGAGAACGCAGTGGG
GCGCGATCAAAACAACGTCGGCCCCAAGGTTTACCCAATAATACTGCGTCTTGGTTCACCGCTCTCACTCAACATGGCAAGGAA
GACCTTAAATTCCCTCGAGGACAAGGCGTTCCAATTAACACCAATAGCAGTCCAGATGACCAAATTGGCTACTACCGAAGAGC
TACCAGACGAATTCGTGGTGGTGACGGTAAAATGAAAGATCTCAGTCCAAGATGGTATTTCTACTACCTAGGAACTGGGCCAG
AAGCTGGACTTCCCTATGGTGCTAACAAAGACGGCATCATATGGGTTGCAACTGAGGGAGCCTTGAATACACCAAAAGATCAC
ATTGGCACCCGCAATCCTGCTAACAATGCTGCAATCGTGCTACAACTTCCTCAAGGAACAACATTGCCAAAAGGCTTCTACGCA
GAAGGGAGCAGAGGCGGCAGTCAAGCCTCTTCTCGTTCCTCATCACGTAGTCGCAACAGTTCAAGAAATTCAACTCCAGGCAG
CAGTAGGGGAACTTCTCCTGCTAGAATGGCTGGCAATGGCGGTGATGCTGCTCTTGCTTTGCTGCTGCTTGACAGATTGAACC
AGCTTGAGAGCAAAATGTCTGGTAAAGGCCAACAACAACAAGGCCAAACTGTCACTAAGAAATCTGCTGCTGAGGCTTCTAAG
AAGCCTCGGCAAAAACGTACTGCCACTAAAGCATACAATGTAACACAAGCTTTCGGCAGACGTGGTCCAGAACAAACCCAAGG
AAATTTTGGGGACCAGGAACTAATCAGACAAGGAACTGATTACAAACATTGGCCGCAAATTGCACAATTTGCCCCCAGCGCTT
CAGCGTTCTTCGGAATGTCGCGCATTGGCATGGAAGTCACACCTTCGGGAACGTGGTTGACCTACACAGGTGCCATCAAATTG
GATGACAAAGATCCAAATTTCAAAGATCAAGTCATTTTGCTGAATAAGCATATTGACGCATACAAAACATTCCCACCAACAGAG
CCTAAAAAGGACAAAAAGAAGAAGGCTGATGAAACTCAAGCCTTACCGCAGAGACAGAAGAAACAGCAAACTGTGACTCTTC
TTCCTGCTGCAGATTTGGATGATTTCTCCAAACAATTGCAACAATCCATGAGCAGTGCTGACTCAACTCAGGCCTAA

FIG. 6C

SARS-CoV-2-S1-3fRS09

ATGTTCGTGTTCTTGGTGCTTCTGCCGTTGGTGAGTTCTCAGTGCGTCAACCTGACCACCCGAACCCAGCTCCCCCC
CGCCTACACCAACAGCATCACCCGGGGCGTCTACTACCCAGACAAGGTGTTTCGGTCTAGCGTGCTGCACTCCACC
CAGGACCTGTTCCTCCCCTTCTTCTCCAACGTGACCTGGTTCCACGCGATCCACGTGTCGGGAACGAACGGAACTA
AGCGCTTCGACAACCCTGTGCTCCCCTTTAACGATGGCGTGTATTTCGCTTCAACCGAGAAATCGAACATCATTCGC
GGTTGGATCTTCGGCACCACCCTGGACAGTAAGACTCAGTCCCTCCTGATCGTGAACAATGCCACAAACGTTGTGA
TCAAGGTCTGCGAGTTCCAGTTTTGCAACGACCCTTTCCTGGGCGTGTACTACCACAAGAATAACAAGTCCTGGAT
GGAGTCAGAATTCAGGGTGTACAGCTCAGCCAACAACTGCACATTCGAGTATGTGTCCCAGCCCTTTCTGATGGAT
CTGGAGGGCAAGCAGGGGAACTTCAAGAATCTACGTGAATTCGTGTTCAAGAACATCGATGGCTATTTCAAAATC
TACTCGAAGCACACGCCCATCAATCTGGTAAGGGACCTGCCTCAGGGGTTCTCGGCCCTGGAGCCACTCGTCGATC
TGCCGATTGGCATCAACATCACCCGCTTTCAAACCCTCCTGGCCCTCCACAGGTCCTACCTGACGCCCGGCGATTCG
TCGAGTGGGTGGACGGCAGGCGCAGCTGCGTACTACGTGGGGTACCTGCAGCCACGAACCTTCCTGCTGAAGTAC
AACGAGAACGGCACGATTACCGACGCGGTTGATTGCGCCTTGGACCCGCTCTCCGAAACCAAGTGCACCCTGAAG
AGCTTCACCGTGGAGAAGGGAATCTACCAGACGAGTAACTTCCGCGTGCAGCCGACCGAGAGTATTGTTCGGTTC
CCCAACATCACCAACTTGTGCCCATTTGGCGAGGTCTTCAACGCCACCCGCTTCGCAAGCGTGTACGCCTGGAACC
GCAAGAGAATCTCCAATTGCGTGGCCGACTACAGCGTCCTGTACAACTCGGCCTCGTTCAGTACGTTCAAGTGCTA
CGGGGTGTCCCCCACCAAGCTCAATGACCTCTGCTTTACCAACGTGTACGCTGATTCGTTCGTAATCAGGGGTGAC
GAGGTGCGCCAGATCGCCCCAGGCCAGACTGGGAAGATCGCTGACTATAACTATAAGCTCCCCGACGACTTTACC
GGCTGCGTCATCGCCTGGAACTCCAACAACCTGGATTCGAAGGTGGGAGGCAACTACAATTACCTGTATCGCCTCT
TCAGGAAGTCAAATCTGAAGCCTTTCGAGAGGGACATATCGACCGAGATCTACCAGGCGGGAAGTACCCCCTGCA
ACGGGGTGGAGGGGTTCAACTGCTACTTCCCGCTGCAGTCGTACGGCTTCCAGCCTACCAACGGGGTCGGGTACC
AGCCCTACCGCGTGGTGGTGCTCAGTTTCGAGCTCTTGCATGCCCCCGCTACAGTGTGCGGACCGAAGAAGTCCAC
AAACCTGGTGAAGAACAAGTGCGTTAACTTTAACTTCAACGGACTCACTGGCACCGGCGTGCTGACTGAGTCGAA
CAAGAAGTTTCTGCCCTTCCAGCAGTTTGGCCGCGACATCGCAGACACCACCGATGCCGTGCGGGACCCCCAGAC
CCTCGAGATCCTGGACATCACCCCCTGCTCCTTCGGCGGAGTCTCCGTCATAACCCCCGGGACAAACACGTCGAAT
CAGGTGGCTGTGCTCTATCAAGATGTAAATTGTACAGAGGTGCCCGTGGCAATCCACGCGGACCAGCTGACCCCA
ACCTGGCGCGTTTACAGCACCGGCAGTAACGTGTTCCAGACACGCGCTGGTTGCCTCATCGGCGCCGAACACGTG
AACAACTCGTATGAGGGATCCGGGTACATCCCCGAGGCCCCTCGCGATGGCCAAGCTTATGTGCGAAAGGACGG
GGAGTGGGTGCTGCTCTCCACCTTCCTGGCCCCCCCCCACGCACTGAGCGAGAACTTATACTTCGAGGGCCACCAT
CACCACCACCATTGA

FIG. 6D

SARS-CoV-2-S1-3fRS09-NP

ATGTTCGTGTTCTTGGTGCTTCTGCCGTTGGTGAGTTCTCAGTGCGTCAACCTGACCACCCGAACCCAGCTCCCCCCCGCCTACA
CCAACAGCATCACCCGGGGCGTCTACTACCCAGACAAGGTGTTTCGGTCTAGCGTGCTGCACTCCACCCAGGACCTGTTCCTCC
CCTTCTTCTCCAACGTGACCTGGTTCCACGCGATCCACGTGTCGGGAACGAACGGAACTAAGCGCTTCGACAACCCTGTGCTCC
CCTTTAACGATGGCGTGTATTTCGCTTCAACCGAGAAATCGAACATCATTCGCGGTTGGATCTTCGGCACCACCCTGGACAGTA
AGACTCAGTCCCTCCTGATCGTGAACAATGCCACAAACGTTGTGATCAAGGTCTGCGAGTTCCAGTTTTGCAACGACCCTTTCC
TGGGCGTGTACTACCACAAGAATAACAAGTCCTGGATGGAGTCAGAATTCAGGGTGTACAGCTCAGCCAACAACTGCACATTC
GAGTATGTGTCCCAGCCCTTTCTGATGGATCTGGAGGGCAAGCAGGGGAACTTCAAGAATCTACGTGAATTCGTGTTCAAGAA
CATCGATGGCTATTTCAAAATCTACTCGAAGCACACGCCCATCAATCTGGTAAGGGACCTGCCTCAGGGGTTCTCGGCCCTGGA
GCCACTCGTCGATCTGCCGATTGGCATCAACATCACCCGCTTTCAAACCCTCCTGGCCCTCCACAGGTCCTACCTGACGCCCGGC
GATTCGTCGAGTGGGTGGACGGCAGGCGCAGCTGCGTACTACGTGGGGTACCTGCAGCCACGAACCTTCCTGCTGAAGTACA
ACGAGAACGGCACGATTACCGACGCGGTTGATTGCGCCTTGGACCCGCTCTCCGAAACCAAGTGCACCCTGAAGAGCTTCACC
GTGGAGAAGGGAATCTACCAGACGAGTAACTTCCGCGTGCAGCCGACCGAGAGTATTGTTCGGTTCCCCAACATCACCAACTT
GTGCCCATTTGGCGAGGTCTTCAACGCCACCCGCTTCGCAAGCGTGTACGCCTGGAACCGCAAGAGAATCTCCAATTGCGTGG
CCGACTACAGCGTCCTGTACAACTCGGCCTCGTTCAGTACGTTCAAGTGCTACGGGGTGTCCCCCACCAAGCTCAATGACCTCT
GCTTTACCAACGTGTACGCTGATTCGTTCGTAATCAGGGGTGACGAGGTGCGCCAGATCGCCCCAGGCCAGACTGGGAAGAT
CGCTGACTATAACTATAAGCTCCCCGACGACTTTACCGGCTGCGTCATCGCCTGGAACTCCAACAACCTGGATTCGAAGGTGG
GAGGCAACTACAATTACCTGTATCGCCTCTTCAGGAAGTCAAATCTGAAGCCTTTCGAGAGGGACATATCGACCGAGATCTAC
CAGGCGGGAAGTACCCCCTGCAACGGGGTGGAGGGGTTCAACTGCTACTTCCCGCTGCAGTCGTACGGCTTCCAGCCTACCAA
CGGGGTCGGGTACCAGCCCTACCGCGTGGTGGTGCTCAGTTTCGAGCTCTTGCATGCCCCCGCTACAGTGTGCGGACCGAAGA
AGTCCACAAACCTGGTGAAGAACAAGTGCGTTAACTTTAACTTCAACGGACTCACTGGCACCGGCGTGCTGACTGAGTCGAAC
AAGAAGTTTCTGCCCTTCCAGCAGTTTGGCCGCGACATCGCAGACACCACCGATGCCGTGCGGGACCCCCAGACCCTCGAGAT
CCTGGACATCACCCCCTGCTCCTTCGGCGGAGTCTCCGTCATAACCCCCGGGACAAACACGTCGAATCAGGTGGCTGTGCTCTA
TCAAGATGTAAATTGTACAGAGGTGCCCGTGGCAATCCACGCGGACCAGCTGACCCCAACCTGGCGCGTTTACAGCACCGGCA
GTAACGTGTTCCAGACACGCGCTGGTTGCCTCATCGGCGCCGAACACGTGAACAACTCGTATGAGGGATCTGGGTACATCCCC
GAGGCCCCTCGCGATGGCCAAGCTTATGTGCGAAAGGACGGGGAGTGGGTGCTGCTCTCCACCTTCCTGGCCCCCCCCCACGC
ACTGAGCGGATCCATGTCTGATAATGGACCCCAAAATCAGCGAAATGCACCCCGCATTACGTTTGGTGGACCCTCAGATTCAA
CTGGCAGTAACCAGAATGGAGAACGCAGTGGGGCGCGATCAAAACAACGTCGGCCCCAAGGTTTACCCAATAATACTGCGTC
TTGGTTCACCGCTCTCACTCAACATGGCAAGGAAGACCTTAAATTCCCTCGAGGACAAGGCGTTCCAATTAACACCAATAGCAG
TCCAGATGACCAAATTGGCTACTACCGAAGAGCTACCAGACGAATTCGTGGTGGTGACGGTAAAATGAAAGATCTCAGTCCAA
GATGGTATTTCTACTACCTAGGAACTGGGCCAGAAGCTGGACTTCCCTATGGTGCTAACAAAGACGGCATCATATGGGTTGCA
ACTGAGGGAGCCTTGAATACACCAAAAGATCACATTGGCACCCGCAATCCTGCTAACAATGCTGCAATCGTGCTACAACTTCCT
CAAGGAACAACATTGCCAAAAGGCTTCTACGCAGAAGGGAGCAGAGGCGGCAGTCAAGCCTCTTCTCGTTCCTCATCACGTAG
TCGCAACAGTTCAAGAAATTCAACTCCAGGCAGCAGTAGGGGAACTTCTCCTGCTAGAATGGCTGGCAATGGCGGTGATGCTG
CTCTTGCTTTGCTGCTGCTTGACAGATTGAACCAGCTTGAGAGCAAAATGTCTGGTAAAGGCCAACAACAACAAGGCCAAACT
GTCACTAAGAAATCTGCTGCTGAGGCTTCTAAGAAGCCTCGGCAAAAACGTACTGCCACTAAAGCATACAATGTAACACAAGC
TTTCGGCAGACGTGGTCCAGAACAAACCCAAGGAAATTTTGGGGACCAGGAACTAATCAGACAAGGAACTGATTACAAACATT
GGCCGCAAATTGCACAATTTGCCCCCAGCGCTTCAGCGTTCTTCGGAATGTCGCGCATTGGCATGGAAGTCACACCTTCGGGA
ACGTGGTTGACCTACACAGGTGCCATCAAATTGGATGACAAAGATCCAAATTTCAAAGATCAAGTCATTTTGCTGAATAAGCAT
ATTGACGCATACAAAACATTCCCACCAACAGAGCCTAAAAAGGACAAAAAGAAGAAGGCTGATGAAACTCAAGCCTTACCGCA
GAGACAGAAGAAACAGCAAACTGTGACTCTTCTTCCTGCTGCAGATTTGGATGATTTCTCCAAACAATTGCAACAATCCATGAG
CAGTGCTGACTCAACTCAGGCCTAA

FIG. 6E

SARS-CoV-2-S1-3fRS09-2ANP

ATGTTCGTGTTCTTGGTGCTTCTGCCGTTGGTGAGTTCTCAGTGCGTCAACCTGACCACCCGAACCCAGCTCCCCCCCGCCTACA
CCAACAGCATCACCCGGGGCGTCTACTACCCAGACAAGGTGTTTCGGTCTAGCGTGCTGCACTCCACCCAGGACCTGTTCCTCC
CCTTCTTCTCCAACGTGACCTGGTTCCACGCGATCCACGTGTCGGGAACGAACGGAACTAAGCGCTTCGACAACCCTGTGCTCC
CCTTTAACGATGGCGTGTATTTCGCTTCAACCGAGAAATCGAACATCATTCGCGGTTGGATCTTCGGCACCACCCTGGACAGTA
AGACTCAGTCCCTCCTGATCGTGAACAATGCCACAAACGTTGTGATCAAGGTCTGCGAGTTCCAGTTTTGCAACGACCCTTTCC
TGGGCGTGTACTACCACAAGAATAACAAGTCCTGGATGGAGTCAGAATTCAGGGTGTACAGCTCAGCCAACAACTGCACATTC
GAGTATGTGTCCCAGCCCTTTCTGATGGATCTGGAGGGCAAGCAGGGGAACTTCAAGAATCTACGTGAATTCGTGTTCAAGAA
CATCGATGGCTATTTCAAAATCTACTCGAAGCACACGCCCATCAATCTGGTAAGGGACCTGCCTCAGGGGTTCTCGGCCCTGGA
GCCACTCGTCGATCTGCCGATTGGCATCAACATCACCCGCTTTCAAACCCTCCTGGCCCTCCACAGGTCCTACCTGACGCCCGGC
GATTCGTCGAGTGGGTGGACGGCAGGCGCAGCTGCGTACTACGTGGGGTACCTGCAGCCACGAACCTTCCTGCTGAAGTACA
ACGAGAACGGCACGATTACCGACGCGGTTGATTGCGCCTTGGACCCGCTCTCCGAAACCAAGTGCACCCTGAAGAGCTTCACC
GTGGAGAAGGGAATCTACCAGACGAGTAACTTCCGCGTGCAGCCGACCGAGAGTATTGTTCGGTTCCCCAACATCACCAACTT
GTGCCCATTTGGCGAGGTCTTCAACGCCACCCGCTTCGCAAGCGTGTACGCCTGGAACCGCAAGAGAATCTCCAATTGCGTGG
CCGACTACAGCGTCCTGTACAACTCGGCCTCGTTCAGTACGTTCAAGTGCTACGGGGTGTCCCCCACCAAGCTCAATGACCTCT
GCTTTACCAACGTGTACGCTGATTCGTTCGTAATCAGGGGTGACGAGGTGCGCCAGATCGCCCCAGGCCAGACTGGGAAGAT
CGCTGACTATAACTATAAGCTCCCCGACGACTTTACCGGCTGCGTCATCGCCTGGAACTCCAACAACCTGGATTCGAAGGTGG
GAGGCAACTACAATTACCTGTATCGCCTCTTCAGGAAGTCAAATCTGAAGCCTTTCGAGAGGGACATATCGACCGAGATCTAC
CAGGCGGGAAGTACCCCCTGCAACGGGGTGGAGGGGTTCAACTGCTACTTCCCGCTGCAGTCGTACGGCTTCCAGCCTACCAA
CGGGGTCGGGTACCAGCCCTACCGCGTGGTGGTGCTCAGTTTCGAGCTCTTGCATGCCCCCGCTACAGTGTGCGGACCGAAGA
AGTCCACAAACCTGGTGAAGAACAAGTGCGTTAACTTTAACTTCAACGGACTCACTGGCACCGGCGTGCTGACTGAGTCGAAC
AAGAAGTTTCTGCCCTTCCAGCAGTTTGGCCGCGACATCGCAGACACCACCGATGCCGTGCGGGACCCCCAGACCCTCGAGAT
CCTGGACATCACCCCCTGCTCCTTCGGCGGAGTCTCCGTCATAACCCCCGGGACAAACACGTCGAATCAGGTGGCTGTGCTCTA
TCAAGATGTAAATTGTACAGAGGTGCCCGTGGCAATCCACGCGGACCAGCTGACCCCAACCTGGCGCGTTTACAGCACCGGCA
GTAACGTGTTCCAGACACGCGCTGGTTGCCTCATCGGCGCCGAACACGTGAACAACTCGTATGAGGGATCTGGGTACATCCCC
GAGGCCCCTCGCGATGGCCAAGCTTATGTGCGAAAGGACGGGGAGTGGGTGCTGCTCTCCACCTTCCTGGCCCCCCCCCACGC
ACTGAGCGGATCCGGCCAGTGTACAAACTACGCCCTGCTTAAATTAGCCGGCGACGTGGAGTCAAACCCCGGCCCCGTCGACG
CCACCATGTCTGATAATGGACCCCAAAATCAGCGAAATGCACCCCGCATTACGTTTGGTGGACCCTCAGATTCAACTGGCAGTA
ACCAGAATGGAGAACGCAGTGGGGCGCGATCAAAACAACGTCGGCCCCAAGGTTTACCCAATAATACTGCGTCTTGGTTCACC
GCTCTCACTCAACATGGCAAGGAAGACCTTAAATTCCCTCGAGGACAAGGCGTTCCAATTAACACCAATAGCAGTCCAGATGA
CCAAATTGGCTACTACCGAAGAGCTACCAGACGAATTCGTGGTGGTGACGGTAAAATGAAAGATCTCAGTCCAAGATGGTATT
TCTACTACCTAGGAACTGGGCCAGAAGCTGGACTTCCCTATGGTGCTAACAAAGACGGCATCATATGGGTTGCAACTGAGGGA
GCCTTGAATACACCAAAAGATCACATTGGCACCCGCAATCCTGCTAACAATGCTGCAATCGTGCTACAACTTCCTCAAGGAACA
ACATTGCCAAAAGGCTTCTACGCAGAAGGGAGCAGAGGCGGCAGTCAAGCCTCTTCTCGTTCCTCATCACGTAGTCGCAACAG
TTCAAGAAATTCAACTCCAGGCAGCAGTAGGGGAACTTCTCCTGCTAGAATGGCTGGCAATGGCGGTGATGCTGCTCTTGCTT
TGCTGCTGCTTGACAGATTGAACCAGCTTGAGAGCAAAATGTCTGGTAAAGGCCAACAACAACAAGGCCAAACTGTCACTAAG
AAATCTGCTGCTGAGGCTTCTAAGAAGCCTCGGCAAAAACGTACTGCCACTAAAGCATACAATGTAACACAAGCTTTCGGCAG
ACGTGGTCCAGAACAAACCCAAGGAAATTTTGGGGACCAGGAACTAATCAGACAAGGAACTGATTACAAACATTGGCCGCAA
ATTGCACAATTTGCCCCCAGCGCTTCAGCGTTCTTCGGAATGTCGCGCATTGGCATGGAAGTCACACCTTCGGGAACGTGGTTG
ACCTACACAGGTGCCATCAAATTGGATGACAAAGATCCAAATTTCAAAGATCAAGTCATTTTGCTGAATAAGCATATTGACGCA
TACAAAACATTCCCACCAACAGAGCCTAAAAAGGACAAAAAGAAGAAGGCTGATGAAACTCAAGCCTTACCGCAGAGACAGA
AGAAACAGCAAACTGTGACTCTTCTTCCTGCTGCAGATTTGGATGATTTCTCCAAACAATTGCAACAATCCATGAGCAGTGCTG
ACTCAACTCAGGCCTAA

FIG. 6F

SARS-CoV-2-S1-3

MFVFLVLLPLVSSQCVNLTTRTQLPPAYTNSITRGVYYPDKVFRSSVLHSTQDLFLPFFSNVTWFHAIHVSGTNGTKRFD
NPVLPFNDGVYFASTEKSNIIRGWIFGTTLDSKTQSLLIVNNATNVVIKVCEFQFCNDPFLGVYYHKNNKSWMESEFRVY
SSANNCTFEYVSQPFLMDLEGKQGNFKNLREFVFKNIDGYFKIYSKHTPINLVRDLPQGFSALEPLVDLPIGINITRFQTLL
ALHRSYLTPGDSSSGWTAGAAAYYVGYLQPRTFLLKYNENGTITDAVDCALDPLSETKCTLKSFTVEKGIYQTSNFRVQP
TESIVRFPNITNLCPFGEVFNATRFASVYAWNRKRISNCVADYSVLYNSASFSTFKCYGVSPTKLNDLCFTNVYADSFVIR
GDEVRQIAPGQTGKIADYNYKLPDDFTGCVIAWNSNNLDSKVGGNYNYLYRLFRKSNLKPFERDISTEIYQAGSTPCNG
VEGFNCYFPLQSYGFQPTNGVGYQPYRVVVLSFELLHAPATVCGPKKSTNLVKNKCVNFNFNGLTGTGVLTESNKKFLP
FQQFGRDIADTTDAVRDPQTLEILDITPCSFGGVSVITPGTNTSNQVAVLYQDVNCTEVPVAIHADQLTPTWRVYSTGS
NVFQTRAGCLIGAEHVNNSYEGS*

FIG. 7A

SARS-CoV-2-S1-3-NP

MFVFLVLLPLVSSQCVNLTTRTQLPPAYTNSITRGVYYPDKVFRSSVLHSTQDLFLPFFSNVTWFHAIHVSGTNGTKRFD
NPVLPFNDGVYFASTEKSNIIRGWIFGTTLDSKTQSLLIVNNATNVVIKVCEFQFCNDPFLGVYYHKNNKSWMESEFRVY
SSANNCTFEYVSQPFLMDLEGKQGNFKNLREFVFKNIDGYFKIYSKHTPINLVRDLPQGFSALEPLVDLPIGINITRFQTLL
ALHRSYLTPGDSSSGWTAGAAAYYVGYLQPRTFLLKYNENGTITDAVDCALDPLSETKCTLKSFTVEKGIYQTSNFRVQP
TESIVRFPNITNLCPFGEVFNATRFASVYAWNRKRISNCVADYSVLYNSASFSTFKCYGVSPTKLNDLCFTNVYADSFVIR
GDEVRQIAPGQTGKIADYNYKLPDDFTGCVIAWNSNNLDSKVGGNYNYLYRLFRKSNLKPFERDISTEIYQAGSTPCNG
VEGFNCYFPLQSYGFQPTNGVGYQPYRVVVLSFELLHAPATVCGPKKSTNLVKNKCVNFNFNGLTGTGVLTESNKKFLP
FQQFGRDIADTTDAVRDPQTLEILDITPCSFGGVSVITPGTNTSNQVAVLYQDVNCTEVPVAIHADQLTPTWRVYSTGS
NVFQTRAGCLIGAEHVNNSYEGSMSDNGPQNQRNAPRITFGGPSDSTGSNQNGERSGARSKQRRPQGLPNNTASW
FTALTQHGKEDLKFPRGQGVPINTNSSPDDQIGYYRRATRRIRGGDGKMKDLSPRWYFYYLGTGPEAGLPYGANKDGII
WVATEGALNTPKDHIGTRNPANNAAIVLQLPQGTTLPKGFYAEGSRGGSQASSRSSSRSRNSSRNSTPGSSRGTSPAR
MAGNGGDAALALLLLDRLNQLESKMSGKGQQQQGQTVTKKSAAEASKKPRQKRTATKAYNVTQAFGRRGPEQTQG
NFGDQELIRQGTDYKHWPQIAQFAPSASAFFGMSRIGMEVTPSGTWLTYTGAIKLDDKDPNFKDQVILLNKHIDAYKT
FPPTEPKKDKKKKADETQALPQRQKKQQTVTLLPAADLDDFSKQLQQSMSSADSTQA*

FIG. 7B

SARS-CoV-2-S1-3-2ANP

MFVFLVLLPLVSSQCVNLTTRTQLPPAYTNSITRGVYYPDKVFRSSVLHSTQDLFLPFFSNVTWFHAIHVSGTNGTKRFD
NPVLPFNDGVYFASTEKSNIIRGWIFGTTLDSKTQSLLIVNNATNVVIKVCEFQFCNDPFLGVYYHKNNKSWMESEFRVY
SSANNCTFEYVSQPFLMDLEGKQGNFKNLREFVFKNIDGYFKIYSKHTPINLVRDLPQGFSALEPLVDLPIGINITRFQTLL
ALHRSYLTPGDSSSGWTAGAAAYYVGYLQPRTFLLKYNENGTITDAVDCALDPLSETKCTLKSFTVEKGIYQTSNFRVQP
TESIVRFPNITNLCPFGEVFNATRFASVYAWNRKRISNCVADYSVLYNSASFSTFKCYGVSPTKLNDLCFTNVYADSFVIR
GDEVRQIAPGQTGKIADYNYKLPDDFTGCVIAWNSNNLDSKVGGNYNYLYRLFRKSNLKPFERDISTEIYQAGSTPCNG
VEGFNCYFPLQSYGFQPTNGVGYQPYRVVVLSFELLHAPATVCGPKKSTNLVKNKCVNFNFNGLTGTGVLTESNKKFLP
FQQFGRDIADTTDAVRDPQTLEILDITPCSFGGVSVITPGTNTSNQVAVLYQDVNCTEVPVAIHADQLTPTWRVYSTGS
NVFQTRAGCLIGAEHVNNSYEGSGQCTNYALLKLAGDVESNPGPVDATMSDNGPQNQRNAPRITFGGPSDSTGSNQ
NGERSGARSKQRRPQGLPNNTASWFTALTQHGKEDLKFPRGQGVPINTNSSPDDQIGYYRRATRRIRGGDGKMKDLS
PRWYFYYLGTGPEAGLPYGANKDGIIWVATEGALNTPKDHIGTRNPANNAAIVLQLPQGTTLPKGFYAEGSRGGSQAS
SRSSSRSRNSSRNSTPGSSRGTSPARMAGNGGDAALALLLLDRLNQLESKMSGKGQQQQGQTVTKKSAAEASKKPRQ
KRTATKAYNVTQAFGRRGPEQTQGNFGDQELIRQGTDYKHWPQIAQFAPSASAFFGMSRIGMEVTPSGTWLTYTGAI
KLDDKDPNFKDQVILLNKHIDAYKTFPPTEPKKDKKKKADETQALPQRQKKQQTVTLLPAADLDDFSKQLQQSMSSAD
STQA*

FIG. 7C

SARS-CoV-2-S1-3fRS09

MFVFLVLLPLVSSQCVNLTTRTQLPPAYTNSITRGVYYPDKVFRSSVLHSTQDLFLPFFSNVTWFHAIHVSGTNGTKRFD
NPVLPFNDGVYFASTEKSNIIRGWIFGTTLDSKTQSLLIVNNATNVVIKVCEFQFCNDPFLGVYYHKNNKSWMESEFRVY
SSANNCTFEYVSQPFLMDLEGKQGNFKNLREFVFKNIDGYFKIYSKHTPINLVRDLPQGFSALEPLVDLPIGINITRFQTLL
ALHRSYLTPGDSSSGWTAGAAAYYVGYLQPRTFLLKYNENGTITDAVDCALDPLSETKCTLKSFTVEKGIYQTSNFRVQP
TESIVRFPNITNLCPFGEVFNATRFASVYAWNRKRISNCVADYSVLYNSASFSTFKCYGVSPTKLNDLCFTNVYADSFVIR
GDEVRQIAPGQTGKIADYNYKLPDDFTGCVIAWNSNNLDSKVGGNYNYLYRLFRKSNLKPFERDISTEIYQAGSTPCNG
VEGFNCYFPLQSYGFQPTNGVGYQPYRVVVLSFELLHAPATVCGPKKSTNLVKNKCVNFNFNGLTGTGVLTESNKKFLP
FQQFGRDIADTTDAVRDPQTLEILDITPCSFGGVSVITPGTNTSNQVAVLYQDVNCTEVPVAIHADQLTPTWRVYSTGS
NVFQTRAGCLIGAEHVNNSYEGSGYIPEAPRDGQAYVRKDGEWVLLSTFLAPPHALSENLYFEGHHHHHH*

FIG. 7D

SARS-CoV-2-S1-3fRS09-NP

MFVFLVLLPLVSSQCVNLTTRTQLPPAYTNSITRGVYYPDKVFRSSVLHSTQDLFLPFFSNVTWFHAIHVSGTNGTKRFD
NPVLPFNDGVYFASTEKSNIIRGWIFGTTLDSKTQSLLIVNNATNVVIKVCEFQFCNDPFLGVYYHKNNKSWMESEFRVY
SSANNCTFEYVSQPFLMDLEGKQGNFKNLREFVFKNIDGYFKIYSKHTPINLVRDLPQGFSALEPLVDLPIGINITRFQTLL
ALHRSYLTPGDSSSGWTAGAAAYYVGYLQPRTFLLKYNENGTITDAVDCALDPLSETKCTLKSFTVEKGIYQTSNFRVQP
TESIVRFPNITNLCPFGEVFNATRFASVYAWNRKRISNCVADYSVLYNSASFSTFKCYGVSPTKLNDLCFTNVYADSFVIR
GDEVRQIAPGQTGKIADYNYKLPDDFTGCVIAWNSNNLDSKVGGNYNYLYRLFRKSNLKPFERDISTEIYQAGSTPCNG
VEGFNCYFPLQSYGFQPTNGVGYQPYRVVVLSFELLHAPATVCGPKKSTNLVKNKCVNFNFNGLTGTGVLTESNKKFLP
FQQFGRDIADTTDAVRDPQTLEILDITPCSFGGVSVITPGTNTSNQVAVLYQDVNCTEVPVAIHADQLTPTWRVYSTGS
NVFQTRAGCLIGAEHVNNSYEGSGYIPEAPRDGQAYVRKDGEWVLLSTFLAPPHALSGSMSDNGPQNQRNAPRITFG
GPSDSTGSNQNGERSGARSKQRRPQGLPNNTASWFTALTQHGKEDLKFPRGQGVPINTNSSPDDQIGYYRRATRRIR
GGDGKMKDLSPRWYFYYLGTGPEAGLPYGANKDGIIWVATEGALNTPKDHIGTRNPANNAAIVLQLPQGTTLPKGFY
AEGSRGGSQASSRSSSRSRNSSRNSTPGSSRGTSPARMAGNGGDAALALLLLDRLNQLESKMSGKGQQQQGQTVTKK
SAAEASKKPRQKRTATKAYNVTQAFGRRGPEQTQGNFGDQELIRQGTDYKHWPQIAQFAPSASAFFGMSRIGMEVTP
SGTWLTYTGAIKLDDKDPNFKDQVILLNKHIDAYKTFPPTEPKKDKKKKADETQALPQRQKKQQTVTLLPAADLDDFSK
QLQQSMSSADSTQA*

FIG. 7E

SARS-CoV-2-S1-3fRS09-2ANP

MFVFLVLLPLVSSQCVNLTTRTQLPPAYTNSITRGVYYPDKVFRSSVLHSTQDLFLPFFSNVTWFHAIHVSGTNGTKRFD
NPVLPFNDGVYFASTEKSNIIRGWIFGTTLDSKTQSLLIVNNATNVVIKVCEFQFCNDPFLGVYYHKNNKSWMESEFRVY
SSANNCTFEYVSQPFLMDLEGKQGNFKNLREFVFKNIDGYFKIYSKHTPINLVRDLPQGFSALEPLVDLPIGINITRFQTLL
ALHRSYLTPGDSSSGWTAGAAAYYVGYLQPRTFLLKYNENGTITDAVDCALDPLSETKCTLKSFTVEKGIYQTSNFRVQP
TESIVRFPNITNLCPFGEVFNATRFASVYAWNRKRISNCVADYSVLYNSASFSTFKCYGVSPTKLNDLCFTNVYADSFVIR
GDEVRQIAPGQTGKIADYNYKLPDDFTGCVIAWNSNNLDSKVGGNYNYLYRLFRKSNLKPFERDISTEIYQAGSTPCNG
VEGFNCYFPLQSYGFQPTNGVGYQPYRVVVLSFELLHAPATVCGPKKSTNLVKNKCVNFNFNGLTGTGVLTESNKKFLP
FQQFGRDIADTTDAVRDPQTLEILDITPCSFGGVSVITPGTNTSNQVAVLYQDVNCTEVPVAIHADQLTPTWRVYSTGS
NVFQTRAGCLIGAEHVNNSYEGSGYIPEAPRDGQAYVRKDGEWVLLSTFLAPPHALSGSGQCTNYALLKLAGDVESNP
GPVDATMSDNGPQNQRNAPRITFGGPSDSTGSNQNGERSGARSKQRRPQGLPNNTASWFTALTQHGKEDLKFPRG
QGVPINTNSSPDDQIGYYRRATRRIRGGDGKMKDLSPRWYFYYLGTGPEAGLPYGANKDGIIWVATEGALNTPKDHIG
TRNPANNAAIVLQLPQGTTLPKGFYAEGSRGGSQASSRSSSRSRNSSRNSTPGSSRGTSPARMAGNGGDAALALLLLD
RLNQLESKMSGKGQQQQGQTVTKKSAAEASKKPRQKRTATKAYNVTQAFGRRGPEQTQGNFGDQELIRQGTDYKH
WPQIAQFAPSASAFFGMSRIGMEVTPSGTWLTYTGAIKLDDKDPNFKDQVILLNKHIDAYKTFPPTEPKKDKKKKADET
QALPQRQKKQQTVTLLPAADLDDFSKQLQQSMSSADSTQA*

FIG. 7F

| Name of Peptide | Amino Acid Sequence |
|---|---|
| | |
| Foldon (F) | GYIPEAPRDGQAYVR KDGEWVLLSTFL |
| RS09 | APPHALS |
| Tobacco Etch Virus Protease (Tp) | ENLYFE*G |

SARS-COV-2 SUBUNIT VACCINE AND MICRONEEDLE ARRAY DELIVERY SYSTEM

CROSS REFERENCE TO RELATED APPLICATIONS

This application claims the benefit if U.S. Provisional Patent Application Nos. 62/985,498 filed Mar. 5, 2020, and 62/989,208 filed Mar. 13, 2020, each of which is incorporated herein by reference in its entirety.

The Sequence Listing associated with this application is filed in electronic format via EFS-Web and is hereby incorporated by reference into the specification in its entirety. The name of the text file containing the Sequence Listing is 2003011_ST25.txt. The size of the text file is 112,846 bytes, and the text file was created on Jun. 3, 2020.

Provided herein are coronavirus, e.g., SARS-CoV-2, immunogens and vaccines, as well as an improved microneedle array able to deliver therapeutic agents, such as coronavirus, e.g., SARS-CoV-2, immunogens, as well as methods of making the microneedle array.

On Dec. 31, 2019, Chinese authorities reported a cluster of pneumonia cases in Wuhan, China, most of which included patients who reported exposure to a large seafood market selling many species of live animals. Emergence of another pathogenic zoonotic HCoV was suspected, and by Jan. 10, 2020, researchers from the Shanghai Public Health Clinical Center & School of Public Health and their collaborators released a full genomic sequence of SARS-CoV-2 (related to coronavirus disease 2019, or COVID-19) to public databases, exemplifying prompt data sharing in outbreak response. Preliminary analyses indicate that SARS-CoV-2 has some amino acid homology to SARS-CoV and may be able to use Angiotensin converting enzyme 2 (ACE2) as a receptor. COVID-19 has reached pandemic status, and, as such, vaccines and therapeutics able to prevent or mitigate the disease are sought.

STATEMENT REGARDING FEDERAL FUNDING

This invention was made with government support under Grant Nos. AR071277and AR068249awarded by the National Institutes of Health. The government has certain rights in this invention.

SUMMARY

An immunogenic pharmaceutical composition is provided for use in eliciting an immune response to SARS-CoV-2 in a patient. The composition comprises a polypeptide having the sequence of amino acids 1-661 of SEQ ID NO: 2, a naturally-occurring variant thereof, or a derivative thereof having at least 95% sequence identity with amino acids 1-661 of SEQ ID NO: 2, and a pharmaceutically-acceptable excipient.

A microneedle array for use in eliciting an immune response to SARS-CoV-2 in a patient is provided. The microneedle array comprises: a backing layer; and a plurality of microneedles, with a polypeptide having the sequence of SEQ ID NO: 2, amino acids 1-661 of SEQ ID NO: 2, a naturally-occurring variant thereof, or a derivative thereof having at least 95% sequence identity with amino acids 1-661 of SEQ ID NO: 2, incorporated into or onto the microneedle.

A method of eliciting an immune response against SARS-CoV-2 in a patient is provided. The method comprises administering to the patient an amount of an immunogenic pharmaceutical composition comprising a polypeptide having the sequence of SEQ ID NO: 2, amino acids 1-661 of SEQ ID NO: 2, a naturally-occurring variant thereof, or a derivative thereof having at least 95% sequence identity with amino acids 1-661 of SEQ ID NO: 2, or with SEQ ID NO: 2, and a pharmaceutically-acceptable excipient effective to elicit an immune response against SARS-CoV-2 in a patient, thereby eliciting an immune response in the patient against SARS-CoV-2.

A method of forming a microneedle array is provided. The method comprises forming a plurality of microneedles having a filleted base attached to a backing, comprising incorporating into or onto microneedles of the microneedle array a polypeptide having the sequence of SEQ ID NO: 2, amino acids 1-661 of SEQ ID NO: 2, a naturally-occurring variant thereof, or a derivative thereof having at least 95% sequence identity with amino acids 1-661 of SEQ ID NO: 2, or with SEQ ID NO: 2.

The following numbered clauses describe various exemplary aspects of the present invention.

Clause 1. A composition for reducing, preventing, treating, or vaccinating a patient, comprising a polypeptide comprising an immunogenic amino acid sequence (e.g., an epitope, antigen, antigenic determinant capable of inducing humoral and/or cell-mediated immune response or immunity) of a SARS-CoV-2 spike (e.g., S1) protein or a conservative derivative thereof able to elicit an immune response to a SARS-CoV-2 spike protein, and optionally an amino acid sequence not from SARS-CoV-2, or a polypeptide having the sequence of SEQ ID NO: 2, of amino acids 1-661 of SEQ ID NO: 2, of a naturally-occurring variant thereof, or a derivative thereof having at least 95% sequence identity with amino acids 1-661 of SEQ ID NO: 2, or with SEQ ID NO: 2, and a pharmaceutically acceptable excipient.

Clause 2. The composition of clause 1, able to elicit neutralizing antibodies for SARS-CoV-2 in a normal, healthy patient.

Clause 3. The composition of clause 1 or 2, wherein the polypeptide comprises a multimerization domain, such as an immunoglobulin Fc domain, a T4 fibritin foldon trimerization domain, or a human collagen XV trimerization domain.

Clause 4. The composition of any one of clauses 1-3, wherein the polypeptide further comprises a Toll-like receptor agonist domain, such as a Toll-like receptor 4 (TLR4) or Toll-like receptor 3 (TLR3) agonist domain.

Clause 5. The composition of clause 4, wherein the Toll-like receptor 4 (TLR-4) agonist domain is an RS09 domain.

Clause 6. The composition of any one of clauses 1-5, wherein the immunogenic amino acid sequence of the SARS-CoV-2 spike protein includes an angiotensin-converting enzyme 2 (ACE2) receptor-binding domain (RBD) of the SARS-CoV-2 S protein.

Clause 7. The composition of any one of clauses 1-6, wherein the composition comprises a trimer structure of the polypeptide.

Clause 8. The composition of clause 1, comprising a polypeptide comprising the amino acid sequence:

(SEQ ID NO: 2)

```
MFVFLVLLPLVSSQCVNLTTRTQLPPAYTNSITRGVYYPDKVFRSSVLHS

TQDLFLPFFSNVTWFHAIHVSGTNGTKRFDNPVLPFNDGVYFASTEKSNI
```

-continued

```
IRGWIFGTTLDSKTQSLLIVNNATNVVIKVCEFQFCNDPFLGVYYHKNNK

SWMESEFRVYSSANNCTFEYVSQPFLMDLEGKQGNFKNLREFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSF

VIRGDEVRQIAPGQTGKIADYNYKLPDDFTGCVIAWNSNNLDSKVGGNYN

YLYRLFRKSNLKPFERDISTEIYQAGSTPCNGVEGFNCYFPLQSYGFQPT

NGVGYQPYRVVVLSFELLHAPATVCGPKKSTNLVKNKCVNFNFNGLTGTG

VLTESNKKFLPFQQFGRDIADTTDAVRDPQTLEILDITPCSFGGVSVITP

GTNTSNQVAVLYQDVNCTEVPVAIHADQLTPTWRVYSTGSNVFQTRAGCL

IGAEHVNNSYEGS.
```

Clause 9. The composition of clause 1 having an amino acid sequence comprising the amino acid sequence of any one of FIG. 2B, 3B, 4B, 5B, or 7A-7F, such as:

```
                                          (SEQ ID NO: 8)
MFVFLVLLPLVSSQCVNLTTRTQLPPAYTNSITRGVYYPDKVFRSSVLHS

TQDLFLPFFSNVTWFHAIHVSGTNGTKRFDNPVLPFNDGVYFASTEKSNI

IRGWIFGTTLDSKTQSLLIVNNATNVVIKVCEFQFCNDPFLGVYYHKNNK

SWMESEFRVYSSANNCTFEYVSQPFLMDLEGKQGNFKNLREFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSF

VIRGDEVRQIAPGQTGKIADYNYKLPDDFTGCVIAWNSNNLDSKVGGNYN

YLYRLFRKSNLKPFERDISTEIYQAGSTPCNGVEGFNCYFPLQSYGFQPT

NGVGYQPYRVVVLSFELLHAPATVCGPKKSTNLVKNKCVNFNFNGLTGTG

VLTESNKKFLPFQQFGRDIADTTDAVRDPQTLEILDITPCSFGGVSVITP

GTNTSNQVAVLYQDVNCTEVPVAIHADQLTPTWRVYSTGSNVFQTRAGCL

IGAEHVNNSYEGSGYIPEAPRDGQAYVRKDGEWVLLSTFLAPPHALSENL

YFEGHHHHHH.
```

Clause 10. A pharmaceutical composition comprising the composition of any one of clauses 1-9, and a pharmaceutically-acceptable excipient, and optionally a molecule with immune stimulant or adjuvant effects, such as TLR3 agonists such as Poly(I:C) or Poly-ICLC; TLR 4 agonists such as LPS or monophosphoryl lipid derivatives; TLR 5 agonists such as flagellin derivatives; TLR 7/8 agonists such as imiquimod or R848; TLR 9 agonists such as CpG sequences; Stimulator of Interferon Genes (STING) pathway agonists such as ADU-S100; stimulatory neuroimmune mediators such as calcitonin gene-related peptide (CGRP); neurokinin 1 (NK1) receptor agonists such as Hemokinin 1 and Substance P; saponin related adjuvants such as QS-21 (*Quillaja saponaria*); purinoergic receptor agonists such as ATP; or oil-in-water emulsion adjuvants such as MF59.

Clause 11. A pharmaceutical composition comprising the composition of any one of clauses 1-10, and optionally a molecule with immune stimulant or adjuvant effects, such as TLR3 agonists such as Poly(I:C) or Poly-ICLC; TLR 4 agonists such as LPS or monophosphoryl lipid derivatives; TLR 5 agonists such as flagellin derivatives; TLR 7/8 agonists such as imiquimod or R848; TLR 9 agonists such as CpG sequences; Stimulator of Interferon Genes (STING) pathway agonists such as ADU-5100; stimulatory neuroimmune mediators such as calcitonin gene-related peptide (CGRP); neurokinin 1 (NK1) receptor agonists such as Hemokinin 1 and Substance P; saponin related adjuvants such as QS-21 (*Quillaja saponaria*); purinoergic receptor agonists such as ATP; or oil-in-water emulsion adjuvants such as MF59, in combination with a matrix composition of a microneedle array.

Clause 12. The pharmaceutical composition the composition of clause 11, wherein the matrix composition of the microneedle array comprises carboxymethyl cellulose (CMC, e.g., 90 kDa MW).

Clause 13. The pharmaceutical composition the composition of clause 12, wherein the matrix composition of the microneedle array further comprises trehalose.

Clause 14. The pharmaceutical composition the composition of clause 11, wherein the matrix composition of the microneedle array comprises carboxymethyl cellulose, trehalose, polyvinylpyrrolidone, maltodextrin, silk, hyaluronic acid, poly(lactic-co-glycolic acid), poly(lactic acid), poly(vinyl alcohol), polyethylene glycol, or a combination of any two or more of the preceding.

Clause 15. A microneedle array for transdermal delivery of a therapeutic agent into a subject, comprising: a backing layer; and a plurality of microneedles comprising a matrix of a dissolvable or bioerodible, biocompatible material extending from the base portion and containing the composition of any one of clauses 1-10, and optionally a molecule with immune stimulant or adjuvant effects, such as TLR3 agonists such as Poly(I:C) or Poly-ICLC; TLR 4 agonists such as LPS or monophosphoryl lipid derivatives; TLR 5 agonists such as flagellin derivatives; TLR 7/8 agonists such as imiquimod or R848; TLR 9 agonists such as CpG sequences; Stimulator of Interferon Genes (STING) pathway agonists such as ADU-S100; stimulatory neuroimmune mediators such as calcitonin gene-related peptide (CGRP); neurokinin 1 (NK1) receptor agonists such as Hemokinin 1 and Substance P; saponin related adjuvants such as QS-21 (*Quillaja saponaria*); purinoergic receptor agonists such as ATP; or oil-in-water emulsion adjuvants such as MF59, the microneedles optionally having a length of 1 mm or less.

Clause 16. The microneedle array of clause 15, wherein the plurality of microneedles have a shape that comprises a first cross-sectional dimension at a head portion distal to the backing layer, a second cross-sectional dimension at a stem portion proximal to the backing layer, and a third cross-sectional dimension at an intermediate portion located between the top portion and the bottom portion having a cross-sectional dimension greater than the first and second cross-sectional dimensions.

Clause 17. The microneedle array of clause 15, wherein the plurality of microneedles comprise a stem portion adjacent or proximal to the backing layer, and a head portion attached to the stem portion distal to the backing layer, the microneedles having a barbed or undercut profile in which the head portion having a cross section adjacent to the stem is larger than a cross section of the stem adjacent to the head.

Clause 18. The microneedle array of any one of clauses 15-17, wherein a plurality of microneedles comprise a plurality of layers of one or more dissolvable or bioerodible, biocompatible material.

Clause 19. The microneedle array of any one of clauses 15-18, wherein a plurality of microneedles comprise carboxymethyl cellulose, trehalose, polyvinylpyrrolidone, maltodextrin, silk, hyaluronic acid, poly(lactic-co-glycolic acid), poly(lactic acid), poly(vinyl alcohol), polyethylene glycol, or a combination of any two or more of the preceding.

Clause 20. The microneedle array of any one of clauses 15-19, wherein the dissolvable or bioerodible, biocompatible material comprises carboxymethylcellulose and, optionally, trehalose.

Clause 21. A method of eliciting an immune response against SARS-CoV-2 in a subject, comprising administering to the subject the immunogenic composition of any one of clauses 1-10, thereby eliciting the immune response against SARS-CoV-2, wherein the immunogenic composition is optionally administered parenterally.

Clause 22. The method of clause 20, comprising contacting the skin of the subject with the microneedle array of any one of clauses 15-20, thereby delivering the immunogen to the skin of the subject and eliciting an immune response against SARS-CoV-2 in the subject, wherein the immunogen is optionally delivered intradermally or subdermally.

Clause 23. The method of clause 21 or 22, wherein the subject is a human.

Clause 24. The method of any one of clauses 21-23, wherein the subject is a female.

Clause 25. The method of clause 24, wherein the female is of an age wherein she can bear children.

Clause 26. The method of clause 25, wherein the female is pregnant.

Clause 27. A method of forming a microneedle array, comprising:

- forming or providing a production mold of a flexible material, the production mold comprising a plurality of cavities that are shaped to define a plurality of respective microneedles having a stem, a head, a filleted base, and at least one undercut feature, the microneedles optionally having a length of 1 mm or less;
- delivering a first dissolvable or bioerodible material into at least the microneedle head portion defined by the respective cavities of the production mold, and prior to or during delivery of the first dissolvable or bioerodible material into at least the microneedle head portion, incorporating a therapeutic agent into the first dissolvable or bioerodible material to provide a biodegradable matrix;
- delivering the first dissolvable or bioerodible material and/or one or more additional dissolvable or bioerodible materials into the cavity and forming a plurality of microneedles in the production mold that include the biodegradable matrix; and removing the microneedles from the production mold by pulling the microneedles out of the mold, wherein the flexible material of the production mold has sufficient elasticity to allow for the molded microneedle array to be removed from the production mold, e.g., in a single pull, without damaging the integrity of the shape of the microneedles as defined by the mold.

Clause 28. The method of clause 27, wherein the therapeutic agent is the composition of any one of clauses 1-10.

Clause 29. The method of clause 27, wherein the at least one undercut feature is directly below the microneedle head.

Clause 30. The method of any one of clauses 27-29, wherein the stem is formed from the first dissolvable or bioerodible material.

Clause 31. The method of any one of clauses 27-30, wherein the first dissolvable or bioerodible material comprises carboxymethyl cellulose, trehalose, polyvinylpyrrolidone, maltodextrin, silk, hyaluronic acid, poly(lactic-co-glycolic acid), poly(lactic acid), poly(vinyl alcohol), polyethylene glycol, or a combination of any two or more of the preceding.

Clause 32. The method of any one of clauses 27-31, wherein the stem is formed from a non-dissolvable material.

Clause 33. The method of any one of clauses 27-28, further comprising delivering a second dissolvable material into the production mold to form a dissolving layer at a portion of the stem, such as adjacent to the microneedle head.

Clause 34. The method of clause 33, wherein the second dissolvable material of the dissolving layer is a material that dissolves more quickly than the biodegradable matrix that contains the therapeutic agent.

Clause 35. The method of clause 34, wherein the second dissolvable material comprises a low molecular weight compound or composition that rapidly dissolves, e.g., dissolves in less than 30 seconds, less than 20 seconds, less than 10 seconds, or less than 5 seconds in water.

Clause 36. The method of clause 35, wherein the second dissolvable material comprises glucose, trehalose, sucrose, maltodextrin, polyvinylpyrrolidone, or a combination of two or more of the preceding.

Clause 37. The method of any one of clauses 27-36, further comprising forming a backing layer adjacent to the stem.

Clause 38. The method of clause 37, wherein the backing layer is formed from a nondissolvable material.

Clause 39. The method of clause 37 or 38, wherein the backing layer is formed from a conformable material that optionally can flex, deform, or bend to conform to non-uniform skin topography.

Clause 40. The method of clause 37, wherein the backing layer is formed from the dissolvable or bioerodible, biocompatible material.

Clause 41. The method of any one of clauses 27-40, further comprising incorporating one or more additional therapeutically active agents into the biodegradable matrix.

Clause 42. The method of any one of clauses 27-41, wherein the plurality of microneedles have a shape that includes a circular obelisk, a square obelisk, a bevel obelisk, a pyramid on a square stem, an arrowhead shape on a stem, a pyramid head on a square obelisk stem, a conical head on a cylindrical obelisk stem, a square obelisk, a 45° pyramid, or a 30° pyramid.

Clause 43. The method of any one of clauses 27-42, wherein the fillet base is located at the intersection of the backing layer and the stem.

Clause 44. The method of any one of clauses 27-43, wherein the microneedles are formed by a method comprising a spin-casting step.

Clause 45. The method of any one of clauses 27-44, formed using a single-pull mold.

Clause 46. A microneedle array formed by the method of any of clauses 27-45.

Clause 47. A microneedle array for transdermal delivery of a therapeutic agent into a subject, comprising: a backing layer; and a plurality of microneedles comprising a stem portion adjacent or proximal to the backing layer and a head portion attached to the stem portion distal to the backing layer, and comprising a matrix of a dissolvable or bioerodible, biocompatible material extending from the backing layer and containing a therapeutic agent, the microneedles optionally having a length of 1 mm or less, wherein:

the plurality of microneedles have a shape that comprises a first cross-sectional dimension at a head portion distal to the backing layer, a second cross-sectional dimension at a stem portion proximal to the backing layer, and a third cross-sectional dimension at an intermediate portion located between the head portion and the stem portion having a cross-sectional dimension greater than the first and second cross-sectional dimensions; or the plurality of microneedles having a barbed or undercut profile in which the head portion has a cross section adjacent to the stem that is larger than a cross section of the stem adjacent to the head.

Clause 48. The microneedle array of clause 47, wherein a plurality of microneedles comprise a plurality of layers of one or more dissolvable or bioerodible, biocompatible material.

Clause 49. The microneedle array of clause 47 or 48, wherein a plurality of microneedles comprise carboxymethyl cellulose, trehalose, polyvinylpyrrolidone, maltodextrin, silk, hyaluronic acid, poly(lactic-co-glycolic acid), poly (lactic acid), poly(vinyl alcohol), polyethylene glycol, or a combination of any two or more of the preceding.

Clause 50. The microneedle array of any one of clauses 47-49, wherein the dissolvable or bioerodible, biocompatible material comprises carboxymethylcellulose and, optionally, trehalose.

Clause 51. The microneedle array of any one of clauses 47-50, wherein the microneedles comprise an undercut feature located at the intersection of the stem and the microneedle head.

Clause 52. The microneedle array of any one of clauses 47-51, wherein the stem is formed from the first dissolvable or bioerodible, biocompatible material.

Clause 53. The microneedle array of any of clauses 47-52, wherein the plurality of microneedles each comprise a second dissolvable material that forms a quick-dissolving layer at a portion of the stem that is adjacent the microneedle tip.

Clause 54. The microneedle array of clause 53, wherein the second dissolvable material of the dissolving layer is selected from a material that dissolves more quickly than the biodegradable matrix that contains the therapeutic agent.

Clause 55. The microneedle array of clause 53 or 54, wherein the second dissolvable material comprises a low molecular weight compound or composition that rapidly dissolves, e.g., dissolves in less than 30 seconds, less than 20 seconds, less than 10 seconds, or less than 5 seconds in water.

Clause 56. The microneedle array of clause 55, wherein the second dissolvable material comprises glucose, trehalose, sucrose, polyvinylpyrrolidone, maltodextrin, or a combination thereof.

Clause 57. The microneedle array of any one of clauses 47-51, wherein the stem is formed from a nondissolvable material.

Clause 58. The microneedle array of clause 57, wherein the backing layer is formed from a conformable material that optionally can flex, deform, or bend to conform to non-uniform skin topography.

Clause 59. The microneedle array of any one of clauses 47-56, wherein the backing layer is formed from the dissolvable or bioerodible, biocompatible material.

Clause 60. The microneedle array of clauses 47-59, wherein the microneedles comprise two or more therapeutically active agents.

Clause 61. The microneedle array of any one of clauses 47-60, wherein the plurality of microneedles has a shape that includes a circular obelisk, a square obelisk, a bevel obelisk, a pyramid on a square stem, an arrowhead shape on a stem, a pyramid head on a square obelisk stem, a conical head on a circular obelisk stem, a square obelisk, a 45° pyramid, or a 30° pyramid.

Clause 62. The microneedle array of any one of clauses 47-61, wherein the fillet base is located at the intersection of the backing layer and the stem.

Clause 63. A method of forming a mold comprising: generating in a computer a 3D-CAD drawing of a microneedle array that includes a plurality of microneedles with at least one undercut feature; forming a master microneedle array using the 3D-CAD drawing; forming at least one replica of the master microneedle array, e.g., by additive manufacturing; and forming a production mold of the microneedle array using the at least one replica, wherein the production mold is formed of a flexible material.

Clause 64. The method of clause 63, wherein the flexible material has sufficient elasticity to allow for a molded microneedle array to be removed from the production mold in a single pull without damaging the integrity of the shape of the plurality microneedles as defined by the production mold.

Clause 65. The method of clause 63 or 64, wherein the at least one replica includes a plurality of replicas, and the forming of the production mold comprises forming a microneedle array holder and combining the plurality of replicas together on the microneedle array holder.

Clause 66. The method of any of clauses 63-65, wherein the microneedle array comprises a holder formed of a resin material.

Clause 67. A method of forming a tissue adhesive patch comprising:

forming or providing a production mold of a flexible material, the production mold comprising a plurality of cavities that are shaped to define a plurality of respective microneedles that each have a stem, a microneedle head, a filleted base, and at least one undercut feature;

incorporating at least one bioactive material or therapeutic agent into a first dissolvable material to provide a biodegradable matrix and during or prior to incorporating the at least one bioactive material or therapeutic agent into the first dissolvable material delivering the biodegradable matrix into at least the microneedle-tip portion defined by the respective cavities of the production mold; forming a plurality of microneedles in the production mold that include the biodegradable matrix; and removing the microneedles from the production mold by pulling the microneedles out of the mold, wherein the flexible material has sufficient elasticity to allow for the molded microneedle array to be removed from the production mold in a single pull without damaging the integrity of the shape of the microneedles as defined by the mold.

Clause 68. A method of forming a tissue adhesive patch or microbarb array comprising: forming a production mold of a flexible material, the production mold comprising a plurality of cavities that are shaped to define a plurality of respective microneedles that each have a stem, a microneedle tip, a filleted base, and at least one undercut feature, incorporating at least one bioactive material into a first dissolvable material to provide a biodegradable matrix, delivering the biodegradable matrix into at least the microneedle-tip portion defined by the respective cavities of the production mold; forming a plurality of microneedles in the production mold that include the biodegradable matrix;

and removing the microneedles from the production mold by pulling the microneedles out of the mold, wherein the flexible material has sufficient elasticity to allow for the molded microneedle array to be removed from the production mold in a single pull without damaging the integrity of the shape of the microneedles as defined by the mold.

Clause 69. A method of forming a microneedle array comprising:

forming a production mold of a flexible material, the production mold comprising a plurality of cavities that are shaped to define a plurality of respective microneedles that each have a stem, a microneedle tip, a filleted base, and at least one undercut feature;

forming a plurality of microneedles in the production mold;

removing the microneedles from the production mold by pulling the microneedles out of the mold; and coating at least a portion of the plurality of microneedles with a bioactive component, wherein the flexible material has sufficient elasticity to allow for the molded microneedle array to be removed from the production mold in a single pull without damaging the integrity of the shape of the microneedles as defined by the mold.

Clause 70. The method of clause 69, wherein the microneedle is coated with the bioactive component by dip-coating, air-spraying, or a combination thereof.

Clause 71. A microneedle array formed according to a method of any one of clauses 63-70.

Clause 72. A method of using a microneedle array, comprising: applying the microneedle array of clause 71 to a targeted skin area of a subject such that the microneedles enter the skin to deliver the at least one therapeutic agent or bioactive component intradermally.

Clause 73. A method of using a microneedle array, comprising: applying the microneedle array of clause 71 to a non-cutaneous tissue to deliver the at least one bioactive component to the non-cutaneous tissue.

Clause 74. A method of preventing infection with SARS-CoV-2, vaccinating a patient for SARS-CoV-2, or treating or reducing a symptom of a SARS-CoV-2 infection in a patient, comprising administering to the patient an amount of the compositions of any one of clauses 1-10, by a route of administration effective to induce an immune response, e.g., a neutralizing immune response, to SARS-CoV-2.

Clause 75. The method of clause 74, wherein the composition is administered to the patient parenterally.

Clause 76. The method of clause 74, wherein the composition is administered to the patient by inhalation or intranasally.

Clause 77. The method of clause 74, wherein the composition is administered to or through the skin, such as intracutaneously or subcutaneously, for example by subcutaneous injection of delivery by a microneedle array, e.g., a microneedle array of any one of clauses 15-20, 46-62, or 71.

Clause 78. The method of any one of clauses 74-77, wherein the composition is administered to the patient more than once.

Clause 79. A nucleic acid, comprising a gene for expressing a polypeptide according to any one of clauses 1-10.

Clause 80. The nucleic acid of clause 79, encoding a recombinant viral vector, such as an adenovirus or adeno-associated virus vector, comprising the gene.

Clause 81. An immunogenic pharmaceutical composition for use in eliciting an immune response to SARS-CoV-2 in a patient, comprising a polypeptide having the sequence of SEQ ID NO: 2, amino acids 1-661 of SEQ ID NO: 2, a naturally-occurring variant thereof, or a derivative thereof having at least 95% sequence identity with amino acids 1-661 of SEQ ID NO: 2, and a pharmaceutically-acceptable excipient.

Clause 82. The composition of clause 81, able to elicit neutralizing antibodies for SARS-CoV-2 in a normal, healthy patient.

Clause 83. The composition of clause 81, wherein the polypeptide is a fusion protein comprising a multimerization domain, a Toll-like receptor agonist domain, or a SARS-CoV-2 nucleoprotein amino acid sequence having the sequence of amino acids 664-1,082 of SEQ ID NO: 16, a naturally-occurring variant thereof, or a derivative thereof having at least 95% sequence identity with amino acids 664-1,082 of SEQ ID NO: 16.

Clause 84. The pharmaceutical composition comprising of clause 81, further comprising a molecule with immune stimulant or adjuvant effect.

Clause 85. The pharmaceutical composition of clause 84, comprising: a TLR3 agonist; a TLR 4 agonists; a TLR 5 agonist; a TLR 7/8 agonist; a TLR 9 agonist; a Stimulator of Interferon Genes (STING) pathway agonist; a stimulatory neuroimmune mediator; a neurokinin 1 (NK1) receptor agonist; a saponin related adjuvant; a purinoergic receptor agonist; or an oil-in-water emulsion adjuvant.

Clause 86. The pharmaceutical composition of clause 81, wherein the polypeptide has at least 99% sequence identity with amino acids SEQ ID NO: 2, 1-661 of SEQ ID NO: 2, or is a naturally-occurring variant of amino acids 1-661 of SEQ ID NO: 2.

Clause 87. A microneedle array for use in eliciting an immune response to SARS-CoV-2 in a patient, comprising: a backing layer; and a plurality of microneedles, with a polypeptide having the sequence of SEQ ID NO: 2, amino acids 1-661 of SEQ ID NO: 2, a naturally-occurring variant thereof, or a derivative thereof having at least 95% sequence identity with amino acids 1-661 of SEQ ID NO: 2 incorporated into or onto the microneedle.

Clause 88. The microneedle array of clause 87, in which the plurality of microneedles comprise a matrix of a dissolvable or bioerodible, biocompatible material extending from the base portion.

Clause 89. The microneedle array of clause 88, wherein a plurality of microneedles comprise a plurality of layers of one or more dissolvable or bioerodible, biocompatible material.

Clause 90. The microneedle array of clause 88, wherein the plurality of microneedles comprise carboxymethyl cellulose, trehalose, polyvinylpyrrolidone, maltodextrin, silk, hyaluronic acid, poly(lactic-co-glycolic acid), poly(lactic acid), poly(vinyl alcohol), polyethylene glycol, or a combination of any two or more of the preceding.

Clause 91. The microneedle array of clause 88, wherein the plurality of microneedles comprise carboxymethyl cellulose.

Clause 92. The microneedle array of clause 91, wherein the plurality of microneedles further comprise trehalose.

Clause 93. The microneedle array of clause 88, wherein the plurality of microneedles have a shape that comprises a first cross-sectional dimension at a head portion distal to the backing layer, a second cross-sectional dimension at a stem portion proximal to the backing layer, and a third cross-sectional dimension at an intermediate portion located between the top portion and the bottom portion having a cross-sectional dimension greater than the first and second cross-sectional dimensions.

Clause 94. The microneedle array of clause 88, wherein the plurality of microneedles comprise a stem portion adjacent or proximal to the backing layer, and a head portion attached to the stem portion distal to the backing layer, the microneedles having a barbed or undercut profile in which the head portion having a cross section adjacent to the stem is larger than a cross section of the stem adjacent to the head.

Clause 95. The microneedle array of clause 88, wherein the microneedles comprise a stem, a head, a filleted base, and at least one undercut feature.

Clause 96. A method of eliciting an immune response against SARS-CoV-2 in a patient, comprising administering to the patient an amount of the pharmaceutical composition of clause 1 effective to elicit an immune response against SARS-CoV-2 in a patient, thereby eliciting an immune response in the patient against SARS-CoV-2.

Clause 97. The method of clause 96, wherein the pharmaceutically-acceptable excipient is a matrix of a microneedle array, and comprising contacting the skin of the patient with the microneedle array to delivering the polypeptide intradermally or subdermally to the patient and eliciting an immune response against SARS-CoV-2 in the patient.

Clause 98. The method of clause 97, wherein the patient is a human.

Clause 99. A method of forming a microneedle array comprising forming a plurality of microneedles having a filleted base attached to a backing, comprising incorporating into or onto microneedles of the microneedle array a polypeptide having the sequence of SEQ ID NO: 2, amino acids 1-661 of SEQ ID NO: 2, a naturally-occurring variant thereof, or a derivative thereof having at least 95% sequence identity with amino acids 1-661 of SEQ ID NO: 2, or of SEQ ID NO: 2.

Clause 100. The method of forming a microneedle array of clause 99, wherein the polypeptide is incorporated into a first dissolvable or bioerodible material.

Clause 101. The method of forming a microneedle array of clause 100, comprising:

- forming or providing a production mold of a flexible material, the production mold comprising a plurality of cavities that are shaped to define a plurality of respective microneedles having a stem, a head, a filleted base, and at least one undercut feature;
- delivering the first dissolvable or bioerodible material into at least the microneedle head portion defined by the respective cavities of the production mold, and prior to or during delivery of the first dissolvable or bioerodible material into at least the microneedle head portion, incorporating the into the first dissolvable or bioerodible material to provide a biodegradable matrix;
- delivering the first dissolvable or bioerodible material and/or one or more additional dissolvable or bioerodible materials into the cavity and forming a plurality of microneedles in the production mold that include the biodegradable matrix; and removing the microneedles from the production mold by pulling the microneedles out of the mold, wherein the flexible material of the production mold has sufficient elasticity to allow for the molded microneedle array to be removed from the production mold, e.g., in a single pull, without damaging the integrity of the shape of the microneedles as defined by the mold.

Clause 102. The method of clause 101, wherein the at least one undercut feature is directly below the microneedle head.

Clause 103. The method of clause 101, wherein the stem is formed from the first dissolvable or bioerodible material.

Clause 104. The method of clause 101, wherein the first dissolvable or bioerodible material comprises carboxymethyl cellulose, trehalose, polyvinylpyrrolidone, maltodextrin, silk, hyaluronic acid, poly(lactic-co-glycolic acid), poly (lactic acid), poly(vinyl alcohol), polyethylene glycol, or a combination of any two or more of the preceding.

Clause 105. The method of clause 101, further comprising delivering a second dissolvable material into the production mold to form a dissolving layer at a portion of the stem, such as adjacent to the microneedle head.

Clause 106. The method of clause 105, wherein the second dissolvable material of the dissolving layer is a material that dissolves more quickly than the biodegradable matrix that contains the therapeutic agent.

Clause 107. The method of clause 101, wherein the microneedles are formed by a method comprising a spincasting step.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 2A-2B: Nucleotide sequence for SARS-CoV-2-S1 (1992 base pairs) (FIG. 2A) (SEQ ID NO: 1) and amino acid sequence for SARS-CoV-2-S1 (663 amino acids) (FIG. 2B) (SEQ ID NO: 2, with bases 1-661 of SEQ ID NO: 2 corresponding to bases 1-661 of the SARS-CoV-2 S1 protein sequence).

FIGS. 3A-3B: Nucleotide sequence for SARS-CoV-2-S1 H (2010 base pairs) (FIG. 3A) (SEQ ID NO: 3) and amino acid sequence for SARS-CoV-2-S1 H (669 amino acids) (FIG. 3B) (SEQ ID NO: 4).

FIGS. 4A-4B: Nucleotide sequence for SARS-CoV-2-S1fRS09 (2094 base pairs) (FIG. 4A) (SEQ ID NO: 5) and amino acid sequence for SARS-CoV-2-S1fRS09 (697 amino acids) (FIG. 4B) (SEQ ID NO: 6).

FIGS. 5A-5B: Nucleotide sequence for SARS-CoV-2-nCoV-S1fRS09H (2133 base pairs) (FIG. 5A) (SEQ ID NO: 7) and amino acid sequence for SARS-CoV-2-nCoV-S1fRS09H (710 amino acids) (FIG. 5B) (SEQ ID NO: 8).

FIGS. 6A-6F: Nucleotide sequences for additional spike and spike+nucleoprotein constructs as shown in FIG. 1 (SEQ ID NOS: 9-14, respectively).

FIGS. 7A-7F: Amino acid sequences for additional spike and spike+nucleoprotein constructs as shown in FIG. 1 (SEQ ID NOS: 15-20, respectively).

(FIG. 11(A)) Biocargo solution is dispensed onto microneedles in PDMS production molds. (FIG. 11(B)) Microneedle wells of MNA molds are filled with biocargo by brief centrifugation without drying (bucket lids on). (FIG. 11(C)) Excess biocargo solution was recovered from the production mold reservoir to be used for fabricating additional MNAs. (FIG. 11(D)) Remaining biocargo in microneedle molds is dried through spin-casting.

(FIG. 16 (D-I)) Intradermal co-delivery of Alexa488-labeled Poly(I:C) and Alexa555-labeled OVA from tip-loaded CMC/trehalose MNAs. Scale bars are 100 μm. Fluorescence microscope composite images demonstrate delivery cavities penetrating the epidermis and upper dermis, and delivery of both antigen and adjuvant to targeted skin microenvironments. (FIG. 16 (D)) DAPI nuclear stain. (FIG. 16 (E)) Alexa488-labeled Poly(I:C). (FIG. 16 (F)) Alexa555-labeled OVA. (FIG. 16 (G)) Brightfield. (FIG. 13(H)) Merged fluorescent images from (FIGS. 16 (D-F)). (FIG. 16 (I)) Merged fluorescent images from (FIGS. 16 (D-F)) overlaid on brightfield image from (FIG. 16 (G)). (FIG. 16 (J)) Low magnification merged fluorescent images showing OVA and Poly(I:C) delivered in two parallel microneedle tracks. Scale bar is 200 μm.

(FIGS. 17 (D-E)) Effective co-delivery of Alexa488-Poly(I:C) (FIG. 17 (D)) and Alexa555-OVA (FIG. 17** (E)) to the mouse skin using MNAs with undercut features.

(FIGS. 26 (A, B): 2.5× optical magnification, FIG. 26(C): 1.6×, FIG. 26 (D): 20×, FIGS. 26 (E, F): 60× optical magnification).

DETAILED DESCRIPTION

Figure 1:
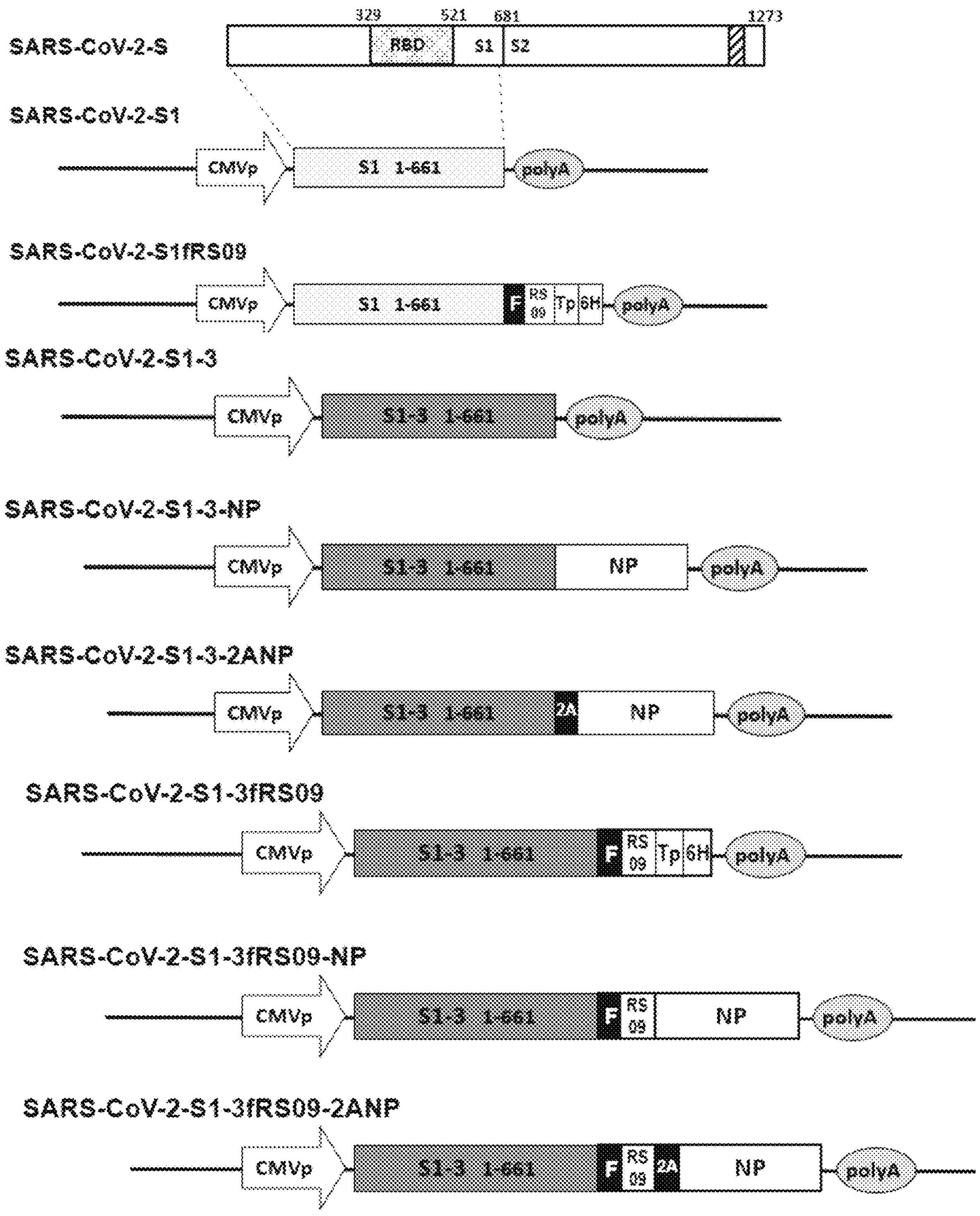
FIG. 1 provides schematic diagrams of various SARS-CoV-2 spike (S1) and spike+nucleoprotein (NP) constructs. S1 is SARS-CoV-2 spike protein, with S1-3 being a codon-optimized version thereof. CMVp is a constitutive CMV promoter. NP is SARS-CoV-2 nucleoprotein. RBD is SARS-CoV-2 S1 receptor binding domain. F is a T4 fibritin foldon trimerization domain. Tp is a Tobacco Etch Virus (TEV) protease. 2A is a self-cleaving peptide sequence. RS09 is a Toll-like receptor 4 (TLR-4) agonist peptide. 6H is a His tag. LoxP is the LoxP recombination site.

Provided herein are subunit monomeric and trimeric SARS-CoV-2 vaccines which are currently under testing in vitro and in vivo. In one example, the vaccine is a multimeric polypeptide immunogen comprising recombinant subunit glycoproteins SARS-CoV-2-S1 fused to the T4 fibritin foldon trimerization domain, with or without the fusion of a Toll-like receptor 4 (TLR-4) agonist peptide (RS09). This recombinant fusion protein is expected to elicit a human immune response able fight and/or neutralize the SARS-CoV-2 virus.

Other than in the operating examples, or where otherwise indicated, the use of numerical values in the various ranges specified in this application are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. Further, as used herein, all numbers expressing dimensions, physical characteristics, processing parameters, quantities of ingredients, reaction conditions, and the like, used in the specification and claims are to be understood as being modified in all instances by the term "about". Moreover, unless otherwise specified, all ranges disclosed herein are to be understood to encompass the beginning and ending range values and any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 3.3, 4.7 to 7.5, 5.5 to 10, and the like.

As used herein "a" and "an" refer to one or more. The term "comprising" is open-ended and may be synonymous with "including", "containing", or "characterized by". The term "consisting essentially of" limits the scope of a claim to the specified materials or steps and those that do not materially affect the basic and novel characteristic(s) of the claimed invention.

As used herein, spatial or directional terms, such as "left", "right", "inner", "outer", "above", "below", "over", "under", and the like, relate to the invention as it is shown in the drawing figures are provided solely for ease of description and illustration, and do not imply directionality, unless specifically required for operation of the described aspect of the invention. It is to be understood that the invention can assume various alternative orientations and, accordingly, such terms are not to be considered as limiting.

As used herein, a "patient" or "subject" is an animal, such as a mammal, including a primate (such as a human, a non-human primate, e.g., a monkey, and a chimpanzee), a non-primate (such as a cow, a pig, a camel, a llama, a horse, a goat, a rabbit, a sheep, a hamster, a guinea pig, a cat, a dog, a rat, a mouse, a horse, and a whale), or a bird (e.g., a duck or a goose). As used herein, the terms "treating", or "treatment" refer to a beneficial or desired result, such as improving one of more functions, or symptoms of a disease.

Unless otherwise explained, all technical and scientific terms used herein have the same meaning as commonly understood by one of ordinary skill in the art to which this disclosure belongs. It is to be understood that all base sizes or amino acid sizes, and all molecular weight or molecular mass values, given for nucleic acids or polypeptides are approximate, and are provided for description. Unless otherwise indicated, polymer molecular weight is expressed as number-average molecular weight (Mn). Although methods and materials similar or equivalent to those described herein can be used in the practice or testing of the present disclosure, suitable methods and materials are described below.

As used herein, 2019-nCoV is synonymous with SARS-CoV-2.

Unless stated otherwise, nucleotide sequences are recited herein in a 5' to 3' direction, and amino acid sequences are recited herein in an N-terminal to C-terminal direction according to convention.

"Therapeutically effective amount," as used herein, is intended to include the amount of a therapeutic agent, such as an immunogen, as described herein that, when administered to a subject having a disease, is sufficient to effect treatment of the disease (e.g., by diminishing, ameliorating or maintaining the existing disease or one or more symptoms of disease). The "therapeutically effective amount" may vary depending on compound or composition, how it is administered, the disease and its severity and the history, age, weight, family history, genetic makeup, the types of preceding or concomitant treatments, if any, and other individual characteristics of the subject to be treated.

A "therapeutically-effective amount" also includes an amount of an agent that produces some desired local or systemic effect at a reasonable benefit/risk ratio applicable to any treatment. Compounds and compositions described herein may be administered in a sufficient amount to produce a reasonable benefit/risk ratio applicable to such treatment. For example, a therapeutically-effective amount of a virus vaccine useful for eliciting an immune response in a subject and/or for preventing infection by the virus. In the context of the present disclosure, a therapeutically effective amount of a coronavirus, e.g., a SARS-CoV-2, virus vaccine, for example, is an amount sufficient to increase resistance to, prevent, ameliorate, and/or treat infection caused by a coronavirus, e.g., a SARS-CoV-2 virus in a subject without causing a substantial cytotoxic effect in the subject. The effective amount of a coronavirus, e.g., a SARS-CoV-2, virus vaccine useful for increasing resistance to, preventing, ameliorating, and/or treating infection in a subject will be dependent on, for example, the subject being treated, the manner of administration of the therapeutic composition and other factors.

A non-limiting range for a therapeutically effective amount of the disclosed immunogen within the methods and immunogenic compositions of the disclosure is about 0.0001 mg/kg body weight to about 10 mg/kg body weight, such as about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.5 mg/kg, about 2 mg/kg, about 2.5 mg/kg, about 3 mg/kg, about 4 mg/kg, about 5 mg/kg, or about 10 mg/kg, for example, 0.01 mg/kg to about 1 mg/kg body weight, about 0.05 mg/kg to about 5 mg/kg body weight, about 0.2 mg/kg to about 2 mg/kg body weight, or about 1.0 mg/kg to about 10 mg/kg body weight. In some embodiments, the dosage includes a set amount of a disclosed immunogen such as from about 1-300 μg, for example, a dosage of about 1, 2, 3, 4, 5, 6, 7, 8, 9, 10, 15, 20, 30, 40, 50, 60, 70, 80, 90, 100, 150, 200, 250, or about 300 μg.

Dosage can be varied by the attending clinician to maintain a desired concentration at a target site (for example, systemic circulation). Higher or lower concentrations can be selected based on the mode of delivery, for example, trans-epidermal, rectal, oral, pulmonary, or intranasal delivery versus intravenous or subcutaneous delivery. The actual dosage of disclosed immunogen will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response. A therapeutically effective amount is also one in which any toxic or detrimental side effects of the disclosed immunogen and/or other biologically active agent is outweighed in clinical terms by therapeutically beneficial effects.

Further, preventing, treating or ameliorating a disease: "Preventing" a disease refers to inhibiting the full development of a disease or infection, such as a coronavirus, e.g., a SARS-CoV-2 infection, from a subsequent exposure. "Treating" refers to a therapeutic intervention that ameliorates a sign or symptom of a disease or pathological condition after it has begun to develop. "Ameliorating" refers to the reduction in the number or severity of one or more signs or symptoms of a disease or infection. Prime-boost vaccination: An immunotherapy including administration of a first immunogenic composition (the primer vaccine) followed by administration of a second immunogenic composition (the booster vaccine) to a subject to elicit an immune response. The primer vaccine and/or the booster vaccine include a vector (such as a viral vector, RNA, or DNA vector) expressing the antigen to which the immune response is directed, or can include a protein immunogen. The booster vaccine is administered to the subject after the primer vaccine; the skilled artisan will understand a suitable time interval between administration of the primer vaccine and the booster vaccine, and examples of such timeframes are disclosed herein. In some embodiments, the primer vaccine, the booster vaccine, or both primer vaccine and the booster vaccine additionally include an adjuvant.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids; (23) serum component, such as serum albumin, HDL and LDL; and (24) other non-toxic compatible substances employed in pharmaceutical formulations. Remington: The Science and Practice of Pharmacy, The University of the Sciences in Philadelphia, Editor, Lippincott, Williams, & Wilkins, Philadelphia, Pa., 21st Edition (2005), describes compositions and formulations suitable for pharmaceutical delivery of one or more therapeutic compositions, such as a chimeric virus, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Therapeutic agents, for example and without limitation, bioactive agents, drugs, active pharmaceutical ingredients, or biologicals, may be incorporated into the compositions and combination devices described herein. Non-limiting examples of therapeutic agents include: anti-inflammatories, such as, without limitation, NSAIDs (non-steroidal anti-inflammatory drugs) such as salicylic acid, indomethacin, sodium indomethacin trihydrate, salicylamide, naproxen, colchicine, fenoprofen, sulindac, diflunisal, diclofenac, indoprofen sodium salicylamide, anti-inflammatory cytokines, and anti-inflammatory proteins or steroidal anti-inflammatory agents); antibiotics; anticlotting factors such as heparin, Pebac, enoxaprin, aspirin, hirudin, plavix, bivalirudin, prasugrel, idraparinux, warfarin, coumadin, clopidogrel, PPACK, GGACK, tissue plasminogen activator, urokinase, and streptokinase; growth factors; or antibiotics, such as, without limitation: acyclovir, afloxacin, ampicillin, amphotericin B, atovaquone, azithromycin, ciprofloxacin, clarithromycin, clindamycin, clofazimine, dapsone, diclazaril, doxycycline, erythromycin, ethambutol, fluconazole, fluoroquinolones, foscarnet, ganciclovir, gentamicin, iatroconazole, isoniazid, ketoconazole, levofloxacin, lincomycin, miconazole, neomycin, norfloxacin, ofloxacin, paromomycin, penicillin, pentamidine, polymixin B, pyrazinamide, pyrimethamine, rifabutin, rifampin, sparfloxacin, streptomycin, sulfadiazine, tetracycline, tobramycin, trifluorouridine, trimethoprim sulphate, Zn-pyrithione, ciprofloxacin, norfloxacin, afloxacin, levofloxacin, gentamicin, tobramycin, neomycin, erythromycin, trimethoprim sulphate, polymixin B, and silver salts such as chloride, bromide, iodide, and periodate; cytokines or chemoattractants; an anti-inflammatory protein; a steroidal anti-inflammatory agent; or an anti-clotting agents, such as heparin. Other therapeutic agents that may promote immunogenicity of the described immunogen may also be included.

As used herein, administering a composition (e.g., an immunogenic composition, such as a vaccine) to a subject means to give, apply or bring the composition into contact with the subject. Administration can be accomplished by any of a number of routes, such as, for example, topical, oral, subcutaneous, intradermal intramuscular, intraperitoneal, intravenous, intrathecal, and intramuscular.

An antibody is an immunoglobulin molecule produced by B lymphoid cells with a specific amino acid sequence. Antibodies are evoked in humans or other animals by a specific antigen (immunogen). Antibodies are characterized by reacting specifically with the antigen in some demonstrable way, antibody and antigen each being defined in terms of the other. "Eliciting an antibody response" refers to the ability of an antigen or other molecule to induce the production of antibodies.

An antigen is a compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In one embodiment, an antigen is a virus antigen, such as a coronavirus spike protein.

In the context of a live virus, a virus is attenuated if its ability to infect a cell or subject and/or its ability to produce disease is reduced (for example, eliminated) compared to a wild-type virus. Typically, an attenuated virus retains at least some capacity to elicit an immune response following administration to an immunocompetent subject. In some cases, an attenuated virus is capable of eliciting a protective immune response without causing any signs or symptoms of infection. In some embodiments, the ability of an attenuated virus to cause disease in a subject is reduced at least about 10%, at least about 25%, at least about 50%, at least about 75%, or at least about 90% relative to wild-type virus. Accordingly, an "attenuating mutation" is a mutation in the viral genome and/or an encoded polypeptide that results in an attenuated virus.

A biological sample is a sample obtained from a subject (such as a human or veterinary subject). Biological samples, include, for example, fluid, cell and/or tissue samples. In some embodiments herein, the biological sample is a fluid sample. Fluid sample include, but are not limited to, serum, blood, plasma, urine, feces, saliva, cerebral spinal fluid (CSF) and bronchoalveolar lavage (BAL) fluid.

Coronaviruses (Coronoviridae) are members of the Nidovirales order, and are enveloped, non-segmented positive-sense RNA viruses. The most prominent feature of coronaviruses is the club-shape spike projections emanating from the surface of the virion. These spikes are a defining feature of the virion and give them the appearance of a solar corona, prompting the name, coronaviruses. Homotrimers of the virus encoded S protein make up the distinctive spike structure on the surface of the virus. The trimeric S glycoprotein is a class I fusion protein and mediates attachment to the host receptor. In most, but not all, coronaviruses, S is cleaved by a host cell furin-like protease into two separate polypeptides noted S1 and S2. S1 makes up the large receptor-binding domain of the S protein while S2 forms the stalk of the spike. Diagrams of exemplary SARS-CoV-2 spike (S1) and SARS-CoV-2 S1+SARS-CoV-2 nucleoprotein (NP) recombinant constructs are depicted in FIG. 1. Constructs, such as those depicted in FIG. 1, may be inserted into, propagated, and/or expressed, in any vector or DNA background, such as, for example and without limitation, a plasmid or viral genome, a chromosome or artificial chromosome, as naked nucleic acid, or inserted into a cell genome. Examples of sequences of the SARS-CoV-2 spike protein are provided in FIGS. 2A, 2B, 3A, 3B, 4A, 4B, 5A, 5B, 6A-6F, and 7A-7F. FIGS. 6A-6F provide codon-optimized S1 (S1-3) nucleotide sequences, which was the highest-expressing version of the S1 ORFs tested.

The first 661 amino acids (amino acids 1-661 of SEQ ID NO: 2) FIG. 2B provides an exemplary SARS CoV-2 spike protein S1 subunit useful as an immunogen as described herein. A "portion" of a protein or sequence refers to less than the complete natural sequence. As such, a polypeptide that comprises a sequence of bases 1-661 of SEQ ID NO: 2 less than 661 amino acids in length comprises a "portion" of the SARS-CoV-2 S1 spike protein subunit. A "naturally-occurring variant" of a specified amino acid or nucleotide sequence or a portion thereof is a variant found in nature and typically has at least 90%, at least 95%, or at least 99% sequence identity with a stated amino acid sequence, e.g., with 1, 2, 3, 4, 5, 6, 7, 8, 9, or 10 amino acid substitutions, insertions, or deletions, e.g., with 1, 2, or 3 amino acid substitutions, or at least 85%, at least 90%, or at least 95% sequence identity with a stated nucleotide sequence or a codon-optimized version thereof. Naturally-occurring variants of SARS-CoV-2 are expected during the evolution of the virus, if they are not already identified (See, e.g., Tang, X., et al., On the origin and continuing evolution of SARS-CoV-2, *National Science Review*, nwaa036, https://doi.org/10.1093/nsr/nwaa036) as is the case with SARS-CoV and MERS-CoV, as well as non-human. A polypeptide having the sequence of amino acids 1-661 of SEQ ID NO: 2 unexpectedly multimerizes, e.g., trimerizes, in physiological aqueous solutions, such as normal saline. Polypeptides having at least 90%, at least 95%, or at least 99% sequence identity with amino acids 1-661 of SEQ ID NO: 2, are, likewise, expected to form multimers, even without combination, in a fusion protein, with an exogenous multimerization domain. Multimerization, e.g., trimerization, can readily be detected, e.g., by Western blot. As such, naturally-occurring variants of the sequence of amino acids 1-661 of SEQ ID NO: 2, as well as polypeptides having at least 90%, at least 95%, or at least 99% sequence identity with amino acids 1-661 of SEQ ID NO: 2, e.g., conservative derivatives of amino acids 1-661 of SEQ ID NO: 2, are readily tested for their ability to both act as an immunogen, their ability to elicit neutralizing antibodies, and their ability to multimerize, based on the present disclosure and testing methods known in the art.

Naturally-occurring variants of the sequence of amino acids 1-661 of SEQ ID NO: 2 as well as polypeptides having at least 90%, at least 95%, or at least 99% sequence identity with amino acids 1-661 of SEQ ID NO: 2, e.g., conservative derivatives of amino acids 1-661 of SEQ ID NO: 2 may be incorporated into fusion proteins according to any variation of the immunogenic SARS-CoV-2 S1 subunit polypeptide, e.g., variants as depicted in FIG. 1.

A "codon-optimized" nucleic acid refers to a nucleic acid sequence that has been altered such that the codons are optimal for expression in a particular system (such as a particular species of group of species). For example, a nucleic acid sequence can be optimized for expression in mammalian cells. Codon optimization does not alter the amino acid sequence of the encoded protein. Codon optimized constructs, e.g., plasmids, may be designed and produced by any suitable method, and constructs may be tested for their expression in any applicable recombinant protein production system.

A conservative substitution is a substitution of one amino acid residue in a protein sequence for a different amino acid residue having similar biochemical properties. Typically, conservative substitutions have little to no impact on the activity of a resulting polypeptide. For example, ideally, a coronavirus protein (such as an S protein) including one or more conservative substitutions (for example 1-10, 2-5, or 10-20, or no more than 2, 5, 10, 20, 30, 40, or 50 substitutions) retains the structure and function of the wild-type protein, namely, in the context of the present disclosure, the ability to elicit an immunological response, such as a neutralizing immunological response to SARS-CoV-2, e.g., the spike protein of SARS-CoV-2. A polypeptide can be produced to contain one or more conservative substitutions by manipulating the nucleotide sequence that encodes that polypeptide using, for example, standard procedures such as site-directed mutagenesis or PCR. In one example, such variants can be readily selected for additional testing by infecting cells with a virus containing a variant protein and determining its ability to replicate, by producing virus containing a variant protein and determining its virulence or cell-invasion properties, and/or by testing antibody cross-reactivity.

The term "contacting" refers to placement in direct physical association; includes both in solid and liquid form. "Contacting" is often used interchangeably with "exposed." In some cases, "contacting" includes transfecting, such as transfecting a nucleic acid molecule into a cell. In other examples, "contacting" refers to incubating a molecule (such as an antibody) with a biological sample.

A fusion protein or fusion polypeptide refers to a protein or polypeptide generated, for example, by expression of a nucleic acid sequence engineered from nucleic acid sequences encoding at least a portion of two different (heterologous) proteins. To create a fusion protein, the nucleic acid sequences are in the same reading frame and contain no internal stop codons. For example, a fusion protein includes a coronavirus S or S1 polypeptide fused to a heterologous protein, that is an amino acid sequence originating synthetically, or from a different genetic source or species.

An immune response is a response of a cell of the immune system, such as a B-cell, T-cell, macrophage or polymorphonucleocyte, to a stimulus, such as an antigen. An immune response may include any cell of the body involved in a host defense response for example, an epithelial cell that secretes an interferon or a cytokine. An immune response includes, but is not limited to, an innate immune response or inflammation.

To immunize a subject refers to rendering a subject protected from an infectious disease, such as by vaccination.

An immunogen refers to a compound, composition, or substance which is capable, under appropriate conditions, of stimulating an immune response, such as the production of antibodies, such as neutralizing antibodies, or a T-cell response in an animal, including compositions that are injected or absorbed into an animal. As used herein, an "immunogenic composition" is a composition comprising an immunogen (such as a coronavirus S1 polypeptide).

An immunoglobulin Fc domain is a polypeptide including the constant region of an antibody excluding the first constant region immunoglobulin domain. Fc domain generally refers to the last two constant region immunoglobulin domains of IgA, IgD, and IgG, and the last three constant region immunoglobulin domains of IgE and IgM. An Fc domain may also include part or all of the flexible hinge N-terminal to these domains. For IgA and IgM, an Fc domain may or may not include the tailpiece, and may or may not be bound by the J chain. For IgG, the Fc domain includes immunoglobulin domains Cgamma2 and Cgamma3 (Cγ2 and Cγ3) and the lower part of the hinge between Cgamma1 (Cγ1) and Cγ2. Although the boundaries of the Fc domain may vary, the human IgG heavy chain Fc domain is usually defined to include residues C226 or P230 to its carboxyl-terminus, wherein the numbering is according to the EU index as in Kabat. For IgA, the Fc domain includes immunoglobulin domains Calpha2 and Calpha3 (Cα2 and Cα3) and the lower part of the hinge between Calpha1 (Cα1) and Cα2.

An "isolated" or "purified" biological component (such as a nucleic acid, peptide, protein, protein complex, or particle) refers to a component that has been substantially separated, produced apart from, or purified away from other components in a preparation or other biological components in the cell of the organism in which the component occurs, that is, other chromosomal and extrachromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. A preparation may be purified such that the biological component represents at least 50%, such as at least 70%, at least 90%, at least 95%, or greater, of the total biological component content of the preparation.

A linker refers to a molecule or group of atoms positioned between two moieties (portions of a molecule). Typically, linkers are bifunctional, e.g., the linker includes a functional group at each end, wherein the functional groups are used to couple the linker to the two moieties. The two functional groups may be the same, e.g., a homobifunctional linker, or different, e.g., a heterobifunctional linker. A peptide linker may be used to link the C-terminus of a first polypeptide to the N-terminus of a second polypeptide in a fusion protein or peptide. Non-limiting examples of peptide linkers include glycine-serine peptide linkers, which are typically not more than 10 amino acids in length. Typically, such linkage is accomplished using molecular biology techniques to genetically manipulate DNA encoding the first polypeptide linked to the second polypeptide by the peptide linker in an open reading frame.

A nucleic acid molecule (a nucleic acid) refers to a polymeric form of nucleotides, which may include both sense and anti-sense strands of RNA, cDNA, genomic DNA, and synthetic forms and mixed polymers of the above. A nucleotide refers to a ribonucleotide, a deoxyribonucleotide or a modified form of either type of nucleotide. The term "nucleic acid molecule" as used herein is synonymous with "nucleic acid" and "polynucleotide." The term includes single- and double-stranded forms of DNA. A polynucleotide may include either or both naturally occurring and modified nucleotides linked together by naturally occurring and/or non-naturally occurring nucleotide linkages.

A first nucleic acid is said to be operably linked to a second nucleic acid when the first nucleic acid is placed in a functional relationship with the second nucleic acid. Generally, operably linked DNA sequences are contiguous (e.g., in cis) and, where the sequences act to join two protein coding regions, in the same reading frame. Operably linked nucleic acids include a first nucleic acid contiguous with the 5' or 3' end of a second nucleic acid. In other examples, a second nucleic acid is operably linked to a first nucleic acid when it is embedded within the first nucleic acid, for example, where the nucleic acid construct includes (in order) a portion of the first nucleic acid, the second nucleic acid, and the remainder of the first nucleic acid.

A polypeptide is a polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include proteins and modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

Conservative amino acid substitutions are those substitutions that, when made, least interfere with the properties of the original protein, that is, the structure and especially the function of the protein is conserved and not significantly changed by such substitutions, and may be identified by use of matrices, such as the BLOSUM series of matrices, and other matrices.

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl, or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

A promoter is an array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor).

A recombinant nucleic acid refers to a nucleic acid molecule (or protein or virus) that is not naturally occurring or has a sequence that is made by an artificial combination of two otherwise separated segments of sequence. This artificial combination is accomplished by chemical synthesis or, more commonly, by the artificial manipulation of isolated segments of nucleic acids, e.g., by genetic engineering techniques. The term recombinant includes nucleic acids and proteins that have been altered solely by addition, substitution, or deletion of a portion of a natural nucleic acid molecule or protein.

"Sequence identity" refers to the similarity between nucleic acid or amino acid sequences is expressed in terms of the similarity between the sequences, otherwise referred to as sequence identity. Sequence identity may be measured in terms of percentage identity (or similarity or homology); the higher the percentage, the more similar the two sequences are. Homologs, orthologs, or variants of a polypeptide will possess a relatively high degree of sequence identity when aligned using standard methods. Methods of alignment of sequences for comparison are well-known in the art. Various programs and alignment algorithms are described in the art.: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. In the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

Once aligned, the number of matches may be determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a peptide sequence that has 1166 matches when aligned with a test sequence having 1554 amino acids is 75.0 percent identical to the test sequence (1166÷15541 00=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

Homologs and variants of a polypeptide are typically characterized by possession of at least about 75%, for example, at least about 80%, 85%, 90%, 91%, 92%, 93%, 94%, 95%, 96%, 97%, 98%, or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85%, at least 90%, or at least 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of Pearson & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. One example of a useful algorithm is PILEUP. PILEUP uses a simplification of the progressive alignment method of Feng & Doolittle, J. Mol. Evol. 35:351-360, 1987. The method used is similar to the method described by Higgins & Sharp, CABIOS 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc. Acids Res. 12:387-395, 1984).

Another example of algorithms that are suitable for determining percent sequence identity and sequence similarity are the BLAST and the BLAST 2.0 algorithm, which are described in Altschul et al., J. Mol. Biol. 215:403-410, 1990 and Altschul et al., Nucleic Acids Res. 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, Proc. Natl. Acad. Sci. USA 89:10915, 1989). An oligonucleotide is a linear polynucleotide sequence of up to about 100 nucleotide bases in length.

As used herein, reference to "at least 80% identity" (or similar language) refers to "at least 80%, at least 85%, at least 90%, at least 91%, at least 92%, at least 93%, at least 94%, at least 95%, at least 96%, at least 97%, at least 98%, at least 99%, or even 100% identity" to a specified reference sequence. As used herein, reference to "at least 90% identity" (or similar language) refers to "at least 90%, at least 91%, at least 92%, at least 93%, at least 94%, at least 95%, at least 96%, at least 97%, at least 98%, at least 99%, or even 100% identity" to a specified reference sequence.

Complementary refers to the ability of polynucleotides (nucleic acids) to hybridize to one another, forming inter-strand base pairs. Base pairs are formed by hydrogen bonding between nucleotide units in polynucleotide strands that are typically in antiparallel orientation. Complementary polynucleotide strands can base pair (hybridize) in the Watson-Crick manner (e.g., A to T, A to U, C to G), or in any other manner that allows for the formation of duplexes. In RNA as opposed to DNA, uracil rather than thymine is the base that is complementary to adenosine. Two sequences comprising complementary sequences can hybridize if they form duplexes under specified conditions, such as in water, saline (e.g., normal saline, or 0.9% w/v saline) or phosphate-buffered saline), or under other stringency conditions, such as, for example and without limitation, 0.1×SSC (saline sodium citrate) to 10×SSC, where 1×SSC is 0.15M NaCl and 0.015M sodium citrate in water. Hybridization of complementary sequences is dictated, e.g., by the nucleobase content of the strands, the presence of mismatches, the length of complementary sequences, salt concentration, temperature, with the melting temperature (Tm) lowering with shorter complementary sequences, increased mismatches, and increased stringency. Perfectly matched sequences are said to be "fully complementary", though one sequence (e.g., a target sequence in an mRNA) may be longer than the other.

A "transformed" cell is a cell into which has been introduced a nucleic acid molecule (such as a heterologous nucleic acid) by any useful molecular biology technique. The term encompasses all techniques by which a nucleic acid molecule might be introduced into such a cell, including, without limitation, transfection with viral vectors, transformation with plasmid vectors, and introduction of naked DNA by electroporation, lipofection, or particle gun acceleration.

A vaccine refers to a preparation of immunogenic material capable of stimulating an immune response, administered for the prevention, inhibition, amelioration, or treatment of infectious, such as coronavirus, e.g., SARS-CoV-2, infections, or other types of disease. The immunogenic material may include attenuated or inactivated (killed) microorganisms (such as bacteria or viruses), or antigenic proteins, peptides or DNA derived from them. An attenuated virus is a virulent organism that has been modified to produce a less virulent form, but nevertheless retains the ability to elicit immunity against the virulent form. An inactivated (killed) virus is a previously virulent organism that has been inactivated with chemicals, heat, or other treatment, but elicits antibodies against the organism. Vaccines may elicit both prophylactic (preventative or protective) and therapeutic responses. Methods of administration vary according to the vaccine, but may include inoculation, ingestion, inhalation or other forms of administration. Vaccines may be administered with an adjuvant to boost the immune response.

A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. An insertional vector is capable of inserting itself into a host nucleic acid. A vector can also include one or more selectable marker genes and other genetic elements. An expression vector is a vector that contains the necessary regulatory sequences to allow transcription and translation of inserted gene or genes.

By "expression" or "gene expression," it is meant the overall flow of information from a gene or functional/structural RNA, and a polyadenylation sequence), to produce a gene product (typically a protein, optionally post-translationally modified or a functional/structural RNA). A "gene" refers to a functional genetic unit for producing a gene product, such as RNA or a protein in a cell, or other expression system encoded on a nucleic acid and comprising: a transcriptional control sequence, such as a promoter and other cis-acting elements, such as transcriptional response elements (TREs) and/or enhancers; an expressed sequence that may encode a protein (referred to as an open-reading frame or ORF), and a polyadenylation sequence. By "expression of genes under transcriptional control of," or alternately "subject to control by," a designated sequence such as TRE or transcription control element, it is meant gene expression from a gene containing the designated sequence operably linked (functionally attached, typically in cis) to the gene. A "gene for expression of" a stated gene product is a gene capable of expressing that stated gene product when placed in a suitable environment—that is, for example, when transformed, transfected, transduced, etc. into a cell, and subjected to suitable conditions for expression. In the case of a constitutive promoter "suitable conditions" means that the gene typically need only be introduced into a host cell. In the case of an inducible promoter, "suitable conditions" means when factors that regulate transcription, such as DNA-binding proteins, are present or absent—for example an amount of the respective inducer is available to the expression system (e.g., cell), or factors causing suppression of a gene are unavailable or displaced—effective to cause expression of the gene.

Immunogens are disclosed herein. These immunogens may be used to induce a neutralizing immune response, and were shown to protect against coronavirus challenge in an animal model of a coronavirus infection. Although the SARS-CoV-2 S1 subunit may multimerize on its own, the immunogens may include a fusion protein, wherein the fusion protein comprises a coronavirus spike polypeptide, and a multimerization domain. The multimerization domain may be an immunoglobulin Fc domain (see, e.g., Yang. C., et al. Engineering of Fc Fragments with Optimized Physicochemical Properties Implying Improvement of Clinical Potentials for Fc-Based Therapeutics Front. Immunol. 8:1860, 8 Jan. 2018, https://doi.org/10.3389/fimmu.2017.01860), a T4 fibritin foldon trimerization domain (see, e.g., Papanikolopoulou, K., et al. "Formation of Highly Stable Chimeric Trimers by Fusion of an Adenovirus Fiber Shaft Fragment with the Foldon Domain of Bacteriophage T4 Fibritin" J. Biol. Chem. 2004 279: 8991. doi:10.1074/jbc.M311791200), or a human collagen XV trimerization domain (See, e.g., Ángel M. Cuesta, David Sánchez-Martín, Ana Blanco-Toribio, Maider Villate, Kelly Enciso-Álvarez, Ana Álvarez-Cienfuegos, Noelia Sainz-Pastor, Laura Sanz, Francisco J. Blanco & Luis Álvarez-Vallina (2012) Improved stability of multivalent antibodies containing the human collagen XV trimerization domain, mAbs, 4:2, 226-232, DOI: 10.4161/mabs.4.2.19140). Any combination of these domains may be utilized.

The multimerization domain may be placed at the C-terminus of the immunogen in the fusion protein. Suitable multimerization domains include, but are not limited to the following exemplary sequences:

1. Immunoglobulin Dimerization Domain

```
                                          (SEQ ID NO: 21)
DKTHTCPSRPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSR

WQ QGNVFSCSVLHEALHSHYTQKSLSLSPGK
```

2. T4 Fibritin Foldon Trimerization Domain

```
                                          (SEQ ID NO: 22)
            GYIPEAPRDGQAYVRKDGEWVLLSTFL;
```

and

3. Human Collagen XV Trimerization Domain

```
                                          (SEQ ID NO: 23)
VTAFSNMDDMLQKAHLVIEGTFIYLRDSTEFFIRVRDGWKKLQLGELIPI

PADSPPPPALSSNP.
```

A multimerization domain may include an amino acid sequence at least 95% identical to any one of the sequences provided in the preceding paragraph, such as an amino acid sequence about 95%, about 96%, about 97%, about 98%, about 99% or 100% identical to any one of the sequences provided in the preceding paragraph, provided the multimerization domain functions, such that dimers or trimers are produced (as appropriate to the native domain). A multimerization domain can include at most 1, 2, 3, or 4 conservative amino acid substitutions in one of any one of the sequences provided in the preceding paragraph, provided the multimerization domain functions, such that dimers or trimers are produced (as appropriate to the native domain). In some embodiments, the multimerization domain consists of the amino acid sequence of any one of the sequences provided in the preceding paragraph.

A signal peptide may be operably linked to the fusion protein to replace its original signal sequence, and can be a premembrane (prM) signal peptide, an IgG signal peptide, or a human secretory signal peptide hidden Markov model.

A Toll-like receptor (TLR) agonist adjuvant, e.g., a Toll-like receptor 4 (TLR4) or Toll-like receptor 3 (TLR3) agonist (alt. ligand) domain may be included in the fusion protein. Sequences of such TLR agonists are known. In one example, TLR3 ligands activate keratinocytes, innate immune cells, and professional APCs and induce cross-presentation of antigen to prime CD8+ T cells (Datta et al. "A subset of toll-like receptor ligands induces cross-presentation by bone marrow-derived dendritic cells", 2003, *J. Immunol.,* 170: 4102-4110; Schulz et al. "Toll-like receptor 3 promotes cross-priming to virus-infected cells", 2005, *Nature,* 433:887-892; Kalali et al. "Double-stranded RNA induces an antiviral defense status in epidermal keratinocytes through TLR3-, PKR-, and MDA5/RIG-I-mediated differential signaling", 2008, *J. Immunol.,* 181: 2694-2704).

In addition or alternately to the inclusion of the TLR agonist sequence in the fusion protein, a Poly(I:C) adjuvant (polyinosinic-polycytidylic acid (poly(I:C)) or Poly-ICLC (poly(I:C)) stabilized with poly lysine and carboxymethylcellulose) also may be included as an adjuvant in a pharmaceutical composition as described herein (See, e.g., Tewari K, Flynn B J, Boscardin S B, et al. Poly(I:C) is an effective adjuvant for antibody and multi-functional $CD4^+$ T cell responses to *Plasmodium falciparum* circumsporozoite protein (CSP) and αDEC-CSP in non-human primates. *Vaccine.* 2010; 28(45):7256-7266. doi:10.1016/j.vaccine.2010.08.098).

Where two or more immunogenic proteins are encoded in a single ORF, a self-cleaving amino acid sequence, such as 2A, may be included between the two immunogenic proteins. This may be exemplified by the SARS-CoV-2-S1-3-2ANP protein depicted in FIG. 1, for which an exemplary nucleotide sequence is provided in FIG. 6C and an exemplary amino acid sequence is provided in FIG. 7C, or by the SARS-CoV-2-51-3fRS09-2ANP protein depicted in FIG. 1, for which an exemplary nucleotide sequence is provided in FIG. 6F and an exemplary amino acid sequence is provided in FIG. 7F.

Additional amino acid sequences, including linkers, spacers, carriers (see, e.g., US 2020/0031874), signal peptides, and tags may be included in the fusion protein, so long as they do not interfere to any significance with the operation of the immunogen in eliciting an appropriate immune response to a coronavirus, e.g., SARS-CoV-2. Portions of the coronavirus spike protein, e.g., the S1 protein, may be utilized so long as immunogenicity is substantially retained. The polypeptide may include two or more iterations of the spike protein, or immunogenic portions thereof, arranged in tandem in the fusion protein. The two or more iterations of the spike protein, or immunogenic portions thereof, spike protein, or immunogenic portions thereof, may have the same sequence, or different sequences, accounting for genetic variation of the spike protein. Likewise, where the immunogen comprises one instance of the spike protein, or immunogenic portions thereof, in a single polypeptide chain, polypeptide chains with different sequences accounting for genetic variation of the spike protein may be prepared and co-multimerized to produce a multi-valent immunogen.

The fusion protein also may include a second immunogenic SARS-CoV-2 polypeptide corresponding to the nucleoprotein, as exemplified in FIGS. 1, 6B, 6C, 6E, 6F, 7B, 7C, 7E, and 7F. An exemplary nucleoprotein sequence corresponds to amino acids 664-1082 of the amino acid sequence of FIG. 7B (SARS-CoV-2-S1-3-NP, SEQ ID NO: 16, bases 664-1,082). Naturally-occurring variants of amino acids 664-1,082 of SEQ ID NO: 16, immunogenic portions thereof, or a derivative thereof having at least 95% or 99% sequence identity with amino acids 664-1,082 of SEQ ID NO: 16 may be used in the fusion proteins as a substitute for amino acids 664-1,082 of SEQ ID NO: 16 in any version of the construct as described herein.

Nucleic acids and vectors encoding these fusion proteins may be provided. In some non-limiting examples, disclosed is a recombinant vector, such as an adenoviral vector, the expresses the disclosed immunogens. Polynucleotides encoding a disclosed immunogen are also provided. These polynucleotides include DNA, cDNA and RNA sequences which encode the antigen. One of skill in the art can readily use the genetic code to construct a variety of functionally equivalent nucleic acids, such as nucleic acids which differ in sequence but which encode the same protein sequence, or encode a conjugate or fusion protein including the nucleic acid sequence. In some embodiments, the polynucleotide is codon-optimized for expression in human cells. In specific non-limiting examples, nucleic acids encoding a coronavirus, e.g., SARS-CoV-2, immunogen as described herein can be codon optimized.

Exemplary nucleic acids may be prepared by cloning techniques, as are broadly-known and implemented either commercially, or in the art. Multiple textbooks and reference manuals describe and provide examples of useful and appropriate cloning and sequencing techniques, and instructions sufficient to direct persons of skill through such techniques are known. Commercial and public product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), Addgene, and Applied Biosystems (Foster City, Calif.), as well as many other commercial sources.

The disclosed immunogens and viral vectors can be delivered to a subject to produce an immune response to a coronavirus, such as a SARS-CoV-2 virus, such as a protective or neutralizing immune response. In some embodiments, delivery can be transcutaneously by microneedle arrays (MNAs), such as carboxymethyl cellulose-(CMC-) containing MNAs.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The polynucleotides encoding a disclosed immunogen can include a recombinant DNA which is incorporated into a vector into an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

Polynucleotide sequences encoding a disclosed immunogen can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (e.g., ATG) in front of a protein-encoding gene, splicing signal for introns, maintenance of the correct reading frame of that gene to permit proper translation of mRNA, and stop codons.

DNA sequences encoding the disclosed immunogen can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Hosts can include microbial, yeast, insect, and mammalian organisms. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevi-*

*siae*, *Salmonella typhimurium*, SF9 cells, C129 cells, 293 cells, *Neurospora*, and immortalized mammalian myeloid and lymphoid cell lines. Techniques for the propagation of mammalian cells in culture are well-known. Examples of commonly used mammalian host cell lines are VERO and HeLa cells, CHO cells, and WI38, BHK, and COS cell lines, although cell lines may be used, such as cells designed to provide higher expression, desirable glycosylation patterns, or other features. In some embodiments, the host cells include HEK293 cells or derivatives thereof, such as GnTI$^{-/-}$ cells (ATCC® No. CRL-3022), or HEK-293F cells.

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$) method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or viral vectors can be used. Eukaryotic cells can also be co-transformed with polynucleotide sequences encoding a disclosed antigen, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. One of skill in the art can readily use an expression systems such as plasmids and vectors of use in producing proteins in cells including higher eukaryotic cells such as the COS, CHO, HeLa and myeloma cell lines.

In one non-limiting example, a disclosed immunogen is expressed using an adenoviral vector, as discussed below.

Modifications may be made to a nucleic acid encoding a disclosed immunogen without diminishing its biological activity. Some modifications may be made to facilitate the cloning, expression, or incorporation of the targeting molecule into a fusion protein. Such modifications include, for example, termination codons, a methionine added at the amino terminus to provide an initiation, site, additional amino acids placed on either terminus to create conveniently located restriction sites, or additional amino acids (such as poly His) to aid in purification steps.

A nucleic acid molecule encoding a disclosed immunogen may be included in a viral vector, for example, for expression of the immunogen in a host cell, or for immunization of a subject as disclosed herein. In some embodiments, the viral vectors are administered to a subject as part of a prime-boost vaccination. The viral vectors may be included in a vaccine, such as a primer vaccine or a booster vaccine for use in a prime-boost vaccination.

The viral vector may be replication-competent. For example, the viral vector may have a mutation in the viral genome that does not inhibit viral replication in host cells. The viral vector also can be conditionally replication-competent. In other examples, the viral vector is replication-deficient in host cells.

A number of viral vectors have been constructed, that may be used to express the immunogen described herein, including polyoma, e.g., SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Natl. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Viral., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,2217,879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Viral., 54:401-407), and human origin (Page et al., 1990, J. Viral., 64:5370-5276; Buchschalcher et al., 1992, J. Viral., 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

The viral vector may include an adenoviral vector that expresses a disclosed immunogen. Adenovirus from various origins, subtypes, or mixture of subtypes can be used as the source of the viral genome for the adenoviral vector. Non-human adenovirus (e.g., simian, chimpanzee, gorilla, avian, canine, ovine, or bovine adenoviruses) may be used to generate the adenoviral vector. For example, a simian adenovirus can be used as the source of the viral genome of the adenoviral vector. A simian adenovirus may be of serotype 1, 3, 7, 11, 16, 18, 19, 20, 27, 33, 38, 39, 48, 49, 50, or any other simian adenoviral serotype. A simian adenovirus can be referred to by using any suitable abbreviation known in the art, such as, for example, SV, SAdV, SAV or sAV. In some examples, a simian adenoviral vector is a simian adenoviral vector of serotype 3, 7, 11, 16, 18, 19, 20, 27, 33, 38, or 39. A chimpanzee serotype C Ad3 vector may be used (see, e.g., Peruzzi et al., Vaccine, 27:1293-1300, 2009) or an Ad5 vector is used (see the Examples Section). Human adenovirus can be used as the source of the viral genome for the adenoviral vector. Human adenovirus can be of various subgroups or serotypes. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22, 23, 24, 25, 26, 27, 28, 29, 30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. The person of ordinary skill in the art is familiar with replication competent and deficient adenoviral vectors (including singly and multiply replication deficient adenoviral vectors). Examples of replication-deficient adenoviral vectors, including multiply replication-deficient adenoviral vectors, are disclosed in U.S. Pat. Nos. 5,837,511; 5,851,806; 5,994,106; 6,127,175; 6,482,616; and 7,195, 896, and International Patent Application Nos. WO 94/28152, WO 95/02697, WO 95/16772, WO 95/34671, WO 96/22378, WO 97/12986, WO 97/21826, and WO 03/022311.

The compositions, methods, and combination devices disclosed herein may include one or more adjuvants or molecules with immune stimulant or adjuvant effect. In other examples, an adjuvant is not included in the composition, but is separately administered to a subject (for example, in combination with a composition disclosed herein) before, after, or substantially simultaneously with administration of one or more of the immunogen-containing compositions disclosed herein. Adjuvants are agents that increase or enhance an immune response in a subject administered an antigen, compared to administration of the antigen in the absence of an adjuvant. One example of an adjuvant is an aluminum salt, such as aluminum hydroxide, aluminum phosphate, aluminum potassium sulfate, or aluminum hydroxyphosphate. Other adjuvants include biological adjuvants, such as cytokines (for example, IL-2, IL-6, IL-12, RANTES, GM-CSF, TNF-α, or IFN-γ), growth factors (for example, GM-CSF or G-CSF), one or more molecules such as OX-40L or 4-1 BBL, immunostimulatory oligonucleotides (for example, CpG oligonucleotides, for example, see U.S. Pat. Nos. 6,194,388; 6,207,646; 6,214,806; 6,218,371; 6,239,116; 6,339,068; 6,406,705; and 6,429,199), Toll-like receptor agonists (for example, TLR2, TLR4, TLR7/8, or TLR9 agonists), and bacterial lipopolysaccharides or their derivatives (such as 3D-MPL). Additional adjuvants include oil and water emulsions, squalene, or other agents. An adjuvant may be a water-in-oil emulsion in which antigen solution is emulsified in mineral oil (for example, Freund's incomplete adjuvant), sometimes with the inclusion of killed mycobacteria (Freund's complete adjuvant) to further enhance antigenicity. In one example, the adjuvant is a mixture of stabilizing detergents, micelle-forming agent, and oil available under the name PROVAX® (IDEC Pharmaceuticals, San Diego, Calif.). One of skill in the art can select a suitable adjuvant or combination of adjuvants to be included in the compositions disclosed herein or administered to a subject in combination with the compositions disclosed herein. Molecules with immune stimulant or adjuvant effects, include, without limitation: TLR3 agonists such as Poly(I:C) or Poly-ICLC; TLR 4 agonists such as LPS or monophosphoryl lipid derivatives; TLR 5 agonists such as flagellin derivatives; TLR 7/8 agonists such as imiquimod or R848; TLR 9 agonists such as CpG sequences; Stimulator of Interferon Genes (STING) pathway agonists such as ADU-S100; stimulatory neuroimmune mediators such as calcitonin gene-related peptide (CGRP); neurokinin 1 (NK1) receptor agonists such as Hemokinin 1 and Substance P; saponin related adjuvants such as QS-21 (*Quillaja saponaria*); purinoergic receptor agonists such as ATP; or oil-in-water emulsion adjuvants such as MF59.

A "polymer composition" is a composition comprising one or more polymers. As a class, "polymers" includes, without limitation, homopolymers, heteropolymers, co-polymers, block polymers, block co-polymers and can be both natural and/or synthetic. Homopolymers contain one type of building block, or monomer, whereas copolymers contain more than one type of monomer. The term "(co) polymer" and like terms refer to either homopolymers or copolymers. A polymer may have any shape for the chain making up the backbone of the polymer, including, without limitation: linear, branched, networked, star, brush, comb, or dendritic shapes. Molecular weight (MW) or molecular mass may refer to either number average molecular weight (Mn) or weight average molecular weight (Mw) unless specified.

A polymer "comprises" or is "derived from" a stated monomer if that monomer is incorporated into the polymer. Thus, the incorporated monomer (monomer residue) that the polymer comprises is not the same as the monomer prior to incorporation into a polymer, in that at the very least, certain groups/moieties are missing and/or modified when incorporated into the polymer backbone. A polymer is said to comprise a specific type of linkage if that linkage is present in the polymer, such as, without limitation: ester, amide, carbonyl, ether, thioester, thioether, disulfide, sulfonyl, amine, carbonyl, or carbamate bonds. The polymer may be a homopolymer, a copolymer, and/or a polymeric blend. A polymer is bioerodible, if it degrades essentially completely in vivo in less than two years, less than one year, less than six months, less than three months, or less than one month.

By "biocompatible", it is meant that a compound, composition, device, etc. is essentially, practically (for its intended use) and/or substantially non-toxic, non-injurious or non-inhibiting or non-inhibitory to cells, tissues, organs, and/or organ systems that would come into contact with the compound, composition, device, etc.

A bioerodible polymer also may be prepared from and therefore may comprise, without limitation, one or more of the following monomer residues: glycolide, lactide, caprolactone, dioxanone, and trimethylene carbonate. In general, useful (co)polymers may comprise monomers derived from alpha-hydroxy acids including polylactide, poly(lactide-co-glycolide), poly(l-lactide-co-caprolactone), polyglycolic acid, poly(dl-lactide-co-glycolide), and poly(l-lactide-co-dl-lactide); monomers derived from esters including polyhydroxybutyrate, polyhydroxyvalerate, polydioxanone, and polyglactin; monomers derived from lactones including polycaprolactone; monomers derived from carbonates including polycarbonate, polyglyconate, poly(glycolide-co-trimethylene carbonate), and poly(glycolide-co-trimethylene carbonate-co-dioxanone); monomers joined through urethane linkages, including poly(ester urethane) urea (PEUU), poly(ether ester urethane)urea (PEEUU), poly(ester carbonate)urethane urea (PECUU), or poly(carbonate) urethane urea (PCUU). Examples of suitable polymers may include, but are not limited to, polyacrylate, polymethacrylates, polyacrylamides, polymethacrylamides, polypeptides, polystyrenes, polyethylene oxides (PEO), poly(organo) phosphazenes, poly-1-lysine, polyethyleneimine (PEI), poly-d,l-lactide-co-glycolide (PLGA), and poly(alkylcyanoacrylate).

Polymer functionality may, for example, be linear or branched, and may include a poly(ethylene glycol) (PEG), a PEG-like group, an amine-bearing group (including primary, secondary, tertiary amine groups), a cationic group (which may generally be any cationic group—examples include a quaternary ammonium group, a guanidine group (guanidinium group), a phosphonium group or a sulfonium group), a dimethylsulfoxide-like (DMSO-like) group including methylsulfinyl-terminated alkyl groups, such as methylsulfinyl-terminated $C_1$-$C_6$ alkyl groups, or a zwitterionic group, such as a betaine, a reactive group for modification of polymer with, for example, small molecules (including, for example, dyes and targeting agents), a polymer, a biomolecule, or a biologically-active agent, such as a therapeutic agent, for example a peptide such as a cytokine or a growth factor, a polysaccharide, an oligonucleotide, a biologic active agent, or a small-molecule active agent.

The pharmaceutical compositions described herein comprise the described immunogen and at least one carrier. The pharmaceutical compositions include the compositions used to form the microneedles and microneedle arrays as described herein. The pharmaceutical compositions may also comprise an adjuvant. The pharmaceutical compositions may also comprise an additional therapeutic agent.

One or more of the disclosed immunogens, or vectors encoding the immunogens, are administered to a subject by any of the routes normally used for introducing a composition into a subject. Methods of administration include, but are not limited to, intradermal, intramuscular, intraperitoneal, parenteral, intravenous, subcutaneous, vaginal, rectal, intranasal, inhalation, or oral. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, and tablets of the kind previously described. Administration can be systemic or local. For example, an immunogenic fusion protein may be administered intracutaneously or subcutaneously by a microneedle array, for example as described herein.

The immunogen, or a vector encoding the immunogen, may be administered using a microneedle array. Thus, the immunogen, or the vector encoding the immunogen, can be administered to the intracutaneous or subcutaneous microenvironment of a subject to elicit an immune response to the immunogen.

An immunogenic compositions may be administered in any suitable manner, such as with a pharmaceutically acceptable carrier. Choice of pharmaceutically acceptable carriers may be determined, at least in part, by the particular composition being administered, as well as by the particular method used to administer the composition. Accordingly, there is a wide variety of suitable formulations of pharmaceutical compositions of the present disclosure.

An immunogenic composition may include an adjuvant. The adjuvant may be a cyclic dinucleotide, such as, but not limited to, 2'3'-cGAMP (cyclic [G(2',5')pA(3',5')p]). However, any adjuvant can be utilized, and efficacy thereof may be determined empirically.

The immunogenic compositions may be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with appropriate carriers. The formulations may be presented in unit-dose or multi-dose containers, for example, sealed ampules, vials, microneedle injection devices, syringes, etc., and optionally and where appropriate, may be stored in a freeze-dried (lyophilized) condition, requiring only the addition of a sterile liquid carrier, for example, water for injections, immediately prior to use. Extemporaneous injection solutions and suspensions may be prepared from sterile powders, granules and tablets commonly used by one of ordinary skill in the art.

Provided herein are methods of eliciting an immune response in a subject by administering to the subject an immunogen, or a vector encoding the immunogen, as disclosed herein. In a particular example, the subject is a human. The immunogen, or a viral vector encoding the immunogen, is used, for examples, to produce an immune response that prevents or inhibits infection with a coronavirus, e.g., a SARS-CoV-2. The subject can be a human. United States Patent Application Publication No. US 2020/0031874, incorporated herein by reference, describes a recombinant immunogen and associated manufacturing and delivery technologies many of which are useful in the context of the present disclosure.

In some examples, the method further includes selecting a subject in need of enhanced immunity to a coronavirus, e.g., a SARS-CoV-2. Subjects in need of enhanced immunity to coronavirus, e.g., a SARS-CoV-2 include subjects who are at risk of coronavirus, e.g., a SARS-CoV-2 infection, subjects who have been exposed to one or more coronavirus, e.g., a SARS-CoV-2, and subjects who have previously been vaccinated with a coronavirus, e.g., a SARS-CoV-2 vaccine. Additional factors that contribute to risk of infection with coronavirus, e.g., a SARS-CoV-2 include the characteristics of the location, presence of coronavirus, e.g., a SARS-CoV-2 in the area, and lack of preventive measures. The subject can be female, such as a human of childbearing age.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The immunogen described herein, or a nucleic acid comprising a gene encoding the immunogen, may be administered by a microneedle array as described herein or elsewhere.

Dissolvable microneedle arrays enable efficient and safe drug and vaccine delivery to the skin and mucosal surfaces. However, inefficient drug delivery can result from the homogenous nature of conventional microneedle array fabrication. Although, the drugs or other cargo that is to be delivered to the patient are generally incorporated into the entire microneedle array matrix, in practice only the microneedles enter the skin and therefore, only cargo contained in the volume of the individual needles is deliverable. Accordingly, the vast majority of the drugs or other cargo that is localized in the non-needle components (e.g., the supporting structure of the array) is never delivered to the patient and is generally discarded as waste.

A fully-dissolvable microneedle array substrate and unique microneedle geometries may be utilized that enable effective delivery of the immunogens, and vectors encoding the disclosed immunogens. This technology can also uniquely enable the simultaneous co-delivery of multiple chemically distinct agents for polyfunctional drug delivery. Examples of the utility of these devices include, for example, (1) simultaneous delivery of the disclosed immunogens and optionally adjuvants to generate a polyvalent immune response relevant to coronavirus disease prevention and (2) localized skin delivery.

A dissolvable microneedle array for transdermal insertion, e.g., local cutaneous delivery, into a subject may be provided for promoting an immune response against a coronavirus in a subject in need thereof. The array includes a base portion and a plurality of microneedles extending from the base portion and containing a disclosed immunogen, or a vector encoding the immunogen, and optionally at least one adjuvant.

The plurality of microneedles may be pre-formed to have a shape that comprises a first cross-sectional dimension at a top portion, a second cross-sectional dimension at a bottom portion, and a third cross-sectional dimension at an intermediate portion, wherein the intermediate portion is located between the top portion and the bottom portion, and the third cross-sectional dimension is greater than the first and second cross-sectional dimensions. Each microneedle may comprise a plurality of layers of dissoluble biocompatible material, such as, but not limited to carboxymethylcellulose.

A fabrication technology may be utilized that results in various active components to be incorporated into the needle tips, see U.S. Published Patent Application No. US 2016/0271381 A1, which is incorporated herein by reference. Thus, by localizing the active components in this manner, the remainder of the microneedle array volume includes less expensive matrix material that is non-active and generally regarded as safe. The net result is greatly improved efficiency of drug delivery based on (1) reduced waste of non-deliverable active components incorporated into the non-needle portions of the microneedle array, and (2) higher drug concentration in the skin penetrating needle tips.

Thus, the active component may be concentrated in the microneedle tips of the respective arrays. In contrast to conventional microneedle arrays, the active component is not present at even concentration throughout the microneedle array since there is little or no active component present in the supporting base structure. In addition, as shown, for example, in FIGS. 3A, 3B, 4A, and 4B of U.S. Published Patent Application No. US 2016/0271381 A1, which is incorporated herein by reference, not only is there little or no active component in the supporting structures, the location of the active component is concentrated in the upper half of the individual microneedles in the array. The active component may be concentrated in the upper half of the individual microneedles. The active component may be concentrated in the tip of the microneedle, with the tip being defined by an area of the microneedle that extends from a base portion in a narrowing and/or tapered manner. The base portion, in turn, extends from the supporting structure of the array.

As noted above, individual microneedles may comprise active components only in the upper half of the microneedle. Individual microneedles may comprise active components only in the tips or in a narrowing portion near the tip of the microneedle. Individual needles may comprise active components throughout the entire microneedle portion that extends from the supporting structure, see U.S. Published Patent Application No. US 2016/0271381 A1, which is incorporated herein by reference.

The disclosed immunogens also may be delivered as disclosed in PCT Application No. PCT/US2016/057363, which is incorporated herein by reference. This PCT application disclosed microneedle arrays that can be configured to penetrate the stratum corneum to deliver their cargo (e.g., biologics or bioactive components) to the epidermis and/or dermis, while minimizing pain and bleeding by preventing penetration to deeper layers that may contain nerve endings and vessels. Pyramidal CMC-microneedles effectively penetrated the stratum corneum, epidermis, and dermis of living human skin, and, thus, can be used for cutaneous delivery. Thus, the microneedle array may include pyramidal CMC-microneedles.

To construct the microneedle arrays, a base material may be used to form portions of each microneedle that have bioactive components and portions that do not. As discussed above, each microneedle can comprise bioactive components only in the microneedles, or in some embodiments, only in the upper half of the microneedles, or in other embodiments, only in a portion of the microneedle that tapers near the tip. Thus, to control the delivery of the bioactive component(s) and to control the cost of the microneedle arrays, each microneedle preferably has a portion with a bioactive component (immunogen and/or adjuvant) and a portion without a bioactive component. In the embodiments described herein, the portion without the bioactive component includes the supporting structure of the microneedle array and, in some embodiments, a base portion (e.g., a lower half) of each microneedle in the array.

Various materials may be used as the base material for the microneedle arrays. The structural substrates of biodegradable solid microneedles may include poly(lactic-co-glycolic acid) (PLGA) or carboxymethylcellulose (CMC) based formulations; however, other bases can be used.

CMC may be preferable to PLGA as the base material of the microneedle arrays described herein. The PLGA based devices can limit drug delivery and vaccine applications due to the relatively high temperature (e.g., 135 degrees Celsius or higher) and vacuum required for fabrication. In contrast, a CMC-based matrix can be formed at room temperature in a simple spin-casting and drying process, making CMC-microneedle arrays more desirable for incorporation of sensitive biologics, peptides, proteins, nucleic acids, and other various bioactive components.

CMC-hydrogel may be prepared from low viscosity sodium salt of CMC with or without active components (as described below) in sterile $dH_2O$. In the exemplary embodiment, CMC can be mixed with sterile distilled water ($dH_2O$) and with the active components to achieve about 25 wt % CMC concentration. The resulting mixture can be stirred to homogeneity and equilibrated at about 4° C. for 24 hours. During this period, the CMC and any other components may be hydrated and a hydrogel can be formed. The hydrogel may be degassed in a vacuum for about an hour and centrifuged at about 20,000 g for an hour to remove residual micro-sized air bubbles that might interfere with a spincasting/drying process of the CMC-microneedle arrays. The dry matter content of the hydrogel can be tested by drying a fraction (10 g) of it at 85° C. for about 72 hours. The ready-to-use CMC-hydrogel is desirably stored at about 4° C. until use.

Active components, such as a disclosed immunogen or a vector encoding the immunogen, and optionally an adjuvant, may be incorporated in a hydrogel of CMC at a relatively high (20-30%) CMC-dry biologics weight ratio before the spin-casting process. Arrays can be spin-cast at room temperature, making the process compatible with the functional stability of a structurally broad range of bioactive components. Since the master and production molds can be reusable for a large number of fabrication cycles, the fabrication costs can be greatly reduced. The resulting dehydrated CMC-microneedle arrays are generally stable at room temperature or slightly lower temperatures (such as about 4° C.), and preserve the activity of the incorporated biologics, facilitating easy, low cost storage and distribution.

In one example, the surface of the production molds may be covered with about 50 μl (for molds with 11 mm diameter) of CMC-hydrogel and spin-casted by centrifugation at 2,500 g for about 5 minutes. After the initial CMC-hydrogel layer, another 50 μl CMC-hydrogel can be layered over the mold and centrifuged for about 4 hours at 2,500 g. At the end of a drying process, the CMC-microneedle arrays are separated from the molds, trimmed off from excess material at the edges, collected and stored at about 4° C. The production molds may be cleaned and reused for further casting of microneedle arrays.

CMC-solids may be formed with layers that do not contain active components and layers that contain active components. FIGS. 11A-D of PCT Application No. PCT/US2016/057363, incorporated herein by reference) illustrate CMC-solids with different shapes (FIGS. 11A and 11B of PCT Application No. PCT/US2016/057363) and embedded active cargos on an upper layer which becomes, after micromilling, the portions of the microneedle with the active components. FIGS. 12A and 12B of PCT/US2016/057363, also illustrate CMC-solids with different shapes, with FIG. 12B showing a square shape and FIG. 12B showing a rectangular shape. Both CMC solids can be milled to dimensions for further processing as described herein. It should be understood that the geometries are not intended to be limiting. Any geometry can be used with the immunogens and vectors disclosed herein.

United States Patent Publication Nos. 2011/0098651; 2014/0350472; 2015/0126923, 2016/0271381, and U.S. Pat. No. 8,834,423, describe certain exemplary microneedle arrays and methods of making and using microneedle arrays. As an example, apparatuses and methods are described for fabricating dissolvable microneedle arrays using master molds formed by micromilling techniques. For example, microneedle arrays can be fabricated based on a mastermold (positive) to production mold (negative) to array (positive) methodology. Micromilling technology can be used to generate various micro-scale geometries on virtually any type of material, including metal, polymer, and ceramic parts. Micromilled mastermolds of various shapes and configurations can be effectively used to generate multiple identical female production molds. The female production molds can then be used to microcast various microneedle arrays. Direct micromilling of mastermolds can replace other exemplary microneedle array production methods that involve expensive, complex and equipment-sensitive SU-8 based lithography or laser etching techniques, which are conventionally used to create mastermolds for dissolvable needle arrays. In addition, as discussed below, micromilling can provide for the construction of more complex mastermold features than can conventional lithography and laser etching processes. Precision-micromilling systems can be used for fabricating a microneedle mastermold, using micro-scale (for example, as small as 10 μm (micrometers or microns)) milling tools within precision computer controlled miniature machine-tool platforms. The system can include a microscope to view the surface of the workpiece that is being cut by the micro-tool. The micro-tool can be rotated at ultra-high speeds (200,000 rpm) to cut the workpiece to create the desired shapes. Micromilling process can be used to create complex geometric features with many kinds of material, which are not possible using conventional lithographic or laser etching processes. Various types of tooling can be used in the micromilling process, including, for example, carbide micro-tools or diamond tools.

Mastermolds can be micromilled from various materials, including, for example, Cirlex® (DuPont, Kapton® polyimide). Mastermolds can be used to fabricate flexible production molds from a suitable material, such as a silicone elastomer, e.g., SYLGARD® 184 (Dow Corning). The mastermold is desirably formed of a material that is capable of being reused so that a single mastermold can be repeatedly used to fabricate a large number of production molds. Similarly each production mold is desirably able to fabricate multiple microneedle arrays.

In one example, production molds are made from SYLGARD® 184 (Dow Corning), and are mixed at a 10:1 SYLGARD® to curing agent ratio. The mixture is degassed for about 10 minutes and poured over the mastermold to form an approximately 8 mm layer, subsequently degassed again for about 30 minutes and cured at 85° C. for 45 minutes. After cooling down to room temperature, the mastermold is separated from the cured silicone, and the silicone production mold is trimmed. From a single mastermold, a large number of production molds (e.g., 100 or more) can be produced with very little, if any, apparent deterioration of the Cirlex® or acrylic mastermolds.

In one example, to construct the microneedle arrays, a base material is used to form portions of each microneedle that have bioactive components and portions that do not. Of course, if desired, each microneedle can comprise only portions that contain bioactive components; however, to control the delivery of the bioactive component(s) and to control the cost of the microneedle arrays, each microneedle optionally is constructed such that a portion of the structure has a bioactive component and a portion does not include a bioactive component. Variations in the size, shape and number of the microneedles, and location of the bioactive component(s) in the microneedles, may be readily varied by varying the mastermold, or by varying the deposition and patterning of the materials used to produce the microarray.

Alternately, the MNA may include microneedles that are not dissolvable, but that include the immunogen-containing composition coated thereon, or contained within a lumen or via thereof, which also allows for access to skin cells.

A large variety of materials useful for preparation of the microneedle array are available, along with variation in the location of such materials in the microarray. Precise positioning and layering of the materials during, e.g., spin casting, of the microneedle array will yield any desired structure.

The microneedle array, both base and needles, may be manufactured from a single carrier composition including a dissolvable composition and a bioactive agent, such as a reporter gene, such as the immunogenic composition comprising a coronavirus, e.g., a SARS-CoV-2, spike protein-based immunogen comprising an immunogenic sequence of a spike S1 protein combined in a chimeric protein with at least one sequence not comprising an immunogenic sequence of a spike S1 protein, such as a multimerization domain, such as an immunoglobulin Fc domain, a T4 fibritin foldon trimerization domain, or a human collagen XV trimerization domain. The "carrier composition" is one or more dissolvable and/or bioerodible compounds or compositions into which a bioactive agent is mixed, and in the context of the present disclosure forms a structure with physical parameters, and lack of negative effects on the bioactive agent as used herein, including sufficient safety to a patient, such that the carrier composition is useful as a component of the microneedles and microneedle arrays described herein.

Figure 8A:
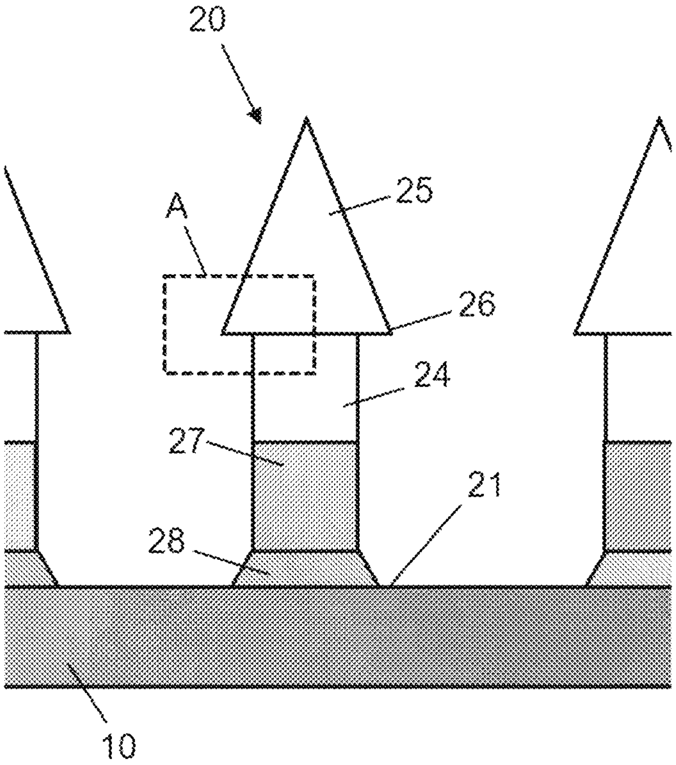
FIGS. 8A and 8B depict schematically exemplary microneedle structures.
Figure 8B:
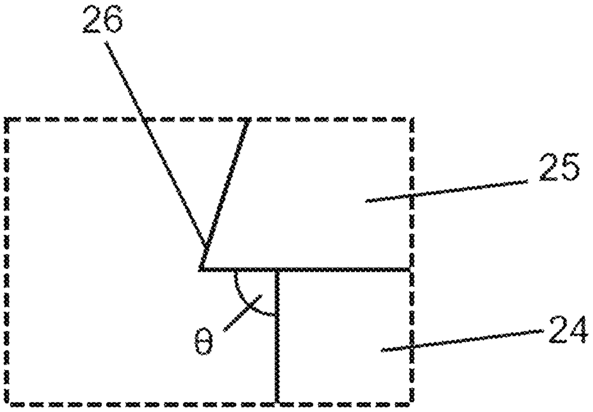

FIGS. 8A and 8B depict a microneedle array 10, in part, having a microneedle 20 and a backing layer 21. Additional, adjacent microneedles are partially depicted. The microneedle 20 comprises a stem 24 and a head 25. The head 25 comprises a ridge 26 extending beyond the peripheral boundary, e.g., circumference, of the stem 24, and as such, the head 25 may be described as undercut or barbed. The head 25, and optionally the stem 24, may comprise a bioactive or therapeutic agent such as the immunogen described herein mixed into, co-deposited in the mold with, absorbed into, or adsorbed onto the microneedle. The stem 24 may comprise a single material, which may be identical to the material of the head 25, or may be different than the material of the head 25. Although the stem 24 may be manufactured from a single material, it may comprise a dissolvable portion 27 that dissolves faster than the material of the head 25, e.g., within seconds under physiological conditions. The dissolvable portion 27 of the stem 24 may comprise a sugar or low molecular-weight dimer, oligomer, or polymer. In use, the microneedle 20 penetrates a patient's skin and the dissolvable portion rapidly-dissolves, either fully releasing the remainder of the microneedle in the patient's skin, or rendering that portion of the stem 24 sufficiently frangible, such that by pulling the backing layer 21 away from the patient's skin, and assisted by the undercutting of the head 25, the heads 25 of the microneedles, and any slower-dissolving portions of the stem 24, as compared to the dissolvable portion 27, will remain in the patient's skin. In embodiments of the microneedle array 10 where the stem 24 does not comprise a dissolvable portion 27, meaning the dissolvable portion 27 is the same material as the stem 24, the stem 24 still remains or is rendered frangible and may be retained in the patient's skin by dissolving and/or breaking of the stem 24.

In use, the microneedles 20 of the microneedle array 10 are pressed into the skin of a patient, and are left in place for a sufficient time to either inoculate the patient, or for the stems 24 and/or the dissolvable portions 27 of the microneedles to be dissolved or rendered sufficiently frangible so that removal of the backing layer would release the heads 25 of the microneedles 20 into the skin of the patient, such that the therapeutic agent(s), such as the immunogen, contained in and/or on the microneedles, is released into the skin of the patient. To prevent breaking off of the microneedles 20 on the patient's skin, prior to piercing of the skin with the microneedles 20, the base of the stem 24 of the microneedles may be reinforced, such as by use of a filleted base 28 as shown in FIG. 8A.

FIG. 8B depicts an enlargement of portion A, within the dashed rectangle as shown in FIG. 8A. Stem 24, head 25, and ridge 26 are depicted. FIG. 8B depicts the ridge 26 extending at an angle θ from the stem 24, where θ is 90°. In practice, θ may vary from 90°, and may range, from 20° to 100°, from 45° to 100°, from 60° to 95°, or 90°±2°, such as, without limitation, 75°, 76°, 77°, 78°, 79°, 80°, 81°, 82°, 83°, 84°, 85°, 86°, 87°, 88°, 89°, 90°, 91°, 92°, 93°, 94°, or 95°. It should be recognized that the undercutting of the head and the transition from the head to the stem may not be perfectly linear, and these angles represent an average or best fit of the relationship between the stem and the underside of the ridge. In aspects, the amount of undercutting will be dictated by the ability to manufacture such structures, for example, using the methods described herein, including the ability to remove the microneedles from the mold after spin-casting. As such, the angle of undercut may be 90°, or may approach 90°, such as 90°±1°, 90°±2°, 90°±3°, 90°±4°, or 90°±5°.

The microneedle array, and elements thereof are depicted in FIGS. 8A and 8B are having specific geometries, such as a cylindrical stem 24 and dissolvable portion 27, a conical head 25, a ridge 26 or undercut extending at a 90° angle (perpendicularly) from the stem 24, and a triangle-profiled filleted base. It would be understood that these geometries are merely exemplary and one of ordinary skill could adapt different shape profiles and still include the structure depicted in FIGS. 8A and 8B, while retaining the functional aspects of those structures.

A nucleic acid molecule or viral vector may be administered to a subject to elicit an immune response to an immunogen, e.g., as described herein, for example with the goal of immunizing or vaccinating a subject against a pathogen such as a coronavirus, such as SARS-CoV-2. One approach to administration of nucleic acids is direct immunization with plasmid DNA, such as with a mammalian expression plasmid. Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and QUIL A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, Immunol. Today 12:383, 1991). Doses of antigen as low as 1 μg encapsulated in ISCOMS™ have been found to produce Class I mediated CTL responses (Takahashi et al., Nature 344:873, 1990).

In another approach to using nucleic acids for immunization, a disclosed fusion protein can be expressed by attenuated viral hosts or vectors or bacterial vectors. Recombinant vaccinia virus, adenovirus, adeno-associated virus (AAV), herpes virus, retrovirus, cytomegalovirus (CMV) or other viral vectors can be used to express the peptide or protein, thereby eliciting a CTL response. For example, vaccinia vectors and methods useful in immunization protocols are described in U.S. Pat. No. 4,722,848. BCG (*Bacillus* Calmette Guerin) provides another vector for expression of the peptides (see Stover, Nature 351:456-460, 1991).

A nucleic acid encoding a disclosed fusion protein may be introduced directly into cells. For example, the nucleic acid may be loaded onto gold microspheres by standard methods and introduced into the skin by a device such as Bio-Rad's HELIOS™ Gene Gun. The nucleic acids may be "naked," consisting of plasmids under control of a strong promoter. Typically, the DNA is injected into muscle, although it can also be injected directly into other sites. Dosages for injection are usually around 0.5 μg/kg to about 50 mg/kg, and typically are about 0.005 mg/kg to about 5 mg/kg (see, e.g., U.S. Pat. No. 5,589,466).

Administration may be accomplished by single or multiple doses. The dose administered to a subject in the context of the present disclosure may be sufficient to induce a beneficial therapeutic response in a subject over time, or to inhibit or prevent coronavirus, e.g., SARS-CoV-2 infection. The dose required may vary from subject-to-subject depending on the species, age, weight and general condition of the subject, the severity of the infection being treated, the particular immunogenic composition being used, and its mode of administration. An appropriate dose may be determined empirically.

The volume of administration may vary depending on the route of administration. By way of example, intramuscular injections may range from about 0.1 ml to about 1.0 ml. Appropriate volumes for different routes of administration may be determined empirically.

Repeated immunizations may be necessary to produce an immune response in a subject. When administered in multiple doses, the booster doses are administered at various time intervals, such as weeks or months to years. In other examples, the a one or more of the disclosed immunogens, or one or more vectors encoding a disclosed immunogen are used as a booster following administration of one or more coronavirus, e.g., SARS-CoV-2, vaccines. In one example, a subject is administered a prime dose of a coronavirus, e.g., SARS-CoV-2, vaccine followed by at least one boost dose of an immunogen, or a vector encoding the immunogen, as disclosed herein. In alternative examples, the immunogen, or the vector encoding the immunogen is administered first, followed by a booster administration of another coronavirus, e.g., SARS-CoV-2, vaccine, such as an inactivated coronavirus, e.g., SARS-CoV-2, vaccine.

A prime boost strategy may be utilized. For example, a boost dose is administered about 14, 30, 60, 90, or more days after administration of the prime dose. Additional boosters can be administered at subsequent time points, if determined to be necessary or beneficial. Immunization protocols (such as amount of immunogen, number of doses and timing of administration) may be determined experimentally, for example by using animal models (such as mice or non-human primates), followed by clinical testing in humans.

Initial injections may range from about 1 μg to about 1 mg, with some embodiments having a range of about 10 μg to about 800 μg, or from about 25 μg to about 500 μg. Following an initial administration of the immune stimulatory composition, subjects may receive one or several booster administrations, adequately spaced. Booster administrations may range from about 1 μg to about 1 mg, with other embodiments having a range of about 10 μg to about 750 μg, and still others a range of about 50 μg to about 500 μg. Periodic boosters at intervals of 1-5 years, for instance three years, may be desirable to maintain the desired levels of protective immunity.

Following immunization, the immune response may be assessed. For example, a biological sample may be obtained from the subject, and antibodies and/or reactive T cells specific for coronavirus, e.g., SARS-CoV-2, can be assessed.

The following examples are provided to illustrate certain particular features and/or embodiments. These examples should not be construed to limit the disclosure to the particular features or embodiments described.

Example 1

The skin is an attractive tissue target for vaccination, as it is readily accessible and contains a dense population of antigen-presenting and immune-accessory cells. Microneedle arrays (MNAs) are emerging as an effective tool for in situ engineering of the cutaneous microenvironment to enable diverse immunization strategies. Here, novel dissolving undercut MNAs and demonstrate their application for effective multicomponent cutaneous vaccination are presented. The MNAs are composed of micron-scale needles featuring pyramidal heads supported by undercut stem regions with filleted bases to ensure successful skin penetration and retention during application. Prior efforts to fabricate dissolving undercut microstructures were limited and required complex and lengthy processing and assembly steps. In the current study, we strategically combine three-dimensional (3D) laser lithography, an emerging micro-additive manufacturing method with unique geometric capabilities and nanoscale resolution, and micromolding with favorable materials. This approach enables reproducible production of dissolving MNAs with undercut microneedles that can be tip-loaded with multiple biocargos, such as antigen (ovalbumin) and adjuvant (Poly(I:C)). The resulting MNAs fulfill the geometric (sharp tips and smooth edges) and mechanical-strength requirements for failure-free penetration of human and murine skin to simultaneously deliver multicomponent (antigen plus adjuvant) vaccines to the same cutaneous microenvironment. Cutaneous vaccination of mice using these MNAs induces more potent antigen-specific cellular and humoral immune responses than those elicited by traditional intramuscular injection. Together, the unique geometric features of these undercut MNAs and the associated manufacturing strategy, which is compatible with diverse drugs and biologics, could enable a broad range of non-cutaneous and cutaneous drug delivery applications, including multicomponent vaccination.

Materials and Methods

Ovalbumin (OVA; #A5503), polyinosinic-polycytidylic acid sodium salt (Poly(I:C); #P1530), carboxymethylcellulose (CMC, 90 kDa MW), D-(+)-trehalose dihydrate, polyvinylpyrrolidone (PVP, 40 kDa MW), polyvinyl alcohol (PVA, 87-90% hydrolyzed, 30-70 kDa MW), Allura Red AC (R40 dye), doxorubicin, 4,4',5,5'-tetramethylbenzidine (TMB) peroxidase substrate, carbonate-bicarbonate buffer (pH 9.6), and Tween20 were purchased from Sigma-Aldrich (St. Louis, Mo.). Polydimethylsiloxane (PDMS) SYLGARD® 184 and VeroWhiteplus-RGD835 UV-curable resin were obtained from Dow Corning (Midland, Mich.) and Stratasys (Eden Prairie, Minn.), respectively. Green fluorescent Degradex PLGA microspheres (10 μm diameter) were acquired from Phosphorex (Hopkinton, Mass.). Alexa 555-labeled OVA (Invitrogen), Alexa 680-labeled OVA (Invitrogen), Texas Red-labeled dextran (40 kDa MW; Invitrogen), Pierce Micro BCA Protein Assay Kit, SYBR Green EMSA nucleic acid stain, endotoxin-free HyClone Cell Culture Grade Water, RNase-free Ambion TE Buffer (pH 8.0), carboxyfluorescein succinimidyl ester (CFSE; Invitrogen), and DAPI were purchased from Thermo Fisher Scientific (Waltham, Mass.). Anti-OVA IgG1 (Cayman Chemical, Ann Arbor, Mich.), anti-OVA IgG2c (Chondrex, Redmond, Wash.), normal goat serum and biotinylated goat anti-mouse IgG1 and IgG2c secondary antibodies (Jackson ImmunoResearch, West Grove, Pa.), streptavidin-HRP (BD Biosciences, San Jose, Calif.), and OVA257-264 (SIINFEKL) peptide (Anaspec, Fremont, Calif.) were used for immune assays.

Fabrication of Dissolving Microneedle Arrays

Figure 9A:
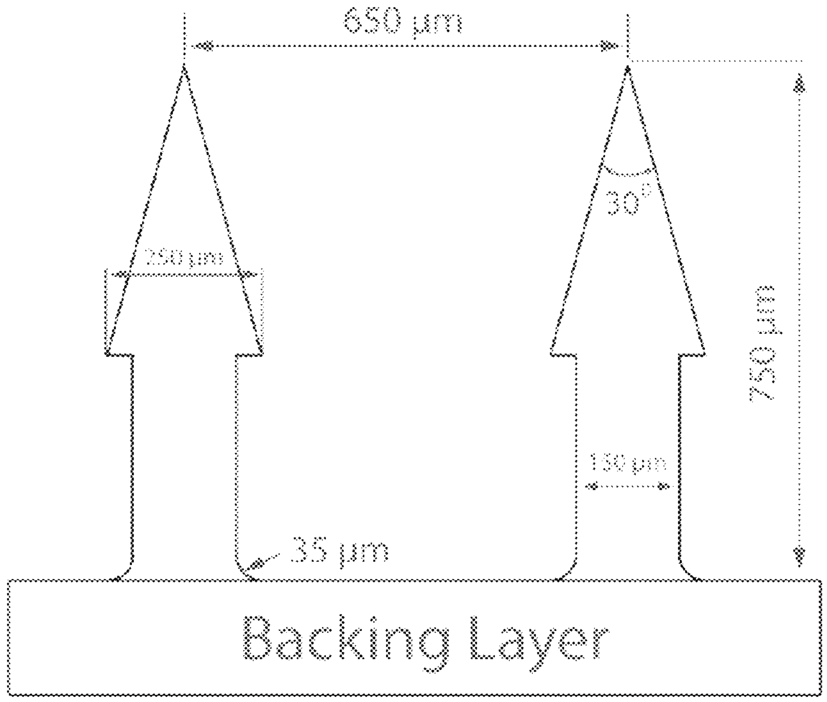
FIGS. 9A-9B: Computer-aided design (CAD) drawing of MNAs that include sharp microneedles with undercut features. Geometric parameters of unique microneedle design are depicted on a 2D-CAD drawing (FIG. 9A). 3D-CAD drawing of a 5×5 MNA (FIG. 6B).
Figure 9B:
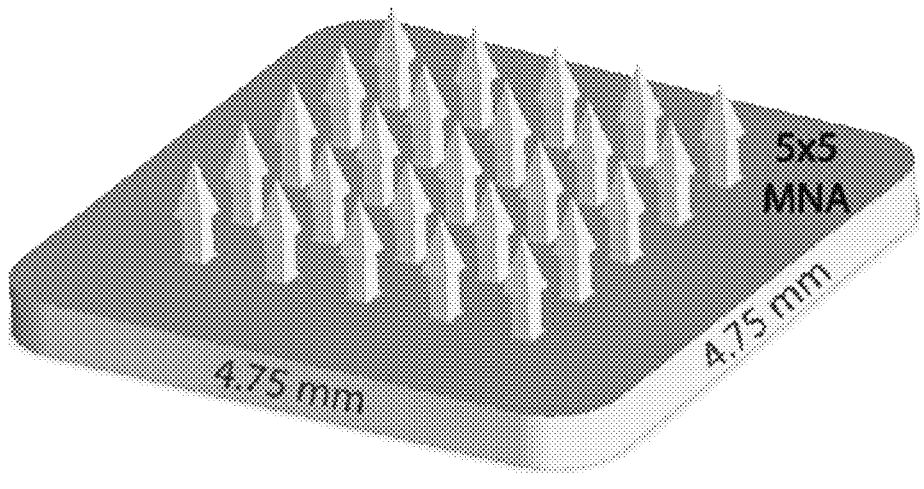

Microneedle and array designs: The unique microneedle array (MNA) design utilized in this study is shown in FIGS. 9A-9B. This particular microneedle design consisted of a sharp-tipped pyramid head and an undercut stem portion with a filleted base. The microneedle was 750 μm in height with a 30° apex angle. The stem portion of the microneedle was 150 μm in width and extended from the bottom of a square pyramid head (250 μm×250 μm base area) to the backing layer of MNA with a 35 μm radius filleted connection. The fillet was specifically designed at the microneedle base to avoid sharp corners and associated mechanical stress concentration, considerably increasing microneedle strength performance during manufacturing processes and skin insertion (Bediz et al. "Dissolvable microneedle arrays for intradermal delivery of biologics: fabrication and application", 2014, *Pharm. Res.*, 31:117-135: Rad et al. "High-fidelity replication of thermoplastic microneedles with open microfluidic channels, 2017, *Microsyst. Nanoeng.*, 3: 17034). The apex angle, width, and height of the microneedles were chosen based on skin anatomy and skin insertion mechanics to ensure failure-free penetration (Bediz et al.; Prausnitz, M. R. "Engineering Microneedle Patches for Vaccination and Drug Delivery to Skin", 2017, *Annu Rev Chem Biomol Eng;* 8:177-200). Notably, this design introduces a novel undercut, or anchor feature, which improves skin retention during application, but still allows direct removal of MNAs from flexible production molds throughout the manufacturing process. The tip-to-tip distance between microneedles in the 5×5 arrays was 650 μm, and the size of MNA was 4.75 mm×4.75 mm. The array design (microneedle spacing) was based on solid mechanics considerations and skin insertion mechanics to avoid a "bed of nails" effect during skin penetration (Bediz et al.; Korkmaz et al. "Therapeutic intradermal delivery of tumor necrosis factor-alpha antibodies using tip-loaded dissolvable microneedle arrays", 2015, *Acta Biomater.*, 24:96-105; Verbaan et al. "Improved piercing of microneedle arrays in dermatomed human skin by an impact insertion method", 2008, *J. Control. Release*, 128: 80-88). The three-dimensional micro-additive manufacturing (3D-μAM) approach provides a simple, reproducible, and revolutionary means to produce the proposed unique MNA design from a 3D-CAD drawing, and allows individuals with no microfabrication expertise to easily create a broad range of MNA designs.

Manufacturing Strategy

Figure 10:
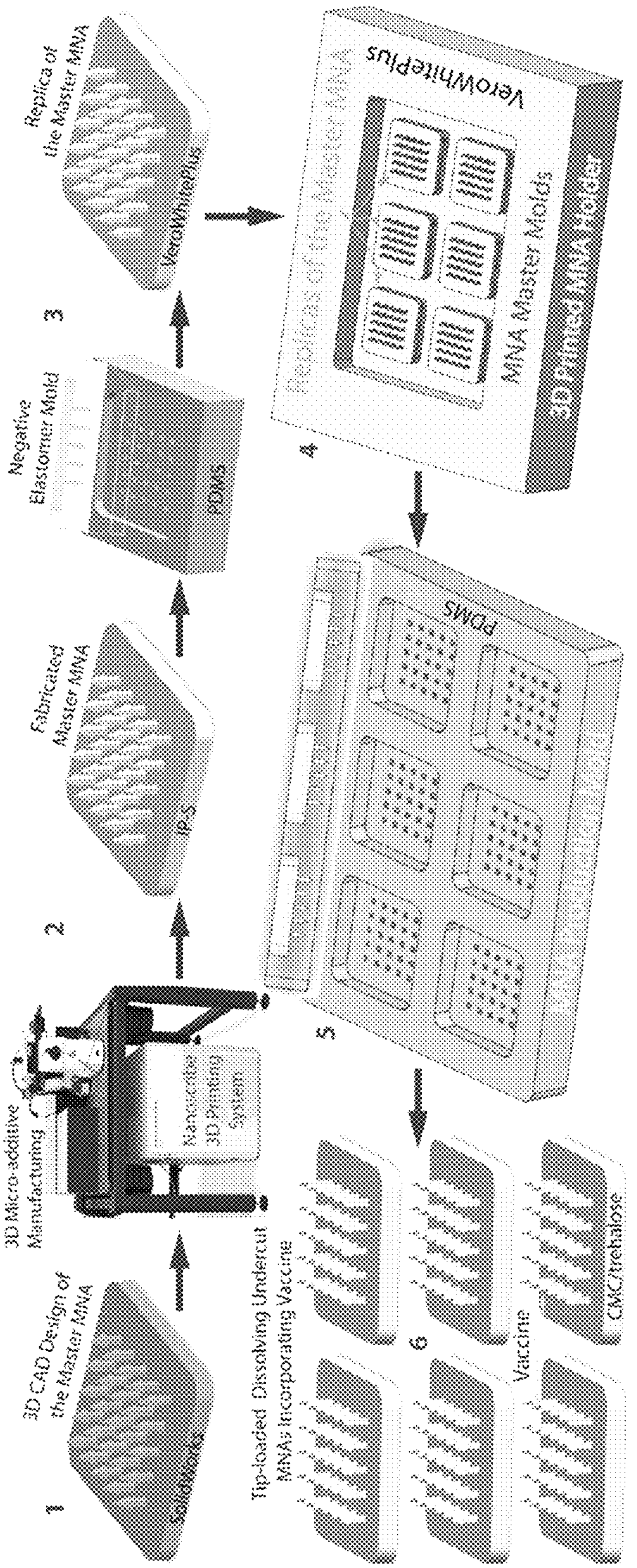
FIG. 10: Microneedle array manufacturing strategy involves six distinct steps. (1) 3D-CAD drawing of the target MNA design. (2) Direct production of the master MNA from the 3D-CAD drawing by 3D direct laser printing. (3) High-fidelity replication of the master MNA using a two-step micromolding approach. (4) Creation of the MNA master molds consisting of multiple master MNA replicas (e.g., six MNA replicas) on 3D-printed MNA holders. (5) Manufacturing of the MNA production molds from PDMS using micromolding. (6) Fabrication of tip-loaded, dissolving undercut MNAs incorporating the target vaccine using the spin-casting method.

The manufacturing strategy used to fabricate dissolving MNAs with novel microneedle designs is graphically summarized in FIG. 10. This strategic six-step approach exploits μAM and micromolding to create dissolving undercut MNAs, while simultaneously achieving high-throughput fabrication: (1) 3D-CAD drawing of the MNA design; (2) direct production of a master MNA from the CAD drawing by 3D direct laser writing using a non-dissolvable resin (IP-S); (3) high-fidelity replication of master MNA with UV-curable resin (VeroWhite) by micromolding; (4) creation of MNA master molds that consist of multiple master MNA replicas on 3D-printed MNA holders; (5) manufacturing of elastomer (PDMS) MNA production molds by micromolding; and (6) fabrication of tip-loaded, dissolving MNAs with undercut microneedles incorporating a vaccine or other biocargo in a water-soluble biocompatible material (e.g., carboxymethylcellulose (CMC) and trehalose) through a spin-casting method. The last step of the process can be modified depending on the biocargo of interest, and typically involves spin-casting cargo (e.g., vaccine) into the tip of the PDMS production molds, followed by spin-casting a dissolvable hydrogel (e.g., CMC/trehalose) into the production molds to serve as the structural material. Notably, the master MNA, master molds consisting of multiple master MNA replicas, and elastomer production molds are reusable, reducing the fabrication costs for dissolving undercut MNAs. At each stage of the fabrication process, optical stereomicroscopy (ZEISS Stemi 2000-C microscope with Olympus OM-D E-M511 camera) was used to assess geometric integrity of the microneedles.

Fabrication of master MNA: The unique MNA geometry was designed in SolidWorks 2018 CAD software and directly created from the 3D-CAD drawing (FIGS. 6A-6B) using 3D laser printing (Nanoscribe Photonic Professional, GT; Nanoscribe Struensee, Germany) with the photopolymeric resist IP-S. The Nanoscribe printing system was equipped with a laser generator, an optical cabinet, a Zeiss optical microscope attached to a lens to focus the laser beam, a Galvo mirror system to direct the laser-beam scanning, a piezoelectric stage for precise motion control, and software (Nanowrite) to execute 3D printing. The whole system was placed on an optical table to eliminate vibrations during the printing process.

To fabricate the master MNA, the CAD design was converted into 'STL' (StereoLithography) format. The STL file was loaded into the specialized software (DeScribe, Germany) for the Nanoscribe system to select the processing conditions (distance of slicing, hatching, and splitting). Finally, the STL file was converted into 'GWL' (General Writing Lithography) format and exported to the Nanowrite software to print the master MNA. The master MNA was fabricated using Galvo-scan mode in XY plane and piezo-scan mode in Z direction. The master MNA was split into 220 μm×220 μm×200 μm blocks within the working range and then stitched together. Laser power and writing speed were set to 100 mW and 6 cm/s, respectively. Minimum and maximum slicing distances of 0.3 μm and 0.5 μm, respectively, were used. The master MNA was then printed through two-photon polymerization of the IP-S photoresist by a femtosecond pulsed laser at a wavelength of 750 nm using a unique deep-in-liquid mode with a 25×NA0.8 objective in Shell and Scaffold mode. After printing, the master MNA was developed in the photoresist solvent propylene glycol monomethyl ether acetate (PGMEA) for 30 min, followed by a 5 min isopropyl alcohol rinse. The master MNA was then air-dried and placed under UV light (365 nm, 16 mW/cm$^2$ intensity) for 30 min to further crosslink the body to make the master MNA structure strong. Replication of Master MNA: A two-stage micromolding method was used to replicate the master MNA with high-fidelity using a UV-curable resin. First, an elastomer mold, which is a negative mold of the master MNA, was manufactured from polydimethylsiloxane (PDMS) by soft-lithography. Elastomer molding with PDMS is a well-established technique for rapid, accurate, and reproducible replication of high-fidelity micron-scale structures (Losic et al. "Rapid fabrication of micro- and nanoscale patterns by replica molding from diatom biosilica", 2007, *Adv. Fund. Mater.*, 17:2439-2446; Gates et al. "Replication of vertical features smaller than 2 nm by soft lithography", 2003, *J. Am. Chem. Soc.*, 125: 14986-14987). Briefly, the master MNA was mounted in a petri-dish with a diameter of 5 cm, and PDMS was prepared using a two-component curable silicone elastomer, SYLGARD® 184 (10:1 base-to-curing agent). The PDMS was poured over the master MNA mounted in the petri-dish and degassed for 15 min. Next, the master MNA with degassed PDMS was cured at 70° C. for 1 h. The cured PDMS was cooled to room temperature for 5 min and then separated from the master MNA to obtain the negative PDMS mold.

The second processing step used the negative PDMS mold to fabricate positive master MNA replicas from a UV-curable resin (VeroWhiteplus-RGD835). For each PDMS mold, 20 μL of liquid resin was poured onto the molds, and then the molds were centrifuged (4500 RPM at 20° C. for 1 min; Thermo Fisher Scientific Sorvall Legend XTR centrifuge with Swinging Bucket Rotor TX-750) to fill the microneedle-shaped wells with resin. The resin was then treated under UV light (365 nm) with 21.7 mW/cm$^2$ intensity for 5 min from both the top and bottom to cure the base and the microneedle tips. To ensure the backing layers of the master MNA replicas were flat, an additional 50 μL of UV-curable resin, which exceeded the remaining volume available, was deposited onto the PDMS mold. A glass slide was placed on top of the mold to get rid of the excess resin, thereby creating a uniform flat surface at the base. The liquid resin was then cured from the top side for 5 min and demolded to obtain a replica of the master MNA.

Creation of MNA master molds and production molds: To improve productivity of the manufacturing process for dissolving MNAs, the MNA master molds were created by assembling six master MNA replicas onto MNA holders fabricated by Stratasys® from a non-dissolvable photopolymer (VeroWhite) using a high-resolution Polyjet 3D printing system (Objet Connex 500 multi-material). A 3D model of the MNA holder was created using SolidWorks 2018 CAD software and then converted into the 'STL' (StereoLithography) file format. Subsequently, the specialized software (Objet Studio) sliced this 3D model into 2D cross-sectional layers, creating a computer file that was sent to the 3D printer system at Stratasys. Channels in the 3D printed MNA holder were designed to serve as pockets in the MNA production molds to assist as reservoirs for both the bioactive cargo (e.g., vaccine) and the structural hydrogel material of dissolving MNAs during the spin-casting process. The MNA master molds were baked at 80° C. overnight in a vacuum oven to facilitate effective molding of elastomer MNA production molds. Subsequently, MNA production molds that included microneedle-shaped wells for six MNAs were fabricated from PDMS as described for replication of the master MNA. Notably, a single MNA master mold can be used repeatedly to fabricate multiple PDMS production molds.

Figure 11:
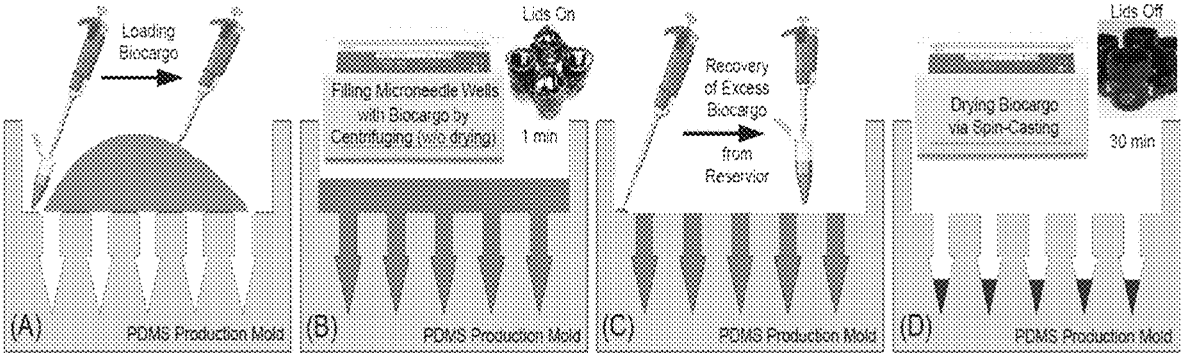
FIG. 11: Steps of the tip-loading process used for MNA fabrication.
Figure 12:
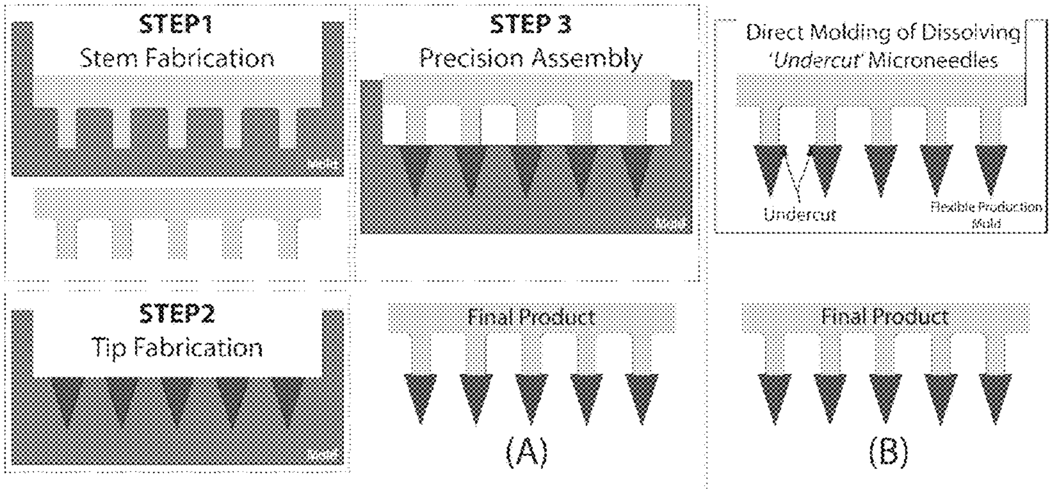
FIG. 12: Summary of traditional and novel fabrication approaches. (A) Traditional engineering approach for the production of undercut structures involves multiple processing and precision assembly steps with the assumption that undercut structures cannot be removed from the molds. (B) Our study, for the first time, demonstrates that it is possible to remove the dissolving undercut microneedles loaded with biocargo from flexible production molds in a single step, resulting in a simpler approach for fabrication of dissolvable undercut MNAs.

Production of dissolving MNAs: Dissolving MNAs with novel undercut microneedles tip-loaded with multicomponent vaccines (OVA antigen±Poly(I:C) adjuvant) were manufactured through a spin-casting technique with centrifugation at room temperature. First, 5 μL of an aqueous solution of OVA (25 mg/mL) was dispensed to each MNA reservoir on the PDMS production molds, and production molds were centrifuged (1 min at 4500 rpm) to fill the microneedle-shaped cavities. Excess OVA solution within the reservoir was then recovered, and production molds were centrifuged (30 min at 4500 rpm) to ensure that dry OVA cargo was located at the tip portion of the microneedle-shaped cavities in the production molds. For MNAs integrating OVA and Poly(I:C), the aforementioned process was repeated with 5 μL of an aqueous solution of Poly(I:C) (62.5 mg/mL). The final MNAs used for cutaneous vaccination experiments included 10 μg OVA and 25 μg Poly(I:C) per MNA. The tip-loading process and recovery of excess biocargo is depicted in FIG. 11.

After loading vaccine biocargo at the tips of microneedles, the MNA structural biomaterial was prepared by dissolving a 70:30 mixture of sodium carboxymethylcellulose (CMC) and D-(+)-trehalose dihydrate in endotoxin-free water at a total solute concentration of 30% w/w. The resulting CMC/trehalose hydrogel was loaded onto each MNA in the PDMS production molds (40 μL each) to fill the remaining volume of the microneedles and to form the MNA backing layer. Hydrogel-loaded production molds were centrifuged (5 h at 4500 rpm) to obtain the final dissolving undercut MNAs for cutaneous vaccination experiments. MNAs were then removed from production molds with tweezers, or forceps, by pulling two diagonal corners of the MNA base away from the mold. To demonstrate the broader material capabilities of our manufacturing strategy for dissolving MNAs with undercut microneedles, MNAs were also fabricated using a 40% w/w hydrogel with a 60:40 mixture of polyvinylpyrrolidone (PVP) and polyvinyl alcohol (PVA) through the spin-casting method.

Quantification of Antigen and Adjuvant Loading

Microneedles were dissolved in TE Buffer, and concentrations of OVA and Poly(I:C) were measured using a Micro BCA protein assay and SYBR Green nucleic acid assay, respectively. Loading error, defined as the difference between measured and theoretical amounts of biocargo in microneedles as a percentage of the theoretical amount, was calculated. To determine loading efficiency, excess biocargo recovered from the MNA production mold reservoir after loading and prior to drying (FIG. 11 (C)) was quantified. Loading efficiency=[biocargo in microneedles/(biocargo loaded to mold−excess biocargo recovered)]×100%. Results are reported as mean±SD (N=6).

Cutaneous Vaccine Delivery to Human Skin Explants Using MNAs

Preparation of ex vivo human skin explants: Human skin explants were prepared as described previously (Morelli et al. "CD4$^+$ T cell responses elicited by different subsets of human skin migratory dendritic cells", 2005, *J. Immunol.*, 175:7905-7915). Briefly, normal human skin from deidentified healthy donors undergoing plastic surgery was acquired through the Pitt Biospecimen Core and used according to University of Pittsburgh Medical Center guidelines. Tissue was rinsed in 70% ethanol and then in phosphate-buffered saline (PBS). Human skin explants (approximately 1 mm thick) were harvested using a Silver's miniature skin graft knife (Padgett, Integra Miltex, Plainsboro, N.J.), and then cut into 20 mm×20 mm square pieces. The resulting human skin samples comprised epidermis and a thin layer of underlying dermis.

Imagining Analysis: To evaluate undercut MNA-directed intradermal biocargo (e.g., vaccine) delivery to living human skin explants, several imaging analyses were performed. Tip-loaded MNAs incorporating a red cargo (Allura Red R40 dye) were fabricated using the manufacturing strategy described above. Prior to application of MNAs to human skin explants, MNAs were imaged using an optical stereomicroscope. Subsequently, MNAs were applied to human skin explants and removed after 10 min. An optical stereomicroscope was then used to image the patterns of colored biocargo deposited from MNAs into the human skin. Remaining MNA materials after application were also imaged. For further qualitative assessment of MNA-directed intradermal vaccine delivery to human skin, MNAs containing both Alexa555-labeled OVA and Alexa488-labeled Poly (I:C) were fabricated, applied to human skin explants for 10 min, and removed. Targeted areas of the human skin explants were fixed in 2% paraformaldehyde, cryopreserved with 30% sucrose solution, flash frozen in optimum cutting temperature (OCT) compound, and cryo-sectioned into 10 μm thick sections. Human skin cross-sections were counterstained with a fluorescent nuclear dye (DAPI) and imaged using a bright-field and epifluorescence microscope (Nikon Eclipse E800) to detect Alexa555-OVA and Alexa488-Poly (I:C), with bright-field images taken to better visualize the stratum corneum breaching.

MNA-Directed Skin Immunization In Vivo

Mice: Female C57BL/6J mice were purchased from The Jackson Laboratory (Bar Harbor, Me.) and used at 8-10 weeks of age. Mice were maintained under specific pathogen-free conditions at the University of Pittsburgh, and all experiments were conducted in accordance with the institutional animal care and use committee (IACUC) guidelines.

Quantification of antigen and adjuvant delivery with MNAs: OVA+Poly(I:C) MNAs were applied to murine abdominal skin for 5, 10, or 20 min, and then remaining MNAs were removed and dissolved in TE Buffer. Concentrations of OVA and Poly(I:C) were measured using a Micro BCA protein assay and SYBR Green nucleic acid assay, respectively. Quantities of OVA and Poly(I:C) delivered to skin were calculated by subtracting the amount remaining from the mean amount loaded, and delivery is reported as percentage of the initial amount loaded (mean±SD, N=6).

In vivo IVIS imaging: In vivo intradermal vaccine delivery with dissolving undercut MNAs was demonstrated on a C57BL/6J mouse. Tip-loaded CMC/trehalose MNAs integrating both Alexa555-labeled OVA and Alexa488-labeled Poly(I:C) were created using the manufacturing strategy described above, applied to the abdomen of an anesthetized mouse for 10 min, and then removed. Fluorescent OVA+Poly(I:C) MNAs were imaged before and after in vivo application by optical stereomicroscopy and epifluorescence microscopy. To show delivery of the fluorescent multicomponent vaccine, the mouse was imaged with an IVIS 200 in vivo imaging system (PerkinElmer, Waltham, Mass.), using the corresponding filters to detect Alexa488-Poly(I:C) and Alexa555-OVA at the MNA application site. Images were then post-processed using Living Image software (PerkinElmer).

Cell-mediated and humoral immune responses: Mice were immunized by application of 10 μg OVA±25 μg Poly(I:C) MNAs to the right and left sides of abdomen (two MNAs per mouse) or by two intramuscular injections of 10 μg OVA in PBS into the hindlimb gastrocnemius muscles. Control mice were left untreated (i.e., naïve), or treated with blank MNAs (without antigen or adjuvant). Cutaneous or intramuscular immunizations were repeated 7 days later. In vivo OVA-specific cytotoxic T-cell activity and OVA-specific antibody responses were evaluated 5 days after the second immunization (booster dose) using well-established techniques (Morelli et al.; Condon et al. "DNA-based immunization by in vivo transfection of dendritic cells", 1996, *Nat. Med.*, 2: 1122-1128).

For OVA-specific antibody responses, blood was collected from anesthetized mice at the time of sacrifice by cardiac puncture, and serum was isolated using BD Microtainer serum separator tubes (BD Biosciences, San Jose, Calif.). OVA-specific IgG1 and IgG2c antibodies in serum were measured by indirect ELISAs. Costar EIA/RIA plates (Corning Inc., Corning, N.Y.) were coated with OVA (100 μg/mL in 0.5 M carbonate-bicarbonate buffer) by overnight incubation at 4° C. Plates were washed (3×) with 0.05% Tween20 in PBS, and blocked with 1% goat serum in PBS for 1 h at 37° C. Serum samples and standards (anti-OVA IgG1 or anti-OVA IgG2c) were diluted with 1% goat serum, added to plates, and incubated 2 h at 37° C. After washing (3×), plates were incubated for 1 h at 37° C. with biotinylated secondary antibodies (goat anti-mouse IgG1 or IgG2c, 1:20,000 in 1% goat serum). Plates were then washed (3×) and incubated for 30 min with streptavidin-HRP (1:1000 in 1% goat serum). Plates were washed (3×) again and incubated at room temperature with TMB peroxidase substrate for 2-3 min, and the reaction quenched with 1.0 M $H_2SO_4$. For all ELISAs, absorbance at 450 nm (OD450) was read with a SpectraMax 340PC plate reader (Molecular Devices, Sunnyvale, Calif.), and serum concentrations calculated from standard curves.

To assess OVA-specific cytotoxic T-cell (CTL) activity, splenocytes from naïve mice were pulsed with 2 μg/mL OVA257-264 (SIINFEKL) peptide, or left unpulsed for 1 h. Antigen pulsed splenocytes were washed and stained with high concentration CFSE (10 μM), while unpulsed splenocytes were labeled with low concentration CFSE (1 μM) for 15 min at 37° C. A 1:1 mixture of pulsed target cells and unpulsed control cells (107 each) was intravenously (IV) injected into immunized and naïve mice. Twenty hours after adoptive transfer, spleens of mice were isolated, and killing of target cells was evaluated by comparison of the antigen pulsed and unpulsed populations by flow cytometry to quantify OVA-specific killing of the high CFSE labeled SIINFEKL-pulsed targets. Specific lysis was calculated and expressed as a percentage of maximum lysis as: % Lysis={1−[(mean $CFSE^{low}/CFSE^{high}$ ratio from naïve mice)/($CFSE^{low}/CFSE^{high}$ ratio from vaccinated mouse)]}×100%.

Statistical analyses: Statistical analyses were performed using Graph Pad Prism v8 (San Diego, Calif.). Data from vaccination experiments were analyzed by one-way independent ANOVA, followed by Tukey's or Dunnett's post-hoc testing. Differences were considered significant if $p<0.05$.

Results and Discussion

Fabrication of dissolving undercut microneedle arrays: Penetration, dissolution, and delivery efficiency are parameters relevant to dissolving MNA-mediated cutaneous immunization. These factors depend on MNA design, and microneedle geometry contributes to the success of MNA-based cutaneous drug delivery. A number of different microneedle geometries such as circular, obelisk, and pyramid microneedles have been used for MNA-directed intradermal drug delivery. MNAs with obelisk microneedle geometries may result in better penetration and cutaneous delivery efficiency as compared to those with prevailing pyramid microneedles. Further, localizing biocargo to the skin-penetrating tip portion of the microneedles enhances delivery efficiency. Maximizing intradermal delivery efficiency is particularly important for effective cutaneous immunization to enable skin microenvironment conditioning while minimizing the necessary quantities of expensive vaccine components. These factors were considered when developing novel MNAs and the associated manufacturing strategy.

Here, we introduce a novel design of dissolving microneedles for cutaneous vaccination, which features undercut geometry and biomolecules localized in the needle apex. This undercut microneedle geometry is believed to result in better retention and other practical advantages in skin and non-cutaneous tissues. Undercut microneedles present complex fabrication challenges (e.g., summarized in FIG. 12). Micromolding is a useful method for high-throughput manufacturing of microstructures; however, fabrication of microstructures with undercut features through micromolding requires complex processing steps and precision assembly of separately molded, or machined, microneedle tips and shafts. Here, we present a manufacturing strategy and materials to fabricate dissolving MNAs with undercut features (FIGS. 6A-6B) through micromolding (FIG. 10), eliminating complicated engineering procedures. Importantly, and counterintuitively, we show that undercut microneedles can be directly removed from the flexible production molds which are reusable for several processing cycles—substantially improving cost and productivity. These results suggest that during the micromolding processes, MNA production molds undergo elastic deflection without permanent deformation, and the mechanical stress distribution (caused by removal forces) is smaller than the strength of the microneedle materials, resulting in failure-free removal of undercut microneedles.

The manufacturing strategy we utilize uniquely enables reproducible fabrication of high-quality, tip-loaded dissolving MNAs with undercut features from different and widely-used dissolving microneedle biomaterials, including CMC/ trehalose and PVP/PVA compositions (See, e.g., Bediz et al.; Lee et al. "Dissolving microneedles for transdermal drug delivery", 2008, Biomaterials, 29:2113-2124; Korkmaz et al.). The manufacturing and processing steps schematically depicted in FIG. 10 result in the final products shown in FIG. 11 (A). Specifically, the master MNA was fabricated from IP-S photoresist by 3D direct laser writing. IP-S is a specific material designed for 3D laser lithography and provides high resolution and mechanical integrity for micro- and nano-structures. We find that 3D laser lithography based on two-photon polymerization provides an effective means for fabrication of undercut MNA designs with smooth edges and sharp tips (~2 μm tip radius), and without any unwanted residues (e.g., machining chips) (FIG. 13 (A, F)). To enable more rapid, parallel fabrication of dissolving MNAs, the master MNA was replicated through a two-step micromolding process (FIG. 13 (C, G)). The IP-S master MNA was used to fabricate a flexible PDMS mold through soft-lithography, and the resulting PDMS molds were used to manufacture several VeroWhite MNA replicas through UV-curable micromolding. PDMS is a commonly used elastomer with tunable flexibility and low cost for molding of micro- and nano-structures (Lee et al.; Losic et al.). VeroWhite resin is a wear-resistant, acrylic-based photopolymer extensively used for 3D Polyjet printers (Lin et al. "3D printed, bio-inspired prototypes and analytical models for structured suture interfaces with geometrically-tuned deformation and failure behavior", 2014, *J. Mech. Phys. Solids,* 73: 166-182), which renders it an ideal material for MNA master molds. Six MNA replicas were then assembled into one MNA master mold, and this master mold was used to produce several PDMS MNA production molds (FIG. 13 (D)). Collectively, these processing steps, along with high geometric capability of 3D direct laser writing, resulted in an effective MNA manufacturing strategy. Furthermore, rapid replication of the 3D printed master MNA using a wear-resistant moldable material improved productivity. Based on these results, it is believed that other undercut features could be achieved with this versatile approach, potentially using materials with different Young's modulus for the elastomer molds or/and polymers with different strength properties for microneedles.

Upon fabrication of the MNA master molds with six MNA replicas, dissolving MNAs that integrate vaccine components in the tip portion of the microneedles were fabricated using the conventional three-stage manufacturing strategy through master mold to production mold to final dissolving MNAs (Bediz et al.; Lee et al.). Dissolving MNAs that incorporated the vaccine components (OVA±Poly(I:C)) in the tip portion of the undercut microneedles were fabricated through the spin-casting process (FIG. 13 (E)). Total OVA and Poly(I:C) content in microneedles was determined to be 10.15±0.87 μg and 24.29±1.60 μg, respectively. With nominal doses of 10 μg OVA and 25 μg Poly(I:C), average loading errors were 5.8% and 6.1%, respectively. During the microneedle tip-loading process, recovery of excess biocargo from MNA production mold reservoirs prior to drying (detailed in FIG. 11) reduces biocargo waste and enables a higher loading efficiency of 77.8±5.8%, which is especially important when working with more expensive vaccine components. For vaccine experiments, we used MNAs made of CMC and trehalose, two FDA-designated "Generally Recognized as Safe" (GRAS) biomaterials. The water-solubility and mechanical strength of CMC make it a good structural material for MNAs (Lee et al.), while trehalose is a disaccharide known to enhance stability of proteins (Kaushik et al. "Why is trehalose an exceptional protein stabilizer? An analysis of the thermal stability of proteins in the presence of the compatible osmolyte trehalose", 2003, *J. Biol. Chem.,* 278: 26458-26465).

Figure 13:
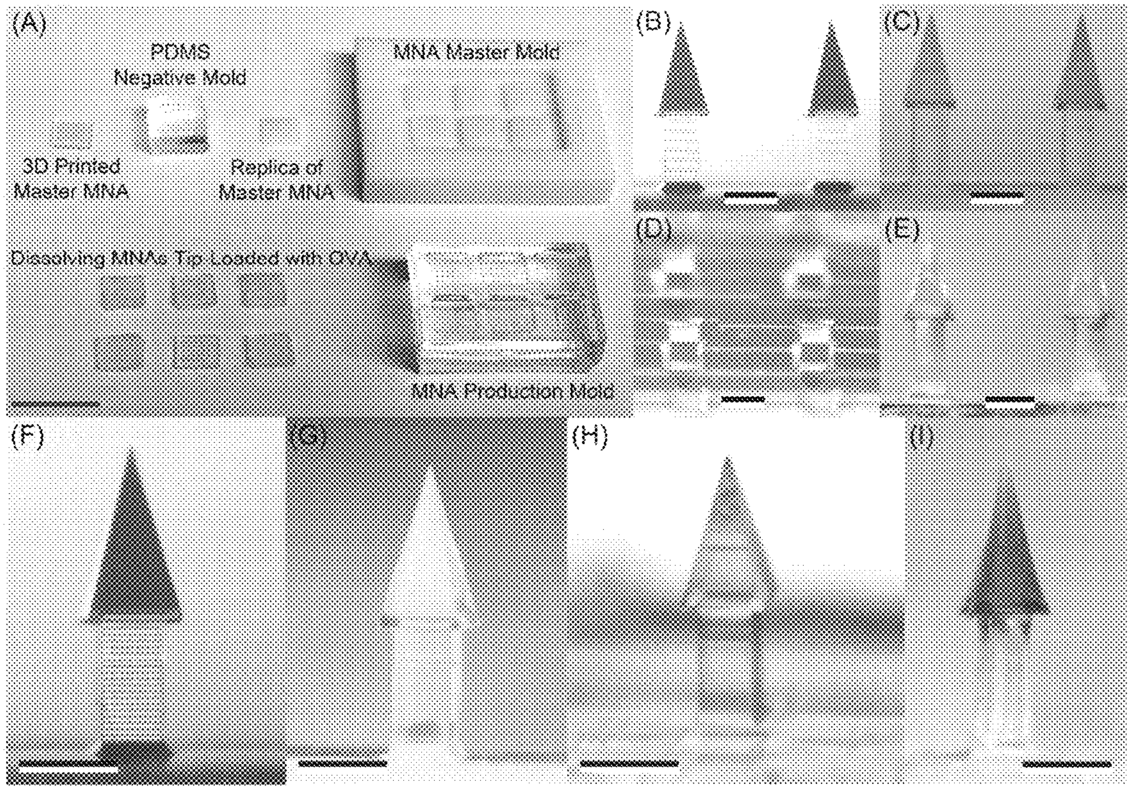
FIG. 13: Fabrication of novel dissolving MNAs with undercut microneedles. Final products corresponding to each step of the presented manufacturing strategy. Scale bar is 10 mm (FIG. 13 (A)). Geometric quality control of the fabricated MNAs using optical stereomicroscopy (FIGS. 13 (B-I)). Scale bars are 250 μm. Master MNA created using 3D direct laser writing (FIG. 13 (B)). Replica of the master MNA created through a two-stage micromolding strategy (elastomer molding combined with UV-curable micromolding) (FIG. 13 (C)). Microneedle-shaped wells in an MNA production mold (FIG. 13 (D)). Final dissolving CMC/trehalose MNA incorporating a multicomponent vaccine (OVA+Poly(I:C)) (FIG. 13 (E)). Higher magnification of an individual undercut microneedle on the 3D printed master MNA (as in FIG. 13 (B)) (FIG. 13 (F)). Higher magnification of an individual undercut microneedle on master MNA replica (as in FIG. 13 (C)) (FIG. 13(G)). Final dissolving PVP/PVA undercut microneedle tip-loaded with Alexa680-labeled OVA (FIG. 13 (H)). Final dissolving CMC/trehalose undercut microneedle tip-loaded with doxorubicin, a red-colored chemotherapeutic small molecule drug (FIG. 13 (I)).

To demonstrate compatibility of our MNA fabrication process and the undercut microneedle geometry with another dissolvable biomaterial composition commonly used in the MNA field, we fabricated some MNAs using a PVP/PVA hydrogel (FIG. 13 (H)). Additionally, MNAs with undercut microneedles tip-loaded with a red colored model drug (doxorubicin) were fabricated to facilitate imaging and demonstrate compatibility of the fabrication process with small molecule agents (FIG. 13 (I)). Demonstrated compatibility of the MNA fabrication process and undercut microneedle geometry with different types of cargos and material compositions makes application-driven optimization possible, as materials can be selected based on compatibility with bioactive cargo, dissolution requirements, and/or necessary mechanical properties for insertion into different types of skin (e.g., normal skin vs. psoriatic plaques).

Figure 14:
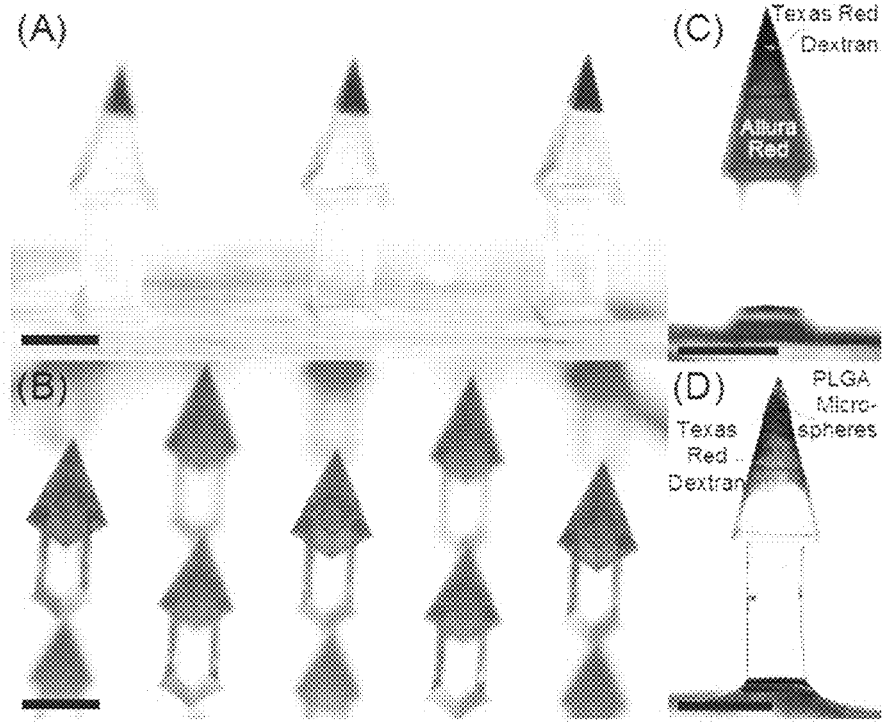
FIG. 14: Successful fabrication of dissolving MNAs with undercut microneedles integrating single or multiple cargos from different dissolvable biomaterial compositions. Scale bars are 250 μm. PVP/PVA MNAs incorporating Texas Red-labeled dextran (40 kDa MW) at the tips of microneedles (FIG. 14 (A)). Tip-loaded CMC/trehalose MNAs integrating Allura Red R40 dye (~500 Da MW) at the pyramid region of microneedles (FIG. 14 (B)). Tip-loaded PVP/PVA MNAs incorporating multiple cargos, such as Texas Red-labeled dextran and Allura Red R40 dye (FIG. 14 (C)). Tip-loaded PVP/PVA MNAs incorporating multiple cargos, such as Texas Red-labeled dextran and green fluorescent PLGA microspheres (FIG. 14 (D)).

In addition to cutaneous vaccination, these dissolving undercut MNAs can be used for a broad range of intradermal and non-cutaneous (e.g., liver, ocular, and cardiac tissues) drug delivery applications (Li et al. "Rapidly separable microneedle patch for the sustained release of a contraceptive", 2019, *Nat. Biomed. Eng.,* 3: 220-229; Than et al. "Self-implantable double-layered micro-drug-reservoirs for efficient and controlled ocular drug delivery", 2018, *Nat. Commun.,* 9: 4433; Tang et al. "Cardiac cell—integrated microneedle patch for treating myocardial infarction", 2018, *Sci. Adv.,* 4:eaat9365). Through the spin-casting process, biocargo(s) of interest can be located either at the tips of microneedles (FIG. 14 (A)), or throughout the entire pyramid region (FIG. 14 (B)), depending on dose requirements. Furthermore, a number of sequential spin-casting steps can be performed to fabricate high-quality MNAs with undercut microneedles that incorporate multiple cargos in their pyramid regions (FIGS. 14 (C) and 14 (D)). As such, the presented approach and novel MNA designs are compatible with single and combination therapies for several cutaneous and non-cutaneous applications. Importantly, same production molds can be re-used to fabricate dissolving MNAs, suggesting that removal of undercut MNAs from flexible PDMS production molds results in elastic deformation for several process cycles without destroying the production molds. For example, the dissolving MNAs in FIGS. 14 (A) and 11 (C) were obtained using the same PDMS production mold at the first and twelfth cycles, respectively. Furthermore, we are currently capable of fabricating 5000+MNAs per day in our laboratories, and these fabrication processes can be scaled up using industrial grade manufacturing strategies.

Additive manufacturing (AM), or 3D printing, has proven useful for the preparation of drug delivery systems (Prasad et al. "3D printing technologies for drug delivery: a review", 2016, *Drug Dev. Ind. Pharm.,* 42:1019-1031; Jonathan et al. "3D printing in pharmaceutics: a new tool for designing customized drug delivery systems", 2016, *Int. J. Pharm.,* 499:376-394). Indeed, there are currently FDA approved, 3D-printed drug delivery systems, such as Spritam® tablets (Prasad et al.; Jonathan et al.). A unique advantage of AM over traditional subtractive fabrication techniques is the possibility for accurate and reproducible manufacturing of 3D complex geometries without design limitations (Johnson et al.). As such, AM offers a high degree of design flexibility and control, and thus enables rapid design-to-fabrication turnaround for optimal application-driven drug delivery systems (Economidou et al. "3D printing applications for transdermal drug delivery", *Int. J. Pharm.*, 2018, 544: 415-424). Indeed, micro-scale AM has been effectively used for accurate and reliable fabrication of intradermal drug delivery systems (Johnson et al.). However, the unique advantages of AM have yet to be exploited for scalable fabrication of high-quality dissolving MNAs with novel designs for a broad range of drug delivery applications.

Figure 15:
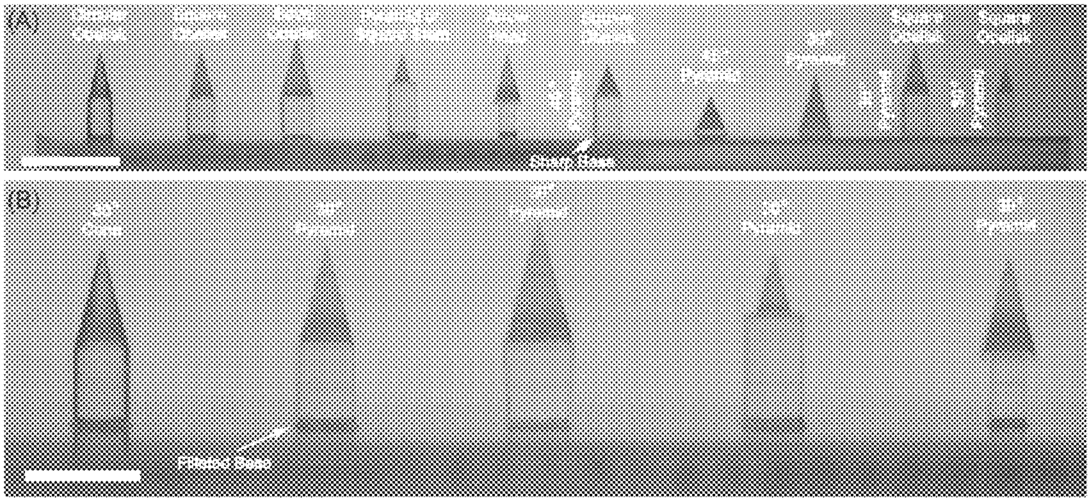
FIG. 15: Geometric capability of 3D direct laser writing for fabricating microneedles. The additive manufacturing approach that enabled fabrication of novel dissolving MNAs introduced by this study is capable of manufacturing high-quality microneedles with diverse geometries. Different microneedle designs fabricated from nondissolvable UV curable resin (IP-S photoresist; same as for master MNAs) using the Nanoscribe (FIG. 15 (A)). Scale bar is 1 mm. Close-up image of printed microneedles with filleted bases (first five from FIG. 14 (A)) (FIG. 15 (B)). Scale bar is 500 μm.

In this study, we utilized the micro-additive manufacturing process, 3D direct laser writing, to enable fabrication of complex, high accuracy, 3D microneedle geometries with smooth edges and sharp tips, as well as undercut features. This technology offers an unprecedented level of flexibility for MNA designs. To demonstrate the range of geometric capability of 3D direct laser writing, we fabricated microneedle designs with diverse geometries. This technology enabled fabrication of a wide range of microneedle geometries with high-fidelity, supporting application-driven optimization. Furthermore, as shown in FIG. 15, it allows a wide range of design changes, including height, width, apex angle, and geometry of the microneedles without requiring complex and custom processing steps. From a strength of materials standpoint, removal of MNAs with different undercut microneedle geometries is governed by needle geometry and material strength, as well as by elasticity and strength of production mold materials. Microneedles with larger undercut geometries may require more flexible production molds with lower Young's moduli for failure-free removal. More flexible PDMS molds can be prepared by adjusting the crosslinker ratio and/or curing temperature (Johnston et al. "Mechanical characterization of bulk Sylgard 184 for microfluidics and microengineering", 2014, *J. Micromech. Microeng.,* 24: 35017; Khanafer et al. "Effects of strain rate, mixing ratio, and stress-strain definition on the mechanical behavior of the polydimethylsiloxane (PDMS) material as related to its biological applications", 2009, *Biomed. Microdevices,* 11:503-508), and hyper-elastic materials, such as Ecoflex, could serve as more flexible alternatives to PDMS (Jeong et al. "PDMS-Based Elastomer Tuned Soft, Stretchable, and Sticky for Epidermal Electronics", 2016, *Adv. Mater.,* 28:5830-5836), allowing removal of even larger undercut features. Collectively, 3D direct laser writing and use of flexible production molds pave the way for fabrication of a broad range of application-driven MNA designs.

Figure 16:
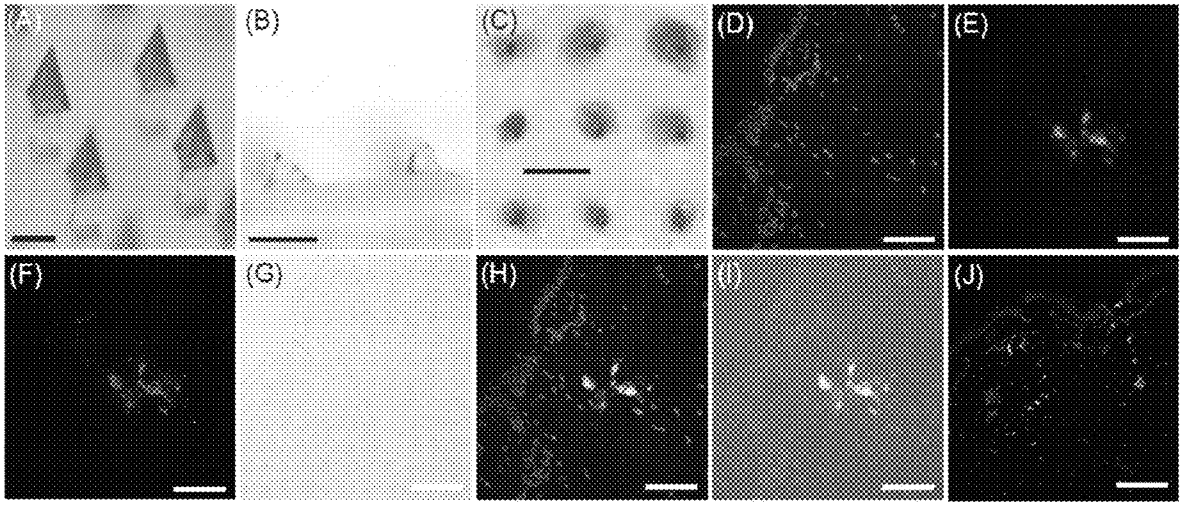
FIG. 16: Intradermal vaccine delivery to freshly-excised human skin explants using tip-loaded, dissolving MNAs with undercut microneedles. Optical stereomicroscopy images of PVP/PVA MNAs incorporating Allura Red R40 dye before (FIG. 16 (A)) and after (FIG. 16 (B)) application to human skin explants. Scale bars are 250 μm. Optical stereomicroscopy image of Allura Red R40 dye microneedle traces on living human skin samples (FIG. 16 (C)). Scale bar is 500 μm.

Dissolving undercut MNAs deliver multicomponent vaccines to human skin: To evaluate cutaneous biocargo delivery characteristics of dissolving MNAs with undercut microneedles, MNAs tip-loaded with Allura Red R40 dye were manufactured using the presented fabrication strategy. Allura Red R40 dye-loaded MNAs were applied to living human skin explants and removed after 10 min. Images of these MNAs before (FIG. 16 (A)) and after (FIG. 16 (B)) application demonstrated high-quality MNAs and complete dissolution of the microneedles, respectively. The corresponding deposits of MNA-embedded Allura Red R40 dye in the targeted skin are shown in FIG. 16 (C).

Successful vaccine delivery through the stratum corneum into the immune cell-rich cutaneous microenvironments is critical for effective intradermal immunization. To anatomically evaluate the delivery of antigen (OVA) and adjuvant (Poly(I:C)) into human skin, MNAs incorporating both Alexa555-labeled OVA and Alexa488-labeled Poly(I:C) were applied to human skin explants for 10 min and then removed. The targeted human skin was cryo-sectioned and imaged using epifluorescence microscopy. The resulting images demonstrated microneedle cavities penetrating through the epidermis into the dermis (FIG. 16 (G)), and delivery of fluorescent labeled OVA and Poly(I:C) to targeted human skin microenvironments (FIGS. 16 (D-J)). Collectively, these results indicate that the MNAs fulfilled the geometric (sharp tips and smooth edges) and mechanical-strength requirements for failure-free human skin penetration (e.g., breaching through the stratum corneum and epidermis), and material requirements for efficient dissolution in the aqueous environment of the skin, thereby presenting an effective cutaneous drug and vaccine delivery platform.

Figure 17:
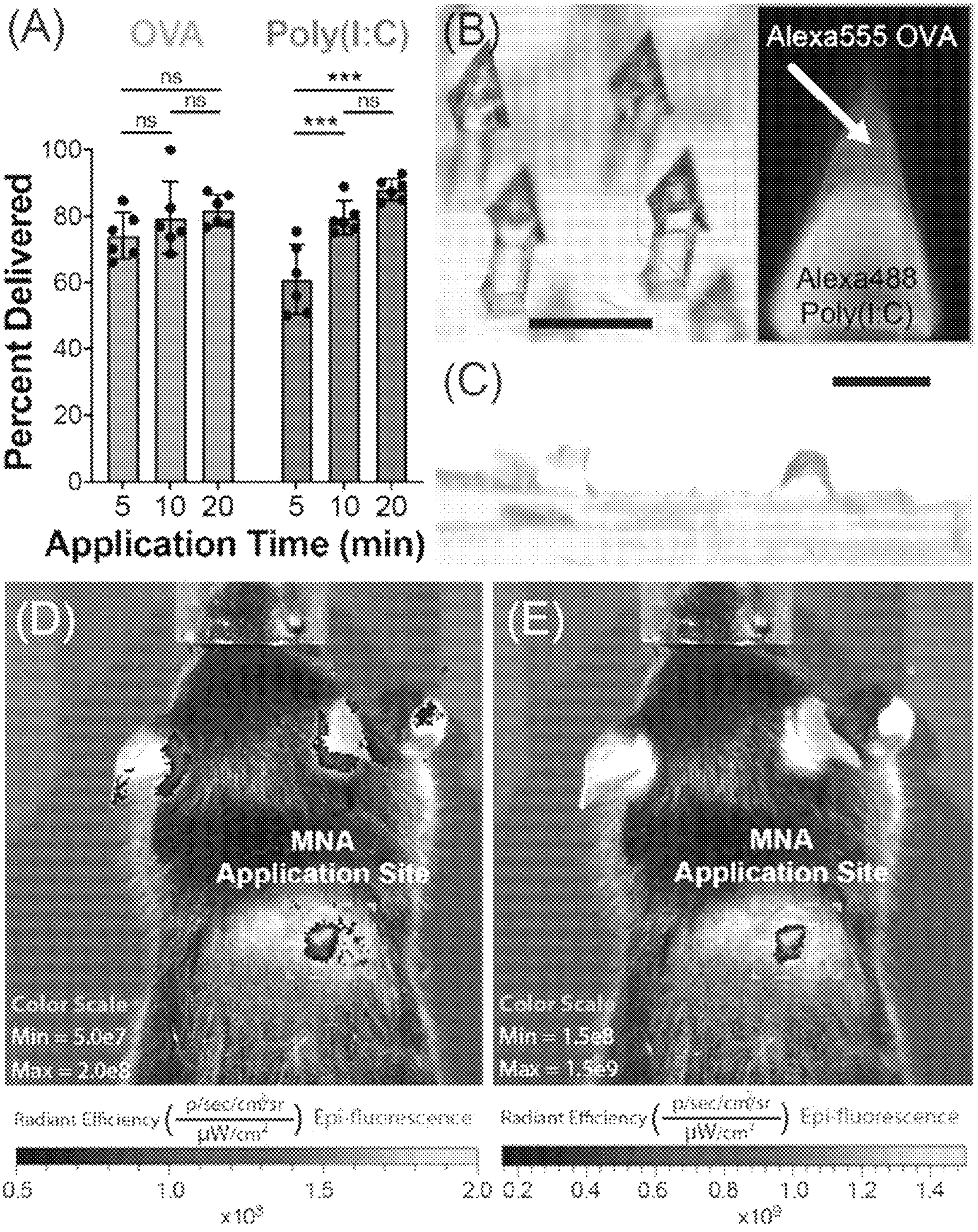
FIG. 17: MNA directed intradermal vaccine delivery in mice. Delivery kinetics for OVA and Poly(I:C) in murine skin (FIG. 17 (A)). OVA+Poly(I:C) MNAs were applied for 5, 10, or 20 min, and then delivery efficiency of OVA and Poly(I:C) with respect to time was quantified. Data represent percent of initial MNA content delivered (mean±SD, N=6). One-way ANOVA and Tukey's post-hoc tests were used for each biocargo, and significant differences are indicated by * $p<0.001$. Optical stereomicroscopy image of MNAs integrating both Alexa555-OVA (red) and Alexa488-Poly(I:C) (green) (FIG. 17 (B)). Scale bar is 500 μm. The fluorescence microscopy inset shows the distribution of both vaccine components in a pyramid microneedle tip. Representative optical stereomicroscopy image of the Alexa555-OVA and Alexa488-Poly(I:C)-loaded MNAs after application to murine skin (FIG. 17 (C)). Scale bar is 250 μm.

Dissolving undercut MNAs deliver multicomponent vaccines to murine skin: To evaluate cutaneous delivery efficiency and kinetics for undercut MNAs, OVA+Poly(I:C) MNAs were applied to murine abdominal skin for 5, 10, or 20 min, then removed and the remaining biocargo content was measured. Within 10 min, MNAs delivered 80.2%±12.5% OVA and 79.6±5.0% Poly(I:C), with nonsignificant additional delivery for either vaccine component by 20 min (FIG. 17 (A)). To visually confirm in vivo intradermal multicomponent vaccine delivery in mice, dissolving MNAs with high-fidelity undercut microneedles incorporating both Alexa555-OVA and Alexa488-Poly(I:C) were fabricated as described above. Prior to application, Alexa555-OVA+Alexa488-Poly(I:C) MNAs were imaged using optical stereomicroscopy and epifluorescence microscopy (FIG. 17 (B)). MNAs were then applied to mice and removed after 10 min. The remaining MNA material after applications was also imaged using optical stereomicroscopy (FIG. 17 (C)). MNA-treated mice were imaged using the IVIS 200 live animal imaging system with filters for detection of both Alexa488-Poly(I:C) and Alexa555-OVA. MNA-directed co-delivery of OVA (antigen) and Poly(I:C) (adjuvant) are shown in FIGS. 17 (D, E). Together, these images demonstrate successful in vivo application of dissolvable undercut MNAs to mice and efficient delivery of both components of a multicomponent vaccine.

Figure 18A:
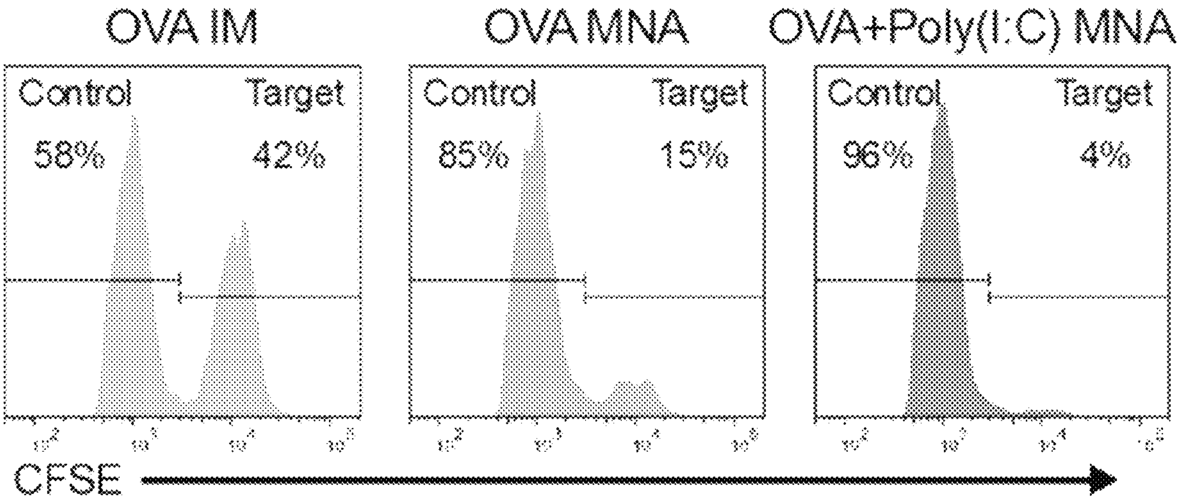
FIGS. 18A-18C: Intradermal delivery of antigen (OVA) ±adjuvant (Poly(I:C)) with MNAs induces antigen-specific cellular and humoral immunity. Mice were immunized by intramuscular (IM) injection of OVA (2×10 μg injections per mouse), or by application of OVA±Poly(I:C) MNAs (10 μg OVA±25 μg Poly(I:C) per MNA, 2 MNAs per mouse) to abdominal skin, and boosted identically seven days later. To determine activity of OVA-specific cytotoxic T lymphocytes (CTLs), equal numbers of unpulsed splenocytes ($CFSE^{low}$ "control" cells) and $OVA_{257-264}$ peptide-pulsed splenocytes ($CFSE^{high}$ "target" cells) were transferred to naïve and immunized mice ($2\times10^7$ total cells per mouse) five days later. Spleens and serum were isolated the next day. Representative flow cytometry histograms showing remaining CFSE-labeled cells in spleens of immunized and unimmunized mice. Specific lysis of peptide-pulsed target cells by OVA-specific CTLs is indicated by a reduction in $CFSE^{high}$ target cells (FIG. 18A). Quantification of specific cell lysis, with 100% lysis corresponding to complete elimination of target cells (mean±SD, N=3 mice per group) (FIG. 18B). Serum concentrations of OVA-specific IgG1 and IgG2c antibodies (bars represent mean values, 3 mice per group) (FIG. 18C). Groups were compared by one-way ANOVA, followed by Tukey's post-hoc tests (FIG. 18B), or Dunnett's comparisons to OVA IM control group (FIG. 18C). Significant differences are indicated by * $p<0.05$,  $p<0.01$, or * $p<0.001$.
Figure 18B:
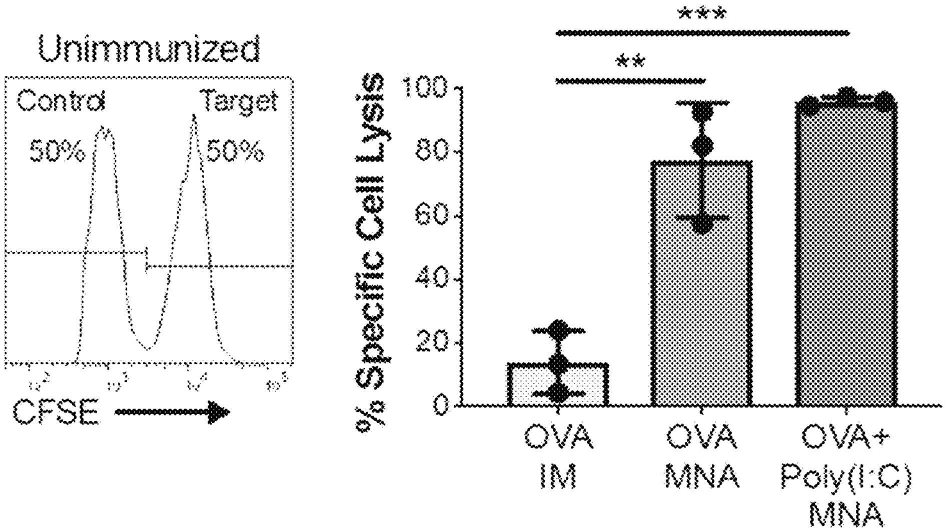
Figure 18C:
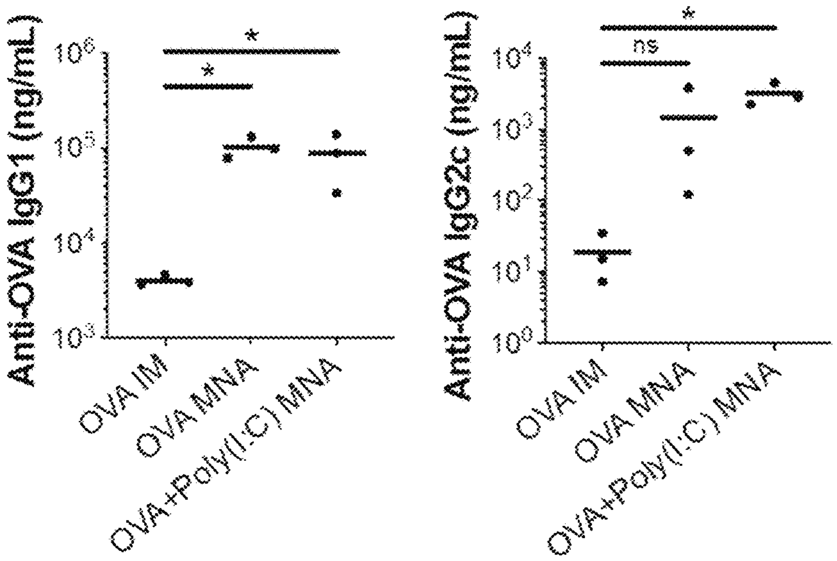

Multicomponent vaccine MNAs induce potent cellular and humoral immunity: Upon demonstration of successful intradermal delivery of the vaccine components to mice, we specifically evaluated immunogenicity of MNA-embedded antigen±adjuvant and compared MNA immunization to vaccination by the clinically common intramuscular (IM) injection route. To this end, MNAs were fabricated with 10 μg OVA±25 μg Poly(I:C) per MNA, as described above. We and others have previously shown that proteins integrated in dissolving MNAs maintain their integrity (Bediz et al.; Korkmaz et al.). Mice were immunized twice with MNAs or by IM injections, as detailed above, and OVA-specific cytotoxic T-cell (CTL) and antibody responses were quantified using standard in vivo lytic assay and ELISAs, respectively (FIGS. 18A-18C). Notably, dissolving MNAs with different geometries have been used to deliver antigens and other adjuvants (Zhao et al. "Enhanced immunization via dissolving microneedle array-based delivery system incorporating subunit vaccine and saponin adjuvant", 2017, *Int. J. Nanomedicine,* 12: 4763-4772; Ding et al. "Microneedle arrays for the transcutaneous immunization of diphtheria and influenza in BALB/c mice", 2009, *J. Control. Release,* 136:71-78; McCrudden et al. "Laser-engineered dissolving microneedle arrays for protein delivery: potential for enhanced intradermal vaccination", 2015, *J. Pharm. Pharmacol.,* 67:409-425), while the Poly(I:C) adjuvant used in this study has only been incorporated in coated or sustained release MNAs (Weldon et al. "Effect of adjuvants on responses to skin immunization by microneedles coated with influenza subunit vaccine", 2012, *PLoS One,* 7: e41501; DeMuth et al. "Composite dissolving microneedles for coordinated control of antigen and adjuvant delivery kinetics in transcutaneous vaccination", 2013, *Adv. Funct. Mater.,* 23: 161-172; DeMuth et al. "Implantable silk composite microneedles for programmable vaccine release kinetics and enhanced immunogenicity in transcutaneous immunization", 2014, *Adv. Healthc. Mater.,* 3: 47-58).

Cutaneous vaccination with MNAs elicited robust antigen-specific cellular immune responses (FIGS. 18A and 18B). As expected, equivalent numbers of antigen-pulsed ($CFSE^{high}$) target cells and unpulsed ($CFSE^{low}$) target cells were recovered from spleens of unimmunized mice (FIG. 18A), indicating the absence of antigen-specific cytolytic activity. Mice treated with Blank MNAs (without antigen or adjuvant) also did not exhibit OVA-specific CTL responses (comparable to naïve). In contrast, specific lysis of antigen-pulsed target cells was dramatically enhanced in immunized mice, as shown by reduced survival of OVA-pulsed targets compared to unpulsed targets (FIG. 18A). While immunization by IM injections of OVA elicited a relatively low antigen-specific cellular immune response (i.e., OVA-specific lysis), cutaneous vaccination with OVA MNAs led to significantly greater OVA-specific lysis (FIGS. 18A and 18B). Importantly, addition of Poly(I:C), a Toll-like receptor 3 (TLR3) agonist adjuvant, to MNAs further improved vaccine immunogenicity, as indicated by a greater CTL response to multicomponent OVA+Poly(I:C) MNAs (FIGS. 18A and 18B). The enhanced CTL response we observed with Poly(I:C) adjuvant is consistent with previous reports that TLR3 ligands activate keratinocytes, innate immune cells, and professional APCs and induce cross-presentation of antigen to prime CD8+ T cells (Datta et al. "A subset of toll-like receptor ligands induces cross-presentation by bone marrow-derived dendritic cells", 2003, *J. Immunol.,* 170: 4102-4110; Schulz et al. "Toll-like receptor 3 promotes cross-priming to virus-infected cells", 2005, *Nature,* 433: 887-892; Kalali et al. "Double-stranded RNA induces an antiviral defense status in epidermal keratinocytes through TLR3-, PKR-, and MDA5/RIG-I-mediated differential signaling", 2008, *J. Immunol.,* 181: 2694-2704). Given these results with a model antigen, multicomponent cutaneous vaccination using dissolving undercut MNAs that incorporate pathogen- or tumor-specific antigens and adjuvants may be expected to induce robust cellular immunity essential for prevention and/or treatment of many infectious diseases and cancer (He et al. "Skin-derived dendritic cells induce potent $CD8^+$ T cell immunity in recombinant lentivector-mediated genetic immunization", 2006, *Immunity,* 24: 643-656; Morelli et al.; Condon et al.).

In addition to cellular immunity, cutaneous vaccination with OVA±Poly(I:C) MNAs elicited robust antigen-specific humoral immune responses (FIG. 15C). While IM immunization resulted in modest OVA-specific serum IgG antibody responses, mice immunized with equivalent doses of OVA antigen in dissolving MNAs had significantly higher IgG levels. Mice not exposed to OVA antigen (i.e., naïve and Blank MNA treated mice) had undetectable levels of OVA-specific antibodies. In particular, we measured serum levels of two subclasses of OVA-specific IgG: IgG1 and IgG2c. Typically, IgG1 antibodies are associated with Th2 type immune responses to extracellular pathogens, while IgG2c antibodies are associated with Th1 type immune responses to viruses and other intracellular pathogens (Nimmerjahn et al. "Divergent immunoglobulin g subclass activity through selective fc receptor binding", 2005, *Science,* 310: 1510-1512). Although both IgG subclasses can potentially neutralize and/or opsonize pathogens, IgG2c antibodies can also activate the complement pathway and typically evoke more potent cellular responses because of a greater affinity for activating Fc receptors (FcγRI, FcγRIII, and FcγRIV) and lower affinity for the inhibitory Fc receptor (FcγRIIB) (Nimmerjahn et al.). In our immunization experiments, the addition of Poly(I:C) adjuvant had minimal effect on OVA MNA induced IgG1 responses, but promoted a modest increase in IgG2c responses, consistent with the enhanced CTL immunity. Compared to IM immunization, the stronger and more balanced IgG1/IgG2c responses to cutaneous vaccination with MNAs could translate into enhanced protection against different types of pathogens. Taken together, these results demonstrate that dissolving MNAs with undercut microneedles can efficiently deliver antigens±adjuvants to APC rich microenvironments within the skin to induce potent cellular and humoral immunity. Ultimately, these undercut MNAs represent a novel modular platform technology for the specific and precise delivery of embedded multicomponent vaccines (antigen±adjuvant) to defined microenvironments within the skin.

Conclusions

We have described a comprehensive approach to fabricate novel dissolving MNAs with undercut microneedles for effective multicomponent cutaneous vaccination. Our manufacturing approach strategically combined 3D laser lithography with nanoscale resolution and micromolding with mechanically flexible molds that allow direct removal of undercut MNAs. Reproducible fabrication of dissolvable MNAs with undercut microneedles incorporating multiple cargos was achieved using different biocompatible and water-soluble polymers, and these MNAs successfully delivered biocargos to murine and human skin microenvironments. Importantly, cutaneous vaccination with antigen-loaded MNAs elicited more potent antigen-specific cellular and humoral immune responses than traditional immunization by intramuscular injection. Simultaneous delivery of adjuvant (Poly(I:C)) to the same skin microenvironment as antigen (OVA) enhanced immune responses and may reduce the amount of antigen and/or adjuvant needed, reducing both the risk of systemic toxicity and cost. Ultimately, our approach to fabrication of dissolving MNAs with diverse geometries, including undercut microneedles, may have a broad range of cutaneous and non-cutaneous vaccination and drug delivery applications.

Example 2

The novel coronavirus, previously dubbed 2019-nCoV, and now officially named SARS-CoV-2 is the causative agent of the current coronavirus disease (COVID-19) outbreak. The virus was first detected in Wuhan, China in December 2019 and is classified as a Betacoronavirus, just as the Middle East Respiratory Syndrome Coronavirus (MERS-CoV), which emerged in Saudi Arabia in 2012 and still poses a serious threat to public health. Safe vaccines that rapidly induce robust, long-lasting, virus-specific immune responses against these infectious agents are urgently needed. The coronavirus spike (S) protein, a characteristic structural component of the viral envelope, is considered a key target for vaccines for the prevention of coronavirus infection.

Coronavirus is an emerging pathogen with exponentially increasing significance due to the high case fatality rate, the large distribution of reservoir, and the lack of medical countermeasures. The public health emergencies caused by Coronavirus (COVID-19, MERS-COV, and SARS-COV)

clearly demonstrate the urgency to evaluate candidate vaccines to combat these outbreaks. Continuous research efforts from previous epidemics have prepared scientists to quickly develop safe vaccines against these emerging infections; however, the outcomes of recent COVID-19 still highlight an important need for the rapid design, production, testing, and clinical translation of candidate vaccines.

Here, the immunogenicity of a trimeric form of MERS-S1 and SARS-CoV-2-S1 subunit vaccines delivered to the immunologically responsive cutaneous microenvironment by dissolvable microneedle arrays (MNAs) is evaluated. Further, to improve the immunogenicity of the vaccines, we constructed S1 subunits with integrated Toll-like receptor (TLR) agonist sequences, specifically RS09 and flagellin C. RS09 is a synthetic form of an LPS mimic 7-mer peptide, which binds to TLR4 and induces nuclear localization of the transcription factor NF-κB, resulting in transcription of inflammatory cytokines and secretion of chemokines (Shanmugam et al. "Synthetic Toll like receptor-4 (TLR-4) agonist peptides as a novel class of adjuvants", 2012, *PloS one;* 7(2): e30839. Flagellin is a highly conserved natural bacterial ligand that binds to TLR5 to activate TLR5 expressing dendritic cells, neutrophils, lung epithelial cells and pneumonocytes, augmenting immunogenicity in several vaccine models (Song et al. "An avian influenza A (H7N9) virus vaccine candidate based on the fusion protein of hemagglutinin globular head and *Salmonella typhimurium* flagellin", 2015, *BMC biotechnology* 2015; 15: 79; Lopez-Boado et al. "*Bordetella bronchiseptica* flagellin is a proinflammatory determinant for airway epithelial cells", 2005, *Infection and immunity;* 73(11): 7525-34; Skountzou et al. "*Salmonella* flagellins are potent adjuvants for intranasally administered whole inactivated influenza vaccine", 2010, *Vaccine;* 28(24): 4103-12).

The skin is an ideal target for immunization since it contains a rich population of antigen presenting and immune accessory cells capable of inducing a proinflammatory microenvironment favoring the induction of robust, potent and durable adaptive immunity (Kashem et al. "Antigen-Presenting Cells in the Skin", 2017, *Annual review of immunology;* 35: 469-99; Kabashima et al. "The immunological anatomy of the skin", 2019, *Nat Rev Immunol;* 19(1): 19-30). Of several emerging skin-targeted drug delivery methods, dissolving MNAs have appeared as a patient-friendly and minimally-invasive intracutaneous approach (Lee et al.). These MNAs are developed from mechanically strong water-soluble polymers to physically breach the outermost layer of skin (stratum corneum) and then rapidly dissolve in the underlying viable epidermis and dermis to deliver biocargos to cutaneous microenvironments (Balmert et al. "Dissolving undercut microneedle arrays for multicomponent cutaneous vaccination", 2020, *Journal of controlled release: official journal of the Controlled Release Society;* 317: 336-46; Korkmaz et al.).

MNA delivery results in high concentrations of vaccine components in the local skin microenvironment, thereby providing a dose-sparing effect that can augment immunogenicity (Sullivan et al. "Dissolving polymer microneedle patches for influenza vaccination", 2010, *Nat Med;* 16(8): 915-20). Further, MNA-embedded vaccines remain stable without expensive "cold chain" requirements. Indeed, a recent Phase 1 clinical trial of an MNA-based influenza vaccine suggests that MNA vaccines are safe, immunogenic, and well accepted by participants and healthcare providers, thereby strongly supporting the clinical feasibility of MNA delivery (Fernando et al. "Safety, tolerability, acceptability and immunogenicity of an influenza vaccine delivered to human skin by a novel high-density microprojection array patch (Nanopatch)", 2018, *Vaccine;* 36(26): 3779-88; Rouphael et al. "The safety, immunogenicity, and acceptability of inactivated influenza vaccine delivered by microneedle patch (TIV-MNP 2015): a randomised, partly blinded, placebo-controlled, phase 1 trial", 2017, *Lancet;* 390(10095): 649-58).

Materials and Methods

Construction of adenoviral vectors and plasmids: The codon-optimized gene encoding MERS-S1 (amino acids 1 to 725 of full-length MERS S, according to the GeneBank JX869059) lacking stop codon flanked with SalI & BamHI was amplified by PCR from pAd/MERS-S1 (Kim et al. "Immunogenicity of an adenoviral-based Middle East Respiratory Syndrome coronavirus vaccine in BALB/c mice", 2014, *Vaccine;* 32(45): 5975-82) and was used to replace the ZIKV-E in in pAd/ZIKV-Efl (Kim et al. "Preventative Vaccines for Zika Virus Outbreak: Preliminary Evaluation", 2016, *EBioMedicine;* 13: 315-20) at SalI & BamHI sites fused with BamH I-linked T4 fibritin foldon trimerization domain (f), Tobacco Etch Virus Protease (Tp), and six histidine tag (6H), generating plasmid pAd/MERS-S1f. For the construction of pAd/MERS-S1fRS09 or pAd/MERS-S1ffliC, BamH I-fTp6H-Not I of pAd/MERS-S1f was replaced with codon optimized BamH I-f-RS09(APPHALS)-Tp6H-Not I or BamH I-f-fliC (GenBank ACY88831)-Tp6H-Not I. Subsequently, replication-defective human adenovirus serotype 5, designated as Ad5.MERS-S1f, Ad5.MERS-S1fRS09, and Ad5.MERS-S1ffliC, were made by loxP homologous recombination and purified and stored as described previously (Gao et al. "Protection of mice and poultry from lethal H5N1 avian influenza virus through adenovirus-based immunization", 2006, *Journal of virology;* 80(4): 1959-64; Steitz et al. "A candidate H1N1 pandemic influenza vaccine elicits protective immunity in mice", 2010, *PloS one;* 5(5): e10492; Hardy et al. "Construction of adenovirus vectors through Cre-lox recombination", 1997, *Journal of virology;* 71(3): 1842-9).

For the construction of pmax/SARS-CoV-2-S1, the codon-optimized gene encoding SARS-CoV-2-S1 amino acids 1 to 661 of full-length from BetaCoV/Wuhan/IPB-CAMS-WH-05/2020 (GISAID accession id. EPI_ISL_403928, amino acids 1 to 661) lacking stop codon flanked with HindIII-SalI & BamHI-6H-NotI was synthesized (GenScript) and generated by subcloning the codon-optimized SARS-CoV-2-S1 gene into pmaxCloning (Lonza), at HindIII/NotI sites. For the construction of pmax/SARS-CoV-2-S1fRS09, BamH I-6H-Not I of pmax/SARS-CoV-2-S1 was replaced with codon optimized BamH I-f-RS09(APPHALS)-Tp6H-Not I.

Purification of recombinant proteins: The recombinant proteins named rMERS-S1f, rMERS-S1fRS09, and rMERSS1ffliC were expressed in Human Embryonic Kidney (HEK) 293 cells infected with Ad5.MERS-S1f, Ad5.MERS-S1fRS09, and Ad5.MERS-S1ffliC, respectively, and purified by His60 Ni Superflow Resin (Clontech) under native conditions from the supernatant as described previously (Kim et al., *EBioMedicine,* 2016). Briefly, the purified recombinant proteins were treated with AcTEV protease (Life Technology) followed by affinity chromatography on a His60 Ni Superflow Resin to remove six-histidine tags and poly-histidine tagged protease from the cleavage reaction. The cleaved native recombinant proteins were collected from the flow-through fraction. The eluted solution was concentrated and desalted with phosphate buffered saline (PBS) in an Amicon Ultra centrifugal filter devices (Millipore).

For expression of recombinant proteins, rSARS-CoV-2-S1 and rSARS-CoV-2-S1fRS09, 293HEK cells were transfected by electroporation (Celetrix). Briefly, 293HEK cells were counted and suspended with plasmids in the electroporation buffer at $5 \times 10^7$ cells, 200 μg/ml. The mixture containing cells and plasmids was transferred into 1 ml Celetrix electroporation cuvette and immediately subjected to electroporation under 930V and 30 ms, and then incubated for 72 hrs at 37° C. in a humidified atmosphere with 5% $CO_2$. The recombinant proteins, rSARS-CoV-2-S1 and rSARS-CoV-2-S1fRS09, were purified by His60 Ni Superflow Resin (Clontech) under native conditions from the supernatant as described previously (Kim et al., EBioMedicine, 2016). The concentrations of the purified recombinant proteins were determined by the Bradford assay using bovine serum albumin (BSA) as a protein standard.

SDS-PAGE and Western blot: To evaluate the recombinant adenoviruses, A549 cells were transduced with ten multiplicity of infection (MOI) of Ad5.MERS-S1f, Ad5.MERS-S1fRS09, and Ad5.MERS-S1fflic. At six hours after infection, cells were washed three times with PBS, and added with serum-free media, and incubated for 4 8 hours. The supernatant of A549 infected with adenoviruses were subjected to sodium dodecyl sulfate polyacrylamide gel electrophoresis (SDS-PAGE) and Western blot. Briefly, after the supernatants were boiled in Laemmli sample buffer containing 2% SDS, or native sample buffer, with or without beta-mercaptoethanol (β-ME), the proteins were separated by 4-20% or 10% Tris-Glycine SDS-PAGE gels and then transferred to polyvinylidene fluoride (PVDF) membrane. After blocking for 1 h at room temperature with 5% non-fat milk in PBST, anti-6×His monoclonal antibody (1:50000) (Invitrogen) were added and incubated overnight with at 4° C. as primary antibody, and horseradish peroxidase (HRP)-conjugated goat anti-mouse IgG (1:10000) (SantaCruz) was added and incubated at RT for 2 h as secondary antibody. After washing three times with PBS, the signals were visualized using ECL Western blot substrate reagents and Amersham Hyperfilm (GE Healthcare).

Fabrication of dissolvable microneedle arrays: Dissolvable microneedle arrays (MNAs) incorporating the protein MERS-S1f, MERS-S1f RS09, MERS-S1ffliC, SARS-CoV-2-S1, or SARS-CoV-2-S1fRS09 (MNA-rMERS-S1f, MNA-rMERS-S1fRS09, MNA-rMERS-S1ffliC, MNA-rSARS-CoV-2-S1, or MNA-rSARS-CoV-2-S1fRS09) were fabricated from carboxymethyl cellulose (CMC, 90 kDa MW) at room temperature (22° C.) using our previously described three-stage MNA manufacturing strategy (Korkmaz et al.; Bediz et al.). Briefly, the elastomer production molds were prepared by casting Polydimethylsiloxane (PDMS, SYLGARD® 184) onto the micromachined MNA master molds that include 100 obelisk-shaped microneedles in a 10×10 array. The height, width, and apex angle of microneedles are chosen to be 750 μm, 225 μm, and 30° C., respectively. Next, CMC-based MNA-rMERS-S1f, MNA-rMERS-S1fRS09, MNA-rMERS-S1ffliC, MNA-rSARS-CoV-2-S1, or MNA-rSARS-CoV-2-S1fRS09 vaccines were produced through a two-step spin-drying technique. First, 20 μl of purified protein was dispensed onto each MNA production mold and centrifuged for 1 min at 2500 g to fill the microneedle cavities. Subsequently, the excess solution was removed and the residual protein solution was spin-dried into the tip of the microneedle cavities of the mold by centrifugation at 2500 g for 30 min The tip-loaded protein in the production molds was overlayered with 75 mg of CMC hydrogel (20 wt %) to form the mechanically strong microneedles and the backing layer of the MNAs. The molds loaded with the CMC-hydrogel were then centrifuged for 2.5 h at 2500 g to obtain final dissolvable MNA vaccines. Each MNA-rMERS-S1f, MNA-rMERS-S1fRS09, MNA-rMERS-S1ffliC, SARS-CoV-2-S1, or SARS-CoV-2-S1fRS09 incorporated 25 μg, 25 μg, 40 μg, 20 μg, or 20 μg proteins, respectively. In one group, the fabricated MNAs were terminally sterilized by gamma irradiation (Cs-137 Mark 1 Model 68A irradiator, JL Shepherd and Associates) at 25 kGy. The geometric integrity of the fabricated MNAs was confirmed through optical stereomicroscopy imaging before the experiments.

Animals and Immunization: BABL/c mice (5 mice per group) were inoculated subcutaneously with 25 μg of MERS-S1f only, 25 μg of MERS-S1f plus 20 μg of MPLA (monophosphoryl lipid A; TLR-4 agonist), 25 μg of MERS-S1fRS09, and 40 μg of MERS-S1ffliC, respectively or PBS as a negative control and $10^{11}$ vp of Ad5.MERS-S1 as a positive control. The microneedle array (MNA) of rMERS-S1f, rMERS-S1fRS09, or rMERS-S1ffliC was administered through intradermal delivery. Two weeks after the primary immunization, mice were boosted intranasally (i.n.) or intracutaneously with the same dose of the corresponding immunogens.

For SARS-CoV-2 study, C57BL/6 female mice (two or five animals per group) were inoculated intracutaneously with MNA or irradiated MNA (iMNA) loaded with 20 μg of SARS-CoV-2-S1 or SARS-CoV-2-S1fRS09 protein, or PBS as a negative control. Mice were bled from the saphenous vein at week 0, 1, and 2, and serum samples were evaluated for SARS-CoV-2-S1 antibody by enzyme-linked immunosorbent assay (ELISA).

All experiments were conducted in accordance with the institutional animal care and use committee (IACUC) guidelines.

FACS Analysis: Two weeks after the prime immunization, pooled sera were obtained from all mice and screened for MERS-S-specific antibodies using fluorescence-activated cell sorter (FACS) analysis of Human Embryonic Kidney (HEK) 293 cells transfected with either pAd/MERS-S or pAd control using Lipofectamine 2000 (Invitrogen) as described previously (Kim et al., *Vaccine,* 2014). Briefly, after 24 hours at 37° C., the transfected cells were harvested, trypsinized, washed with phosphate buffered saline (PBS), and stained with mouse antiserum of each groups followed by a PE-conjugated anti-mouse secondary antibody (Jackson Immuno Research). Data acquisition and analysis were performed using LSRII (BD) and FlowJo (Tree Star) software.

ELISA: Sera from the animals were collected every two weeks and tested for MERS-S1 protein-specific IgG by conventional ELISA as previously described (Kim et al., *Vaccines,* 2014). For long-lasting immunity, sera from the animals were collected at week 23 and week 55 after primary inoculation and tested for MERS-S1 protein-specific IgG by ELISA. Briefly, 96-well plates were coated with the serum-free media from A549 cells infected with 10 MOI of Ad5.MERS-S1 for 48 hours overnight at 4° C. in carbonating buffer (pH 9.5) and then blocked with PBS containing 0.05% Tween 20 (PBS-T) and 2% bovine serum albumin (BSA) for 1 hour. Mouse sera were diluted 1:200 in PBS-T with 1% BSA and incubated for two hours. After the plates were washed, anti-mouse IgG-horseradish peroxidase (HRP) (1:2000, SantaCruz) were added to each well and incubated for one hour. The plates were washed three times and developed with 3,3'5,5'-tetramethylbenzidine, and the reaction was stopped with 1M $H_2SO_4$ and absorbance at 450 nm was determined using an ELISA reader (PerkinElmer 2030). For the binding of the recombinant proteins and mouse sera against Ad5.MERS-S1, the 96-well plates were coated with 200 ng of the purified recombinant proteins per well overnight at 4° C. in carbonate coating buffer (pH 9.5), followed by addition of diluted pre-immunized sera and sera from the mouse infected with AdΨ5 or Ad5.MERS-S1 (Kim et al., *Vaccine,* 2014), and carried out sequentially based on a protocol similar to that described above. For ELISA of SARS-CoV-2-S1 antibody, the 96-well plates were coated with 200 ng of the purified rSARS-CoV-2-S1 per well overnight at 4° C. in carbonate coating buffer (pH 9.5), followed by addition of 1:100 diluted mouse sera, and carried out sequentially based on a protocol similar to that described above.

MERS-CoV neutralization assay: We tested the MERS-CoV neutralization activity of sera derived from mice immunized with rMERS-S1f only, rMERS-S1fRS09, rMERS-S1ffliC, MERS-S1f with MPLA, MNA-MERS-S1f, MNA-MERS-S1f RS09, MNA-MERS-S1ffliC. Ad5.MERS-S1, and PBS, respectively, as previously described (Kim et al., *Vaccine,* 2014). Mouse sera were obtained from the retro-orbital plexus every two weeks for six weeks and tested for their ability to neutralize MERS-CoV (EMC isolate). Briefly, virus (200 PFU) was premixed 1:1 with serial dilutions of sera from animal groups prior to inoculation onto Vero cells, and viral infection was monitored by the occurrence of a cytopathic effect at 72 hours post-infection. Virus neutralization titers (VNTs) were determined as the highest serum dilutions that showed full protection against the cytopathic effect of MERS-CoV.

Statistical analysis: For statistical analysis, the two-way analysis of variance (ANOVA) and Bonferroni post-tests were performed using Prism software (San Diego, Calif., USA). For neutralizing antibody titers, $\log_2$ transformed values were analyzed using one-way ANOVA and Tukey multiple comparison tests. Results were considered statistically significant when the p value was <0.05. Symbols *, , and * are used to indicate the p values <0.05, <0.01, <0.001, respectively.

Results

Figure 19A:
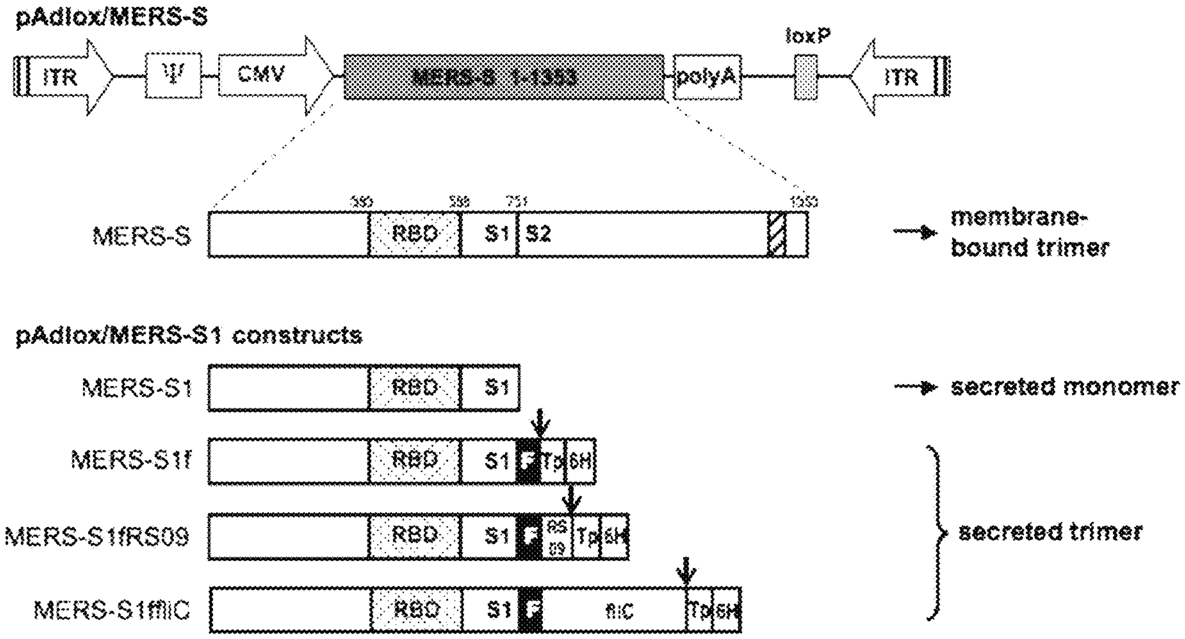
FIGS. 19A-19C: Construction of recombinant MERS-S1 Foldon subunit vaccines. Schematic diagram of rMERS-S1s (FIG. 19A). The positions of the RBD (small dots) and transmembrane domain (stripes) are indicated and S is divided into two subdomains, S1 and S2, at position 751. The vector was used to generate recombinant replication-deficient adenoviruses by homologous recombination with the adenoviral genomic DNA. Arrows showed the cleavage site by TEV protease. Abbreviations are as follows: ITR, inverted terminal repeat; RBD, receptor binding domain; F, T4 fibritin foldon trimerization domain; Tp, Tobacco Etch Virus (TEV) protease; fliC; *Salmonella typhimurium* flagellin C. Western blot of the supernatant of A549 cells infected (10 MOI) with mock (lane 1 and 5), Ad5.MERS-S1f (lane 2 and 6), Ad5.MERS-S1f RS09 (lane 3 and 7), or Ad5.MERS-S1ffliC (lane 4 and 8), respectively, with anti-6His monoclonal antibody (FIG. 19B). The supernatants were resolved on SDS-4~20% polyacrylamide gel after being boiled in 2% SDS sample buffer with or without β-ME. Detection of purified rMERS-S1fs with mouse sera against Ad5.MERS-S1 (FIG. 19C). The recombinant MERS-S1f proteins were purified using His60 Ni Superflow Resin under native conditions. After cleavage of the fusion protein by TEV protease, 6×His tag and protease were removed from the cleavage reaction by affinity chromatography on a nickel chelating resin. Three rMERS-S1fs were coated in 96-well plate with 200 ng/well ELISA and detected with mouse sera against Ad5.MERS-S1. Statically significant differences (Tukey's test) are marked by bars and asterisks. ***, $P<0.001$.
Figure 19B:
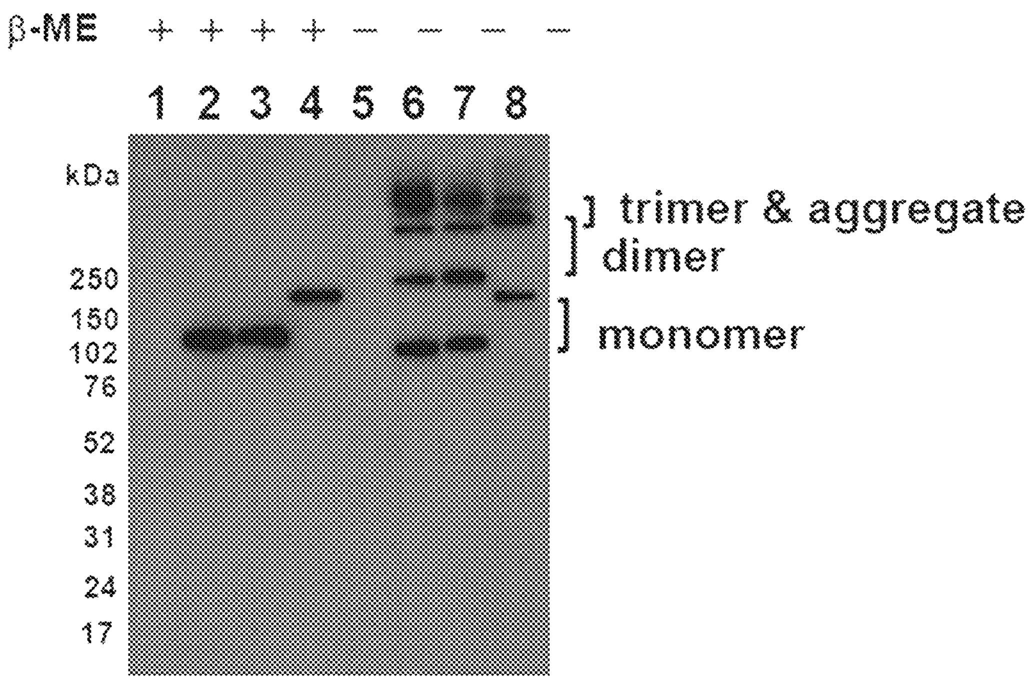
Figure 19C:
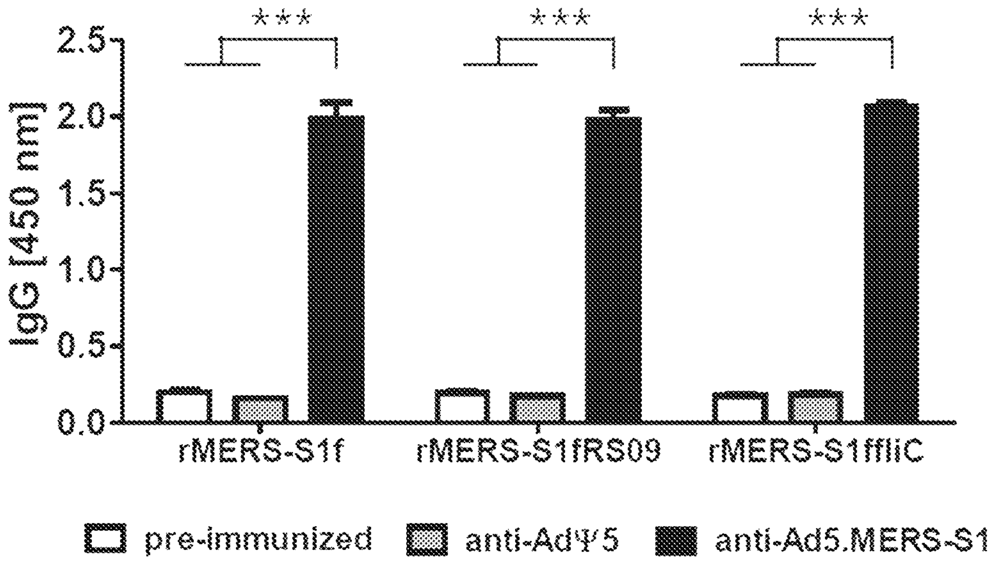

Construction and characterization of recombinant proteins: To construct the recombinant trimeric MERS-S1 proteins, codon-optimized MERS-S1 was fused to the T4 fibritin foldon trimerization domain. Two additional variants were engineered by integrating the TLR4 agonist peptide (RS09) or *Salmonella typhimurium* flagellin C (fliC) fragment at the C-terminal of the foldon. Moreover, all three antigens were designed with a 6-histidine tag and a Tobacco Etch Virus (TEV) protease cleavage sequence at the carboxy terminus to allow for metal chelating affinity purification and to facilitate downstream large-scale purification compatible with clinical manufacturing (FIG. 19A). A shuttle vector (pAd/MERS-S1f) was generated and a replication-defective adenovirus 5, designated as Ad5.MERS-S1f, was produced by loxP homologous recombination to use as a positive control. To determine whether MERS-S1f, MERS-S1f RS09, and MERS-S1ffliC would form trimeric structures, the serum-free supernatants from A549 cells infected with each adenovirus were characterized by SDS-PAGE and Western blot analysis. Three recombinant proteins designed with a 6-histidine tag at the carboxy-terminal ends were recognized by a monoclonal anti-6His antibody at the expected glycosylated monomer molecular weights of about 130 kDa, 135 kDa, and 200 kDa under the denaturing reduced (with β-ME) conditions. The higher molecular-weight bands (dimers or trimers) were evident under the denatured non-reduced (without β-ME) condition, and were 2 or 3 times that of the reduced proteins (monomer), as expected (FIG. 19B) (Yang et al. "Highly stable trimers formed by human immunodeficiency virus type 1 envelope glycoproteins fused with the trimeric motif of T4 bacteriophage fibritin", 2002, *Journal of virology,* 76(9): 4634-42; Yu et al. "Intranasal vaccination of recombinant H5N1 HA1 proteins fused with foldon and Fc induces strong mucosal immune responses with neutralizing activity: Implication for developing novel mucosal influenza vaccines", 2015, *Human vaccines & Immunotherapeutics,* 11(12): 2831-8). After being boiled in the sample buffer, the proteins still migrated to the position of the trimer, indicating the remarkable stability of these proteins. These results demonstrate that recombinant MERS-S1 formed a trimeric conformation in the presence of the Fd trimerization motif. In addition, to delete the six-histidine tag, the purified recombinant proteins were treated with AcTEV protease (Life Technology) followed by affinity chromatography on a nickel chelating resin to remove the six-histidine tags and poly-histidine tagged protease from the cleavage reaction. The cleaved native recombinant proteins were collected from the flow-through fraction and used as coating antigens followed by detection with mouse serum. Three purified recombinant proteins were detected using serum from mice immunized with Ad5.MERS-S1 (***, p<0.001) prepared in our laboratory previously (Kim et al., *Vaccines,* 2014), while no specific antibody binding activity was detected in the serum of pre-immunized naïve mice or from control mice inoculated with AdΨ5 (FIG. 19C). ELISA data revealed that the three recombinant MERS-S1 proteins had strong reactivity with MERS-S1-specific antibodies.

Figure 20A:
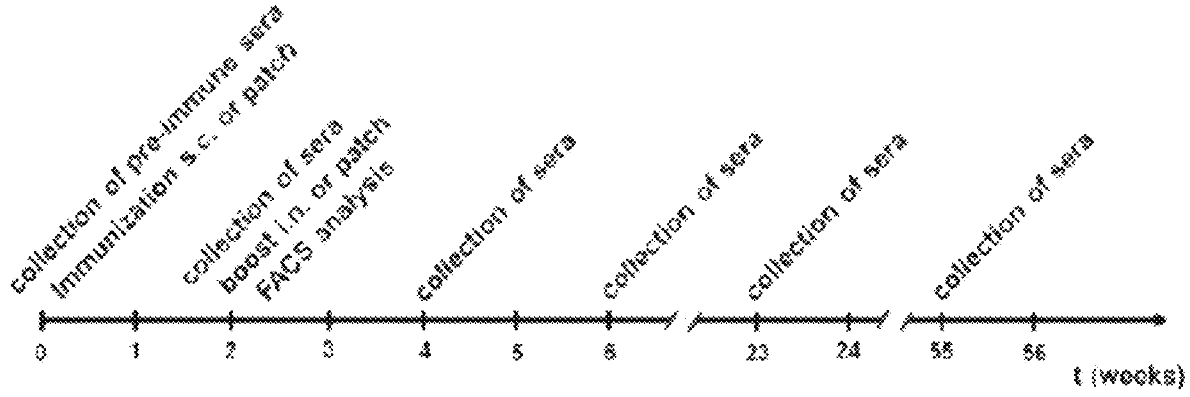
FIGS. 20A-20B: MNA delivered subunit vaccines elicit antibodies recognizing cell surface MERS-S proteins. The experimental schedule representing the time line for the immunizations (FIG. 20A). Flow cytometry assay of 293 cells expressing MERS-S at the cell surface. HEK 293 cells were transfected with pAd/MERS-S or control pAd (FIG. 20B). At 36 hours post-transfection, binding to MERS-S at the cell surface was analyzed by incubation with mice sera obtained at week 2 after immunization followed by staining with PE-conjugated anti-mouse IgG. Statically significant differences (Tukey's test) are marked by bars and asterisks. *, $P<0.05$; , $P<0.01$; *, $P<0.001$; n.s., not significant.
Figure 20B:
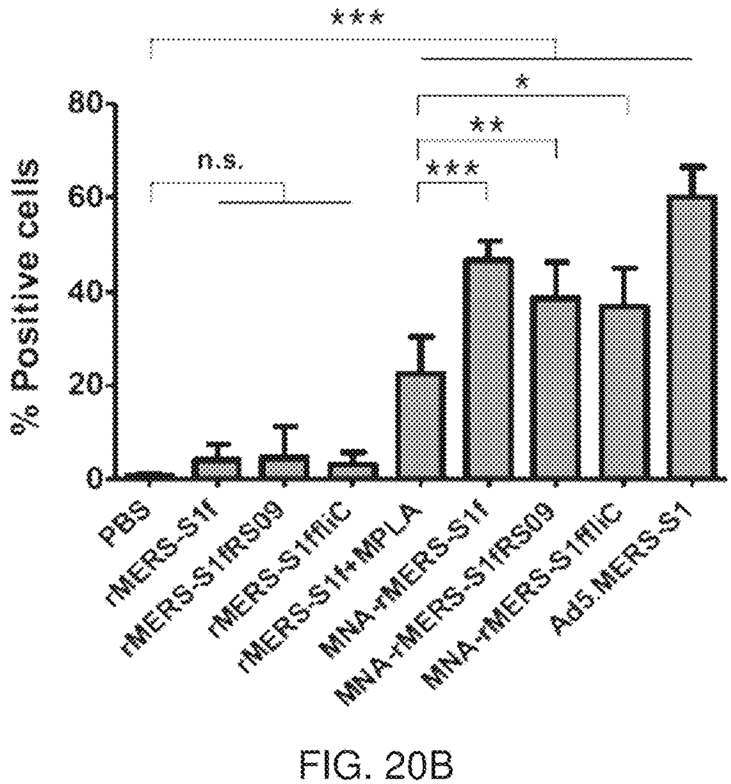

Detection of membrane-bound MERS-S-specific antibodies: We next determined whether these recombinant subunit vaccines could elicit an antigen-specific immune response in vivo. BALB/c mice were inoculated subcutaneously with 25 μg of MERS-S1f, 25 μg of MERS-S1fRS09, 40 μg of MERS-S1ffliC, or 25 μg of MERS-S1f plus 20 μg of the MPLA adjuvant to deliver the same molar ratio of immunogen, or PBS as a negative control on day 0. The experimental schedule is shown in FIG. 20A. Two weeks after immunization, we obtained sera and examined binding to membrane-bound MERS-S by measuring the reactivity against 293 cells transfected with pAd/MERS-S or pAd using flow cytometry. As shown in FIG. 20B, in the presence of MPLA adjuvant, rMERS-S1f induced a strong membrane-bound MERS-S-specific IgG antibody response (*, p<0.001), while no significant antibody response was detectable in the mouse sera of rMERS-S1f, rMERS-S1fRS09, and rMERS-S1ffliC, when compared with PBS-immunized mouse sera. On the other hand, in the absence of adjuvant, MNA intracutaneous delivery of MERS-S1f, MERS-S1f RS09, or MERS-S1ffliC, at the same molar ratio, elicited stronger IgG antibody responses (*, p<0.001) that were significantly stronger than those seen in s.c. immunized mice with MPLA adjuvant (MNA-rMERS-S1f, *, P<0.001; MNA-rMERS-S1fRS09, , P<0.001; MNA-rMERS-S1ffliC, *, P<0.05), indicating the potential of MNA delivery as an effective vaccine delivery platform for these subunit vaccines (FIG. 20B). Mice immunized with Ad5.MERS-S1 as a positive control developed robust levels of IgG antibody against cell membrane-bound MERS-S, while control mice inoculated with PBS did not. Antibodies were not detected bound to cells transfected with pAd without the immunogen insert (data not shown). These data indicate that MERS-S1f protein with MPLA adjuvant and MNA delivered rMERS-S1f, rMERS-S1fRS09, and rMERS-S1ffliC induced strong antibody response to membrane-bound MERS-S two weeks after a single immunization.

Figure 21A:
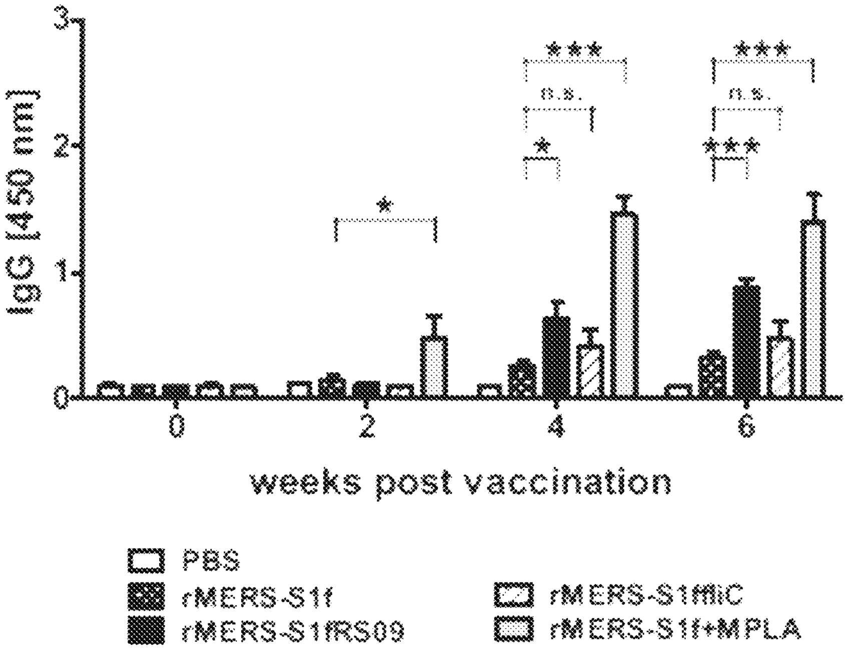
FIGS. 21A-21D: Induction of humoral immune response in mice vaccinated with recombinant MERS-S1 vaccines. BALB/c mice were immunized subcutaneously (s.c.) or intracutaneously with 20 μg of each rMERS-S1 subunit vaccines s.c., with or without 20 μg of MPLA, or by MNA delivery of the same subunit proteins, or with $10^{11}$vp of Ad5.MERS-S1 as a positive control. On day 14 mice were boosted using the same regimen as the prime immunization. On weeks 0, 2, 4, and 6 after treatment, immune sera from mice were collected and tested for the presence of MERS-S1-specific antibodies by ELISA (FIGS. 21A and 21B) or by MERS-CoV-neutralization assay (FIGS. 21C and 21D). MERS-CoV virus-neutralizing titers (VNTs) were measured every week after primary immunization using Vero cells by determining the highest dilution inhibiting MERS-CoV infection by 100%. Statically significant differences (Tukey's test) are marked by bars and asterisks. *, $P<0.05$; , $P<0.01$; *, $P<0.001$; n.s., not significant. Gray asterisks in FIGS. 21C and 21D represented statistical differences compared with PBS group.
Figure 21B:
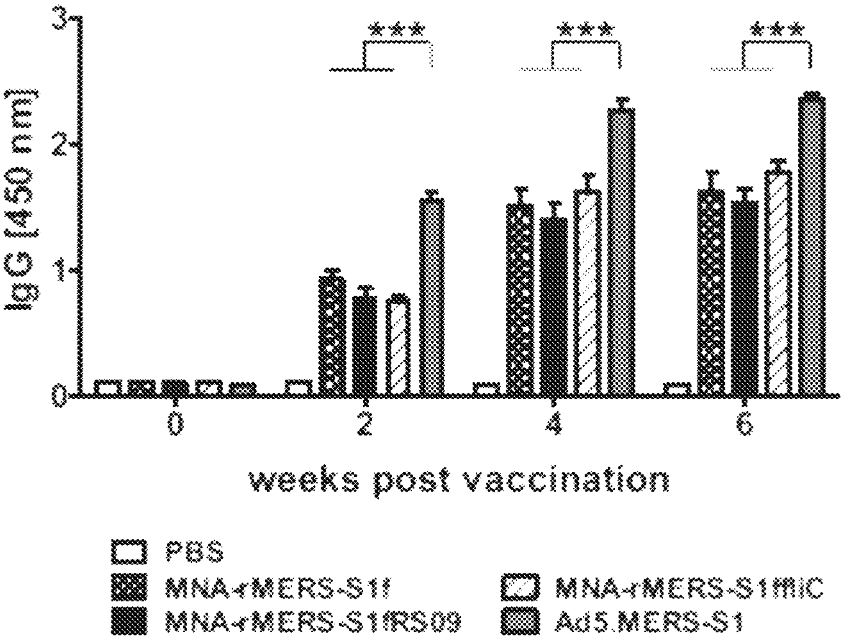

Induction of humoral immune response to MERS-S1: To investigate the immunogenicity of trimeric MERS-S1f proteins, at two and four weeks after a boosting immunization, sera were obtained from all mice and screened for MERS-S1 specific antibodies by ELISA as previously described. As shown in FIG. 21A, following s.c. vaccination only Ad5.MERS-S1 elicited a MERS-S1-specific IgG antibody response (*, p<0.05) at week 2, while no antibody response was detectable in the mouse sera of rMERS-S1f, rMERS-S1fRS09, and rMERS-S1ffliC vaccinated mice when compared with PBS-immunized mouse sera. However, 2 weeks after boosting, antigen specific IgG was detected in the sera of all s.c. immunized mice, although the antibody titers were generally low. As an exception to this, s.c. delivered MERS-S1fRS09 induced a relatively strong MERS-S1-specific IgG antibody response (*, p<0.001 at week 4 & 6). Most importantly, mice immunized with each of the vaccine variants by MNA delivery demonstrated high levels of antigen-specific IgG (*, P<0.001) compared with the sera of mice immunized with PBS, with no significant differences between the vaccine variants (FIG. 21B).

Figure 21C:
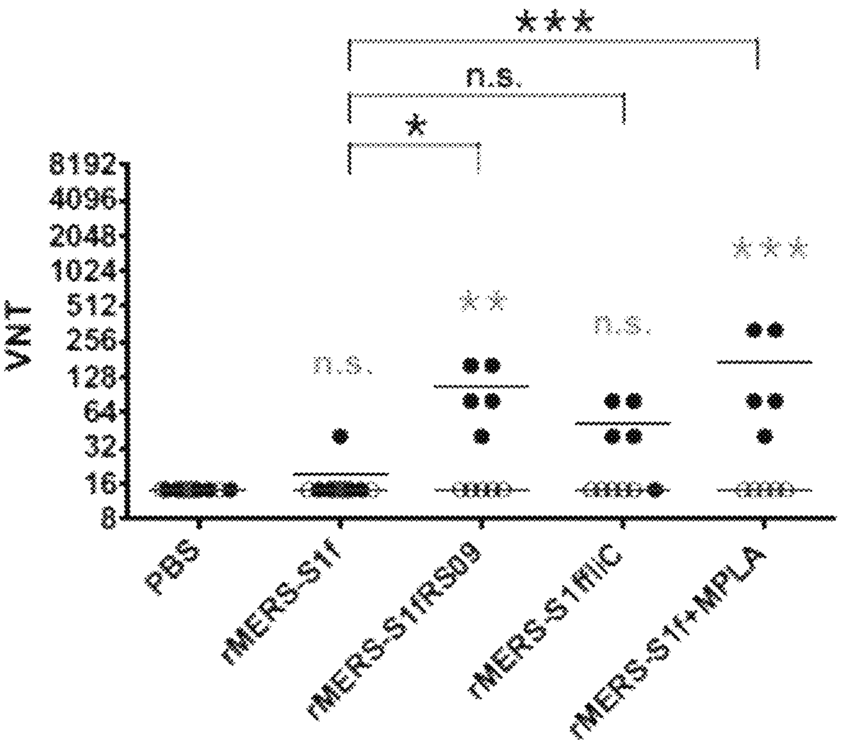
Figure 21D:
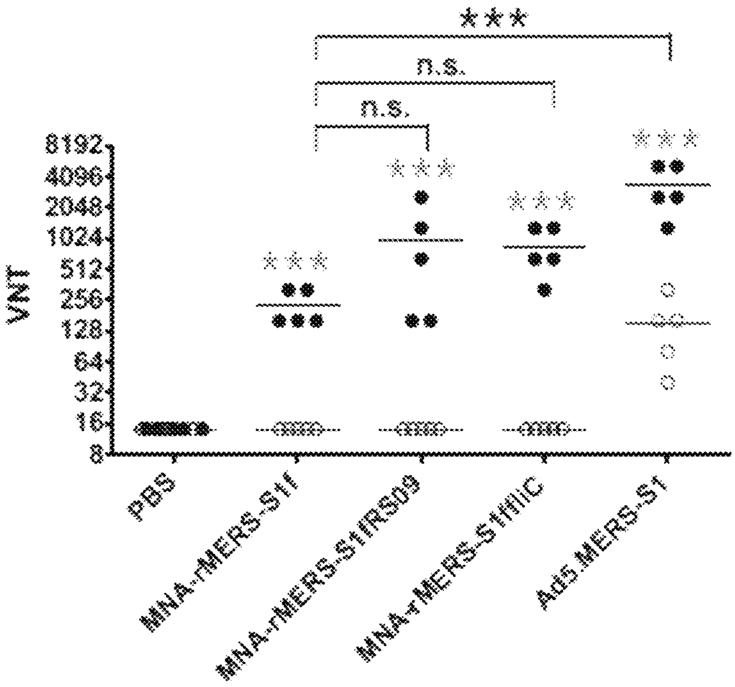

Mouse sera were also tested for their ability to neutralize MERS-CoV (EMC isolate). As shown in FIG. 21C, there were no detectable MERS-CoV-neutralizing antibodies in the sera of mice immunized s.c. with MERS-S1f-, MERS-S1f RS09-, or MERS-S1ffliC at week 4. However, at week 6, sera of animals immunized with rMERS-S1fRS09, rMERS-S1ffliC, or rMERS-S1f+MPLA had significant and comparable levels of virus neutralizing activity, with geometric mean neutralizing titers of 104, 50.8, and 168, respectively. These titers were 5.4, 2.6, and 8.8 fold higher than that of sera from the mice immunized with MERS-S1f only (VNT mean, 19.2). As shown in FIG. 18D, at week 6 all groups of MNA immunized mice developed robust levels of neutralizing antibodies (***, P<0.001). Animals immunized with MNA-rMERS-S1f RS09, MNA-rMERS-S1ffliC, and Ad5.MERS-S1 had geometric mean neutralizing titers of 960, 832, and 3328, respectively. No neutralizing activity was detected in the sera of mice immunized with PBS. These results suggest that MNA delivery of these candidate subunit vaccines induces strong antibody-mediated neutralizing activity that approaches that induced by live adenovector immunization and exceeds that observed by s.c. delivery, even when a potent exogenous adjuvant is added to the s.c. vaccine.

Figure 22A:
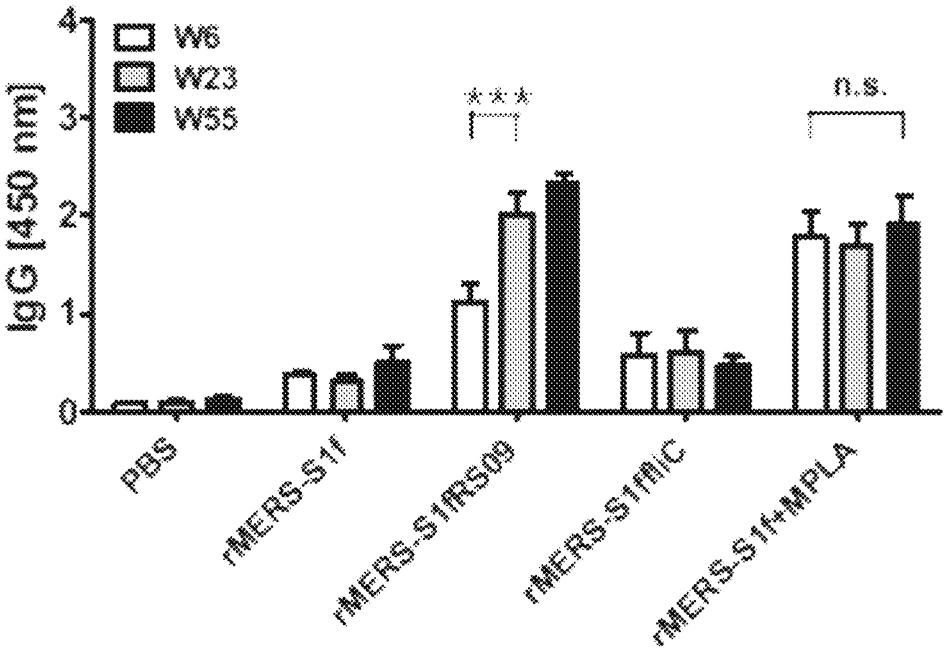
FIGS. 22A-22B: Longevity of immune response in mice vaccinated with subunit vaccines. BALB/c mice were immunized with subunit vaccines as described in the FIGS. 21A-21D legend. On week 23 and 55 after immunization sera were collected and tested for the presence of MERS-S1-specific antibodies by ELISA. Statically significant differences (Tukey's test) are marked by bars and asterisks. , $P<0.01$; *, $P<0.001$; n.s., not significant.
Figure 22B:
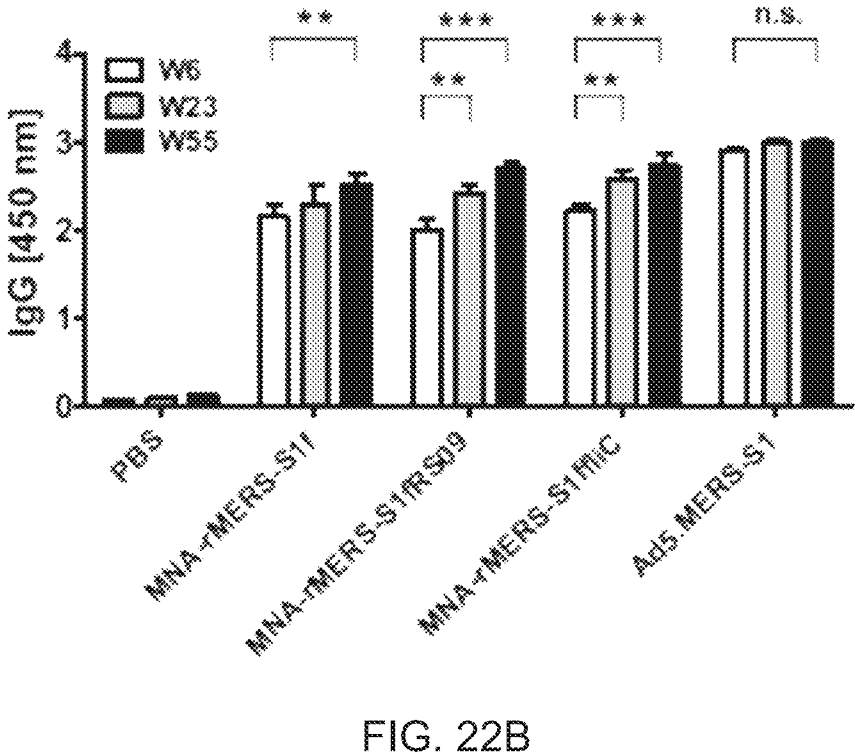

Longevity of the immune response in mice vaccinated with subunit vaccines: To evaluate the persistence of MERS-S1-specific immunity, mouse sera was collected at weeks 23 and 55 after immunization and evaluated for the presence of MERS-S1-specific IgG by ELISA. All animal groups immunized s.c. with recombinant subunit vaccine demonstrated the same or more levels of MERS-S1 IgG specific antibodies at the later time points as those observed at week 6. Surprisingly, mice immunized s.c. with rMERS-S1fRS09 had significantly higher levels of IgG (*, P<0.001) at week 23 compared with those observed at week 6 (FIG. 22A), and this was sustained through 55 weeks. Importantly, MNA delivered vaccines demonstrated generally increasing (statistically significant) levels of MERS-S1-specific antibody through the 23 and 55 week time points (FIG. 22**B). No significant difference was observed in the mice immunized with PBS or Ad5.MERS-S1 at any time point evaluated. These results indicate that MNA-delivered subunit vaccines induce long-lasting MERS-S1 specific antibody responses.

Figure 23A:
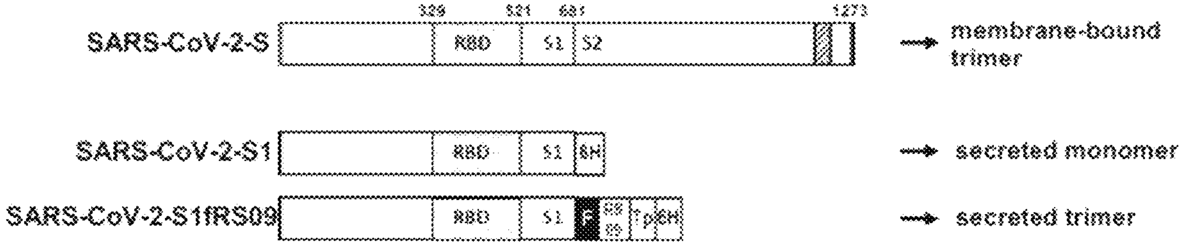
FIGS. 23A-23C: Induction of humoral immune response in mice immunized with MNA delivered SARS-CoV-2-S vaccines. Schematic diagram of rSARS-CoV-2-S1s (FIG. 23A). The positions of the RBD (small dots) and transmembrane domain (stripes) are indicated and S is divided into two subdomains, S1 and S2, at position 681. The SARS-CoV-2-S1 or SARS-CoV-2-S1fRS09 gene was inserted into pmaxCloning expression vector. Western blot of the purified rSARS-CoV-2-S1 (lane 1 and 3) or rSARS-CoV-2-S1fRS09 (lane 2 and 4) proteins with anti-6His monoclonal antibody (FIG. 23B). The purified proteins were resolved on 10% Tris/Glycine gel after being boiled in 2% SDS sample buffer with β-ME or in native sample buffer without β-ME. C57BL/6 mice were immunized intradermally with native and irradiated MNAs containing 20 μg of rSARS-CoV-2-S1 or rSARS-CoV-2-S1fRS09 (FIG. 23C). On weeks 0, 1, and 2 after treatment, immune sera from mice were collected and tested for the presence of SARS-CoV-2-S1-specific antibodies by ELISA. Statically significant differences (Tukey's test) are marked by bars and asterisks. ***, $P<0.001$; n.s., not significant.
Figure 23B:
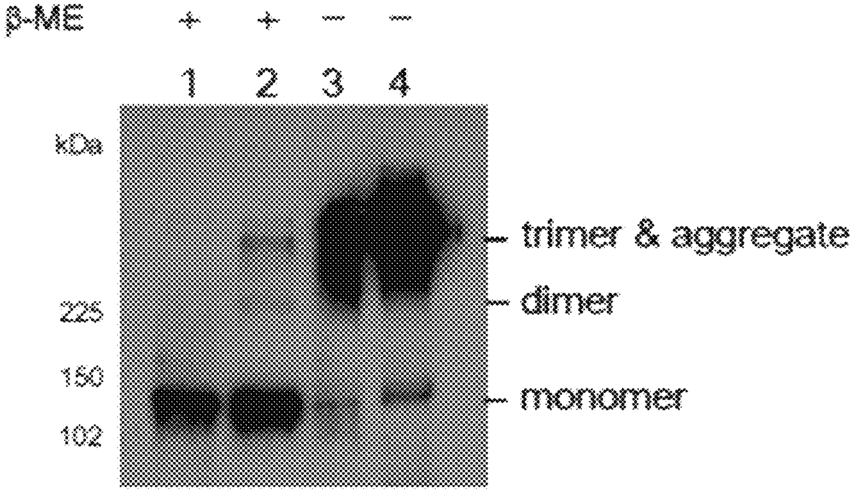
Figure 23C:
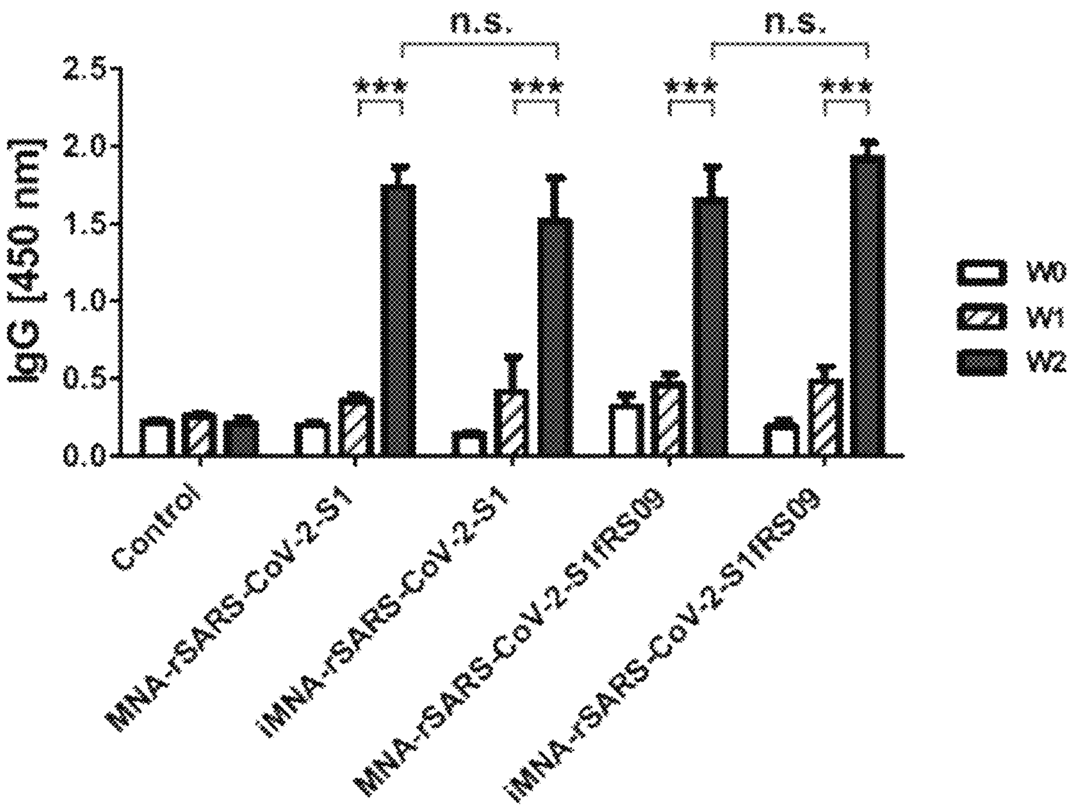

Immunogenicity of MNA delivered SARS-CoV-2-S1 subunit vaccines: Based on these MERS-S1 vaccine results and the urgency of the public health threat, we focused our efforts on the development of SARS-CoV-2-S1 and SARS-CoV-2-S1fRS09 subunit vaccines (schematically shown in FIG. 23A). The size and trimerization product of the vaccine was confirmed by western blot (FIG. 23B). We used MNAs to vaccinate mice with SARS-CoV-2-S1 and SARS-CoV-2-S1fRS09 subunit vaccines via intracutaneous delivery. In addition, to reproduce sterility protocols that would be used for clinical vaccines, we gamma irradiated groups of MNAs with each vaccine. Sera was collected prior to immunization (week 0) and at weeks 1 and 2, and evaluated for the presence of SARS-CoV-2-S1 specific antibodies by ELISA as previously described. As shown in FIG. 23C, robust and statistically significant (*, P<0.001) SARS-CoV-2 IgG responses were detected as early as week 2 for all subunit vaccines. As shown in FIG. 23C, robust and statistically significant (*, P<0.001) SARS-CoV-2 IgG responses were detected as early as week 2 for all subunit vaccines. At this time point, inclusion of the RS09 ligand in the trimer subunit did not have a significant effect on SARS-CoV-2 specific IgG titers. Further, the immunogenicity of gamma irradiation sterilized MNA vaccines was comparable to that of unirradiated MNA vaccines (FIG. 23C), thereby providing additional feasibility for clinical translation and testing.

Pilot manufacturing of a clinical SARS-CoV-2-S1 subunit vaccine: Relying on our experience with MERS-CoV and SARS-CoV vaccines, and our clinical trial experience with MNA delivery, we developed a strategy for the production of clinic grade MNA delivered SARS-CoV-2 subunit vaccines. First, we designed, optimized, and cloned the S1 subunits beginning when the sequence became publicly available. Subsequently, we produced S1 subunit proteins, purified them, and then fabricated dissolvable MNAs integrating the protein subunits for pre-clinical testing in the animal model. Upon confirmation that the MNAs satisfied quality release characteristics, we vaccinated mice with MNA-rSARS-CoV-2 vaccines and began analysis of antibody responses induced in immunized animals. These preclinical studies were initiated within 3 weeks of the vaccine becoming publicly available. In parallel, to enable regulatory approval and rapid clinical testing, we employed Good Manufacturing Processes to expanded S1 subunit protein production, purification, and validation, and incorporated the subunits into dissolvable MNAs or syringes. This was followed by gamma irradiation to assure sterilization of the vaccine loaded MNAs and syringes, and analysis of established release criteria, the latter of which is now ongoing and will be used for an application for IND approval that will enable a safety focused phase I clinical trial.

Discussion

Here we describe the design and production of trimeric recombinant subunit vaccines against MERS—CoV-S1 and SARS-CoV-2-S1 with and without integrated immunostimulatory TLR ligand sequences. We tested the immunogenicity of these vaccine variants delivered either by traditional subcutaneous needle injections, or using MNAs to more specifically target vaccine components to the immune fertile skin microenvironment. We found that MNA delivery of MERS—CoV-S1 vaccines induced stronger humoral responses than traditional needle injections regardless of the inclusion of TLR ligand binding sequences (FIGS. 18A-18B). On the other hand, integration of the RS09 TLR4 binding sequence in the subunit trimer resulted in relatively stronger antibody responses than those without RS09 when vaccines were delivered by subcutaneous injection (FIG. 21A). Interestingly, inclusion of the flagellin TLR5 binding sequence had no effect on the immunogenicity of the subcutaneously (s.c.) delivered vaccines (FIG. 21A). Importantly, significant neutralizing activity was observed in vaccinated animals at week 6. Consistent with previous IgG results, the presence of RS09 in the subunit trimer improved the neutralization function of antibodies from s.c. immunized mice, and this was the only immunogen that resulted in significant neutralization. Notably, MNA delivery was substantially more effective in eliciting neutralizing antibodies for all vaccines. All MNA vaccines generated higher levels of neutralizing antibody, even beyond those induced by an s.c. delivered MPLA adjuvanted vaccine, and similar to those seen following the delivery of the rMERS-S1f construct via an infectious adenovirus vector. Though levels of neutralizing antibody were elevated in mice immunized with trimers including either RS09 or flagellin, these increases were not statistically significant when compared to the MNA vaccine alone (FIGS. 18C and 18D). Thus, though the contributions of the integrated TLR ligands to the strong immune responses induced by MNA vaccines appear to be minimal, they provide promising benefit for s.c. vaccine administration, and their potential for contribution to immunogenicity in humans has yet to be determined.

Based on our results with MERS—CoV-S1 vaccines, we focused our efforts to develop MNASARS-CoV-2 vaccines. Using the described approach, within two weeks of publication of the SARS-CoV-2-S1 sequence we produced both rBetaCoV-S1 and rBetaCoV-S1fRS09 immunogens and fabricated MNAs using GMP conditions in quantities sufficient for testing. For clinical evaluation, we also gamma irradiated several MNAs of each vaccine component to assure sterility. MNA delivery of either rBetaCoV-S1 or rBetaCoV-S1fRS09 induced substantial and statistically significant increases in antigen-specific antibodies responses at week 2 compared to pre-immunization and week 1 responses. Inclusion of RS09 did not have a significant effect on antibody titer at the 2-week time point. Further, immunogenicity of MNA vaccines was maintained after gamma irradiation sterilization. The significant antibody titers we observed at the early time points without boosting strongly supports the feasibility of our MNA-SARS-CoV-2 vaccines, particularly in the context of similar results obtained with the analogous MERS—CoV-S1 constructs under the same conditions.

Neutralization assays are important to validate antibody function; however, at this early timepoint, we do not have access to validated assays for neutralizing antibodies against SARS-CoV2. Further, at the time of submission of this manuscript, we are just over two weeks post-immunization and based on our MERS-CoV studies, the reliable detection of neutralizing SARS-CoV-2 antibodies may require at least six weeks post immunization. We speculate that this delay in the neutralizing response is likely a result of the time needed for affinity maturation of the SARS-CoV-2 neutralizing IgG antibodies. However, we believe that MNA-SARS-CoV2 vaccines will very likely induce neutralizing immunity as suggested by the vigorous early week 2 antibody responses, and commonalities between both the vaccines and the viruses. Accordingly, even though it is still relatively early to predict that humans immunized with these vaccine candidates will have similar responses and be protected from SARS-CoV-2 or MERS-CoV infections, our studies clearly demonstrate that development, production, and initial animal testing of clinical grade vaccine candidates against SARS-CoV-2 and other emerging infections can be rapidly accomplished.

Microneedle array mediated immunization has several mechanistic advantages over traditional intramuscular or subcutaneous needle injections (Zhao et al. "Transdermal immunomodulation: Principles, advances and perspectives", 2018, *Adv Drug Deliv Rev;* 127:3-19; Prausnitz, *Annu Rev Chem Biomol Eng,* 2017). The skin is immunologically reactive and contains a high density of antigen presenting and immune-accessory cells with innate immune function including keratinocytes, mast cells, and innate lymphocytes. Redundant skin immunoregulatory circuits can respond to a wide variety of damage or infection related signals to rapidly orchestrate an innate immune response. Further, MNA deliver vaccine components to a defined 3D space within the skin microenvironment which results in very high vaccine concentrations with relatively low dose antigen delivery. MNA delivery of vaccines to targeted skin microenvironments results in both higher and prolonged exposure of skin resident antigen presenting cells and other innate immune cells to vaccine components. Moreover, transient mechanical stress from microneedle insertion can induce a natural local innate immune response which can serve as a physical adjuvant to enhance antigen-specific adaptive immunity. An additional advantage is that delivery of lower doses to a localized 3D space improves safety by reducing systemic exposure. Further, MNA delivery has the potential to accelerate the process of vaccine production and to significantly reduce cost by considerably reducing the required vaccine doses. Vaccine components including proteins are typically stabilized by integration into the MNA polymer matrix, and maintain their conformational structures, as evidenced by maintenance of antibody binding function (Korkmaz et al. "Tip-Loaded Dissolvable Microneedle Arrays Effectively Deliver Polymer-Conjugated Antibody Inhibitors of Tumor-Necrosis-Factor-Alpha Into Human Skin", 2016*, J Pharm Sci-Us;* 105(11): 3453-7). Thus, MNA vaccines can be stored at room temperature, eliminating the substantial costs associated with the "cold chain" necessary for current vaccines. Finally, the MNAs described here are designed to be applied without the need for an applicator or any specialized equipment, supporting the potential for self-administration. Together, these features provide several important advantages that support the future development of MNA vaccines for global protection from rapidly emerging infectious diseases.

Taken together, our studies demonstrate the speed at which vaccines against emerging infections can be designed and produced using the recent extraordinary advances in recombinant DNA technology. Combining emerging biotechnology methods with bioengineering advances in vaccine delivery strategies, it may now be possible to produce clinical grade vaccines against novel pathogens for human testing and subsequent global distribution in time to significantly impact the spread of disease.

Added-value of this study: These studies demonstrate the immunogenicity and clinical manufacturing of microneedle array (MNA) delivered novel recombinant subunit vaccines against coronaviruses, specifically vaccines targeting SARS-CoV-2 and MERS—CoV-S1, that eliciting potent virus-specific antibody responses. Toward addressing the need for urgency in translational efforts, batch production of clinical MNA SARS-CoV-2 subunit vaccines was completed within four weeks of identification of the novel SARS-CoV-2 sequence. MNA delivered MERS S1 and SARS-CoV-2 S1 subunit vaccines induced long-lasting antigen-specific antibody responses that appeared as early as 2 weeks after vaccination. Importantly, MNA delivery of these coronavirus vaccines generated significantly stronger immune responses than those administered by traditional subcutaneous injection, indicating improved immunogenicity by skin-targeted delivery. Collectively, these studies demonstrate the rapid design, production, and pre-clinic testing of clinically applicable MNA subunit vaccines the prevention of SARS-CoV-2 and other emerging infectious diseases.

Implications of all the available evidence: MNA delivery of coronaviruses-S1 subunit vaccines is a promising immunization strategy against MERS-CoV and SARS-CoV-2 infection, and ready to begin the regulatory process required for the initiation of phase I clinical trials. The described approach can be readily adapted to produce other protein-based virus-specific vaccines against a broad range of emerging infectious diseases. This is one of several novel vaccine approaches now under development, including vaccines delivering antigens in the form of inactivated virus, mRNA, DNA, or protein immunogens. Together by combining recent advances in our understanding of immunobiology, recombinant DNA technology, and vaccine delivery technologies it may now be possible to produce clinical grade vaccines against novel pathogens for human testing and subsequent global distribution in time to significantly impact the spread of emerging infectious diseases.

Example 3—Exemplary Clinical Trial

On Dec. 31, 2019, Chinese authorities reported a cluster of pneumonia cases in Wuhan, China, most of which included patients who reported exposure to a large seafood market selling many species of live animals. Emergence of another pathogenic zoonotic HCoV was suspected, and by Jan. 10, 2020, researchers from the Shanghai Public Health Clinical Center & School of Public Health and their collaborators released a full genomic sequence of SARS-CoV-2 to public databases, exemplifying prompt data sharing in outbreak response. Preliminary analyses indicate that SARS-CoV-2 has some amino acid homology to SARS-CoV and may be able to use ACE2 as a receptor. This has important implications for predicting pandemic potential moving forward. The situation with SARS-CoV-2 is evolving rapidly, with the case count currently growing into the hundreds. Human-to-human transmission of SARS-CoV-2 occurs, as evidenced by the infection of 15 health care practitioners in a Wuhan hospital. The extent, if any, to which such transmission might lead to a sustained epidemic remains an open and critical question. So far, it appears that the fatality rate of SARS-CoV-2 is lower than that of SARS-CoV and MERS-CoV; however, the ultimate scope and effects of the outbreak remain to be seen. Drawing on experience from prior zoonotic CoV outbreaks, public health authorities have initiated preparedness and response activities. Wuhan leaders closed and disinfected the first identified market. The United States and several other countries have initiated entry screening of passengers from Wuhan at major ports of entry. Health practitioners in other Chinese cities, Thailand, Japan, and South Korea promptly identified travel-related cases, isolating individuals for further care. The first travel-related case in the United States occurred on January 21 in a young Chinese man who had visited Wuhan.

Additionally, biomedical researchers are initiating countermeasure development for SARS-CoV-2 using SARS-CoV and MERS-CoV as prototypes. For example, platform diagnostic modalities are being rapidly adapted to include SARS-CoV-2, allowing early recognition and isolation of cases. Broad spectrum antivirals, such as remdesivir, an RNA polymerase inhibitor, as well as lopinavir/ritonavir and interferon beta have shown promise against MERSCoV in animal models and are being assessed for activity against SARS-CoV-2. Vaccines, which have adapted approaches used for SARS-CoV or MERS-CoV, are also being pursued. While the trajectory of this outbreak is impossible to predict, effective response requires prompt action from the standpoint of classic public health strategies to the timely development and implementation of effective countermeasures. The emergence of yet another outbreak of human disease caused by a pathogen from a viral family formerly thought to be relatively benign underscores the perpetual challenge of emerging infectious diseases and the importance of sustained preparedness.

The proposal is to test the hypothesis that MNA-based skin targeted delivery of SARS-CoV-2 virus S1 antigen formulation will stimulate in vivo-specific humoral immunity in human volunteer, as has been observed in BALB/c mice for a closely related beta coronavirus MERS-CoV vaccine. Our approach will combine rationally designed subunit SARS-CoV-2 S1 vaccines with a promising delivery strategy. Importantly, we have designed this skin-targeting vaccine delivery technology specifically to afford advantages in immunogenicity, economy, and safety that will enable broad clinical deployment. The dissolvable MNAs that we have developed enable efficient, precise, and reproducible delivery of biologically-active vaccines to the skin. This MNA delivery platform is directly applicable to patient-friendly, clinical vaccination. Because the microneedles in these arrays have been engineered to not penetrate to the depth of vascular or neural structures, it is expected that delivery to human skin will be both painless and bloodless. The fabrication process is flexible and enables simple and rapid low-cost production with efficient scale-up potential. These structural and manufacturing advantages, coupled with a final product that is stable at room temperature and inexpensive to transport and store, makes this technology, enabling broad and rapid clinical vaccine deployment, applicable to the prevention and/or treatment of a broad range of other zoonotic and human diseases.

The studies proposed in this clinical study are highly significant and that a successful outcome will be a timely contribution to the advancement of the SARS-CoV-2 vaccine development field. This proposal is founded on the following three scientific premises: (1) SARS-CoV-2 is a zoonotic virus that sporadically infects human resulting in a high mortality rate; (2) skin represents a highly immunogenic target for vaccine delivery; and, (3) needle-free delivery of thermostable vaccine products would fulfill a global, unmet public health need in several priority disease areas for which WHO encourages vaccines development, including Human-CoV.

Product Name: The study product is a recombinant subunit spike 1 glycoproteins from SARS-CoV-2 fused to the T4 fibritin foldon trimerization domain with the fusion of a Toll-like receptor 4 (TLR-4) agonist peptide (RS09).

Figure 24:
FIG. 24: The schematic diagram of a SARS-CoV-2-S1fRS09 polypeptide.

Chemical name and structure: The schematic diagram of an exemplary immunogen can be found in FIG. 24.

The 2019nCoV-S1 from BetaCoV/Wuhan/IPBCAMS-WH-05/2020 (GISAID accession id. EPI_ISL_403928 amino acids 1 to 661) gene was codon-optimized for optimal expression in mammalian cells by the UpGene codon optimization algorithm and synthesized by GenScript. The recombinant subunit glycoproteins 2019nCoV-S1 is fused to the T4 fibritin foldon trimerization domain with the fusion of a Toll-like receptor 4 (TLR-4) agonist peptide (RS09). Moreover, this antigen was designed with a polyhistidine-tag sequence to facilitate downstream large-scale purification compatible with clinical manufacturing.

Objectives

Primary: (1) Evaluate the safety and tolerability of the preventative SARS-CoV-2 subunit vaccine in a randomized, placebo-controlled Phase I trial in healthy volunteers.

Secondary: (2) To assess the immunogenicity of the SARS-CoV-2 subunit vaccine vaccination is measured by the detection of spike specific humoral and T-cell responses.

Study Design

This study will be a randomized, placebo controlled, double-blind, Phase I trial that will evaluate the safety and immunogenicity of the SARS-CoV-2 subunit vaccine.

Selection and Enrollment of Subjects: Eligible subjects will be identified, willing to participate in vaccine research. All adults who meet the entry criteria will be eligible for this trial. No patient will be excluded due to race, ethnicity, or gender. The participation of women and minority patients is encouraged. Children will not be included in this initial safety trial. Eligible subjects will meet with the research coordinator and physician investigator for discussion and review of the details of the study. The physician investigator will obtain written informed consent from each subject prior to any study-related procedures including screening.

Inclusion Criteria: (1) Male or female adults, age 18-50 years; (2) Negative Hepatitis B antigen; (3) Negative Hepatitis C antibody; (4) All women of reproductive potential must have a negative urine pregnancy test within 30 days of study entry. All subjects must agree to practice adequate birth control to prevent pregnancy throughout the study period. Acceptable methods of birth control should include barrier methods such as the male or female condom, and diaphragm; (5) General good health as determined by medical history, physical exam and laboratory evaluations; (6) The following laboratory values obtained within 30 days prior to study entry:

Hemoglobin≥9 g/dL

Platelet count ≥100,000/$mm^3$

ANC≥1000/$mm^3$

PT<1.2×ULN and PTT<1.5×ULN

Alkaline phosphatase, AST, ALT, and total bilirubin<1.5×ULN

Creatitine phosphokinase<2.0×ULN

Serum creatinine, lipase, calcium, phosphate within normal limits

Negative anti-ds DNA

ANA≥1:40;

(7) Ability and Willingness to Give Written Informed Consent.

Exclusion Criteria: (1) current or recent (within 60 days of study entry) of any immunomodulatory drugs including but not limited to the following: systemic corticosteroids or other immunosuppressive (cyclosporin, tacrolimus, methotrexate, azothiaprine), interferons, interleukins, thalidomide, GM-CSF, immunoglobulin. Subjects must not have any underlying disease that may require the use of such medications during the study period; (2) Receipt of live attenuated vaccine within 30 days of first study vaccination or inactivated vaccine within 14 days of first study vaccination; (3) Use of any investigational agent within 30 days prior to study entry; (4) Receipt of blood products within 120 days of study entry; (5) Pregnant or breastfeeding women; (6) Active alcohol or drug use, which in the opinion of the investigators, would interfere with adherence to the study requirements; (7) Any current or past medical condition which, in the opinion of the investigator, may interfere with the conduct of the study or evaluation of adverse events.

Study Procedures

A total of 36 subjects will be enrolled into this study. Three dose levels will be studied as follows: Group I at 5 μg of the immunogenic composition per dose; Group II at 20 μg of the immunogenic composition per dose; and Group III at 80 μg of the immunogenic composition per dose.

The trial is designed as randomized, placebo-controlled double-blinded phase I trial in healthy volunteers. The primary goal is to determine the safety and tolerability of 3 dose levels of a SARS-CoV-2 subunit vaccine. A dose level will be considered safe if no more than 2 of 9 subjects have relatively severe vaccine-related grade 2 toxicities during the 12 week period following the first vaccination (see Table 1 below).

TABLE 1

Decision Rules for Dose Level Escalation

| No. of subjects with grade 2 toxicities at this dose level | No. of subjects treated at this dose level | Action |
|---|---|---|
| 0 or 1 | 3 | Treat 6 more subjects at this dose level. |
| >1 | 3 | Halt the trial, and review toxicity data; see below. If the trial is continued, treat 6 more subjects at this dose level. |
| 0, 1 or 2 (observation period: 12 weeks after the first vaccination) | 9 | Treat 3 subjects at the next higher level, or if at the highest level, declare this level to be safe, and close the trial. |
| >2 (observation period: 12 weeks after the first vaccination) | 9 | Halt the trial, and review toxicity data; see below. If the trial is not closed due to toxicity, treat 3 subjects at the next higher level; if at the highest level, declare this level to be safe, and close the trial. |

Subjects will be accrued in block sizes of 4 or 8, and randomly assigned to treatment or placebo in the ratio of 3:1. At the start of the trial, 3 subjects will be treated at the lowest dose level. The decision rules given in the table below are based on the grade 2 toxicities observed in this and subsequent cohorts; to affect decisions, toxicities must be judged to be possibly, probably or definitely related to vaccination. The occurrence of two grade 2 or any grade 3 or 4 toxicities will result in interruption of the trial until an interim safety review can be conducted. The observation period will begin immediately following the first vaccination, and will last no less than 8 weeks (4 weeks after the boost). Because subjects in a cohort are not expected to be accrued simultaneously, the time available for observing some subjects will be greater than the minimum of 4 weeks. All grade 2 toxicities occurring during the time available for observing subjects will be used to determine how to treat a new cohort.

If the trial is halted due to toxicity, all toxicity data accumulated during the trial will be reviewed to decide whether to continue or close the trial. If the toxicities are grade 3 or relatively severe grade 2, and the patterns of occurrence of similar toxicities of all grades suggests that they are vaccine-related, the trial will be closed. (Patterns to be considered will include temporal relationship to vaccination, frequency of various grades among subjects, and comparisons to placebo-treated subjects.) Otherwise the trial will continue. The interim safety reviews will be conducted by the protocol team and reviewed with the DSMB as needed.

Cohorts need not be completed if decisions can be made on the basis of an incomplete cohort. If, for example, the first two subjects treated at a dose level experience grade 2 toxicities, the trial can be halted without accruing the third member of the cohort. Clinical and Laboratory Evaluations Screening/Pre-entry: Eligible subjects will have a screening visit 30 to 60 days before study entry. Written informed consent will be obtained prior to the initiation of any study procedures (including screening). The screening evaluation will include medical history, vital signs, weight and height. Blood will be collected for HIV antibody testing, CBC with differential and platelet count, liver function tests (AST, ALT, alkaline phosphatase, total bilirubin), serum chemistries (CPK, creatinine, lipase, calcium, phosphorus), anti-ds-DNA, ANA, HbsAg, HCV Ab, and urine pregnancy test for women with childbearing potential. The medical history will include all prior and current medical diagnoses. All prescription medications taken in the past 30 days (with doses) will be recorded.

Eligible subjects will return to the clinic within 14 days of study entry for the pre-entry visit. At this time blood will be obtained for T-lymphocyte phenotyping and for storage of plasma and PBMC. The pre-entry visit will include a physical exam and review of the study procedures.

On-Study, Clinical Evaluations: A complete physical exam will be performed at Pre-entry and then at Week 8, and for early study discontinuation. A symptom directed examination will be performed as needed at all other visits.

On-Study, Laboratory Evaluations: Hematology and/or serum liver function tests will be obtained every four weeks until week 16 and at week 24 and 48 (or early discontinuation). Urine pregnancy tests will be done prior to each vaccination (Week 0 and 8) and at any time that pregnancy is suspected. Serum chemistries will be done at Weeks 24 and 48. Serum will be collected for SARS-CoV-2 neutralizing antibodies and T cell testing at each visit post-vaccination.

On-Study, Immunologic Monitoring: Immunologic monitoring of response to the MNA-based vaccine will include the following assays performed with specimens collected prior to, during and after the administration of the vaccine, as indicated in the study calendar:

a) SARS-CoV-2 neutralizing antibodies assay.

b) Direct ELISPOT for IFN-γ secretion in response to the overlapping peptides matching the vaccine immunogen.

Whole blood will be collected in sodium heparin tubes and PBMC isolated using Accuspin tubes. PBMC will be cryopreserved in 10% DMSO and Fetal Bovine Serum at a concentration of 12-15×$10^6$ PBMC per vial. Control samples from a placebo-vaccinated individual will be drawn at the same time and stored in parallel. These samples will serve as storage controls where viability and recovery will be calculated prior to thawing vaccine samples. This will facilitate monitoring of the effects of storage over time. PBMC will be stored in the vapour phase of liquid nitrogen.

SARS-CoV-2 neutralizing antibodies assay: Serum specimens will be heat-inactivated at 56° C. for 30 minutes prior to testing. Serially diluted serum samples (1:20, 1:40, 1:80, 1:160, 1:320, and 1:640) from the 36 vaccinated volunteers at different time points, will be seeded in triplicate into 96-well tissue culture plates. Neutralization titers will be measured as the reciprocal of the highest dilution of serum that completely inhibited infection of Vero cells agglutination of 1% horse erythrocytes by 10e6 pfu of SARS-CoV-2 virus.

IFN-γ ELISPOT assay: Antigen-specific T cell responses will be identified using IFN-γ ELISPOT assay. A series of overlapping peptides matching the vaccine gene inserts will be used as immunogens in the assay. Vaccine responses will be measured from cryopreserved PBMC and can thus be batched over time and assayed simultaneously cryopreserved PBMC will be thawed and rested overnight prior to use in the ELISPOT assay. Cell viability and counting will be performed using a Guava Counter. PBMC yields and recoveries will be recorded according to the SOP used for the ELISPOT assay. The IFN-g ELISPOT assay will be used to screen thawed PBMC for responses to overlapping peptides matching the vaccine immunogen. PBMC will be assayed for IFN-g production in response to peptide stimulation using synthesized peptides. The advantage of this assay is that a large panel of peptides can be used to screen for T cell recognition. The basis of the assay is that cells responding to short peptide fragments (9-20 amino-acids in length) for between 6-16 hours will secrete IFN-g when there is T cell receptor engagement with the MHC-bound peptide. This response will provide an approximation to which peptides (epitopes) are recognized by CTL using sets of 15mers overlapping by 11 amino-acids. High protein binding 96-well plates (Millipore) will be coated with IFN-g monoclonal antibody (Mabtech). To each well 2×$10^5$ PBMC will be added plus peptide and incubated at 37° C. for 16 hours. After washing biotinylated IFN-g will be added and incubated at room temperature for 3 hours. Strepatavidin horseradish peroxidase will be added and subsequently developed with NovaRed substrate after further washing. The number of dark red spots will be enumerated using the CTL Immunospot Reader. The frequency of cells responding to short-term incubation with peptide will allow quantitation of peptide-responses at the single cell level. The number of antigen-specific T cells will be calculated by subtracting the negative control values and the number of positive responses will be deemed greater than 55 spot forming units per $10^6$ PBMC or three times the background spots/well, but with at least 20 spot per $10^6$ PBMC. Positive responses will be verified by CD3-depletion of PBMC to observe whether there is >50% reduction of response. Cell depletions will be performed using Dynal Beads according to the manufacturer's instructions. Positive controls in the assay will consist of PHA (assay control) and a pool of optimal peptides to CMV, EBV and 'Flu (CEF). Positive control PBMC samples will also be used on every plate to control for plate and operator variability. Positive PBMC samples will be obtained from buffy coat bloods where there is a known response to CEF pools.

Study Treatment

Vaccine Description and Preparation: The vaccine product may be a recombinant subunit glycoproteins SARS-CoV-2 fused to the T4 fibritin foldon trimerization domain with the fusion of a Toll-like receptor 4 (TLR-4) agonist peptide (RS09). The subunit vaccine is formulated in microneedle array patches.

Placebo: The placebo will consist in empty MNA patches.

Vaccine Administration: One administrations (Week 0) of the vaccine (or placebo) will be given percutaneously. Subjects will be observed for at least one hour following immunization for the occurrence of any acute hypersensitivity reaction. Subjects will be instructed on the use of a thermometer for temperature monitoring and the symptom diary card prior to discharge from the clinic. Subjects will be contacted by telephone 48 hours after vaccination. If telephone contact is not possible, subjects will return to the research unit for assessment of vaccine related side effects.

Evaluation and Management of Toxicity

Anticipated Toxicities: Subunit recombinant vaccine have been used for vaccine studies in a number of human diseases since 1950. Data from these studies indicate intradermal administration of subunit vaccines has been generally well tolerated with minor local reactions but no serious events. A dose escalation trial of percutaneous MNA-based drug administration in humans was associated with moderate sporadic reactions. These events resolved without residual effect within 24-48 hours following vaccination. In several preclinical study recombinant subunit vaccines were given without evidence of toxicity. Formal toxicity studies will be conducted prior to the initiation of the trial.

Toxicity Grading: All toxicities will be graded using the FDA Table for Grading Severity of Adverse Experiences. Adverse events not included in these tables will be graded as follows: 0=none, 1=mild, 2=moderate, 3=severe, 4=Potentially life-threatening.

Local Reactions: Local reactions of mild to moderate severity (grades 1 and 2) will usually resolve spontaneously. Conservative measures such as cold compresses, oral acetaminophen or non-steroidal anti-inflammatory agents may be used as needed. Subjects who experience Grade 3 or 4 local reactions will not receive additional vaccinations. All grade 3 or 4 reactions must be monitored closely until resolution. Local therapy including medical or surgical intervention will be undertaken as appropriate.

Systemic Reactions: Subjects with mild to moderate systemic reactions thought to be possibly, probably or definitely related to the vaccination may continue to receive subsequent vaccinations with close monitoring at the discretion of the investigator. Subjects with grade 3 or 4 systemic reactions will be followed closely until resolution of the symptoms. Subsequent vaccinations may not be administered to subjects with grade 3 or 4 systemic reactions that are considered possibly, probably or definitely related to the vaccination. Subjects who discontinue vaccination will continue to be monitored on the study protocol and will adhere to the same study visit schedule.

Dose Modification: There will be no dose modification in this protocol.

Therapy Modification/Stopping Rules: (A) Subjects will be withdrawn from the study intervention (e.g. will receive no further vaccination) in the following circumstances: (1) Subjects with evidence of an untoward response including allergic or atopic responses will be treated as appropriate symptomatically. Subjects with any Grade 3 or 4 clinical or laboratory adverse events considered definitely, probably or possibly related to study vaccination will not be further subjected to vaccination; (2) Subjects experiencing any treatment related toxicity will be monitored as indicated clinically until resolved; or (3) other criteria for Discontinuation of subjects from the study treatment.

(B) Subjects will be withdrawn from the study intervention (e.g., will receive no further vaccination) in the following circumstances: (1) the subject becomes pregnant; (2) The investigator determines that further participation would be detrimental to his/her health or well-being; (3) the subject fails to adhere to the study regimen or other study requirements so as to cause harm to self or seriously interfere with the validity of the study results; or (4) the subject requires treatment with medications that are disallowed while on this study.

(C) Subjects may be permanently discontinued from the study for the following reasons: (1) withdrawal of consent by the subject with refusal to continue with study related procedures or follow-up evaluations; (2) completion of the study; or (3) termination of the study by the investigator, the Food and Drug Administration.

(D) Dose Escalation criteria/Stopping rules: Enrollment into this protocol will be halted in the event of any severe (grade 3 or 4) clinical or laboratory event for which a relationship to the study product cannot be ruled out. The study investigator will consult with the DSMB prior to continuation of enrollment. Additionally, the occurrence of moderate (grade 2) unexpected events in 2 or more subjects will result in the halting of enrollment pending further investigation of the events. Following such investigation, the protocol may resume after consultation with the DSMB and if necessary, the FDA.

Statistical Considerations

The primary objectives of this phase I study are a) to determine the safety and tolerability of 3 dose levels of the SARS-CoV-2 subunit vaccine, b) to document the observed toxicities, and c) to establish preliminary point estimates and upper bounds for the incidence rates of toxicity. The secondary objective is assessing immunogenicity of the vaccine in a preliminary manner.

Trial Design: The trial is designed as randomized, placebo-controlled double-blinded phase I trial in healthy volunteers. There will be 9 vaccine-treated and 3 placebo-treated subjects in each of 3 dose levels. Section 3 describes the trial design and defines tolerability. The design has the following property: if 0, 1 or 2 of the 9 subjects treated at a dose level experiences grade 2 toxicities, there would be 90% confidence that the true rate of toxicity in the population will be less than 23%, 37%, or 49%, respectively. If there is no evidence of a dose-toxic response relationship, and no toxicity is observed in the 27 treated subjects, there would be 90% confidence that the true rate of toxicity will be less than 8%.

Statistical Analyses of Safety and Tolerability Data: Descriptive statistics will be calculated on the safety parameters for all subjects enrolled in the study who receive at least one vaccination. Data listings and tables will be presented and a safety analysis will be performed on the occurrence of local and systemic toxicities. These summaries will be competed for the three dose groups separately and also for the pooled data. In addition, if toxicity data are sufficient, the relationship between dose and the severity of the observed toxicity will be assessed with the Jonckheere-Terpstra test. Point estimates of toxicity will be computed; estimates corrected for toxicity observed in the placebo-treated subjects will also be computed.

Statistical Analyses of Immunogenicity Data: Data on humoral and cellular immune response to vaccination will be presented in tables that are stratified on dose level. The primary indicator of immune response will be taken to be the development of neutralizing antibodies raised against the SARS-CoV-2 virus. It is assumed that, prior to the first vaccination, subjects will have no detectable SARS-CoV-2 specific antibodies. (If this assumption were to be proven incorrect, analyses would be modified appropriately.) The analysis goals are 1) to determine for each dose level the fraction of subjects that achieve detectable levels of neutralizing antibodies (>1:8), 2) to determine whether that fraction increases with dose, and 3) to determine for each dose level whether that fraction increases after the second vaccination. The last two goals will be addressed with the trend and McNemar's tests, respectively. Since the trial is not specifically designed to achieve these goals, it is likely that the results will be primarily useful as pilot data for the design of a subsequent trial. To augment these analyses, we will also carry out similar, but more sensitive analyses based on the antibody levels as measured by the endpoint titers of the Vero cells neutralization assay. The antibody levels will be tabulated as a function of dose tier, as will changes in levels resulting from the second vaccination. Inference will be based on the Jonckheere-Terpstra and Wilcoxon signed rank tests. The placebo-treated individuals will provide valuable data on the within-subject variability of all measures of immune response.

Schedule of events: The schedule of events can be found in Table 2.

TABLE 2

Schedule of Events

| Evaluations | Screening/ Pre-entry | Entry Week 0 | Wk 2 | Wk 4 | Wk 8 | Wk 12 | Wk 16 | Wk 20 | Wk 24 | Wk 36 | Wk 48 | Early Disc |
|---|---|---|---|---|---|---|---|---|---|---|---|---|
| Written IC | X | | | | | | | | | | | |
| Complete H + P | X | | | | | | | | | | | X |
| Medical History | X | | | | | | | | | | | |
| Targeted H + P | | X | | X | X | | | | X | | | X |
| HIV Ab | X | | | | | | | | | | | |
| CBC/D/P | X | | | X | X | X | X | | X | | X | |
| PT/PTT | X | | | | | | | | | | | |
| Liver function | X | | | X | | X | | | | | | |
| Chemistries | X | | | | | X | | | | | | |
| HbsAg, HCV Ab | X | | | | | | | | | | | |
| Pregnancy test[1] | | X | | X | | | | | | | | |
| T-cell phenotyping | X | | | | | | | | | | | |
| Plasma/PBMC | X | X | X | X | X | X | X | X | X | X | X | X |
| Telephone follow-up for symptoms | | X | | X | | | | | | | | |
| Vaccination | | X | | X | | | | | | | | |

[1]Urine pregnancy test will be performed on all women with childbearing potential at the screening visit and prior to each vaccination. This test should be performed at any other time points if pregnancy is suspected.
[2]Early discontinuation visit should be performed in subjects who discontinue from the study prior to study Week 96

Data Summary

Figure 25:
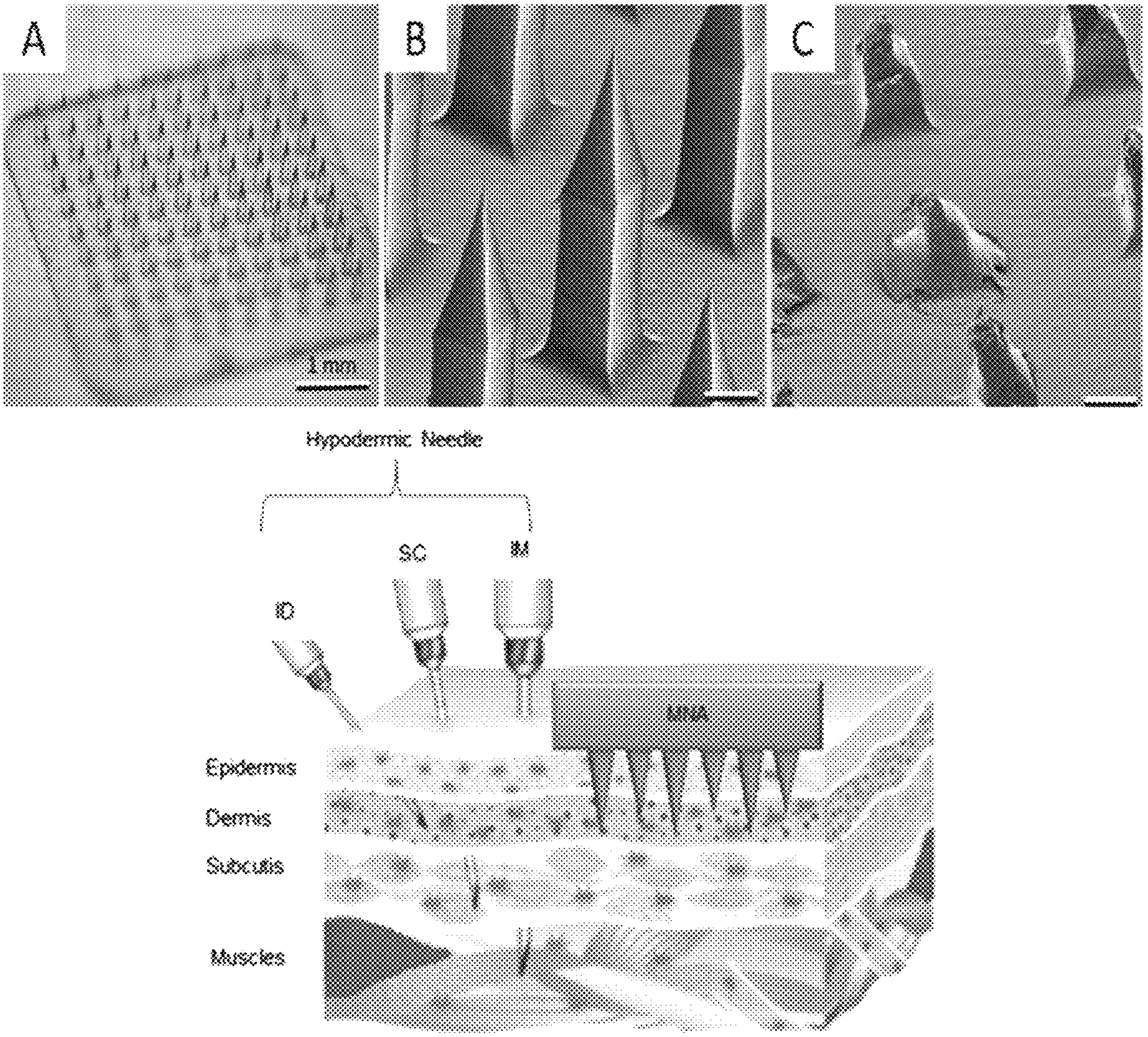
FIG. 25: Microscopic images of an MNA and Schematic representation of needle based vaccine delivery approaches. An MNA (FIG. 25 (A)). Obelisk-shaped needles before (FIG. 25 (B)) and after (FIG. 25 (C)) application of the MNA to the skin. Notice the efficient degradation of the needles in (FIG. 25 (C)). Scanning electron microscopy ×100.

Animal Studies, Preliminary Work: The preliminary work we present below directly support our hypothesis and the rationale for our experimental approach. Briefly, our data demonstrate that we have designed and fabricated highly reproducible, biocompatible, dissolvable CMC-based MNAs that effectively penetrate and deliver integrated cargo to mouse and human skin. The cargo is taken up by APCs and transported to the draining lymph node, where transgenic antigen associated with APC populations can be defined. Novel MNA fabrication technology has been developed and published by Dr. Falo. Briefly, they have demonstrated fabrication of MNAs, integration of several protein and small molecule cargos, and efficient delivery to both mouse and human skin. This novel delivery system integrates cargo into dissolvable CMC microneedles. Each MNA is composed of a 10×10 array of microneedles covering a 6×6 mm area (FIG. 25 (A)). Each individual needle is 700 μm high with a 30-degree apex angle and a 200 μm base (FIG. 25 (B)). Several features of the design, including the obelisk geometry and filet angles (FIG. 25 (B)), have been designed to optimize skin penetration and delivery efficiency. When the MNA is applied to the skin, the microneedles rapidly dissolve (~5 min), depositing the cargo in the localized area of skin penetration (FIG. 25 (C)). To evaluate penetration capability, MNAs were initially tested for piercing on water-based model elastic substrates and on full thickness human skin (FIGS. 25 (A, C)).

Figure 26:
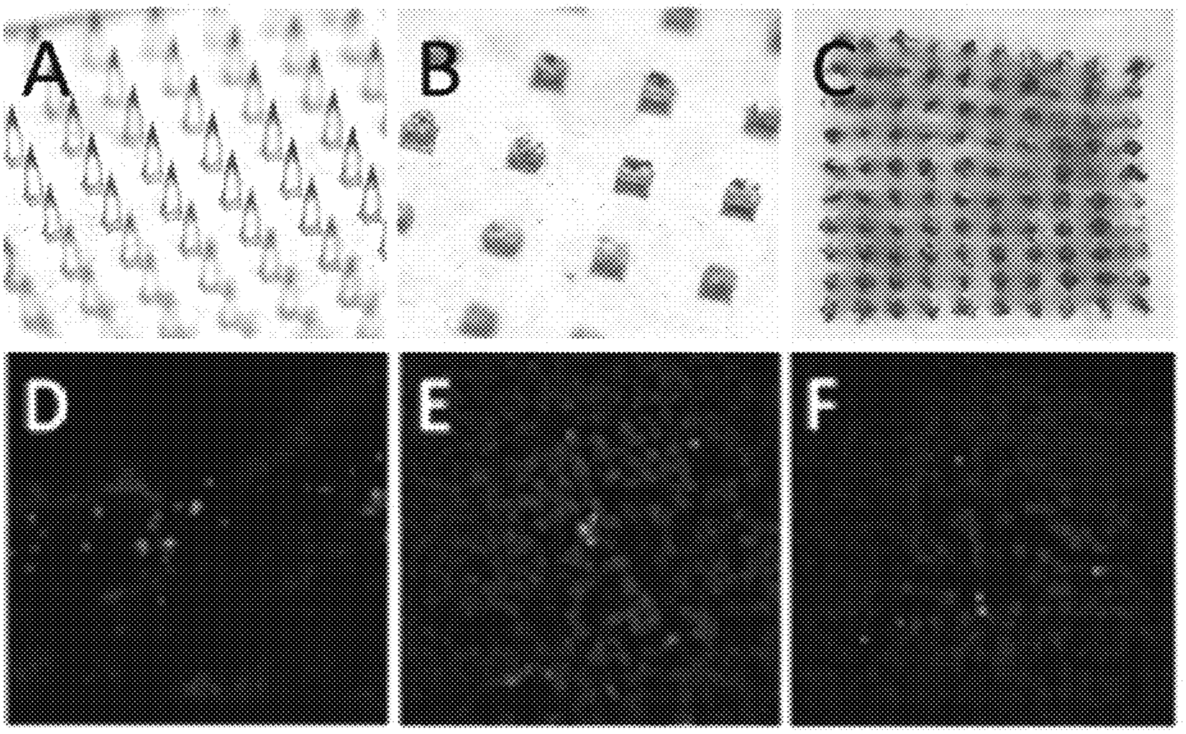
FIG. 26: Penetration and delivery of CMC microneedle cargo to mouse and human skin. Stereo micrographs of sharp pillar type patches before application to human skin (FIG. 26 (A)) and after 5 min. exposure (FIG. 26 (B)) to freshly excised human skin explants where the tracer dye is deposited (FIG. 26 (C)). Cross section of a mouse ear at the MNA insertion site demonstrating delivery of fluorescent tracer beads (FIG. 26 (D), DAPI (blue) and fluorescent particles (green)). After 48 h, the fluorescent tracers were also detectable in the draining lymph nodes, where they were associated with macrophages (FIG. 26 (E), DAPI (blue), F4/80 (red) and fluorescent particles (green)) and dendritic cells (FIG. 26 (F), DAPI (blue), CD11c (red), and fluorescent particles (green)).

The model elastic substrate consisted of 10% CMC and 10% porcine gelatin in phosphate buffered saline (PBS) gelled at 4° C. for 24 hours or longer. The surface of the elastics was covered with 100 μm thick Parafilm to prevent immediate contact of the needle-tips and the patch materials with the water-based model elastics. To enhance stereo microscopic-imaging, trypan blue tracer dye (Sigma Chem., cat #T6146) was incorporated into the CMC-hydrogel at 0.1% concentration. The patches were applied to the targets using a specifically designed spring-loaded applicator and analyzed after 4 min. exposure. Based on gross observation, the microneedles penetrated and released a substantial amount of tracer dye into the artificial substrate, full thickness human skin (FIGS. 26 (B) and 26 (C)), and mouse skin (not shown and below). Images of recovered patches revealed considerable degradation of the needles (FIG. 26 (A)), indicating the dissolution of the CMC matrix. To evaluate cutaneous delivery of particulate antigen in vivo, we applied fluorescent particle-containing MNAs to the dorsal aspect of the ears of anesthetized mice. After five minutes, the patches were removed and the mice resumed their normal activity. Two days later, mice were sacrificed and ear skin and draining lymph nodes were analyzed for the presence of fluorescent particles. Consistent with observations of human skin, particulates were evident in the skin excised from the array application site (FIG. 26 (D)). Further, at the two day time point, a substantial number of particles were evident in the draining lymph node cells in close association with APCs, including macrophages (FIG. 26 (E)) and DCs (FIG. 26 (F)). The skin is rich in readily-accessible DCs and has long been regarded as a highly immunogenic target for vaccine delivery.

We have successfully generated the recombinant MERS-S1f, MERS-S1f-RS09, and MERS-S1f-fliC, subunit vaccines and purified from the supernatant of human embryonic kidney (HEK) 293 cells, and tested them in vitro and in vivo.

Figure 27A:
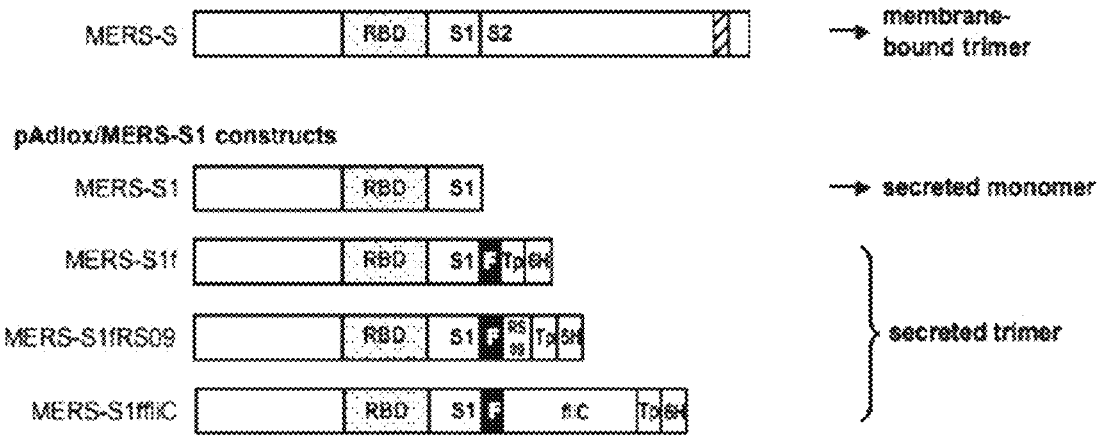
FIGS. 27A-27B: Construction of recombinant MERS-S1 foldon subunit vaccines. Schematic diagram of rMERS-S1s (FIG. 27A). The positions of the RBD (small dots) and transmembrane domain (stripes) are indicated and S is divided into two subdomains, S1 and S2, at position 751. The vector was used to generate recombinant replication-deficient adenoviruses by homologous recombination with the adenoviral genomic DNA. Abbreviations are as follows: ITR, inverted terminal repeat; RBD, receptor binding domain; F, T4 fibritin foldon trimerization domain; Tp, Tobacco Etch Virus (TEV) protease; fliC; *Salmonella typhimurium* flagellin C. Amino acid sequences of peptides in construction *; cleavage site (FIG. 27B).
Figures 27B, 28A:
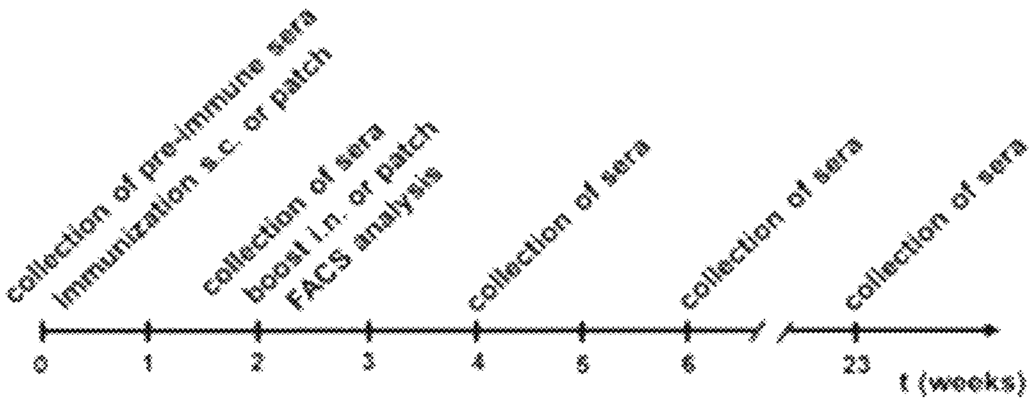
FIGS. 28A-28D: Induction of immune response in mice vaccinated with recombinant MERS-S1fs. Experimental schedule representing the immunization timeline (FIG. 28A). Mice were immunized on week 0 and week 2 with 25 μg of MERS-S1f, MERS-S1f plus 20 μg of MPLA, 25 μg of MERS-S1fRS09, 40 μg of MERS-S1ffliC, respectively, or PBS as a negative control and $10^{11}$vp of Ad5.MERS-S1 as a positive control. MNAs of MERS-S1f, MERS-S1fRS09, or MERS-S1ffliC were administered through intradermal delivery. Flow cytometry assay on HEK 293 cells transfected with pAd.MERS-S1 using 1:20 diluted sera on week 2 (FIG. 28B), week 2, 4, and 6 (FIG. 28C), or on week 23 (FIG. 28D) were collected and tested for the presence of MERS-S1-specific antibodies using ELISA.

The MERS-S1 (GenBank JX869059 amino acids 1 to 725, according to GenBank database) gene was codon-optimized for optimal expression in mammalian cells by the UpGene codon optimization algorithm and synthesized by GenScript. The three recombinant subunit glycoproteins MERS-S1 are fused to the T4 fibritin foldon trimerization domain with or without the fusion of a Toll-like receptor 4 (TLR-4) agonist peptide (RS09) or *Salmonella Typhimurium* flagellin C (fliC, GenBank ACY88831) (FIGS. 27A-27B). Flagellin is a highly conserved bacterial protein that elicits TLR5-dependent inflammatory responses and plays a role as adjuvant because of the presence of TLR5 in the mucosal surfaces of the respiratory compartment to induce robust and broad immune responses. Moreover, all the antigens were designed with a polyhistidine-tag and a Tobacco Etch Virus (TEV) protease cleavage sequence to facilitate downstream large-scale purification compatible with clinical manufacturing. pAd/MERS-S1f, pAd/MERS-S1fRS09, and pAd/MERS-S1ffliC were generated by subcloning each codon-optimized gene into the shuttle vector, pAd (GenBank U62024) at SalI/NotI sites. Recombinant histidine-tagged MERS-S1 foldon was purified from the supernatant of HEK 293 cells using His60 Ni Resin under native conditions. With the purified 3 subunit vaccines we examined whether they could elicit an antigen-specific immune response in vivo. To prepare the native proteins, the purified recombinant proteins were treated with AcTEV protease (Life Technology) followed by affinity chromatography on a nickel chelating resin to remove six-histidine tags and poly-histidine tagged protease from the cleavage reaction. The cleaved native recombinant proteins were collected from the flow-through fraction. BALB/c mice were inoculated subcutaneously with 25 μg of MERS-S1f, MERS-S1f plus 20 μg of MPLA, 25 μg of MERS-S1fRS09, 40 μg of MERS-S1ffliC, respectively, or PBS as a negative control and $10^{11}$vp of Ad5.MERS-S1 as a positive control.

Figure 28B:
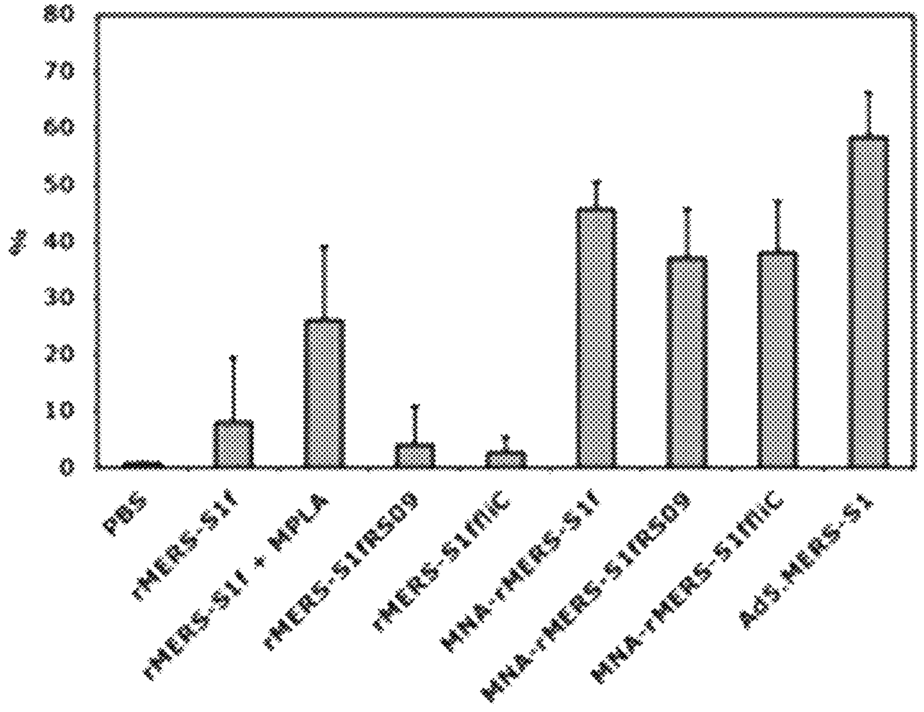
Figure 28C:
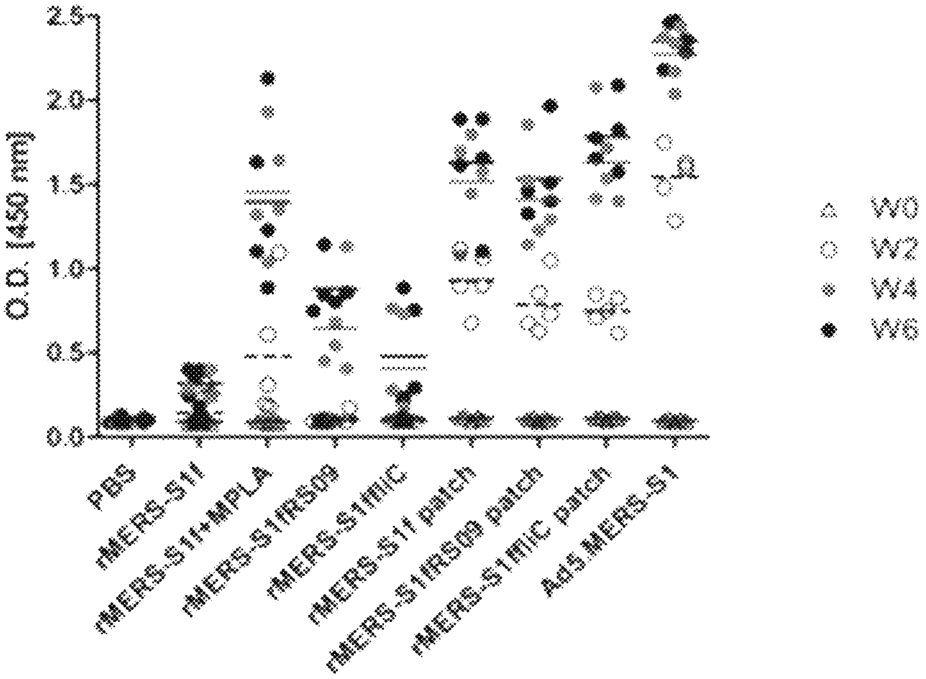
Figure 28D:
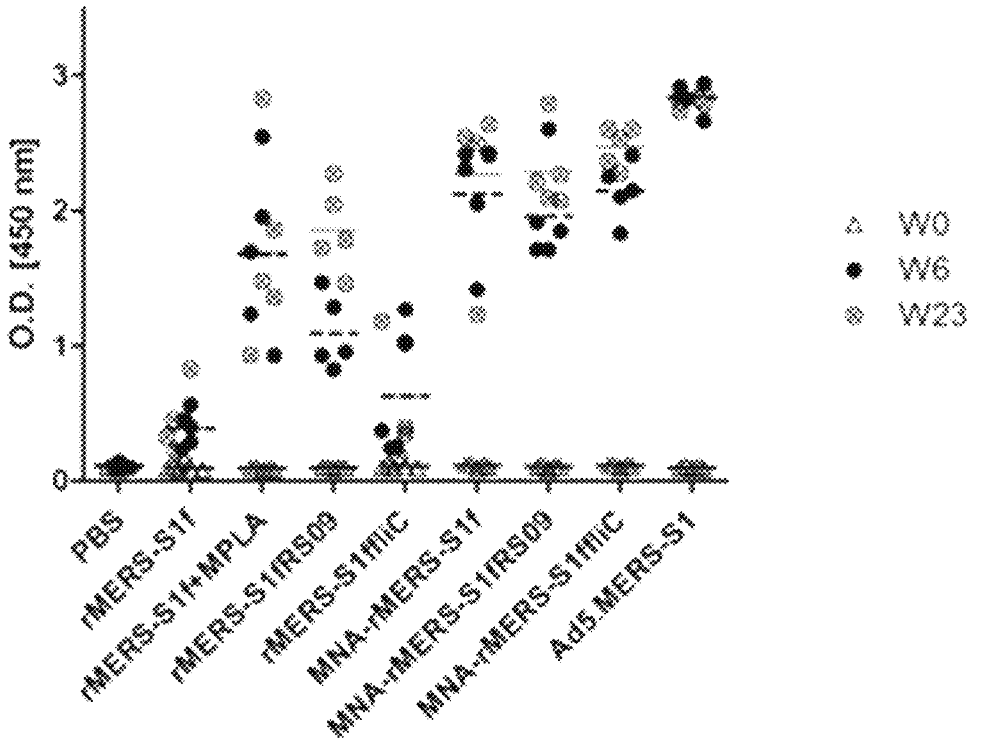

MNAs of MERS-S1f, MERS-S1fRS09, or MERS-S1ffliC were administered through intradermal delivery (FIGS. 28B-28D)

The experimental schedule is represented in FIG. 28A. Two weeks after immunization, we examined whether these antibodies could bind membrane-bound MERS-S by measuring reactivity on HEK 293 cells transfected with pAd/MERS-S or pAd using flow cytometry. The MERS-S1f+MPLA- (*, P<0.05), MNA-MERS-S1f-, MNA-MERS-S1fRS09-, MNA-MERS-S1ffliC-, and Ad5.MERS-S1-immunized mice developed membrane-bound MERS-S-specific antibodies (*, P<0.0001), while no or low specific antibody response was detected in serum samples from animals inoculated with MERS-S1f, MERS-S1f RS09, or MERS-S1ffliC compared with PBS-immunized mouse sera (FIG. 28**B).

Figure 29:
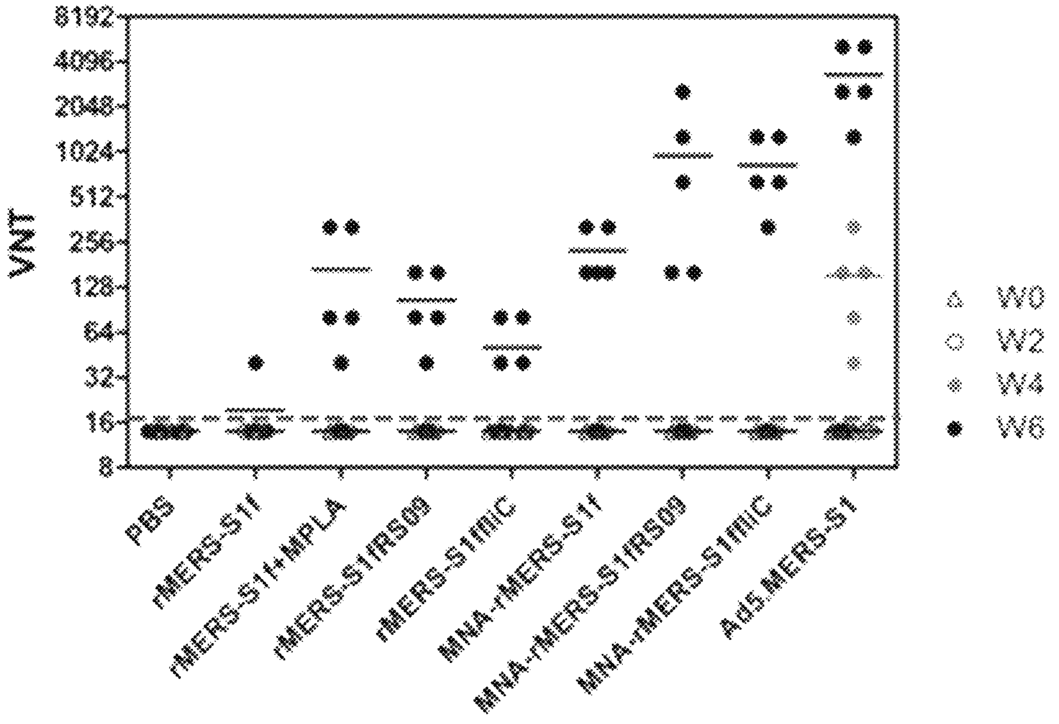
FIG. 29: Induction of neutralizing antibodies in mice with rMERS-S1 foldon proteins. MERS-CoV virus-neutralizing titers (VNTs) were measured every two weeks using Vero cells by determining the highest dilution inhibiting MERS-CoV infection by 90%.

No antibodies were detected on cells transfected with pAd without insert (data not shown). Two, four, and six weeks after immunization, sera were obtained from all mice and screened for MERS-S1-specific antibodies using ELISA. Briefly, A549 cells were infected with 10 MOI of Ad5.MERS-S1. At six hours after infection, cells were washed three times with PBS, serum-free media was added, and the cells were incubated for 48 hours. ELISA plates were coated with this supernatant from A549 cells infected with Ad5.MERS-S1 overnight at 4° C. in carbonate coating buffer (pH 9.5). Mouse sera were diluted 1:200 and followed by HRP-conjugated anti-mouse IgG (1:2000, Santa Cruz). MERS-S1 specific antibodies were detected as soon as two weeks after the first immunization. The induction of MERS-S1-specific IgG antibodies were comparable between immunized groups. As shown in FIG. 28C, a highly significant difference was observed between the sera of mice vaccinated with rMERS-S1fRS09, rMERS-S1f+MPLA, MNA-rMERS-S1fRS09, MNA-rMERS-S1ffliC, Ad5.MERs-S1 (*, P<0.0001 at week 6) and those vaccinated with rMERS-S1f, or rMERS-S1ffliC (ns; non-significant) when compared with the sera of mice immunized with PBS. In fact, IgG levels in the sera of mice vaccinated with all animal groups immunized with MNA showed a highly significant difference (*, P<0.0001) compared with the sera of mice immunized with only rMERS-S1f, although rMERS-S1fRS09-immunized mice showed a significant difference (*, P<0.05). Twenty-three weeks after immunization, sera were obtained from all mice and screened for MERS-S1 specific IgG using ELISA analysis. All animal groups lost the similar immunity response against MERS-S1 compared at week 6. Interestingly, mice immunized rMERS-S1fRS09 showed a highly significant elevation of IgG (*, P<0.0001) compared at week 6 (FIG. 28D). Mouse sera were also tested for their ability to neutralize MERS-CoV (EMC isolate). At week two post-booster, only mice immunized with Ad5.MERS-S1 vaccines induced detectable levels of MERS-CoV-neutralizing antibodies (*, P<0.0001), although other animal groups did not produce the neutralizing antibodies yet. After week four of booster immunization (W6), animals developed robust levels of neutralizing antibodies (rMERS-S1fRS09; , P<0.001, rMERS-S1f+MPLA, MNA-MERS-S1f, MNA-MERS-S1fRS09, MNA-MERS-S1ffliC, and Ad5.MERS-S1; *, P<0.0001), while animals inoculated with PBS, rMERS-S1f, and rMERS-S1ffliC did (FIG. 28D). As shown in FIG. 28C, a highly significant difference was observed between the sera of mice vaccinated with MNA-rMERS-S1f, MNA-rMERS-S1fRS09, MNA-rMERS-S1ffliC, Ad5.MERs-S1 (***, P<0.0001 at week 6) and those vaccinated with rMERS-S1fRS09 (*, P<0.05 or rMERS-S1ffliC (ns; non-significant) when compared with the sera of mice immunized with only rMERS-S1f. This result might suggest that the MNA-delivered MERS-CoV subunit vaccine candidate induced a stronger antibody-mediated neutralizing activity than i.m. administered vaccine, almost comparable with adenovirus-based vaccine delivered vaccine (FIG. 29).

Having described this invention, it will be understood to those of ordinary skill in the art that the same can be performed within a wide and equivalent range of conditions, formulations and other parameters without affecting the scope of the invention or any embodiment thereof. References incorporated herein by reference are incorporated for their technical disclosure and only to the extent that they are consistent with the present disclosure.

What is claimed is:

1. A pharmaceutical composition comprising (a) a polypeptide having the sequence of amino acids 1-661 of SEQ ID NO: 2 or a derivative thereof having at least 95% sequence identity with amino acids 1-661 of SEQ ID NO: 2, and (b) a TLR3 agonist, a TLR 4 agonist, a TLR 5 agonist, a TLR 7/8 agonist, a TLR 9 agonist, a Stimulator of Interferon Genes (STING) pathway agonist, a stimulatory neuroimmune mediator, a neurokinin 1 (NK1) receptor agonist, a saponin related adjuvant, a purinoergic receptor agonist, or an oil-in-water emulsion adjuvant.

2. The composition of claim 1, wherein said composition comprises said polypeptide having the sequence of amino acids 1-661 of SEQ ID NO: 2.

3. The composition of claim 2, wherein the polypeptide is a fusion protein comprising a multimerization domain, a Toll-like receptor agonist domain, or a SARS-CoV-2 nucleoprotein amino acid sequence having the sequence of amino acids 664-1,082 of SEQ ID NO:16 or a derivative thereof having at least 95% sequence identity with amino acids 664-1,082 of SEQ ID NO: 16.

4. The composition of claim 1, wherein said composition comprises said derivative having at least 95% sequence identity with amino acids 1-661 of SEQ ID NO:2.

5. The composition of claim 1, wherein said composition comprises said oil-in-water emulsion adjuvant.

6. The composition of claim 1, wherein said derivative has at least 99% sequence identity with amino acids 1-661 of SEQ ID NO:2.

7. A microneedle array comprising: a backing layer; and a plurality of microneedles, with a polypeptide having (a) the sequence of SEQ ID NO: 2, (b) amino acids 1-661 of SEQ ID NO: 2, (c) a sequence at least 95% sequence identity with amino acids 1-661 of SEQ ID NO: 2, or (d) a sequence having at least 95% sequence identity with SEQ ID NO: 2, incorporated into or onto each of said plurality of microneedles.

8. The microneedle array of claim 7, wherein each of said plurality of microneedles comprises a matrix of a dissolvable or bioerodible, biocompatible material extending from said backing layer.

9. The microneedle array of claim 8, wherein each of said plurality of microneedles comprises a plurality of layers of one or more dissolvable or bioerodible, biocompatible material.

10. The microneedle array of claim 8, wherein each of said plurality of microneedles comprises carboxymethyl cellulose, trehalose, polyvinylpyrrolidone, maltodextrin, silk, hyaluronic acid, poly(lactic-co-glycolic acid), poly(lactic acid), poly(vinyl alcohol), polyethylene glycol, or a combination of any two or more of the preceding.

11. The microneedle array of claim 8, wherein each of said plurality of microneedles comprises carboxymethyl cellulose.

12. The microneedle array of claim 11, wherein each of said plurality of microneedles further comprises trehalose.

13. The microneedle array of claim 8, wherein each of said plurality of microneedles has a shape that comprises a first cross-sectional dimension at a head portion distal to the backing layer, a second cross-sectional dimension at a stem portion proximal to the backing layer, and a third cross-sectional dimension at an intermediate portion located between said head portion and said stem portion having a cross-sectional dimension greater than the first and second cross-sectional dimensions.

14. The microneedle array of claim 8, wherein each of said plurality of microneedles comprises a stem portion adjacent or proximal to the backing layer and a head portion attached to the stem portion distal to the backing layer, wherein each of the plurality of microneedles has a barbed or undercut profile in which the head portion having a cross section adjacent to the stem portion is larger than a cross section of the stem portion adjacent to the head portion.

15. The microneedle array of claim 8, wherein each of said plurality of microneedles comprises a stem, a head, a filleted base, and at least one undercut feature.

16. A method of eliciting an immune response against SARS-CoV-2 in a patient, comprising administering to the patient an amount of the pharmaceutical composition of claim 1 effective to elicit an immune response against SARS-CoV-2 in a patient, thereby eliciting an immune response in the patient against SARS-CoV-2.

17. The method of claim 16, wherein said composition comprises said polypeptide having the sequence of amino acids 1-661 of SEQ ID NO:2.

18. The method of claim 17, wherein the patient is a human.

19. A method of forming a microneedle array comprising forming a plurality of microneedles having a filleted base attached to a backing, comprising incorporating into or onto each of said plurality of microneedles a polypeptide having (a) the sequence of SEQ ID NO: 2, (b) amino acids 1-661 of SEQ ID NO:2, (c) a sequence having at least 95% sequence identity with amino acids 1-661 of SEQ ID NO: 2, or (d) a sequence having at least 95% sequence identity with SEQ ID NO: 2.

20. The method of forming a microneedle array of claim 19, wherein the polypeptide is incorporated into a first dissolvable or bioerodible material.

21. The method of forming a microneedle array of claim 20, comprising:

forming or providing a production mold of a flexible material, the production mold comprising a plurality of cavities that are shaped to define a plurality of respective microneedles having a stem, a head, a filleted base, and at least one undercut feature;

delivering the first dissolvable or bioerodible material into at least a microneedle head portion defined by the respective cavities of the production mold, and prior to or during delivery of the first dissolvable or bioerodible material into at least the microneedle head portion, incorporating the polypeptide into the first dissolvable or bioerodible material to provide a biodegradable matrix;

delivering (a) the first dissolvable or bioerodible material, (b) one or more additional dissolvable or bioerodible materials, or (c) a combination thereof, into the cavity and forming a plurality of microneedles in the production mold that include the biodegradable matrix; and removing the microneedles from the production mold by pulling the microneedles out of the mold, wherein the flexible material of the production mold has sufficient elasticity to allow for the molded microneedle array to be removed from the production mold in a single pull, without damaging the integrity of the shape of the microneedles as defined by the mold.

22. The method of claim 21, wherein the at least one undercut feature is directly below the microneedle head.

23. The method of claim 21, wherein the stem is formed from the first dissolvable or bioerodible material.

24. The method of claim 21, wherein the first dissolvable or bioerodible material comprises carboxymethyl cellulose, trehalose, polyvinylpyrrolidone, maltodextrin, silk, hyaluronic acid, poly(lactic-co-glycolic acid), poly(lactic acid), poly(vinyl alcohol), polyethylene glycol, or a combination of any two or more of the preceding.

25. The method of claim 21, further comprising delivering a second dissolvable material into the production mold to form a dissolving layer at a portion of the stem.

26. The method of claim 25, wherein the second dissolvable material of the dissolving layer is a material that dissolves more quickly than the biodegradable matrix that contains the polypeptide.

27. The method of claim 21, wherein the microneedles are formed by a method comprising a spin-casting step.

* * * * *

SEQUENCE LISTING

<160> NUMBER OF SEQ ID NOS: 23

<210> SEQ ID NO 1
<211> LENGTH: 1992

<212> TYPE: DNA
<213> ORGANISM: Artificial Sequence
<220> FEATURE:
<223> OTHER INFORMATION: SARS-CoV-2-Immunogenic Protein

<400> SEQUENCE: 1

```
atgttcgtgt tcctggtcct gctcccactg gtgtcctcgc agtgcgtgaa cctgaccacc     60
cgcacccagc tgccccctgc gtacaccaac tccatcacca ggggcgtcta ctatcccgac    120
aaggtgtttc gaagttccgt tctgcactcg acccaagacc tgttcctccc cttcttcagc    180
aacgtgacct ggttccatgc tatccacgta tcgggtacga acgggaccaa gcgcttcgac    240
aaccccgtcc tgcccttcaa cgacggcgtg tactttgcat ccaccgagaa gtcgaacatt    300
atcagggggt ggattttcgg caccacccta gactcgaaga cacagtcgct gctgatcgtg    360
aacaacgcga ccaatgtcgt catcaaggtt tgcgaattcc agttctgcaa tgaccccttc    420
ctgggagtct actaccacaa gaacaacaag agctggatgg agagtgagtt cagagtgtat    480
tcctccgcta acaattgcac cttcgagtac gtatcccagc ccttcctgat ggacctggag    540
ggcaagcagg ggaactttaa aaatctgcgc gagttcgtgt ttaagaacat cgacggctac    600
ttcaagatct atagtaagca cacacccata aatctggtcc gcgacctgcc gcaaggcttc    660
tccgctttgg aacccctcgt ggacctgccg attgggatca acatcacacg ttttcagact    720
ctcctggccc tgcaccggag ttacctgaca cccggtgact cctcctcagg ctggactgcc    780
ggggccgccg cttactacgt cggctatttg cagcccagaa ctttcctcct gaagtataac    840
gagaacggca cgatcaccga tgccgtggat tgtgcgctgg acccgctgtc ggagacaaag    900
tgcacgctga agtcgtttac cgtggagaag ggatctacc agacatctaa cttccgggtt    960
cagcccactg agtccatcgt gcgcttcccc aacatcacga atctctgccc cttcggcgag   1020
gtgttcaacg caactcgctt cgccagtgtg tacgcctgga accgcaagcg gatttccaat   1080
tgtgtcgctg actacagtgt gctttacaac tctgcctcat tcagtacgtt caagtgttac   1140
ggcgtgtccc cgaccaagct gaatgatctg tgcttcacca acgtatacgc cgactcgttt   1200
gtcatccgcg gcgatgaagt gaggcagatc gcgcccggcc agacgggcaa gatcgccgac   1260
tacaactaca agctgcccga tgatttcact ggctgtgtta ttgcttggaa tagtaacaat   1320
ctggactcga aggtcggggg gaactacaac tatctctata ggctcttcag aaaaagtaat   1380
ctgaagcctt tcgagcgcga catctcgact gagatatatc aggcaggctc caccccctgc   1440
aacggcgtgg aggggtttaa ttgctacttc cccttcaga gctacggctt tcagccaaca   1500
aacggcgtag gctatcagcc ctaccgcgtg gtggtgctgt cattcgaact cctgcacgcc   1560
cccgcaaccg tctgcggccc taagaagagt acgaacctgg tgaagaacaa gtgcgtcaac   1620
ttcaatttca acggcctcac cggcacaggg gtgctgaccg agtccaacaa gaagtttctc   1680
ccgttccagc agtttgggag ggacatcgca gacactaccg acgcggtgag ggacccacag   1740
accttggaga tactggacat cactccttgc agcttcgggg gcgtgtcggt cataactccc   1800
ggcactaaca cctcaaacca ggtcgccgtg ctctaccagg acgtgaactg taccgaggtg   1860
cccgtggcga ttcacgccga ccagctgaca cccacgtgga gggtgtactc caccggaagt   1920
aatgtcttcc agacccgcgc cgggtgtctg ataggcgccg agcacgtcaa caactcgtac   1980
gagggatcct ga                                                       1992
```

<210> SEQ ID NO 2
<211> LENGTH: 663
<212> TYPE: PRT

-continued

<213> ORGANISM: Artificial Sequence
<220> FEATURE:
<223> OTHER INFORMATION: SARS-CoV-2-Immunogenic Protein

<400> SEQUENCE: 2

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Ile
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
```

```
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Gly Ser
            660
```

<210> SEQ ID NO 3
<211> LENGTH: 2010
<212> TYPE: DNA
<213> ORGANISM: Artificial Sequence
<220> FEATURE:
<223> OTHER INFORMATION: SARS-CoV2-Immunogenic Protein

<400> SEQUENCE: 3

```
atgttcgtgt tcctggtcct gctcccactg gtgtcctcgc agtgcgtgaa cctgaccacc     60

cgcacccagc tgccccctgc gtacaccaac tccatcacca ggggcgtcta ctatcccgac    120

aaggtgtttc gaagttccgt tctgcactcg acccaagacc tgttcctccc cttcttcagc    180

aacgtgacct ggttccatgc tatccacgta tcgggtacga acgggaccaa gcgcttcgac    240

aaccccgtcc tgcccttcaa cgacggcgtg tactttgcat ccaccgagaa gtcgaacatt    300

atcagggggt ggattttcgg caccacccta gactcgaaga cacagtcgct gctgatcgtg    360

aacaacgcga ccaatgtcgt catcaaggtt tgcgaattcc agttctgcaa tgaccccttc    420

ctgggagtct actaccacaa gaacaacaag agctggatgg agagtgagtt cagagtgtat    480
```

-continued

```
tcctccgcta acaattgcac cttcgagtac gtatcccagc ccttcctgat ggacctggag    540
ggcaagcagg ggaactttaa aaatctgcgc gagttcgtgt ttaagaacat cgacggctac    600
ttcaagatct atagtaagca cacacccata aatctggtcc gcgacctgcc gcaaggcttc    660
tccgctttgg aacccctcgt ggacctgccg attgggatca acatcacacg ttttcagact    720
ctcctggccc tgcaccggag ttacctgaca cccggtgact cctcctcagg ctggactgcc    780
ggggccgccg cttactacgt cggctatttg cagcccagaa ctttcctcct gaagtataac    840
gagaacggca cgatcaccga tgccgtggat tgtgcgctgg acccgctgtc ggagacaaag    900
tgcacgctga agtcgtttac cgtggagaag ggatctaccc agacatctaa cttccgggtt    960
cagcccactg agtccatcgt gcgcttcccc aacatcacga atctctgccc cttcggcgag   1020
gtgttcaacg caactcgctt cgccagtgtg tacgcctgga accgcaagcg gatttccaat   1080
tgtgtcgctg actacagtgt gctttacaac tctgcctcat tcagtacgtt caagtgttac   1140
ggcgtgtccc cgaccaagct gaatgatctg tgcttcacca acgtatacgc cgactcgttt   1200
gtcatccgcg gcgatgaagt gaggcagatc gcgcccggcc agacgggcaa gatcgccgac   1260
tacaactaca agctgcccga tgatttcact ggctgtgtta ttgcttggaa tagtaacaat   1320
ctggactcga aggtcggggg gaactacaac tatctctata ggctcttcag aaaaagtaat   1380
ctgaagcctt tcgagcgcga catctcgact gagatatatc aggcaggctc cacccccctgc   1440
aacggcgtgg aggggtttaa ttgctacttc ccccttcaga gctacggctt tcagccaaca   1500
aacggcgtag gctatcagcc ctaccgcgtg gtggtgctgt cattcgaact cctgcacgcc   1560
cccgcaaccg tctgcggccc taagaagagt acgaacctgg tgaagaacaa gtgcgtcaac   1620
ttcaatttca acggcctcac cggcacaggg gtgctgaccg agtccaacaa gaagtttctc   1680
ccgttccagc agtttgggag ggacatcgca gacactaccg acgcggtgag ggacccacag   1740
accttggaga tactggacat cactccttgc agcttcgggg gcgtgtcggt cataactccc   1800
ggcactaaca cctcaaacca ggtcgccgtg ctctaccagg acgtgaactg taccgaggtg   1860
cccgtggcga ttcacgccga ccagctgaca cccacgtgga gggtgtactc caccggaagt   1920
aatgtcttcc agacccgcgc cgggtgtctg ataggcgccg agcacgtcaa caactcgtac   1980
gagggatccc accatcacca ccaccactga                                    2010
```

```
<210> SEQ ID NO 4
<211> LENGTH: 669
<212> TYPE: PRT
<213> ORGANISM: Artificial Sequence
<220> FEATURE:
<223> OTHER INFORMATION: SARS-CoV2-Immunogenic Protein

<400> SEQUENCE: 4

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Ile
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95
```

-continued

```
Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510
```

-continued

```
Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Gly Ser His His His His His His
            660                 665


<210> SEQ ID NO 5
<211> LENGTH: 2094
<212> TYPE: DNA
<213> ORGANISM: Artificial Sequence
<220> FEATURE:
<223> OTHER INFORMATION: SARS-CoV2-Immunogenic Protein

<400> SEQUENCE: 5

atgttcgtgt tcctggtcct gctcccactg gtgtcctcgc agtgcgtgaa cctgaccacc      60

cgcacccagc tgccccctgc gtacaccaac tccatcacca ggggcgtcta ctatcccgac     120

aaggtgtttc gaagttccgt tctgcactcg acccaagacc tgttcctccc cttcttcagc     180

aacgtgacct ggttccatgc tatccacgta tcgggtacga acgggaccaa gcgcttcgac     240

aaccccgtcc tgcccttcaa cgacggcgtg tactttgcat ccaccgagaa gtcgaacatt     300

atcagggggt ggattttcgg caccacccta gactcgaaga cacagtcgct gctgatcgtg     360

aacaacgcga ccaatgtcgt catcaaggtt tgcgaattcc agttctgcaa tgaccccttc     420

ctgggagtct actaccacaa gaacaacaag agctggatgg agagtgagtt cagagtgtat     480

tcctccgcta acaattgcac cttcgagtac gtatcccagc ccttcctgat ggacctggag     540

ggcaagcagg ggaactttaa aaatctgcgc gagttcgtgt ttaagaacat cgacggctac     600

ttcaagatct atagtaagca cacacccata aatctggtcc gcgacctgcc gcaaggcttc     660

tccgctttgg aacccctcgt ggacctgccg attgggatca acatcacacg ttttcagact     720

ctcctggccc tgcaccggag ttacctgaca cccggtgact cctcctcagg ctggactgcc     780

ggggccgccg cttactacgt cggctatttg cagcccagaa ctttcctcct gaagtataac     840

gagaacggca cgatcaccga tgccgtggat tgtgcgctgg acccgctgtc ggagacaaag     900

tgcacgctga agtcgtttac cgtggagaag ggatctacc agacatctaa cttccgggtt     960

cagcccactg agtccatcgt gcgcttcccc aacatcacga atctctgccc cttcggcgag    1020

gtgttcaacg caactcgctt cgccagtgtg tacgcctgga accgcaagcg gatttccaat    1080

tgtgtcgctg actacagtgt gctttacaac tctgcctcat tcagtacgtt caagtgttac    1140

ggcgtgtccc cgaccaagct gaatgatctg tgcttcacca acgtatacgc cgactcgttt    1200
```

```
gtcatccgcg gcgatgaagt gaggcagatc gcgcccggcc agacgggcaa gatcgccgac    1260

tacaactaca agctgcccga tgatttcact ggctgtgtta ttgcttggaa tagtaacaat    1320

ctggactcga aggtcggggg gaactacaac tatctctata ggctcttcag aaaaagtaat    1380

ctgaagcctt tcgagcgcga catctcgact gagatatatc aggcaggctc cacccctgc    1440

aacggcgtgg aggggtttaa ttgctacttc ccccttcaga gctacggctt tcagccaaca    1500

aacggcgtag gctatcagcc ctaccgcgtg gtggtgctgt cattcgaact cctgcacgcc    1560

cccgcaaccg tctgcggccc taagaagagt acgaacctgg tgaagaacaa gtgcgtcaac    1620

ttcaatttca acggcctcac cggcacaggg gtgctgaccg agtccaacaa gaagtttctc    1680

ccgttccagc agtttgggag ggacatcgca gacactaccg acgcggtgag ggacccacag    1740

accttggaga tactggacat cactccttgc agcttcgggg gcgtgtcggt cataactccc    1800

ggcactaaca cctcaaacca ggtcgccgtg ctctaccagg acgtgaactg taccgaggtg    1860

cccgtggcga ttcacgccga ccagctgaca cccacgtgga gggtgtactc caccggaagt    1920

aatgtcttcc agacccgcgc cgggtgtctg ataggcgccg agcacgtcaa caactcgtac    1980

gagggatccg ggtacatccc cgaggcccct cgcgatggcc aagcttatgt gcgaaaggac    2040

ggggagtggg tgctgctctc caccttcctg gccccccccc acgcactgag ctga         2094
```

<210> SEQ ID NO 6
<211> LENGTH: 697
<212> TYPE: PRT
<213> ORGANISM: Artificial Sequence
<220> FEATURE:
<223> OTHER INFORMATION: SARS-CoV2-Immunogenic Protein

<400> SEQUENCE: 6

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Ile
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205
```

```
Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620
```

-continued

```
His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Gly Ser Gly Tyr Ile Pro Glu Ala Pro Arg Asp
            660                 665                 670

Gly Gln Ala Tyr Val Arg Lys Asp Gly Glu Trp Val Leu Leu Ser Thr
        675                 680                 685

Phe Leu Ala Pro Pro His Ala Leu Ser
    690                 695


<210> SEQ ID NO 7
<211> LENGTH: 2133
<212> TYPE: DNA
<213> ORGANISM: Artificial Sequence
<220> FEATURE:
<223> OTHER INFORMATION: SARS-CoV2-Immunogenic Protein

<400> SEQUENCE: 7

atgttcgtgt tcctggtcct gctcccactg gtgtcctcgc agtgcgtgaa cctgaccacc     60

cgcacccagc tgcccccctgc gtacaccaac tccatcacca ggggcgtcta ctatcccgac    120

aaggtgtttc gaagttccgt tctgcactcg acccaagacc tgttcctccc cttcttcagc    180

aacgtgacct ggttccatgc tatccacgta tcgggtacga acgggaccaa gcgcttcgac    240

aaccccgtcc tgcccttcaa cgacggcgtg tactttgcat ccaccgagaa gtcgaacatt    300

atcagggggt ggattttcgg caccacccta gactcgaaga cacagtcgct gctgatcgtg    360

aacaacgcga ccaatgtcgt catcaaggtt tgcgaattcc agttctgcaa tgaccccttc    420

ctgggagtct actaccacaa gaacaacaag agctggatgg agagtgagtt cagagtgtat    480

tcctccgcta acaattgcac cttcgagtac gtatcccagc ccttcctgat ggacctggag    540

ggcaagcagg ggaactttaa aaatctgcgc gagttcgtgt ttaagaacat cgacggctac    600

ttcaagatct atagtaagca cacacccata aatctggtcc gcgacctgcc gcaaggcttc    660

tccgctttgg aacccctcgt ggacctgccg attgggatca acatcacacg ttttcagact    720

ctcctggccc tgcaccggag ttacctgaca cccggtgact cctcctcagg ctggactgcc    780

ggggccgccg cttactacgt cggctatttg cagcccagaa ctttcctcct gaagtataac    840

gagaacggca cgatcaccga tgccgtggat tgtgcgctgg acccgctgtc ggagacaaag    900

tgcacgctga agtcgtttac cgtggagaag ggatctacc agacatctaa cttccgggtt     960

cagcccactg agtccatcgt gcgcttcccc aacatcacga atctctgccc cttcggcgag   1020

gtgttcaacg caactcgctt cgccagtgtg tacgcctgga accgcaagcg gatttccaat   1080

tgtgtcgctg actacagtgt gctttacaac tctgcctcat tcagtacgtt caagtgttac   1140

ggcgtgtccc cgaccaagct gaatgatctg tgcttcacca acgtatacgc cgactcgttt   1200

gtcatccgcg gcgatgaagt gaggcagatc gcgcccggcc agacgggcaa gatcgccgac   1260

tacaactaca agctgcccga tgatttcact ggctgtgtta ttgcttggaa tagtaacaat   1320

ctggactcga aggtcggggg gaactacaac tatctctata ggctcttcag aaaaagtaat   1380

ctgaagcctt tcgagcgcga catctcgact gagatatatc aggcaggctc caccccctgc   1440

aacggcgtgg aggggtttaa ttgctacttc cccttcaga gctacggctt tcagccaaca    1500

aacggcgtag gctatcagcc ctaccgcgtg gtggtgctgt cattcgaact cctgcacgcc   1560

cccgcaaccg tctgcggccc taagaagagt acgaacctgg tgaagaacaa gtgcgtcaac   1620
```

```
ttcaatttca acggcctcac cggcacaggg gtgctgaccg agtccaacaa gaagtttctc   1680

ccgttccagc agtttgggag ggacatcgca gacactaccg acgcggtgag ggacccacag   1740

accttggaga tactggacat cactccttgc agcttcgggg gcgtgtcggt cataactccc   1800

ggcactaaca cctcaaacca ggtcgccgtg ctctaccagg acgtgaactg taccgaggtg   1860

cccgtggcga ttcacgccga ccagctgaca cccacgtgga gggtgtactc caccggaagt   1920

aatgtcttcc agacccgcgc cgggtgtctg ataggcgccg agcacgtcaa caactcgtac   1980

gagggatccg ggtacatccc cgaggcccct cgcgatggcc aagcttatgt gcgaaaggac   2040

ggggagtggg tgctgctctc caccttcctg gcccccccccc acgcactgag cgagaactta   2100

tacttcgagg gccaccatca ccaccaccat tga                                2133


<210> SEQ ID NO 8
<211> LENGTH: 710
<212> TYPE: PRT
<213> ORGANISM: Artificial Sequence
<220> FEATURE:
<223> OTHER INFORMATION: SARS-CoV2-Immunogenic Protein

<400> SEQUENCE: 8

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Ile
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270
```

-continued

```
Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Gly Ser Gly Tyr Ile Pro Glu Ala Pro Arg Asp
            660                 665                 670

Gly Gln Ala Tyr Val Arg Lys Asp Gly Glu Trp Val Leu Leu Ser Thr
        675                 680                 685

Phe Leu Ala Pro Pro His Ala Leu Ser Glu Asn Leu Tyr Phe Glu Gly
```

690 695 700

His His His His His His
705 710

<210> SEQ ID NO 9
<211> LENGTH: 1992
<212> TYPE: DNA
<213> ORGANISM: Artificial Sequence
<220> FEATURE:
<223> OTHER INFORMATION: SARS-CoV2-Immunogenic Protein

<400> SEQUENCE: 9
atgttcgtgt tcttggtgct tctgccgttg gtgagttctc agtgcgtcaa cctgaccacc 60
cgaacccagc tcccccccgc ctacaccaac agcatcaccc ggggcgtcta ctacccagac 120
aaggtgtttc ggtctagcgt gctgcactcc acccaggacc tgttcctccc cttcttctcc 180
aacgtgacct ggttccacgc gatccacgtg tcgggaacga acggaactaa gcgcttcgac 240
aaccctgtgc tccccttaa cgatggcgtg tatttcgctt caaccgagaa atcgaacatc 300
attcgcggtt ggatcttcgg caccaccctg gacagtaaga ctcagtccct cctgatcgtg 360
aacaatgcca caaacgttgt gatcaaggtc tgcgagttcc agttttgcaa cgaccctttc 420
ctgggcgtgt actaccacaa gaataacaag tcctggatgg agtcagaatt cagggtgtac 480
agctcagcca acaactgcac attcgagtat gtgtcccagc cctttctgat ggatctggag 540
ggcaagcagg ggaacttcaa gaatctacgt gaattcgtgt tcaagaacat cgatggctat 600
ttcaaaatct actcgaagca cacgcccatc aatctggtaa gggacctgcc tcaggggttc 660
tcggccctgg agccactcgt cgatctgccg attggcatca acatcacccg ctttcaaacc 720
ctcctggccc tccacaggtc ctacctgacg cccggcgatt cgtcgagtgg gtggacggca 780
ggcgcagctg cgtactacgt ggggtacctg cagccacgaa ccttcctgct gaagtacaac 840
gagaacggca cgattaccga cgcggttgat tgcgccttgg acccgctctc cgaaaccaag 900
tgcaccctga agagcttcac cgtggagaag ggaatctacc agacgagtaa cttccgcgtg 960
cagccgaccg agagtattgt tcggttcccc aacatcacca acttgtgccc atttggcgag 1020
gtcttcaacg ccacccgctt cgcaagcgtg tacgcctgga accgcaagag aatctccaat 1080
tgcgtggccg actacagcgt cctgtacaac tcggcctcgt tcagtacgtt caagtgctac 1140
ggggtgtccc ccaccaagct caatgacctc tgctttacca acgtgtacgc tgattcgttc 1200
gtaatcaggg gtgacgaggt gcgccagatc gccccaggcc agactgggaa gatcgctgac 1260
tataactata agctccccga cgactttacc ggctgcgtca tcgcctggaa ctccaacaac 1320
ctggattcga aggtgggagg caactacaat tacctgtatc gcctcttcag gaagtcaaat 1380
ctgaagcctt tcgagaggga catatcgacc gagatctacc aggcgggaag taccccctgc 1440
aacggggtgg aggggttcaa ctgctacttc ccgctgcagt cgtacggctt ccagcctacc 1500
aacggggtcg ggtaccagcc ctaccgcgtg gtggtgctca gtttcgagct cttgcatgcc 1560
cccgctacag tgtgcggacc gaagaagtcc acaaacctgg tgaagaacaa gtgcgttaac 1620
tttaacttca acggactcac tggcaccggc gtgctgactg agtcgaacaa gaagtttctg 1680
cccttccagc agtttggccg cgacatcgca gacaccaccg atgccgtgcg ggaccccccag 1740 accctcgaga tcctggacat cacccccctgc tccttcggcg gagtctccgt cataaccccc 1800
gggacaaaca cgtcgaatca ggtggctgtg ctctatcaag atgtaaattg tacagaggtg 1860
cccgtggcaa tccacgcgga ccagctgacc ccaacctggc gcgtttacag caccggcagt 1920

-continued aacgtgttcc agacacgcgc tggttgcctc atcggcgccg aacacgtgaa caactcgtat 1980
gagggatcct ga 1992

<210> SEQ ID NO 10
<211> LENGTH: 3249
<212> TYPE: DNA
<213> ORGANISM: Artificial Sequence
<220> FEATURE:
<223> OTHER INFORMATION: SARS-CoV2-Immunogenic Protein

<400> SEQUENCE: 10
atgttcgtgt tcttggtgct tctgccgttg gtgagttctc agtgcgtcaa cctgaccacc 60
cgaacccagc tcccccccgc ctacaccaac agcatcaccc ggggcgtcta ctacccagac 120
aaggtgtttc ggtctagcgt gctgcactcc acccaggacc tgttcctccc cttcttctcc 180
aacgtgacct ggttccacgc gatccacgtg tcgggaacga acggaactaa gcgcttcgac 240
aaccctgtgc tcccctttaa cgatggcgtg tatttcgctt caaccgagaa atcgaacatc 300
attcgcggtt ggatcttcgg caccaccctg gacagtaaga ctcagtccct cctgatcgtg 360
aacaatgcca caaacgttgt gatcaaggtc tgcgagttcc agttttgcaa cgaccctttc 420
ctgggcgtgt actaccacaa gaataacaag tcctggatgg agtcagaatt cagggtgtac 480
agctcagcca acaactgcac attcgagtat gtgtcccagc cctttctgat ggatctggag 540
ggcaagcagg ggaacttcaa gaatctacgt gaattcgtgt tcaagaacat cgatggctat 600
ttcaaaatct actcgaagca cacgcccatc aatctggtaa gggacctgcc tcaggggttc 660
tcggccctgg agccactcgt cgatctgccg attggcatca acatcacccg ctttcaaacc 720
ctcctggccc tccacaggtc ctacctgacg cccggcgatt cgtcgagtgg gtggacggca 780
ggcgcagctg cgtactacgt ggggtacctg cagccacgaa ccttcctgct gaagtacaac 840
gagaacggca cgattaccga cgcggttgat tgcgccttgg acccgctctc cgaaaccaag 900
tgcaccctga agagcttcac cgtggagaag ggaatctacc agacgagtaa cttccgcgtg 960
cagccgaccg agagtattgt tcggttcccc aacatcacca acttgtgccc atttggcgag 1020
gtcttcaacg ccacccgctt cgcaagcgtg tacgcctgga accgcaagag aatctccaat 1080
tgcgtggccg actacagcgt cctgtacaac tcggcctcgt tcagtacgtt caagtgctac 1140
ggggtgtccc ccaccaagct caatgacctc tgctttacca acgtgtacgc tgattcgttc 1200
gtaatcaggg gtgacgaggt gcgccagatc gccccaggcc agactgggaa gatcgctgac 1260
tataactata agctccccga cgactttacc ggctgcgtca tcgcctggaa ctccaacaac 1320
ctggattcga aggtgggagg caactacaat tacctgtatc gcctcttcag gaagtcaaat 1380
ctgaagcctt tcgagaggga catatcgacc gagatctacc aggcgggaag tacccccctgc 1440 aacggggtgg aggggttcaa ctgctacttc ccgctgcagt cgtacggctt ccagcctacc 1500
aacggggtcg ggtaccagcc ctaccgcgtg gtggtgctca gtttcgagct cttgcatgcc 1560
cccgctacag tgtgcggacc gaagaagtcc acaaacctgg tgaagaacaa gtgcgttaac 1620
tttaacttca acggactcac tggcaccggc gtgctgactg agtcgaacaa gaagtttctg 1680
cccttccagc agtttggccg cgacatcgca gacaccaccg atgccgtgcg ggaccccccag 1740 accctcgaga tcctggacat cacccccctgc tccttcggcg gagtctccgt cataaccccc 1800
gggacaaaca cgtcgaatca ggtggctgtg ctctatcaag atgtaaattg tacagaggtg 1860
cccgtggcaa tccacgcgga ccagctgacc ccaacctggc gcgtttacag caccggcagt 1920
aacgtgttcc agacacgcgc tggttgcctc atcggcgccg aacacgtgaa caactcgtat 1980
gagggatcca tgtctgataa tggaccccaa aatcagcgaa atgcaccccg cattacgttt 2040
ggtggaccct cagattcaac tggcagtaac cagaatggag aacgcagtgg ggcgcgatca 2100
aaacaacgtc ggccccaagg tttacccaat aatactgcgt cttggttcac cgctctcact 2160
caacatggca aggaagacct taaattccct cgaggacaag gcgttccaat taacaccaat 2220
agcagtccag atgaccaaat tggctactac cgaagagcta ccagacgaat tcgtggtggt 2280
gacggtaaaa tgaaagatct cagtccaaga tggtatttct actacctagg aactgggcca 2340
gaagctggac ttccctatgg tgctaacaaa gacggcatca tatgggttgc aactgaggga 2400
gccttgaata caccaaaaga tcacattggc acccgcaatc ctgctaacaa tgctgcaatc 2460
gtgctacaac ttcctcaagg aacaacattg ccaaaaggct tctacgcaga agggagcaga 2520
ggcggcagtc aagcctcttc tcgttcctca tcacgtagtc gcaacagttc aagaaattca 2580
actccaggca gcagtagggg aacttctcct gctagaatgg ctggcaatgg cggtgatgct 2640
gctcttgctt tgctgctgct tgacagattg aaccagcttg agagcaaaat gtctggtaaa 2700
ggccaacaac aacaaggcca aactgtcact aagaaatctg ctgctgaggc ttctaagaag 2760
cctcggcaaa aacgtactgc cactaaagca tacaatgtaa cacaagcttt cggcagacgt 2820
ggtccagaac aaacccaagg aaattttggg gaccaggaac taatcagaca aggaactgat 2880
tacaaacatt ggccgcaaat tgcacaattt gcccccagcg cttcagcgtt cttcggaatg 2940
tcgcgcattg gcatggaagt cacaccttcg ggaacgtggt tgacctacac aggtgccatc 3000
aaattggatg acaaagatcc aaatttcaaa gatcaagtca ttttgctgaa taagcatatt 3060
gacgcataca aaacattccc accaacagag cctaaaaagg acaaaaagaa gaaggctgat 3120
gaaactcaag ccttaccgca gagacagaag aaacagcaaa ctgtgactct tcttcctgct 3180
gcagatttgg atgatttctc caaacaattg caacaatcca tgagcagtgc tgactcaact 3240
caggcctaa 3249

<210> SEQ ID NO 11
<211> LENGTH: 3324
<212> TYPE: DNA
<213> ORGANISM: Artificial Sequence
<220> FEATURE:
<223> OTHER INFORMATION: SARS-CoV2-Immunogenic Protein

<400> SEQUENCE: 11
atgttcgtgt tcttggtgct tctgccgttg gtgagttctc agtgcgtcaa cctgaccacc 60
cgaacccagc tcccccccgc ctacaccaac agcatcaccc ggggcgtcta ctacccagac 120
aaggtgtttc ggtctagcgt gctgcactcc acccaggacc tgttcctccc cttcttctcc 180
aacgtgacct ggttccacgc gatccacgtg tcgggaacga acggaactaa gcgcttcgac 240
aaccctgtgc tcccctttaa cgatggcgtg tatttcgctt caaccgagaa atcgaacatc 300
attcgcggtt ggatcttcgg caccaccctg gacagtaaga ctcagtccct cctgatcgtg 360
aacaatgcca caaacgttgt gatcaaggtc tgcgagttcc agttttgcaa cgaccctttc 420
ctgggcgtgt actaccacaa gaataacaag tcctggatgg agtcagaatt cagggtgtac 480
agctcagcca acaactgcac attcgagtat gtgtcccagc cctttctgat ggatctggag 540
ggcaagcagg ggaacttcaa gaatctacgt gaattcgtgt tcaagaacat cgatggctat 600
ttcaaaatct actcgaagca cacgcccatc aatctggtaa gggacctgcc tcaggggttc 660
tcggccctgg agccactcgt cgatctgccg attggcatca acatcacccg ctttcaaacc 720

-continued

```
ctcctggccc tccacaggtc ctacctgacg cccggcgatt cgtcgagtgg gtggacggca    780
ggcgcagctg cgtactacgt ggggtacctg cagccacgaa ccttcctgct gaagtacaac    840
gagaacggca cgattaccga cgcggttgat tgcgccttgg acccgctctc cgaaaccaag    900
tgcaccctga agagcttcac cgtggagaag ggaatctacc agacgagtaa cttccgcgtg    960
cagccgaccg agagtattgt tcggttcccc aacatcacca acttgtgccc atttggcgag   1020
gtcttcaacg ccacccgctt cgcaagcgtg tacgcctgga accgcaagag aatctccaat   1080
tgcgtggccg actacagcgt cctgtacaac tcggcctcgt tcagtacgtt caagtgctac   1140
ggggtgtccc ccaccaagct caatgacctc tgctttacca acgtgtacgc tgattcgttc   1200
gtaatcaggg gtgacgaggt gcgccagatc gccccaggcc agactgggaa gatcgctgac   1260
tataactata agctccccga cgactttacc ggctgcgtca tcgcctggaa ctccaacaac   1320
ctggattcga aggtgggagg caactacaat tacctgtatc gcctcttcag gaagtcaaat   1380
ctgaagcctt tcgagaggga catatcgacc gagatctacc aggcgggaag tacccccctgc   1440
aacggggtgg aggggttcaa ctgctacttc ccgctgcagt cgtacggctt ccagcctacc   1500
aacggggtcg ggtaccagcc ctaccgcgtg gtggtgctca gtttcgagct cttgcatgcc   1560
cccgctacag tgtgcggacc gaagaagtcc acaaacctgg tgaagaacaa gtgcgttaac   1620
tttaacttca acggactcac tggcaccggc gtgctgactg agtcgaacaa gaagtttctg   1680
cccttccagc agtttggccg cgacatcgca gacaccaccg atgccgtgcg ggacccccag   1740
accctcgaga tcctggacat caccccctgc tccttcggcg gagtctccgt cataaccccc   1800
gggacaaaca cgtcgaatca ggtggctgtg ctctatcaag atgtaaattg tacagaggtg   1860
cccgtggcaa tccacgcgga ccagctgacc ccaacctggc gcgtttacag caccggcagt   1920
aacgtgttcc agacacgcgc tggttgcctc atcggcgccg aacacgtgaa caactcgtat   1980
gagggatccg gccagtgtac aaactacgcc ctgcttaaat tagccggcga cgtggagtca   2040
aaccccggcc ccgtcgacgc caccatgtct gataatggac cccaaaatca gcgaaatgca   2100
ccccgcatta cgtttggtgg accctcagat tcaactggca gtaaccagaa tggagaacgc   2160
agtggggcgc gatcaaaaca acgtcggccc caaggtttac ccaataatac tgcgtcttgg   2220
ttcaccgctc tcactcaaca tggcaaggaa gaccttaaat tccctcgagg acaaggcgtt   2280
ccaattaaca ccaatagcag tccagatgac caaattggct actaccgaag agctaccaga   2340
cgaattcgtg gtggtgacgg taaaatgaaa gatctcagtc caagatggta tttctactac   2400
ctaggaactg ggccagaagc tggacttccc tatggtgcta acaaagacgg catcatatgg   2460
gttgcaactg agggagcctt gaatacacca aaagatcaca ttggcacccg caatcctgct   2520
aacaatgctg caatcgtgct acaacttcct caaggaacaa cattgccaaa aggcttctac   2580
gcagaaggga gcagaggcgg cagtcaagcc tcttctcgtt cctcatcacg tagtcgcaac   2640
agttcaagaa attcaactcc aggcagcagt aggggaactt ctcctgctag aatggctggc   2700
aatggcggtg atgctgctct tgctttgctg ctgcttgaca gattgaacca gcttgagagc   2760
aaaatgtctg gtaaaggcca acaacaacaa ggccaaactg tcactaagaa atctgctgct   2820
gaggcttcta agaagcctcg gcaaaaacgt actgccacta aagcatacaa tgtaacacaa   2880
gctttcggca gacgtggtcc agaacaaacc caaggaaatt ttggggacca ggaactaatc   2940
agacaaggaa ctgattacaa acattggccg caaattgcac aatttgcccc cagcgcttca   3000
gcgttcttcg gaatgtcgcg cattggcatg gaagtcacac cttcgggaac gtggttgacc   3060
tacacaggtg ccatcaaatt ggatgacaaa gatccaaatt tcaaagatca agtcattttg   3120
```

ctgaataagc atattgacgc atacaaaaca ttcccaccaa cagagcctaa aaaggacaaa 3180
aagaagaagg ctgatgaaac tcaagcctta ccgcagagac agaagaaaca gcaaactgtg 3240
actcttcttc ctgctgcaga tttggatgat ttctccaaac aattgcaaca atccatgagc 3300
agtgctgact caactcaggc ctaa 3324

<210> SEQ ID NO 12
<211> LENGTH: 2133
<212> TYPE: DNA
<213> ORGANISM: Artificial Sequence
<220> FEATURE:
<223> OTHER INFORMATION: SARS-CoV2-Immunogenic Protein

<400> SEQUENCE: 12
atgttcgtgt tcttggtgct tctgccgttg gtgagttctc agtgcgtcaa cctgaccacc 60
cgaacccagc tcccccccgc ctacaccaac agcatcaccc ggggcgtcta ctacccagac 120
aaggtgtttc ggtctagcgt gctgcactcc acccaggacc tgttcctccc cttcttctcc 180
aacgtgacct ggttccacgc gatccacgtg tcgggaacga acggaactaa gcgcttcgac 240
aaccctgtgc tccccttttaa cgatggcgtg tatttcgctt caaccgagaa atcgaacatc 300
attcgcggtt ggatcttcgg caccaccctg gacagtaaga ctcagtccct cctgatcgtg 360
aacaatgcca caaacgttgt gatcaaggtc tgcgagttcc agttttgcaa cgaccctttc 420
ctgggcgtgt actaccacaa gaataacaag tcctggatgg agtcagaatt cagggtgtac 480
agctcagcca acaactgcac attcgagtat gtgtcccagc cctttctgat ggatctggag 540
ggcaagcagg ggaacttcaa gaatctacgt gaattcgtgt tcaagaacat cgatggctat 600
ttcaaaatct actcgaagca cacgcccatc aatctggtaa gggacctgcc tcaggggttc 660
tcggccctgg agccactcgt cgatctgccg attggcatca acatcacccg ctttcaaacc 720
ctcctggccc tccacaggtc ctacctgacg cccggcgatt cgtcgagtgg gtggacggca 780
ggcgcagctg cgtactacgt ggggtacctg cagccacgaa ccttcctgct gaagtacaac 840
gagaacggca cgattaccga cgcggttgat tgcgccttgg acccgctctc cgaaaccaag 900
tgcaccctga agagcttcac cgtggagaag ggaatctacc agacgagtaa cttccgcgtg 960
cagccgaccg agagtattgt tcggttcccc aacatcacca acttgtgccc atttggcgag 1020
gtcttcaacg ccacccgctt cgcaagcgtg tacgcctgga accgcaagag aatctccaat 1080
tgcgtggccg actacagcgt cctgtacaac tcggcctcgt tcagtacgtt caagtgctac 1140
ggggtgtccc ccaccaagct caatgacctc tgctttacca acgtgtacgc tgattcgttc 1200
gtaatcaggg gtgacgaggt gcgccagatc gccccaggcc agactgggaa gatcgctgac 1260
tataactata agctccccga cgactttacc ggctgcgtca tcgcctggaa ctccaacaac 1320
ctggattcga aggtgggagg caactacaat tacctgtatc gcctcttcag gaagtcaaat 1380
ctgaagcctt tcgagaggga catatcgacc gagatctacc aggcgggaag taccccctgc 1440
aacggggtgg aggggttcaa ctgctacttc ccgctgcagt cgtacggctt ccagcctacc 1500
aacggggtcg ggtaccagcc ctaccgcgtg gtggtgctca gtttcgagct cttgcatgcc 1560
cccgctacag tgtgcggacc gaagaagtcc acaaacctgg tgaagaacaa gtgcgttaac 1620
tttaacttca acggactcac tggcaccggc gtgctgactg agtcgaacaa gaagtttctg 1680
cccttccagc agtttggccg cgacatcgca gacaccaccg atgccgtgcg ggacccccag 1740
accctcgaga tcctggacat cacccccctgc tccttcggcg gagtctccgt cataaccccc 1800
gggacaaaca cgtcgaatca ggtggctgtg ctctatcaag atgtaaattg tacagaggtg 1860
cccgtggcaa tccacgcgga ccagctgacc ccaacctggc gcgtttacag caccggcagt 1920
aacgtgttcc agacacgcgc tggttgcctc atcggcgccg aacacgtgaa caactcgtat 1980
gagggatccg ggtacatccc cgaggcccct cgcgatggcc aagcttatgt gcgaaaggac 2040
ggggagtggg tgctgctctc caccttcctg gccccccccc acgcactgag cgagaactta 2100
tacttcgagg gccaccatca ccaccaccat tga 2133

<210> SEQ ID NO 13
<211> LENGTH: 3357
<212> TYPE: DNA
<213> ORGANISM: Artificial Sequence
<220> FEATURE:
<223> OTHER INFORMATION: SARS-CoV2-Immunogenic Protein

<400> SEQUENCE: 13
atgttcgtgt tcttggtgct tctgccgttg gtgagttctc agtgcgtcaa cctgaccacc 60
cgaacccagc tcccccccgc ctacaccaac agcatcaccc ggggcgtcta ctacccagac 120
aaggtgtttc ggtctagcgt gctgcactcc acccaggacc tgttcctccc cttcttctcc 180
aacgtgacct ggttccacgc gatccacgtg tcgggaacga acggaactaa gcgcttcgac 240
aaccctgtgc tcccctttaa cgatggcgtg tatttcgctt caaccgagaa atcgaacatc 300
attcgcggtt ggatcttcgg caccaccctg gacagtaaga ctcagtccct cctgatcgtg 360
aacaatgcca caaacgttgt gatcaaggtc tgcgagttcc agttttgcaa cgaccctttc 420
ctgggcgtgt actaccacaa gaataacaag tcctggatgg agtcagaatt cagggtgtac 480
agctcagcca acaactgcac attcgagtat gtgtcccagc cctttctgat ggatctggag 540
ggcaagcagg ggaacttcaa gaatctacgt gaattcgtgt tcaagaacat cgatggctat 600
ttcaaaatct actcgaagca cacgcccatc aatctggtaa gggacctgcc tcaggggttc 660
tcggccctgg agccactcgt cgatctgccg attggcatca acatcacccg ctttcaaacc 720
ctcctggccc tccacaggtc ctacctgacg cccggcgatt cgtcgagtgg gtggacggca 780
ggcgcagctg cgtactacgt ggggtacctg cagccacgaa ccttcctgct gaagtacaac 840
gagaacggca cgattaccga cgcggttgat tgcgccttgg acccgctctc cgaaaccaag 900
tgcaccctga agagcttcac cgtggagaag ggaatctacc agacgagtaa cttccgcgtg 960
cagccgaccg agagtattgt tcggttcccc aacatcacca acttgtgccc atttggcgag 1020
gtcttcaacg ccacccgctt cgcaagcgtg tacgcctgga accgcaagag aatctccaat 1080
tgcgtggccg actacagcgt cctgtacaac tcggcctcgt tcagtacgtt caagtgctac 1140
ggggtgtccc ccaccaagct caatgacctc tgctttacca acgtgtacgc tgattcgttc 1200
gtaatcaggg gtgacgaggt gcgccagatc gccccaggcc agactgggaa gatcgctgac 1260
tataactata agctccccga cgactttacc ggctgcgtca tcgcctggaa ctccaacaac 1320
ctggattcga aggtgggagg caactacaat tacctgtatc gcctcttcag gaagtcaaat 1380
ctgaagcctt tcgagaggga catatcgacc gagatctacc aggcgggaag taccccctgc 1440
aacggggtgg aggggttcaa ctgctacttc ccgctgcagt cgtacggctt ccagcctacc 1500
aacggggtcg ggtaccagcc ctaccgcgtg gtggtgctca gtttcgagct cttgcatgcc 1560
cccgctacag tgtgcggacc gaagaagtcc acaaacctgg tgaagaacaa gtgcgttaac 1620
tttaacttca acggactcac tggcaccggc gtgctgactg agtcgaacaa gaagtttctg 1680
cccttccagc agtttggccg cgacatcgca gacaccaccg atgccgtgcg ggacccccag 1740
accctcgaga tcctggacat caccccctgc tccttcggcg gagtctccgt cataaccccc 1800
gggacaaaca cgtcgaatca ggtggctgtg ctctatcaag atgtaaattg tacagaggtg 1860
cccgtggcaa tccacgcgga ccagctgacc ccaacctggc gcgtttacag caccggcagt 1920
aacgtgttcc agacacgcgc tggttgcctc atcggcgccg aacacgtgaa caactcgtat 1980
gagggatctg ggtacatccc cgaggcccct cgcgatggcc aagcttatgt gcgaaaggac 2040
ggggagtggg tgctgctctc caccttcctg gccccccccc acgcactgag cggatccatg 2100
tctgataatg gaccccaaaa tcagcgaaat gcaccccgca ttacgtttgg tggaccctca 2160
gattcaactg gcagtaacca gaatggagaa cgcagtgggg cgcgatcaaa acaacgtcgg 2220
ccccaaggtt tacccaataa tactgcgtct tggttcaccg ctctcactca acatggcaag 2280
gaagacctta aattccctcg aggacaaggc gttccaatta acaccaatag cagtccagat 2340
gaccaaattg gctactaccg aagagctacc agacgaattc gtggtggtga cggtaaaatg 2400
aaagatctca gtccaagatg gtatttctac tacctaggaa ctgggccaga agctggactt 2460
ccctatggtg ctaacaaaga cggcatcata tgggttgcaa ctgagggagc cttgaataca 2520
ccaaaagatc acattggcac ccgcaatcct gctaacaatg ctgcaatcgt gctacaactt 2580
cctcaaggaa caacattgcc aaaaggcttc tacgcagaag ggagcagagg cggcagtcaa 2640
gcctcttctc gttcctcatc acgtagtcgc aacagttcaa gaaattcaac tccaggcagc 2700
agtaggggaa cttctcctgc tagaatggct ggcaatggcg gtgatgctgc tcttgctttg 2760
ctgctgcttg acagattgaa ccagcttgag agcaaaatgt ctggtaaagg ccaacaacaa 2820
caaggccaaa ctgtcactaa gaaatctgct gctgaggctt ctaagaagcc tcggcaaaaa 2880
cgtactgcca ctaaagcata caatgtaaca caagctttcg gcagacgtgg tccagaacaa 2940
acccaaggaa attttgggga ccaggaacta atcagacaag gaactgatta caaacattgg 3000
ccgcaaattg cacaatttgc ccccagcgct tcagcgttct tcggaatgtc gcgcattggc 3060
atggaagtca caccttcggg aacgtggttg acctacacag gtgccatcaa attggatgac 3120
aaagatccaa atttcaaaga tcaagtcatt ttgctgaata agcatattga cgcatacaaa 3180
acattcccac caacagagcc taaaaaggac aaaaagaaga aggctgatga aactcaagcc 3240
ttaccgcaga gacagaagaa acagcaaact gtgactcttc ttcctgctgc agatttggat 3300
gatttctcca aacaattgca acaatccatg agcagtgctg actcaactca ggcctaa 3357

<210> SEQ ID NO 14
<211> LENGTH: 3432
<212> TYPE: DNA
<213> ORGANISM: Artificial Sequence
<220> FEATURE:
<223> OTHER INFORMATION: SARS-CoV2-Immnogenic Protein

<400> SEQUENCE: 14
atgttcgtgt tcttggtgct tctgccgttg gtgagttctc agtgcgtcaa cctgaccacc 60
cgaacccagc tcccccccgc ctacaccaac agcatcaccc ggggcgtcta ctacccagac 120
aaggtgtttc ggtctagcgt gctgcactcc acccaggacc tgttcctccc cttcttctcc 180
aacgtgacct ggttccacgc gatccacgtg tcgggaacga acggaactaa gcgcttcgac 240
aaccctgtgc tcccctttaa cgatggcgtg tatttcgctt caaccgagaa atcgaacatc 300
attcgcggtt ggatcttcgg caccaccctg gacagtaaga ctcagtccct cctgatcgtg 360
aacaatgcca caaacgttgt gatcaaggtc tgcgagttcc agttttgcaa cgaccctttc 420

-continued

```
ctgggcgtgt actaccacaa gaataacaag tcctggatgg agtcagaatt cagggtgtac    480
agctcagcca acaactgcac attcgagtat gtgtcccagc cctttctgat ggatctggag    540
ggcaagcagg ggaacttcaa gaatctacgt gaattcgtgt tcaagaacat cgatggctat    600
ttcaaaatct actcgaagca cacgcccatc aatctggtaa gggacctgcc tcaggggttc    660
tcggccctgg agccactcgt cgatctgccg attggcatca acatcacccg ctttcaaacc    720
ctcctggccc tccacaggtc ctacctgacg cccggcgatt cgtcgagtgg gtggacggca    780
ggcgcagctg cgtactacgt ggggtacctg cagccacgaa ccttcctgct gaagtacaac    840
gagaacggca cgattaccga cgcggttgat tgcgccttgg acccgctctc cgaaaccaag    900
tgcaccctga agagcttcac cgtggagaag ggaatctacc agacgagtaa cttccgcgtg    960
cagccgaccg agagtattgt tcggttcccc aacatcacca acttgtgccc atttggcgag   1020
gtcttcaacg ccacccgctt cgcaagcgtg tacgcctgga accgcaagag aatctccaat   1080
tgcgtggccg actacagcgt cctgtacaac tcggcctcgt tcagtacgtt caagtgctac   1140
ggggtgtccc ccaccaagct caatgacctc tgctttacca acgtgtacgc tgattcgttc   1200
gtaatcaggg gtgacgaggt gcgccagatc gccccaggcc agactgggaa gatcgctgac   1260
tataactata agctccccga cgactttacc ggctgcgtca tcgcctggaa ctccaacaac   1320
ctggattcga aggtgggagg caactacaat tacctgtatc gcctcttcag gaagtcaaat   1380
ctgaagcctt tcgagaggga catatcgacc gagatctacc aggcgggaag taccccctgc   1440
aacggggtgg aggggttcaa ctgctacttc ccgctgcagt cgtacggctt ccagcctacc   1500
aacggggtcg ggtaccagcc ctaccgcgtg gtggtgctca gtttcgagct cttgcatgcc   1560
cccgctacag tgtgcggacc gaagaagtcc acaaacctgg tgaagaacaa gtgcgttaac   1620
tttaacttca acggactcac tggcaccggc gtgctgactg agtcgaacaa gaagtttctg   1680
cccttccagc agtttggccg cgacatcgca gacaccaccg atgccgtgcg ggacccccag   1740
accctcgaga tcctggacat caccccctgc tccttcggcg gagtctccgt cataaccccc   1800
gggacaaaca cgtcgaatca ggtggctgtg ctctatcaag atgtaaattg tacagaggtg   1860
cccgtggcaa tccacgcgga ccagctgacc ccaacctggc gcgtttacag caccggcagt   1920
aacgtgttcc agacacgcgc tggttgcctc atcggcgccg aacacgtgaa caactcgtat   1980
gagggatctg ggtacatccc cgaggcccct cgcgatggcc aagcttatgt gcgaaaggac   2040
ggggagtggg tgctgctctc caccttcctg gcccccccc acgcactgag cggatccggc   2100
cagtgtacaa actacgccct gcttaaatta gccggcgacg tggagtcaaa ccccggcccc   2160
gtcgacgcca ccatgtctga taatggaccc caaaatcagc gaaatgcacc ccgcattacg   2220
tttggtggac cctcagattc aactggcagt aaccagaatg gagaacgcag tggggcgcga   2280
tcaaaacaac gtcggcccca aggtttaccc aataatactg cgtcttggtt caccgctctc   2340
actcaacatg gcaaggaaga ccttaaattc cctcgaggac aaggcgttcc aattaacacc   2400
aatagcagtc cagatgacca aattggctac taccgaagag ctaccagacg aattcgtggt   2460
ggtgacggta aaatgaaaga tctcagtcca agatggtatt tctactacct aggaactggg   2520
ccagaagctg gacttcccta tggtgctaac aaagacggca tcatatgggt tgcaactgag   2580
ggagccttga atacaccaaa agatcacatt ggcacccgca atcctgctaa caatgctgca   2640
atcgtgctac aacttcctca aggaacaaca ttgccaaaag gcttctacgc agaagggagc   2700
agaggcggca gtcaagcctc ttctcgttcc tcatcacgta gtcgcaacag ttcaagaaat   2760
tcaactccag gcagcagtag gggaacttct cctgctagaa tggctggcaa tggcggtgat   2820
```

gctgctcttg ctttgctgct gcttgacaga ttgaaccagc ttgagagcaa aatgtctggt 2880
aaaggccaac aacaacaagg ccaaactgtc actaagaaat ctgctgctga ggcttctaag 2940
aagcctcggc aaaaacgtac tgccactaaa gcatacaatg taacacaagc tttcggcaga 3000
cgtggtccag aacaaaccca aggaaatttt ggggaccagg aactaatcag acaaggaact 3060
gattacaaac attggccgca aattgcacaa tttgccccca gcgcttcagc gttcttcgga 3120
atgtcgcgca ttggcatgga agtcacacct tcgggaacgt ggttgaccta cacaggtgcc 3180
atcaaattgg atgacaaaga tccaaatttc aaagatcaag tcattttgct gaataagcat 3240
attgacgcat acaaaacatt cccaccaaca gagcctaaaa aggacaaaaa gaagaaggct 3300
gatgaaactc aagccttacc gcagagacag aagaaacagc aaactgtgac tcttcttcct 3360
gctgcagatt tggatgattt ctccaaacaa ttgcaacaat ccatgagcag tgctgactca 3420
actcaggcct aa 3432

<210> SEQ ID NO 15
<211> LENGTH: 663
<212> TYPE: PRT
<213> ORGANISM: Artificial Sequence
<220> FEATURE:
<223> OTHER INFORMATION: SARS-CoV2-Immunogenic Protein

<400> SEQUENCE: 15

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Ile
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser

-continued

```
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Gly Ser
            660
```

<210> SEQ ID NO 16
<211> LENGTH: 1082
<212> TYPE: PRT
<213> ORGANISM: Artificial Sequence
<220> FEATURE:
<223> OTHER INFORMATION: SARS-CoV2-Immunogenic Protein

<400> SEQUENCE: 16

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Ile
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

Gly Trp Thr Ala Gly Ala Ala Ala Tyr Tyr Val Gly Tyr Leu Gln Pro
260 265 270

Arg Thr Phe Leu Leu Lys Tyr Asn Glu Asn Gly Thr Ile Thr Asp Ala
275 280 285

Val Asp Cys Ala Leu Asp Pro Leu Ser Glu Thr Lys Cys Thr Leu Lys
290 295 300

Ser Phe Thr Val Glu Lys Gly Ile Tyr Gln Thr Ser Asn Phe Arg Val
305 310 315 320

Gln Pro Thr Glu Ser Ile Val Arg Phe Pro Asn Ile Thr Asn Leu Cys
325 330 335

Pro Phe Gly Glu Val Phe Asn Ala Thr Arg Phe Ala Ser Val Tyr Ala
340 345 350

Trp Asn Arg Lys Arg Ile Ser Asn Cys Val Ala Asp Tyr Ser Val Leu
355 360 365

-continued

```
Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Gly Ser Met Ser Asp Asn Gly Pro Gln Asn Gln
            660                 665                 670

Arg Asn Ala Pro Arg Ile Thr Phe Gly Gly Pro Ser Asp Ser Thr Gly
        675                 680                 685

Ser Asn Gln Asn Gly Glu Arg Ser Gly Ala Arg Ser Lys Gln Arg Arg
    690                 695                 700

Pro Gln Gly Leu Pro Asn Asn Thr Ala Ser Trp Phe Thr Ala Leu Thr
705                 710                 715                 720

Gln His Gly Lys Glu Asp Leu Lys Phe Pro Arg Gly Gln Gly Val Pro
                725                 730                 735

Ile Asn Thr Asn Ser Ser Pro Asp Asp Gln Ile Gly Tyr Tyr Arg Arg
            740                 745                 750

Ala Thr Arg Arg Ile Arg Gly Gly Asp Gly Lys Met Lys Asp Leu Ser
        755                 760                 765

Pro Arg Trp Tyr Phe Tyr Tyr Leu Gly Thr Gly Pro Glu Ala Gly Leu
    770                 775                 780
```

```
Pro Tyr Gly Ala Asn Lys Asp Gly Ile Ile Trp Val Ala Thr Glu Gly
785                 790                 795                 800

Ala Leu Asn Thr Pro Lys Asp His Ile Gly Thr Arg Asn Pro Ala Asn
                805                 810                 815

Asn Ala Ala Ile Val Leu Gln Leu Pro Gln Gly Thr Thr Leu Pro Lys
            820                 825                 830

Gly Phe Tyr Ala Glu Gly Ser Arg Gly Gly Ser Gln Ala Ser Ser Arg
        835                 840                 845

Ser Ser Ser Arg Ser Arg Asn Ser Ser Arg Asn Ser Thr Pro Gly Ser
    850                 855                 860

Ser Arg Gly Thr Ser Pro Ala Arg Met Ala Gly Asn Gly Gly Asp Ala
865                 870                 875                 880

Ala Leu Ala Leu Leu Leu Leu Asp Arg Leu Asn Gln Leu Glu Ser Lys
                885                 890                 895

Met Ser Gly Lys Gly Gln Gln Gln Gln Gly Gln Thr Val Thr Lys Lys
            900                 905                 910

Ser Ala Ala Glu Ala Ser Lys Lys Pro Arg Gln Lys Arg Thr Ala Thr
        915                 920                 925

Lys Ala Tyr Asn Val Thr Gln Ala Phe Gly Arg Arg Gly Pro Glu Gln
    930                 935                 940

Thr Gln Gly Asn Phe Gly Asp Gln Glu Leu Ile Arg Gln Gly Thr Asp
945                 950                 955                 960

Tyr Lys His Trp Pro Gln Ile Ala Gln Phe Ala Pro Ser Ala Ser Ala
                965                 970                 975

Phe Phe Gly Met Ser Arg Ile Gly Met Glu Val Thr Pro Ser Gly Thr
            980                 985                 990

Trp Leu Thr Tyr Thr Gly Ala Ile  Lys Leu Asp Asp Lys  Asp Pro Asn
        995                 1000                1005

Phe Lys  Asp Gln Val Ile Leu  Leu Asn Lys His Ile  Asp Ala Tyr
    1010                1015                1020

Lys Thr  Phe Pro Pro Thr Glu  Pro Lys Lys Asp Lys  Lys Lys Lys
    1025                1030                1035

Ala Asp  Glu Thr Gln Ala Leu  Pro Gln Arg Gln Lys  Lys Gln Gln
    1040                1045                1050

Thr Val  Thr Leu Leu Pro Ala  Ala Asp Leu Asp Asp  Phe Ser Lys
    1055                1060                1065

Gln Leu  Gln Gln Ser Met Ser  Ser Ala Asp Ser Thr  Gln Ala
    1070                1075                1080


<210> SEQ ID NO 17
<211> LENGTH: 1107
<212> TYPE: PRT
<213> ORGANISM: Artificial Sequence
<220> FEATURE:
<223> OTHER INFORMATION: SARS-CoV2-Immunogenic Protein

<400> SEQUENCE: 17

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Ile
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60
```

-continued

```
Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
```

-continued

```
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Gly Ser Gly Gln Cys Thr Asn Tyr Ala Leu Leu
            660                 665                 670

Lys Leu Ala Gly Asp Val Glu Ser Asn Pro Gly Pro Val Asp Ala Thr
        675                 680                 685

Met Ser Asp Asn Gly Pro Gln Asn Gln Arg Asn Ala Pro Arg Ile Thr
    690                 695                 700

Phe Gly Gly Pro Ser Asp Ser Thr Gly Ser Asn Gln Asn Gly Glu Arg
705                 710                 715                 720

Ser Gly Ala Arg Ser Lys Gln Arg Arg Pro Gln Gly Leu Pro Asn Asn
                725                 730                 735

Thr Ala Ser Trp Phe Thr Ala Leu Thr Gln His Gly Lys Glu Asp Leu
            740                 745                 750

Lys Phe Pro Arg Gly Gln Gly Val Pro Ile Asn Thr Asn Ser Ser Pro
        755                 760                 765

Asp Asp Gln Ile Gly Tyr Tyr Arg Arg Ala Thr Arg Arg Ile Arg Gly
    770                 775                 780

Gly Asp Gly Lys Met Lys Asp Leu Ser Pro Arg Trp Tyr Phe Tyr Tyr
785                 790                 795                 800

Leu Gly Thr Gly Pro Glu Ala Gly Leu Pro Tyr Gly Ala Asn Lys Asp
                805                 810                 815

Gly Ile Ile Trp Val Ala Thr Glu Gly Ala Leu Asn Thr Pro Lys Asp
            820                 825                 830

His Ile Gly Thr Arg Asn Pro Ala Asn Asn Ala Ala Ile Val Leu Gln
        835                 840                 845

Leu Pro Gln Gly Thr Thr Leu Pro Lys Gly Phe Tyr Ala Glu Gly Ser
    850                 855                 860

Arg Gly Gly Ser Gln Ala Ser Ser Arg Ser Ser Ser Arg Ser Arg Asn
865                 870                 875                 880

Ser Ser Arg Asn Ser Thr Pro Gly Ser Ser Arg Gly Thr Ser Pro Ala
                885                 890                 895

Arg Met Ala Gly Asn Gly Gly Asp Ala Ala Leu Ala Leu Leu Leu Leu
            900                 905                 910
```

Asp Arg Leu Asn Gln Leu Glu Ser Lys Met Ser Gly Lys Gly Gln Gln
915 920 925

Gln Gln Gly Gln Thr Val Thr Lys Lys Ser Ala Ala Glu Ala Ser Lys
930 935 940

Lys Pro Arg Gln Lys Arg Thr Ala Thr Lys Ala Tyr Asn Val Thr Gln
945 950 955 960

Ala Phe Gly Arg Arg Gly Pro Glu Gln Thr Gln Gly Asn Phe Gly Asp
965 970 975

Gln Glu Leu Ile Arg Gln Gly Thr Asp Tyr Lys His Trp Pro Gln Ile
980 985 990

Ala Gln Phe Ala Pro Ser Ala Ser Ala Phe Phe Gly Met Ser Arg Ile
995 1000 1005

Gly Met Glu Val Thr Pro Ser Gly Thr Trp Leu Thr Tyr Thr Gly
1010 1015 1020

Ala Ile Lys Leu Asp Asp Lys Asp Pro Asn Phe Lys Asp Gln Val
1025 1030 1035

Ile Leu Leu Asn Lys His Ile Asp Ala Tyr Lys Thr Phe Pro Pro
1040 1045 1050

Thr Glu Pro Lys Lys Asp Lys Lys Lys Lys Ala Asp Glu Thr Gln
1055 1060 1065

Ala Leu Pro Gln Arg Gln Lys Lys Gln Gln Thr Val Thr Leu Leu
1070 1075 1080

Pro Ala Ala Asp Leu Asp Asp Phe Ser Lys Gln Leu Gln Gln Ser
1085 1090 1095

Met Ser Ser Ala Asp Ser Thr Gln Ala
1100 1105

<210> SEQ ID NO 18
<211> LENGTH: 710
<212> TYPE: PRT
<213> ORGANISM: Artificial Sequence
<220> FEATURE:
<223> OTHER INFORMATION: SARS-CoV2-Immunogenic Protein

<400> SEQUENCE: 18

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Ile
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

```
Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575
```

```
Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Gly Ser Gly Tyr Ile Pro Glu Ala Pro Arg Asp
            660                 665                 670

Gly Gln Ala Tyr Val Arg Lys Asp Gly Glu Trp Val Leu Leu Ser Thr
        675                 680                 685

Phe Leu Ala Pro Pro His Ala Leu Ser Glu Asn Leu Tyr Phe Glu Gly
    690                 695                 700

His His His His His His
705                 710


<210> SEQ ID NO 19
<211> LENGTH: 1118
<212> TYPE: PRT
<213> ORGANISM: Artificial Sequence
<220> FEATURE:
<223> OTHER INFORMATION: SARS-CoV2-Immunogenic Protein

<400> SEQUENCE: 19

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Ile
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220
```

-continued

```
Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
```

-continued

```
                645                 650                 655

Asn Asn Ser Tyr Glu Gly Ser Gly Tyr Ile Pro Glu Ala Pro Arg Asp
            660                 665                 670

Gly Gln Ala Tyr Val Arg Lys Asp Gly Glu Trp Val Leu Leu Ser Thr
        675                 680                 685

Phe Leu Ala Pro Pro His Ala Leu Ser Gly Ser Met Ser Asp Asn Gly
    690                 695                 700

Pro Gln Asn Gln Arg Asn Ala Pro Arg Ile Thr Phe Gly Gly Pro Ser
705                 710                 715                 720

Asp Ser Thr Gly Ser Asn Gln Asn Gly Glu Arg Ser Gly Ala Arg Ser
                725                 730                 735

Lys Gln Arg Arg Pro Gln Gly Leu Pro Asn Asn Thr Ala Ser Trp Phe
            740                 745                 750

Thr Ala Leu Thr Gln His Gly Lys Glu Asp Leu Lys Phe Pro Arg Gly
        755                 760                 765

Gln Gly Val Pro Ile Asn Thr Asn Ser Ser Pro Asp Asp Gln Ile Gly
    770                 775                 780

Tyr Tyr Arg Arg Ala Thr Arg Arg Ile Arg Gly Gly Asp Gly Lys Met
785                 790                 795                 800

Lys Asp Leu Ser Pro Arg Trp Tyr Phe Tyr Tyr Leu Gly Thr Gly Pro
                805                 810                 815

Glu Ala Gly Leu Pro Tyr Gly Ala Asn Lys Asp Gly Ile Ile Trp Val
            820                 825                 830

Ala Thr Glu Gly Ala Leu Asn Thr Pro Lys Asp His Ile Gly Thr Arg
        835                 840                 845

Asn Pro Ala Asn Asn Ala Ala Ile Val Leu Gln Leu Pro Gln Gly Thr
    850                 855                 860

Thr Leu Pro Lys Gly Phe Tyr Ala Glu Gly Ser Arg Gly Gly Ser Gln
865                 870                 875                 880

Ala Ser Ser Arg Ser Ser Ser Arg Ser Arg Asn Ser Ser Arg Asn Ser
                885                 890                 895

Thr Pro Gly Ser Ser Arg Gly Thr Ser Pro Ala Arg Met Ala Gly Asn
            900                 905                 910

Gly Gly Asp Ala Ala Leu Ala Leu Leu Leu Leu Asp Arg Leu Asn Gln
        915                 920                 925

Leu Glu Ser Lys Met Ser Gly Lys Gly Gln Gln Gln Gln Gly Gln Thr
    930                 935                 940

Val Thr Lys Lys Ser Ala Ala Glu Ala Ser Lys Lys Pro Arg Gln Lys
945                 950                 955                 960

Arg Thr Ala Thr Lys Ala Tyr Asn Val Thr Gln Ala Phe Gly Arg Arg
                965                 970                 975

Gly Pro Glu Gln Thr Gln Gly Asn Phe Gly Asp Gln Glu Leu Ile Arg
            980                 985                 990

Gln Gly Thr Asp Tyr Lys His Trp  Pro Gln Ile Ala Gln  Phe Ala Pro
        995                 1000                 1005

Ser Ala  Ser Ala Phe Phe Gly  Met Ser Arg Ile Gly  Met Glu Val
    1010                 1015                 1020

Thr Pro  Ser Gly Thr Trp Leu  Thr Tyr Thr Gly Ala  Ile Lys Leu
    1025                 1030                 1035

Asp Asp  Lys Asp Pro Asn Phe  Lys Asp Gln Val Ile  Leu Leu Asn
    1040                 1045                 1050

Lys His  Ile Asp Ala Tyr Lys  Thr Phe Pro Pro Thr  Glu Pro Lys
    1055                 1060                 1065
```

```
Lys Asp  Lys Lys Lys Lys Ala  Asp Glu Thr Gln Ala  Leu Pro Gln
    1070                 1075                 1080

Arg Gln  Lys Lys Gln Gln Thr  Val Thr Leu Leu Pro  Ala Ala Asp
    1085                 1090                 1095

Leu Asp  Asp Phe Ser Lys Gln  Leu Gln Gln Ser Met  Ser Ser Ala
    1100                 1105                 1110

Asp Ser  Thr Gln Ala
    1115


<210> SEQ ID NO 20
<211> LENGTH: 1143
<212> TYPE: PRT
<213> ORGANISM: Artificial Sequence
<220> FEATURE:
<223> OTHER INFORMATION: SARS-CoV2-Immunogenic Protein

<400> SEQUENCE: 20

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Ile
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300
```

-continued

```
Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Gly Ser Gly Tyr Ile Pro Glu Ala Pro Arg Asp
            660                 665                 670

Gly Gln Ala Tyr Val Arg Lys Asp Gly Glu Trp Val Leu Leu Ser Thr
        675                 680                 685

Phe Leu Ala Pro Pro His Ala Leu Ser Gly Ser Gly Gln Cys Thr Asn
    690                 695                 700

Tyr Ala Leu Leu Lys Leu Ala Gly Asp Val Glu Ser Asn Pro Gly Pro
705                 710                 715                 720
```

```
Val Asp Ala Thr Met Ser Asp Asn Gly Pro Gln Asn Gln Arg Asn Ala
                725                 730                 735

Pro Arg Ile Thr Phe Gly Gly Pro Ser Asp Ser Thr Gly Ser Asn Gln
            740                 745                 750

Asn Gly Glu Arg Ser Gly Ala Arg Ser Lys Gln Arg Arg Pro Gln Gly
        755                 760                 765

Leu Pro Asn Asn Thr Ala Ser Trp Phe Thr Ala Leu Thr Gln His Gly
    770                 775                 780

Lys Glu Asp Leu Lys Phe Pro Arg Gly Gln Gly Val Pro Ile Asn Thr
785                 790                 795                 800

Asn Ser Ser Pro Asp Asp Gln Ile Gly Tyr Tyr Arg Arg Ala Thr Arg
                805                 810                 815

Arg Ile Arg Gly Gly Asp Gly Lys Met Lys Asp Leu Ser Pro Arg Trp
            820                 825                 830

Tyr Phe Tyr Tyr Leu Gly Thr Gly Pro Glu Ala Gly Leu Pro Tyr Gly
        835                 840                 845

Ala Asn Lys Asp Gly Ile Ile Trp Val Ala Thr Glu Gly Ala Leu Asn
    850                 855                 860

Thr Pro Lys Asp His Ile Gly Thr Arg Asn Pro Ala Asn Asn Ala Ala
865                 870                 875                 880

Ile Val Leu Gln Leu Pro Gln Gly Thr Thr Leu Pro Lys Gly Phe Tyr
                885                 890                 895

Ala Glu Gly Ser Arg Gly Gly Ser Gln Ala Ser Ser Arg Ser Ser Ser
            900                 905                 910

Arg Ser Arg Asn Ser Ser Arg Asn Ser Thr Pro Gly Ser Ser Arg Gly
        915                 920                 925

Thr Ser Pro Ala Arg Met Ala Gly Asn Gly Gly Asp Ala Ala Leu Ala
    930                 935                 940

Leu Leu Leu Leu Asp Arg Leu Asn Gln Leu Glu Ser Lys Met Ser Gly
945                 950                 955                 960

Lys Gly Gln Gln Gln Gln Gly Gln Thr Val Thr Lys Lys Ser Ala Ala
                965                 970                 975

Glu Ala Ser Lys Lys Pro Arg Gln Lys Arg Thr Ala Thr Lys Ala Tyr
            980                 985                 990

Asn Val Thr Gln Ala Phe Gly Arg  Arg Gly Pro Glu Gln  Thr Gln Gly
        995                 1000                1005

Asn Phe  Gly Asp Gln Glu Leu  Ile Arg Gln Gly Thr  Asp Tyr Lys
    1010                 1015                 1020

His Trp  Pro Gln Ile Ala Gln  Phe Ala Pro Ser Ala  Ser Ala Phe
    1025                 1030                 1035

Phe Gly  Met Ser Arg Ile Gly  Met Glu Val Thr Pro  Ser Gly Thr
    1040                 1045                 1050

Trp Leu  Thr Tyr Thr Gly Ala  Ile Lys Leu Asp Asp  Lys Asp Pro
    1055                 1060                 1065

Asn Phe  Lys Asp Gln Val Ile  Leu Leu Asn Lys His  Ile Asp Ala
    1070                 1075                 1080

Tyr Lys  Thr Phe Pro Pro Thr  Glu Pro Lys Lys Asp  Lys Lys Lys
    1085                 1090                 1095

Lys Ala  Asp Glu Thr Gln Ala  Leu Pro Gln Arg Gln  Lys Lys Gln
    1100                 1105                 1110

Gln Thr  Val Thr Leu Leu Pro  Ala Ala Asp Leu Asp  Asp Phe Ser
    1115                 1120                 1125

Lys Gln  Leu Gln Gln Ser Met  Ser Ser Ala Asp Ser  Thr Gln Ala
```

```
    1130                1135                1140


<210> SEQ ID NO 21
<211> LENGTH: 229
<212> TYPE: PRT
<213> ORGANISM: Artificial Sequence
<220> FEATURE:
<223> OTHER INFORMATION: Immunoglobulin Dimerization Domain

<400> SEQUENCE: 21

Asp Lys Thr His Thr Cys Pro Ser Arg Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Asp Glu Leu Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Leu His Glu Ala Leu His Ser His Tyr Thr Gln Lys Ser Leu Ser
    210                 215                 220

Leu Ser Pro Gly Lys
225


<210> SEQ ID NO 22
<211> LENGTH: 27
<212> TYPE: PRT
<213> ORGANISM: Artificial Sequence
<220> FEATURE:
<223> OTHER INFORMATION: T4 Fibritin Foldon Trimerization Domain

<400> SEQUENCE: 22

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25


<210> SEQ ID NO 23
<211> LENGTH: 64
<212> TYPE: PRT
<213> ORGANISM: Artificial Sequence
<220> FEATURE:
```

-continued

```
<223> OTHER INFORMATION: Colagen XV Trimerization Domain

<400> SEQUENCE: 23

Val Thr Ala Phe Ser Asn Met Asp Asp Met Leu Gln Lys Ala His Leu
1               5                   10                  15

Val Ile Glu Gly Thr Phe Ile Tyr Leu Arg Asp Ser Thr Glu Phe Phe
            20                  25                  30

Ile Arg Val Arg Asp Gly Trp Lys Lys Leu Gln Leu Gly Glu Leu Ile
        35                  40                  45

Pro Ile Pro Ala Asp Ser Pro Pro Pro Pro Ala Leu Ser Ser Asn Pro
    50                  55                  60
```